(12) United States Patent
Ryu et al.

(10) Patent No.: US 11,066,391 B1
(45) Date of Patent: Jul. 20, 2021

(54) ATORVASTATIN DERIVED HMG-COA REDUCTASE DEGRADATION INDUCING COMPOUND

(71) Applicant: UPPTHERA, Incheon (KR)

(72) Inventors: Soo Hee Ryu, Incheon (KR); Hwa Jin Lee, Incheon (KR); Seong Hoon Kim, Incheon (KR); Hye Guk Ryu, Incheon (KR); Eun Bin Lee, Incheon (KR)

(73) Assignee: UPPTHERA, Incheon (KR)

( * ) Notice: Subject to any disclaimer, the term of this patent is extended or adjusted under 35 U.S.C. 154(b) by 0 days.

(21) Appl. No.: 17/210,512

(22) Filed: Mar. 24, 2021

(30) Foreign Application Priority Data

Mar. 25, 2020 (KR) ........................ 10-2020-0036498

(51) Int. Cl.
*C07D 401/14* (2006.01)
(52) U.S. Cl.
CPC .................................. *C07D 401/14* (2013.01)
(58) Field of Classification Search
CPC .................................................. C07D 401/14
See application file for complete search history.

(56) References Cited

FOREIGN PATENT DOCUMENTS

WO   WO 2019/109415 A1   6/2019

OTHER PUBLICATIONS

WO 2019109415 (2019) ProQuest English Machine translation p. 1-64.*
Maple, H. J., "Developing degraders: principles and perspectives on design and chemical space." MedChemComm 10.10 (2019): 1755-1764.*
Burslem, George M., and Craig M. Crews. "Small-molecule modulation of protein homeostasis." Chemical reviews 117.17 (2017): 11269-11301.
Ito, Takumi, et al. "Identification of a primary target of thalidomide teratogenicity." Science 327.5971 (2010): 1345-1350.
Chamberlain, Philip P., and Brian E. Cathers. "Cereblon modulators: Low molecular weight inducers of protein degradation." Drug Discovery Today: Technologies 31 (2019): 29-34.
Akuffo, Afua A., et al. "Ligand-mediated protein degradation reveals functional conservation among sequence variants of the CUL4-type E3 ligase substrate receptor cereblon." Journal of Biological Chemistry 293.16 (2018): 6187-6200.
Burslem, George M., et al. "Efficient Synthesis of Immunomodulatory Drug Analogues Enables Exploration of Structure Degradation Relationships." ChemMedChem 13.15 (2018): 1508.
Schneekloth, John S., et al. "Chemical genetic control of protein levels: selective in vivo targeted degradation." Journal of the American Chemical Society 126.12 (2004): 3748-3754.
Rodriguez-Gonzalez, A., et al. "Targeting steroid hormone receptors for ubiquitination and degradation in breast and prostate cancer." Oncogene 27.57 (2008): 7201-7211.
Buckley, Dennis L., et al. "Targeting the von Hippel-Lindau E3 ubiquitin ligase using small molecules to disrupt the VHL/HIF-1α interaction." Journal of the American Chemical Society 134.10 (2012): 4465-4468.
Buckley, Dennis L., et al. "Small-Molecule Inhibitors of the Interaction between the E3 Ligase VHL and HIF1α." Angewandte Chemie International Edition 51.46 (2012): 11463-11467.
Galdeano, Caries, et al. "Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities." Journal of Medicinal Chemistry 57.20 (2014): 8657-8663.
Soares, Pedro, et al. "Group-based optimization of potent and cell-active inhibitors of the von Hippel-Lindau (VHL) E3 ubiquitin ligase: structure-activity relationships leading to the chemical probe (2 S, 4 R)-1-((S)-2-(1-cyanocyclopropanecarboxamido)-3,3-dimethylbutanoyl)-4-hydroxy-N-(4-(4-methylthiazol-5-yl) benzyl) pyrrolidine-2-carboxamide (VH298)." Journal of medicinal chemistry 61.2 (2018): 599-618.
Istvan, Eva S., and Johann Deisenhofer. "Structural mechanism for statin inhibition of HMG-CoA reductase." Science 292.5519 (2001): 1160-1164.
Istvan, Eva. "Statin inhibition of HMG-CoA reductase: a 3-dimensional view." Atherosclerosis Supplements 4.1 (2003): 3-8.

* cited by examiner

*Primary Examiner* — John M Mauro
(74) *Attorney, Agent, or Firm* — Nicholas Park

(57) ABSTRACT

The present invention relates to bifunctional compounds that induce HMG-CoA reductase degradation, in which in which atorvastatin and E3 ubiquitin ligase binding moiety are chemically linked. The present invention also relates to a preparation method of the compounds, a method for degrading HMG-CoA reductase using the compounds, and a composition for the prevention or treatment of HMG-CoA reductase-related diseases comprising the compounds.

3 Claims, 2 Drawing Sheets

ATORVASTATIN DERIVED HMG-COA REDUCTASE DEGRADATION INDUCING COMPOUND

CROSS-REFERENCE TO RELATED APPLICATIONS

This application claims priority to Korean Patent Application No. 10-2020-0036498 filed on Mar. 25, 2020 and all the benefits accruing therefrom under 35 U.S.C. § 119, the contents of which are incorporated by reference in their entirety.

BACKGROUND

The present invention relates to a 3-hydroxy-3-methyl-glutaryl-coenzyme A reductase (HMG-CoA reductase) degradation inducing compound, a method for preparing the same, and the use thereof. Intracellular cholesterol homeostasis may be maintained through transcriptional regulation of HMG-CoA reductase through a sterol regulatory element-binding protein (SREBP) pathway. The SREBP is a transcriptional regulator present in the endoplasmic reticulum membrane,—which forms a complex with SREBP cleavage-activating protein (SCAP). When the concentration of the intracellular cholesterol drops, the complex moves to the Golgi apparatus to induce cleavage of the SREBP, and the activated SREBP enters cell's nucleus to promote transcription of HMG-CoA reductase. On the other hand, when the concentration of the intracellular cholesterol elevates, INSIG (insulin-induced gene) binds to SCAP and inhibits the movement of the SREBP-SCAP complex to the Golgi apparatus, thereby inhibiting the transcription of HMG-CoA reductase.

The HMG-CoA reductase is involved in conversion of HMG-CoA to mevalonate in a mevalonate pathway, which is a pathway for cholesterol biosynthesis in hepatocytes, with the cholesterol as the end product. Statin-based compounds are designed to bind the active site of HMG-CoA reductase, thereby inhibiting enzyme activity. Through the drug mechanism, the statin-based compounds may inhibit intracellular cholesterol production and lower blood cholesterol concentration and reduce the risk of cardiovascular disease. However, when the intracellular cholesterol concentration is lowered by statin, the SREBP pathway may be activated to increase expression of the HMG-CoA as a compensatory mechanism. As a result, in addition to weakening effect of statin, higher dose of statin is necessary, which may lead to risk of type 2 diabetes, muscle pain, or the like. In addition, patients taking high dose of statins for a long period of time in which HMG-CoA reductase are induced, the prognosis may worsen if the patient stops taking the drug. Therefore, there is a demand for alternative drug capable of solving the disadvantages of statin therapy as described above.

Recently, a proteolysis targeting chimera (PROTAC) has been proposed as a small molecule-based platform technology capable of inducing proteolysis of a target protein in the human body. The PROTAC is a bifunctional compound in which a ligand molecule that binds to disease-related target protein and an E3 ubiquitin ligase binding moiety are linked by a chemical linker. Theoretically, the PROTAC compound is capable of inducing degradation of the target protein by placing the disease-related target protein near the E3 ubiquitin ligase. In the case of the PROTAC compound having the HMG-CoA reductase as a target protein, International Patent Publication No. WO2019/109415 A1 discloses some bifunctional compounds in which atorvastatin and a binding moiety for E3 ubiquitin ligase CRBN are linked by a triazole group linker.

However, the above document only describes a synthesis example of statin-derived PROTAC compound including 1 type of atorvastatin. In addition, the above document merely shows partial confirmation of degradation effects of HMG-CoA reductase in CHO cell line (SRD-15) artificially mutated to lack the function of INSIG, etc. The CHO cell line is histologically different from the hepatocyte environment in which statins actually act, and has basically different expression and activity characteristics of HMG-CoA reductase. In addition, the cell line is engineered to maintain a constant level of expression of HMG-CoA reductase through artificially mutating a gene. Thus, unlike the hepatocyte environment, the compensatory mechanism of HMG-CoA reductase depending on the intracellular cholesterol concentration does not occur. In other words, in actual hepatocytes, when the intracellular cholesterol concentration is lowered by administering statins, the HMG-CoA reductase is overexpressed as a compensatory mechanism, and as a result, the pharmacological effect of statins is weakened, but the SRD-15 cell line does not reflect these hepatocyte characteristics. Therefore, it is not sufficient to conclude from the above document that the PROTAC compound using atorvastatin as a binding moiety to the HMG-CoA reductase effectively induces degradation of the HMG-CoA reductase while overcoming the compensation mechanism caused by atorvastatin action in the actual hepatocyte environment.

In addition, the target protein degradation effect of the PROTAC compound may vary significantly depending on the type and length of the linker, and the attachment position of the linker in the target protein ligand, etc., in addition to the type of the target protein ligand and the type of the E3 ubiquitin ligase ligand binding moiety constituting the PROTAC compound (see Burslem and Crews, 2017, etc.). Therefore, it is extremely difficult to predict a structure of a compound capable of effectively inducing the degradation of the HMG-CoA reductase among a wide range of statin-derived PROTAC compounds that are not described in WO2019/109415 A1.

SUMMARY

An object of the present invention is to provide HMG-CoA reductase degradation inducing compounds.

Another object of the present invention is to provide a method for preparing the compounds.

Still another object of the present invention is to provide a use of the compounds.

HMG-CoA Reductase Degradation Inducing Compounds

The present invention provides novel compounds that induce HMG-CoA reductase protein degradation. Specifically, the present invention provides a bifunctional compound in which a HMG-CoA reductase binding moiety and an E3 ubiquitin ligase-binding moiety are linked by a chemical linker.

In one general aspect, there is provided a compound represented by the following Formula I or a pharmaceutically acceptable salt thereof:

ULM-Linker-PTM  [Formula I]

in the Formula I,

ULM is CRBN or VHL E3 ubiquitin ligase binding moiety,

PTM is

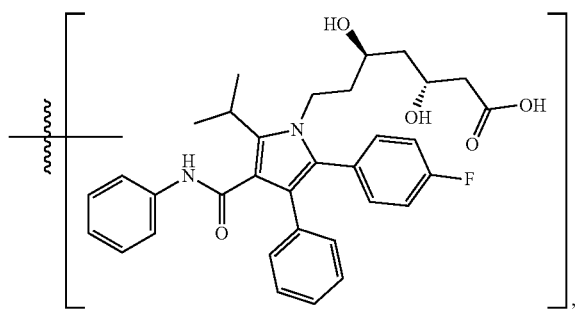

Linker is a chemical group that links ULM and PTM, wherein the PTM is connected to the Linker in the form of the one selected from the group consisting of:

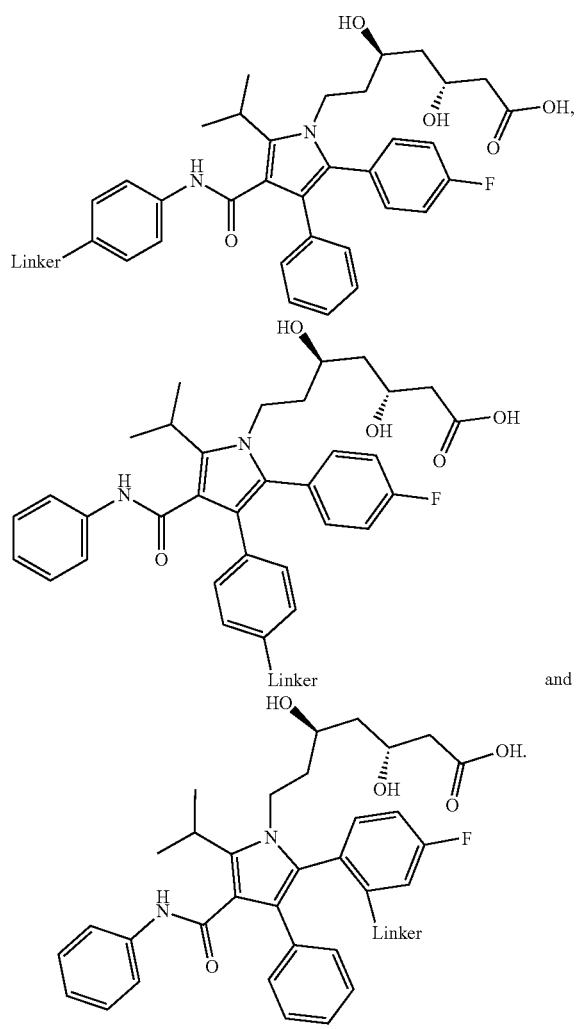

(1) E3 Ubiquitin Ligase Binding Moiety (ULM)

According to an embodiment of the present invention, ULM is a CRBN E3 ubiquitin ligase binding moiety. In the present invention, CRBN means Cereblon E3 ubiquitin ligase.

In one embodiment, the CRBN E3 ubiquitin ligase binding moiety of the present invention is represented by Formula A:

[Formula A]

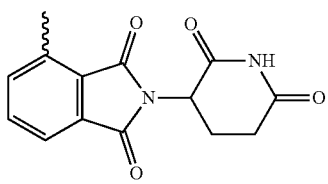

The moiety represented by the Formula A is covalently linked to the Linker as defined in Formula I through ～～～.

According to another embodiment of the present invention, ULM is a VHL E3 ubiquitin ligase ligand binding moiety. In the present invention, VHL means a von Hippel-Lindau tumor suppressor.

In one embodiment, the VHL E3 ubiquitin ligase binding moiety of the present invention is represented by Formula B:

[Formula B]

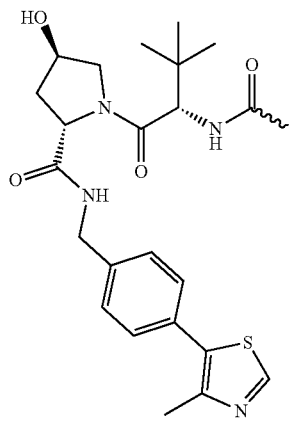

The moiety represented by the Formula B is covalently linked to the Linker as defined in Formula I through ～～～.

(2) Protein Target Moiety (PTM)

In the compound represented by Formula I, the PTM, a moiety that performs a target protein ligand function, is a statin-based compound called atorvastatin, and its preparation method is known in the art.

(3) Linker

According to an embodiment of the present invention, the Linker as defined in Formula I is a chemical structure selected from the group consisting of:

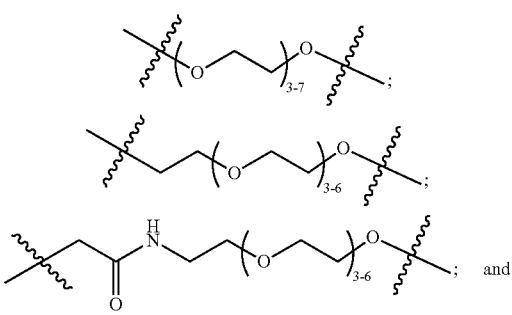

-continued

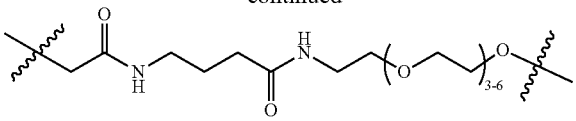

wherein, the left end of the structure is connected to ULM, and the right end is connected to PTM.

In one embodiment, the compound represented by Formula I is selected from the group consisting of Compounds 1-14 below:

(3R,5R)-7-(3-((4-(2-(2-(2-(2-((2-(2,6-dioxopiperidin-3-yl)-1,3-dioxoisoindolin-4-yl)amino)ethoxy)ethoxy)ethoxy)ethoxy)phenyl)carbamoyl)-5-(4-fluorophenyl)-2-isopropyl-4-phenyl-1H-pyrrol-1-yl)-3,5-dihydroxyheptanoic acid (Compound 1)

(3R,5R)-7-(3-((4-((14-((2-(2,6-dioxopiperidin-3-yl)-1,3-dioxoisoindolin-4-yl)amino)-3,6,9,12-tetraoxatetradecyl)oxy)phenyl)carbamoyl)-5-(4-fluorophenyl)-2-isopropyl-4-phenyl-1H-pyrrol-1-yl)-3,5-dihydroxyheptanoic acid (Compound 2)

(3R,5R)-7-(3-((4-((17-((2-(2,6-dioxopiperidin-3-yl)-1,3-dioxoisoindolin-4-yl)amino)-3,6,9,12,15-pentaoxaheptadecyl)oxy)phenyl)carbamoyl)-5-(4-fluorophenyl)-2-isopropyl-4-phenyl-1H-pyrrol-1-yl)-3,5-dihydroxyheptanoic acid (Compound 3)

(3R,5R)-7-(3-((4-((20-((2-(2,6-dioxopiperidin-3-yl)-1,3-dioxoisoindolin-4-yl)amino)-3,6,9,12,15,18-hexaoxaicosyl)oxy)phenyl)carbamoyl)-5-(4-fluorophenyl)-2-isopropyl-4-phenyl-1H-pyrrol-1-yl)-3,5-dihydroxyheptanoic acid (Compound 4)

(3R,5R)-7-(3-((4-((1-((2-(2,6-dioxopiperidin-3-yl)-1,3-dioxoisoindolin-4-yl)oxy)-2-oxo-6,9,12,15,18,21-hexaoxa-3-azatricosan-23-yl)oxy)phenyl)carbamoyl)-5-(4-fluorophenyl)-2-isopropyl-4-phenyl-1H-pyrrol-1-yl)-3,5-dihydroxyheptanoic acid (Compound 5)

(3R,5R)-7-(3-((4-((25-((2-(2,6-dioxopiperidin-3-yl)-1,3-dioxoisoindolin-4-yl)oxy)-19,24-dioxo-3,6,9,12,15-pentaoxa-18,23-diazapentacosyl)oxy)phenyl)carbamoyl)-5-(4-fluorophenyl)-2-isopropyl-4-phenyl-1H-pyrrol-1-yl)-3,5-dihydroxyheptanoic acid (Compound 6)

(3R,5R)-7-(3-((4-((28-((2-(2,6-dioxopiperidin-3-yl)-1,3-dioxoisoindolin-4-yl)oxy)-22,27-dioxo-3,6,9,12,15,18-hexaoxa-21,26-diazaoctacosyl)oxy)phenyl)carbamoyl)-5-(4-fluorophenyl)-2-isopropyl-4-phenyl-1H-pyrrol-1-yl)-3,5-dihydroxyheptanoic acid (Compound 7)

(3R,5R)-7-(3-(4-((1-((2-(2,6-dioxopiperidin-3-yl)-1,3-dioxoisoindolin-4-yl)oxy)-2-oxo-6,9,12,15,18,21-hexaoxa-3-azatricosan-23-yl)oxy)phenyl)-2-(4-fluorophenyl)-5-isopropyl-4-(phenylcarbamoyl)-1H-pyrrol-1-yl)-3,5-dihydroxyheptanoic acid (Compound 8)

(3R,5R)-7-(2-(2-((1-((2-(2,6-dioxopiperidin-3-yl)-1,3-dioxoisoindolin-4-yl)oxy)-2-oxo-6,9,12,15,18,21-hexaoxa-3-azatricosan-23-yl)oxy)-4-fluorophenyl)-5-isopropyl-3-phenyl-4-(phenylcarbamoyl)-1H-pyrrol-1-yl)-3,5-dihydroxyheptanoic acid (Compound 9)

(3S,5S)-7-(2-(4-fluorophenyl)-4-((4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)phenyl)carbamoyl)-5-isopropyl-3-phenyl-1H-pyrrol-1-yl)-3,5-dihydroxyheptanoic acid (Compound 10)

(3S,5S)-7-(2-(4-fluorophenyl)-4-((4-(((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl)oxy)phenyl)carbamoyl)-5-isopropyl-3-phenyl-1H-pyrrol-1-yl)-3,5-dihydroxyheptanoic acid (Compound 11)

(3S,5S)-7-(2-(4-fluorophenyl)-4-((4-(((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)oxy)phenyl)carbamoyl)-5-isopropyl-3-phenyl-1H-pyrrol-1-yl)-3,5-dihydroxyheptanoic acid (Compound 12)

(3S,5S)-7-(2-(4-fluorophenyl)-4-((4-(((S)-22-((2S,4R)-4-hydroxy-2-((4-(4-methylthiazol-5-yl)benzyl)carbamoyl)pyrrolidine-1-carbonyl)-23,23-dimethyl-20-oxo-3,6,9,12,15,18-hexaoxa-21-azatetracosyl)oxy)phenyl)carbamoyl)-5-isopropyl-3-phenyl-1H-pyrrol-1-yl)-3,5-dihydroxyheptanoic acid (Compound 13) and (3S,5S)-7-(2-(4-fluorophenyl)-4-((4-(((S)-25-((2S,4R)-4-hydroxy-2-((4-(4-methylthiazol-5-yl)benzyl)carbamoyl)pyrrolidine-1-carbonyl)-26,26-dimethyl-23-oxo-3,6,9,12,15,18,21-heptaoxa-24-azaheptacosyl)oxy)phenyl)carbamoyl)-5-isopropyl-3-phenyl-1H-pyrrol-1-yl)-3,5-dihydroxyheptanoic acid (Compound 14).

A pharmaceutically acceptable salt in the present invention refers to any organic or inorganic acid addition salt with a concentration that is relatively non-toxic, is harmless, and has effective action to patients, wherein side effects caused by this salt does not deteriorate beneficial efficacy of the compound represented by Formula I. For example, the pharmaceutically acceptable salt may be an inorganic acid such as hydrochloric acid, phosphoric acid, sulfuric acid, nitric acid, or the like, or an organic acid such as methanesulfonic acid, p-toluenesulfonic acid, acetic acid, trifluoroacetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid or hydroiodic acid, but is not limited thereto.

Method for Preparing the HMG-CoA Reductase Degradation Inducing Compounds

The compound represented by Formula I may be prepared through Examples in the specification with reference to known literatures.

In one embodiment, Compounds 1 to 7 represented by Formula I may be prepared with reference to Reaction Scheme 1 below:

[Reaction Scheme 1]
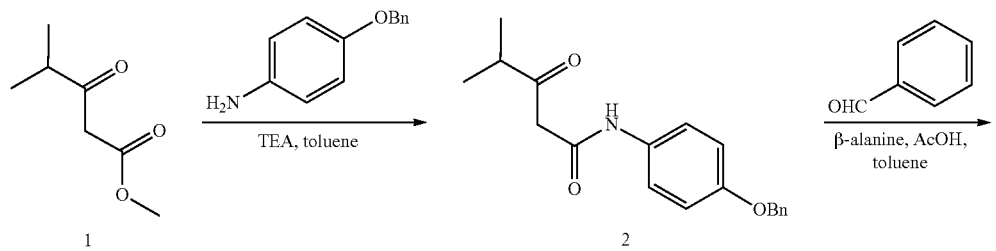
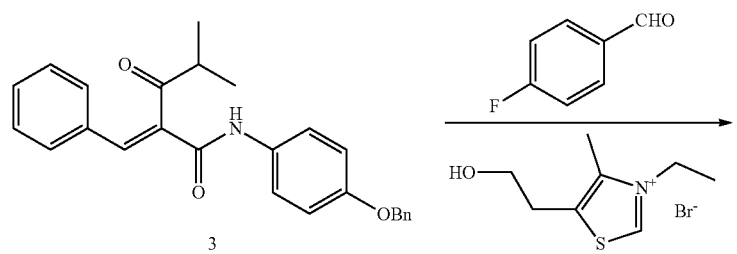
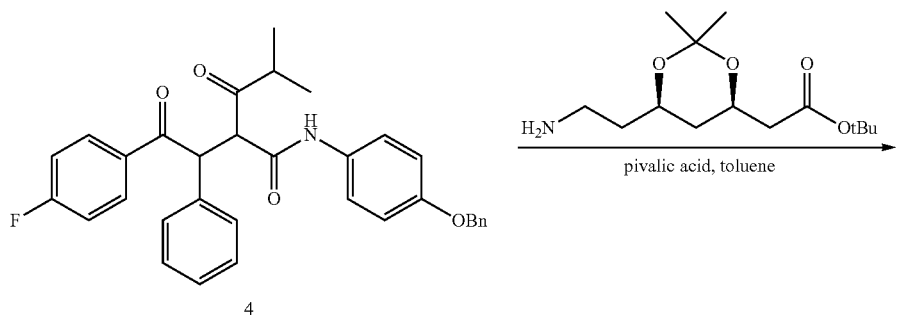
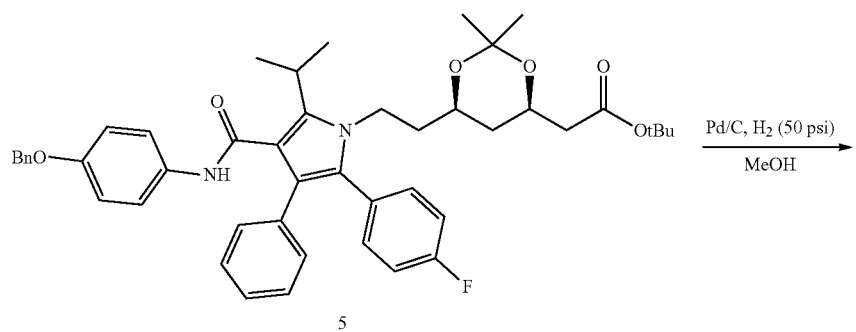
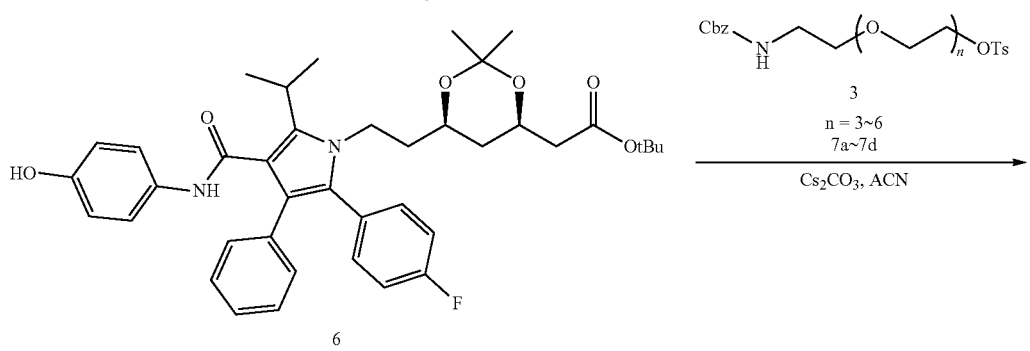

-continued
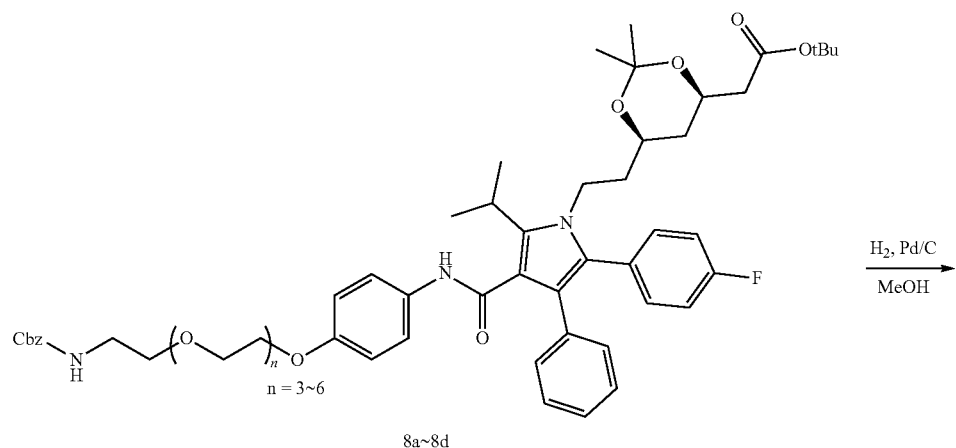
8a~8d
H₂, Pd/C
MeOH
→
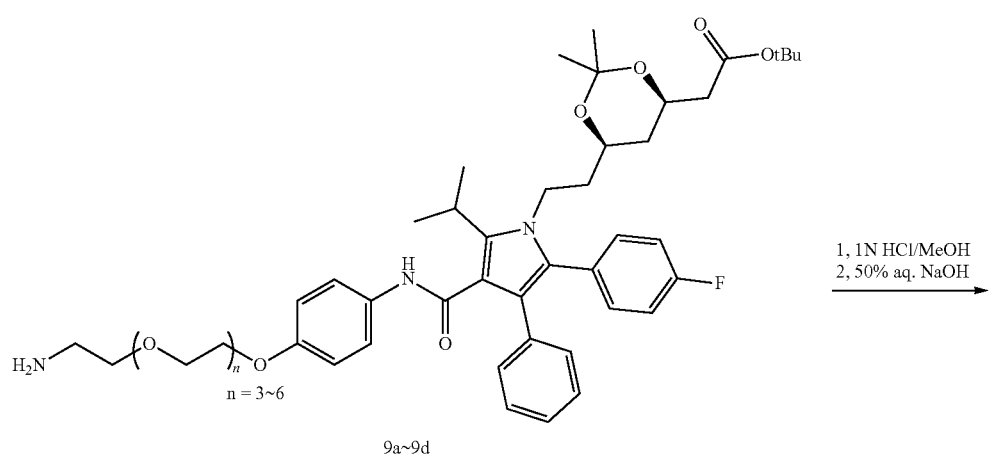
9a~9d
1, 1N HCl/MeOH
2, 50% aq. NaOH
→
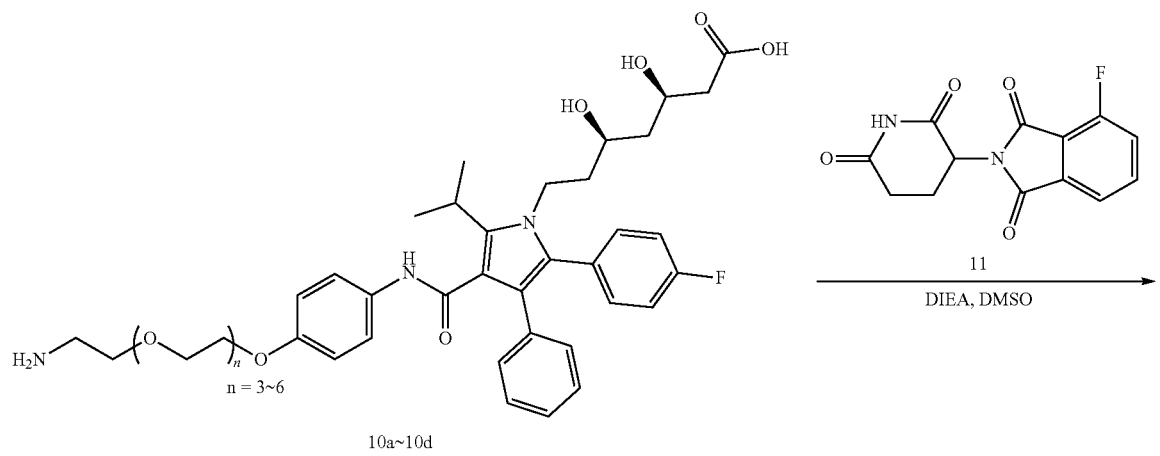
10a~10d
DIEA, DMSO
→

-continued
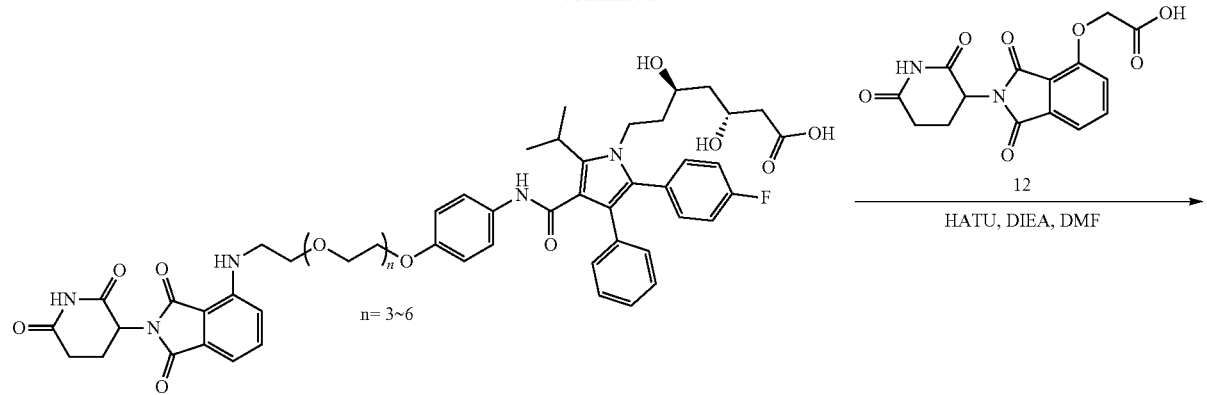
Example 1-4
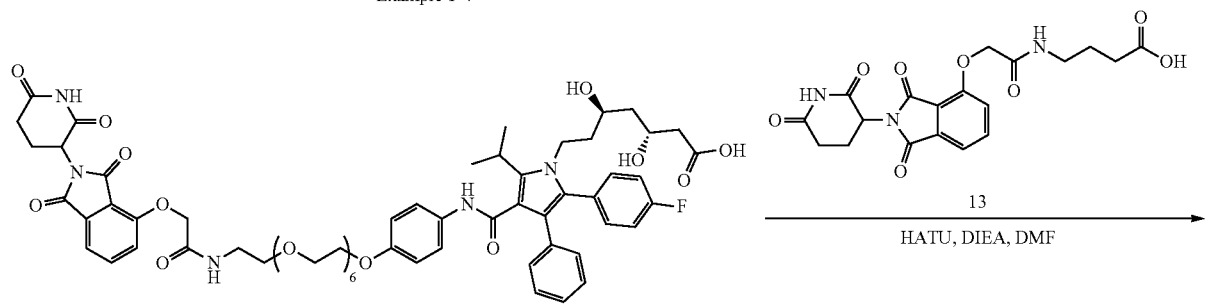
Example 5
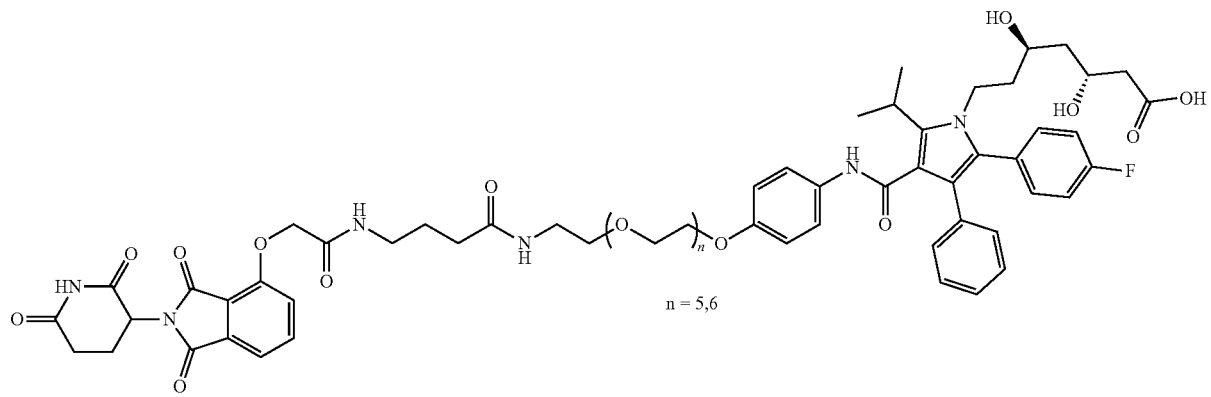
Example 6,7
In one embodiment, Compound 8 represented by Formula I may be prepared with reference to Reaction Scheme 2 below:
[Reaction Scheme 2]
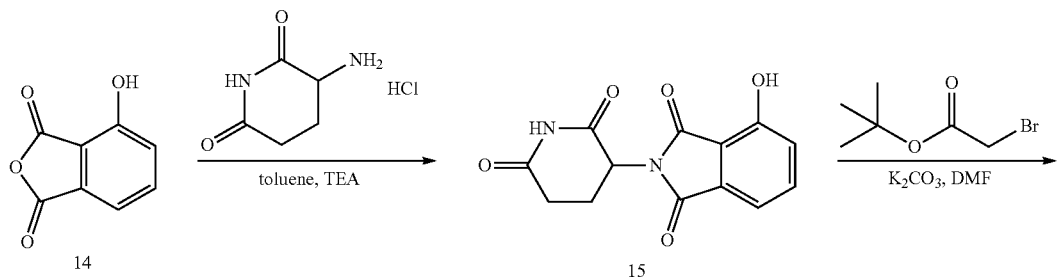

-continued
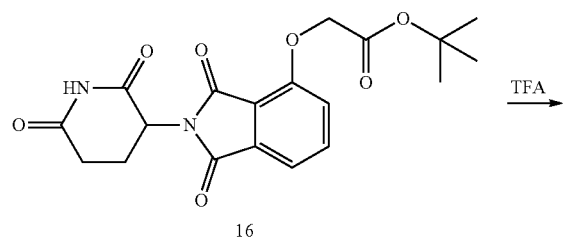
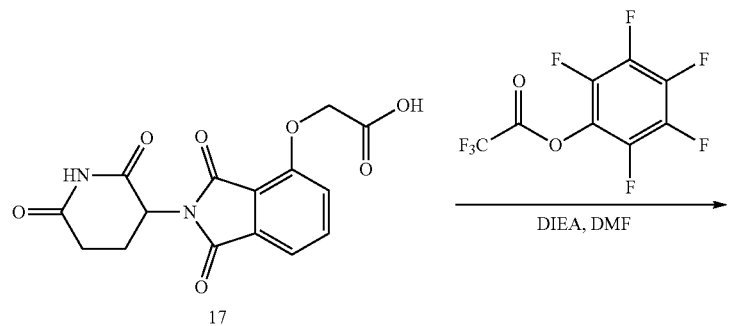
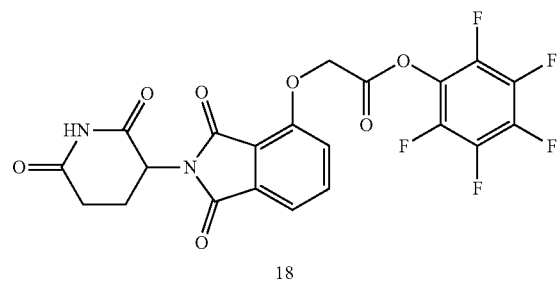
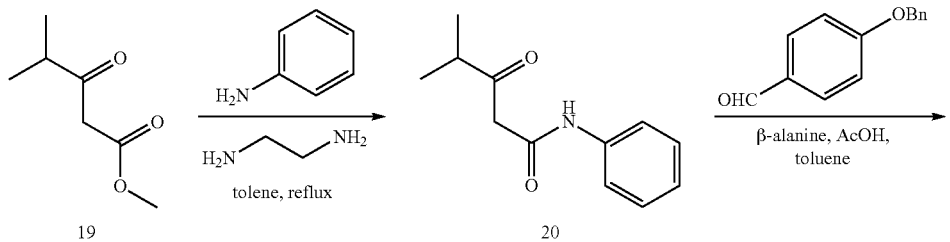
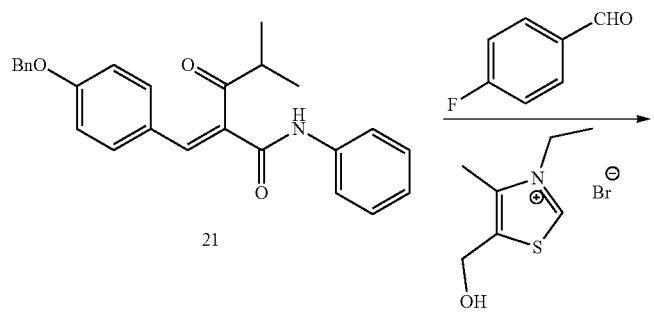

-continued
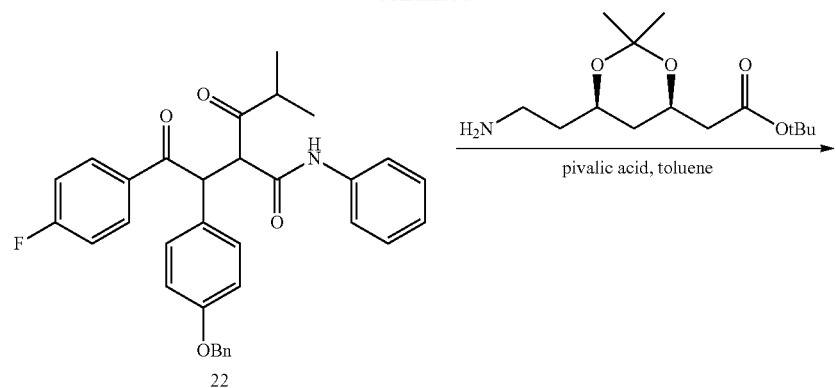
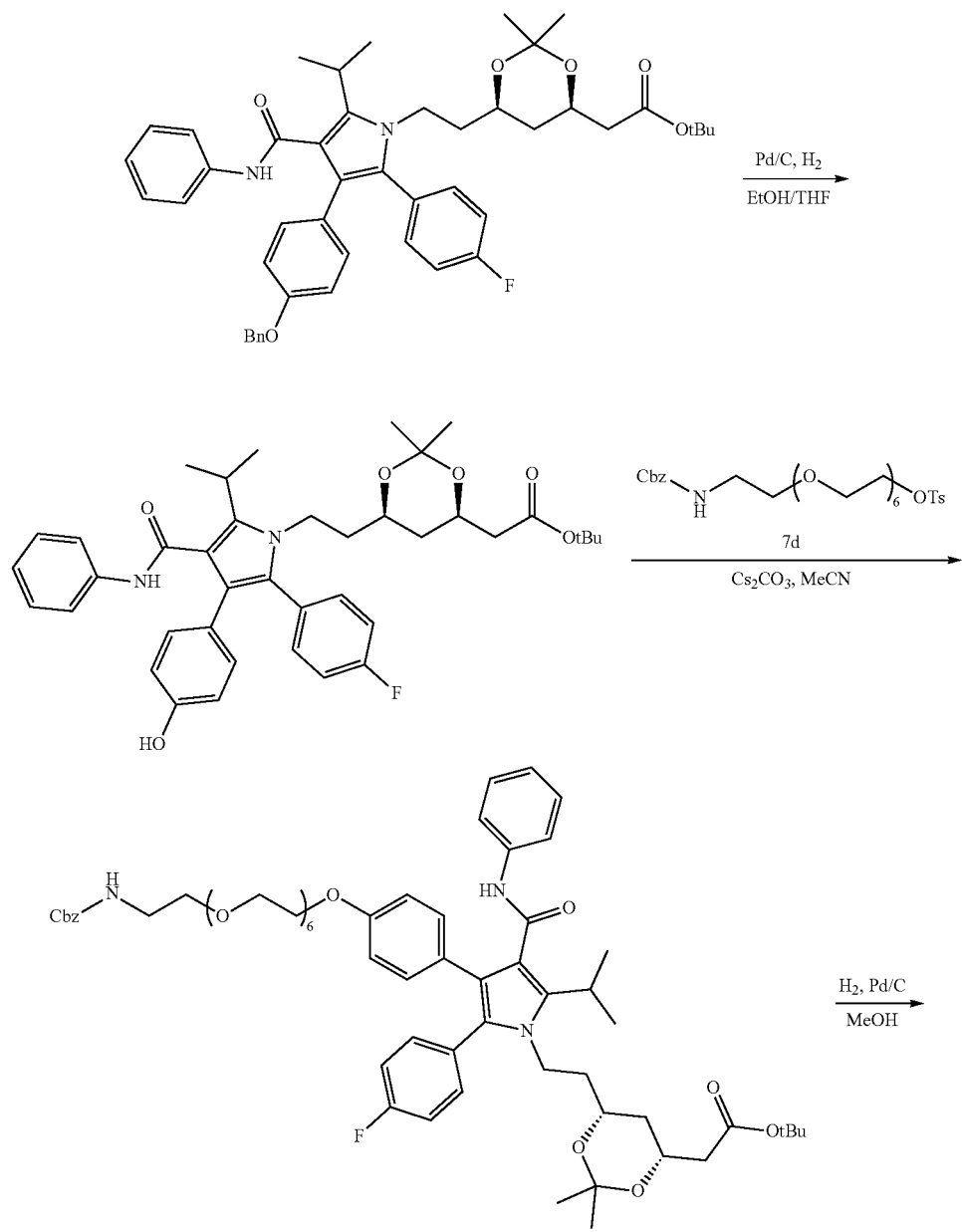

-continued
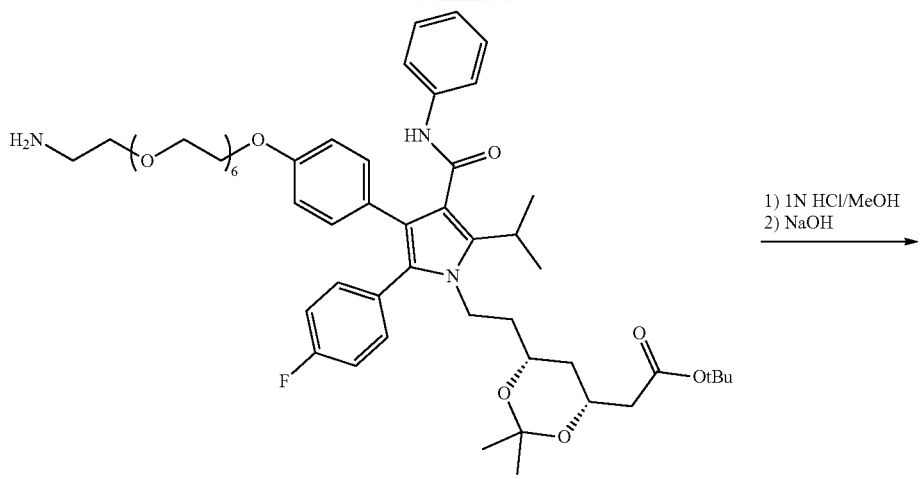
26
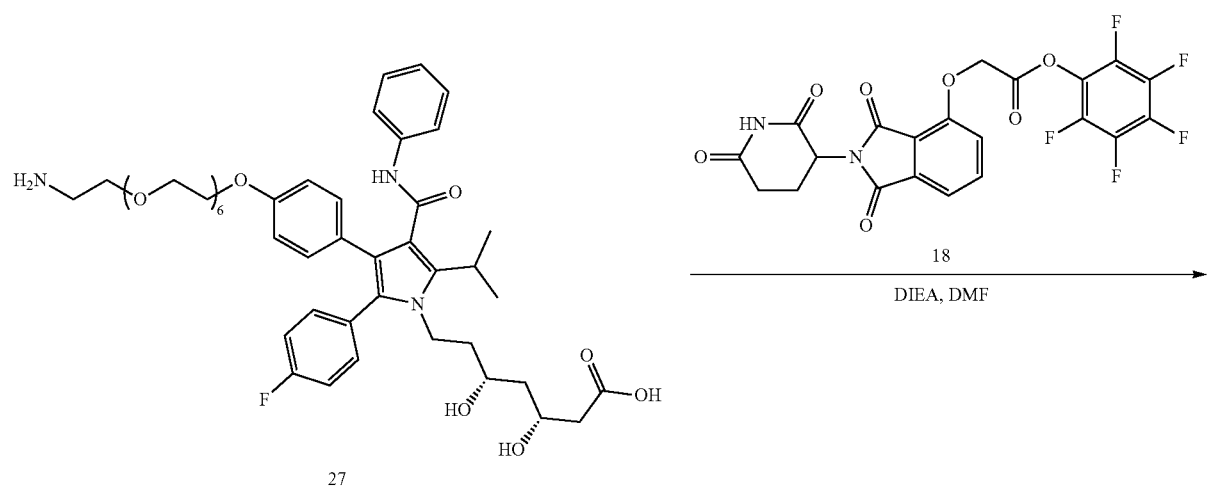
27
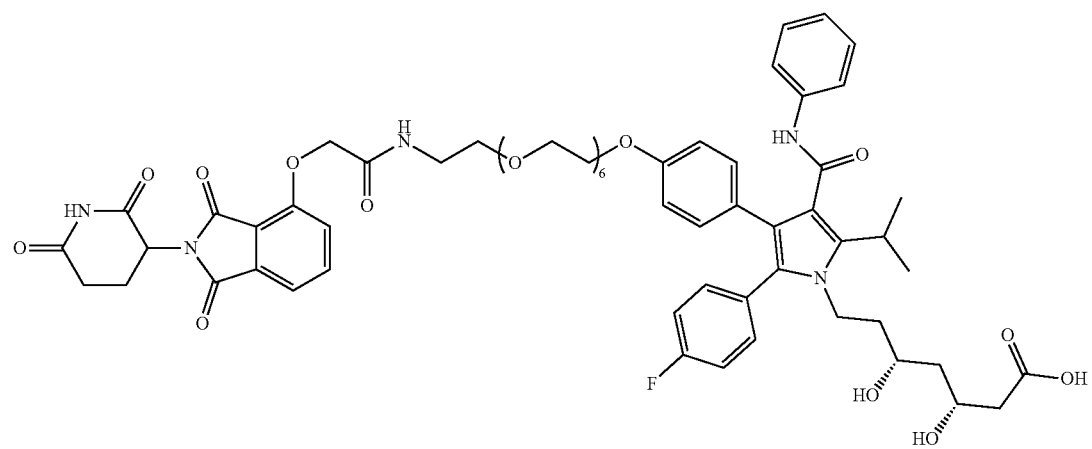
Example 8

In one embodiment, Compound 9 represented by Formula I may be prepared with reference to Reaction Scheme 3 below:
[Reaction Scheme 3]
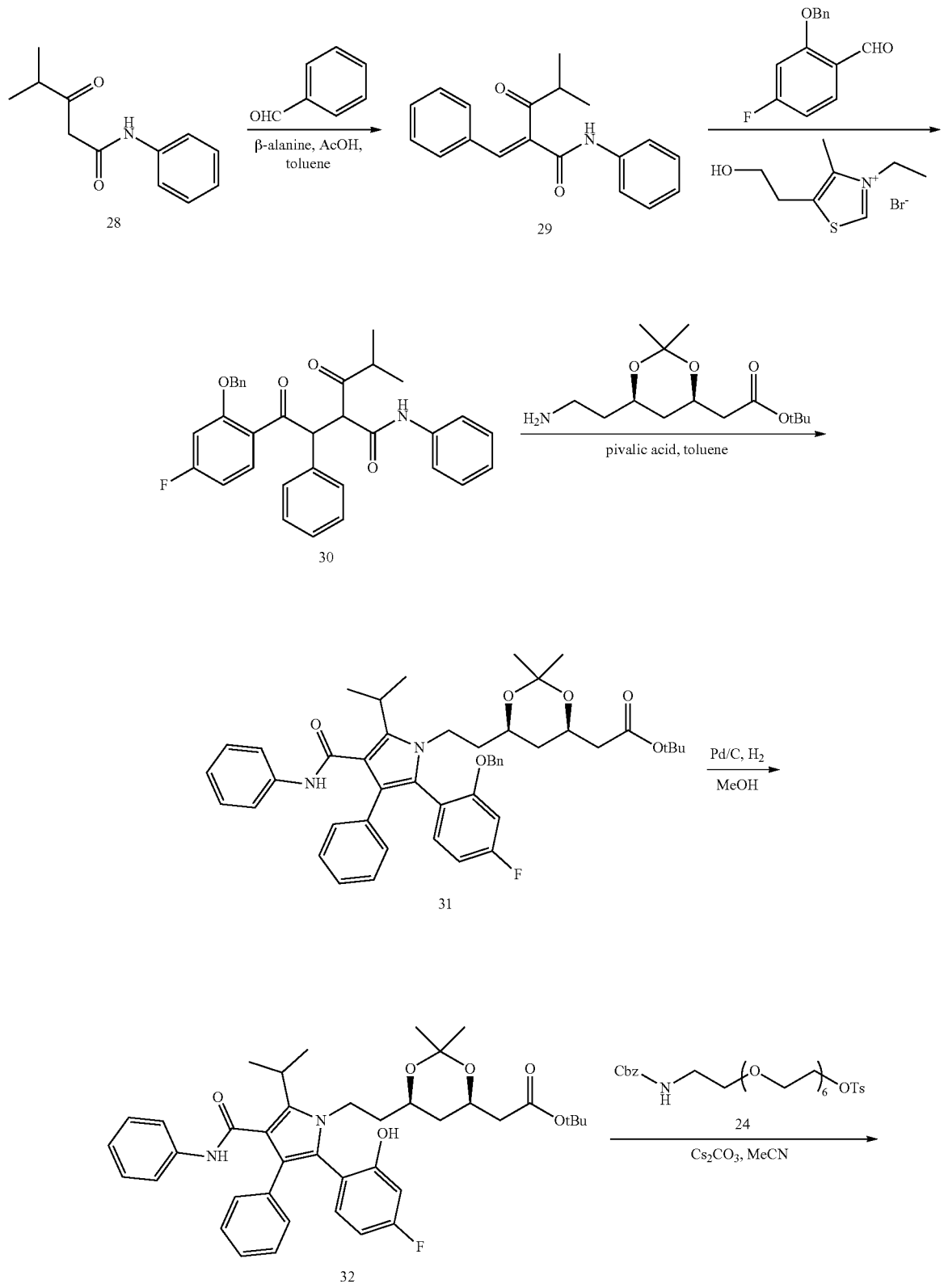

-continued
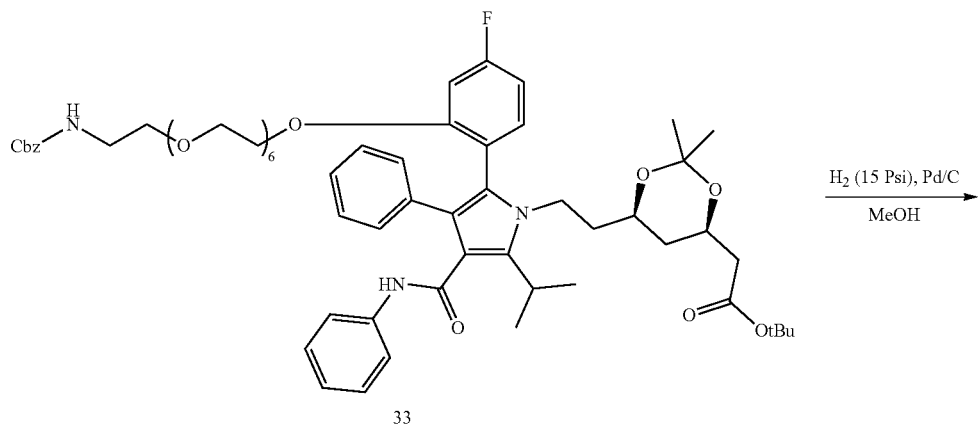
33
H₂ (15 Psi), Pd/C
MeOH
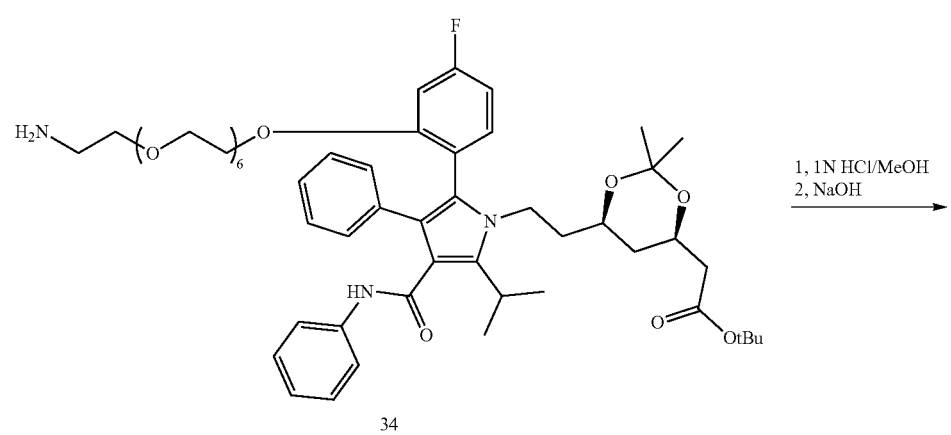
34
1, 1N HCl/MeOH
2, NaOH
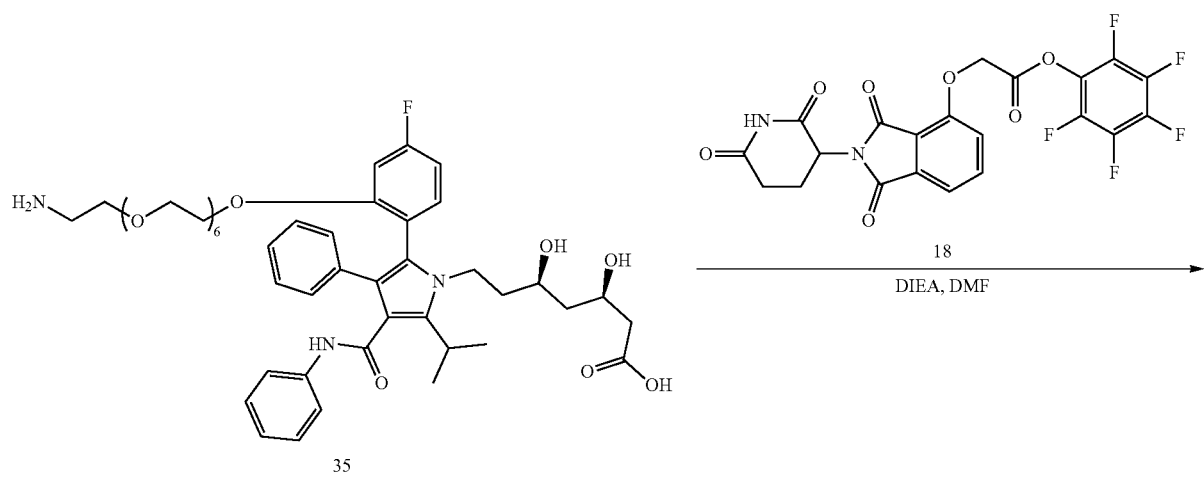
35
18
DIEA, DMF -continued
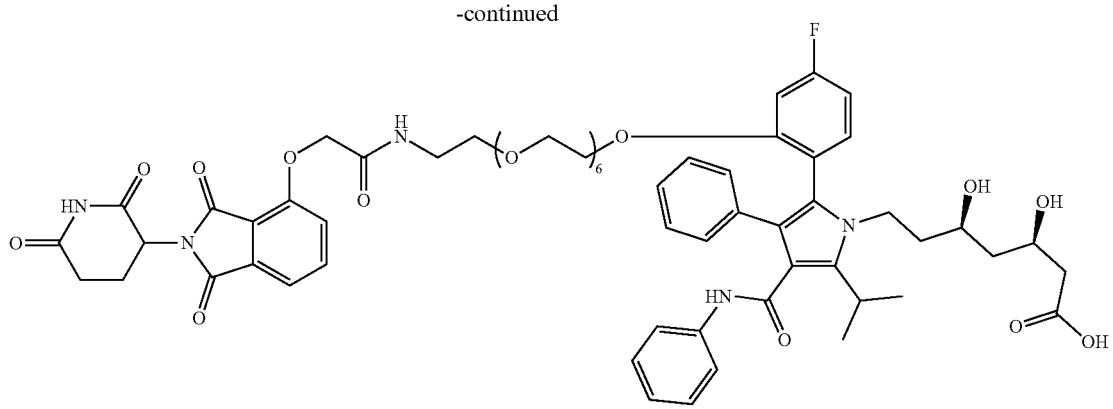
Example 9
In one embodiment, Compounds 10-14 represented by Formula I may be prepared with reference to Reaction Scheme 4 below:
[Reaction Scheme 4]
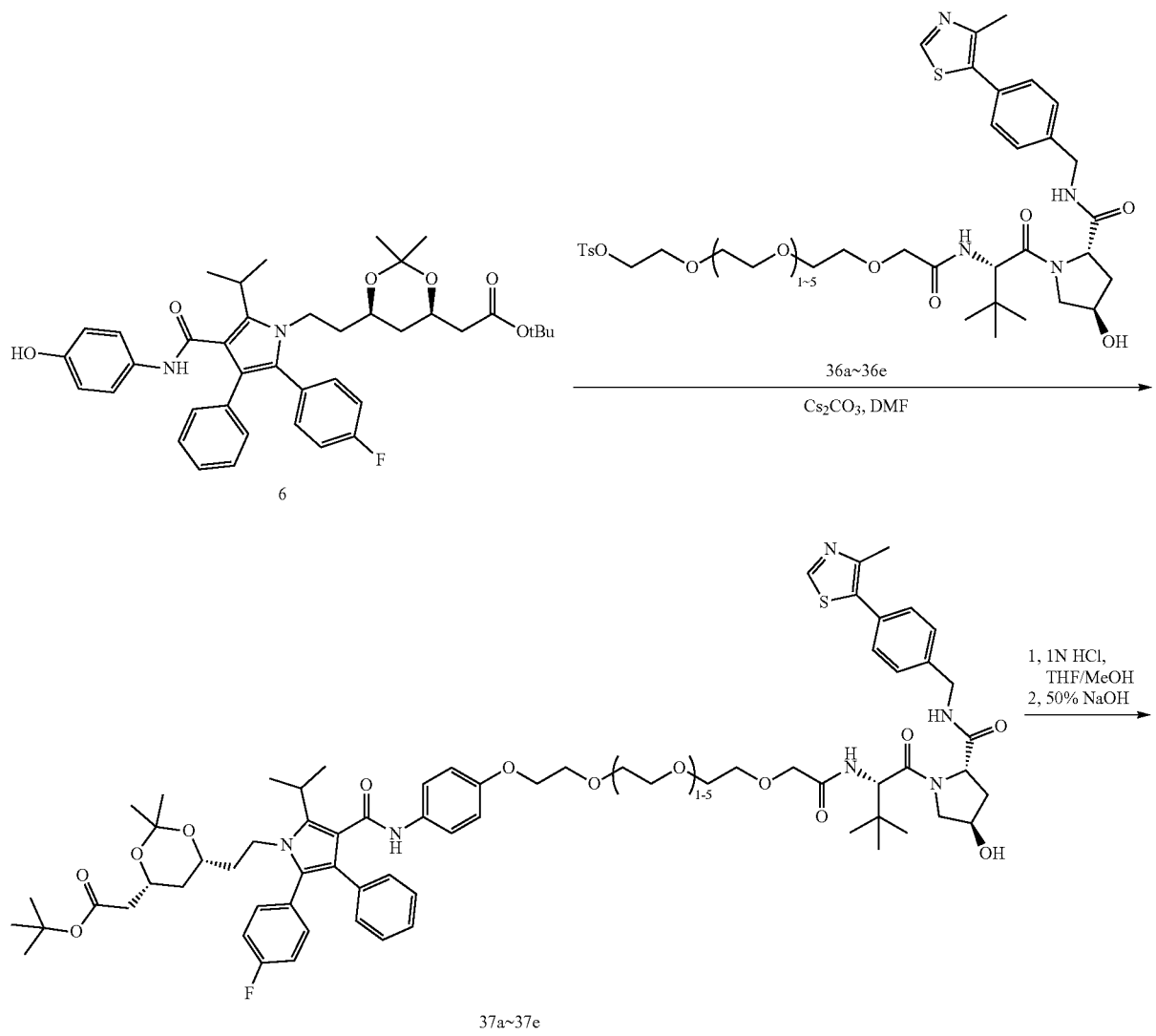

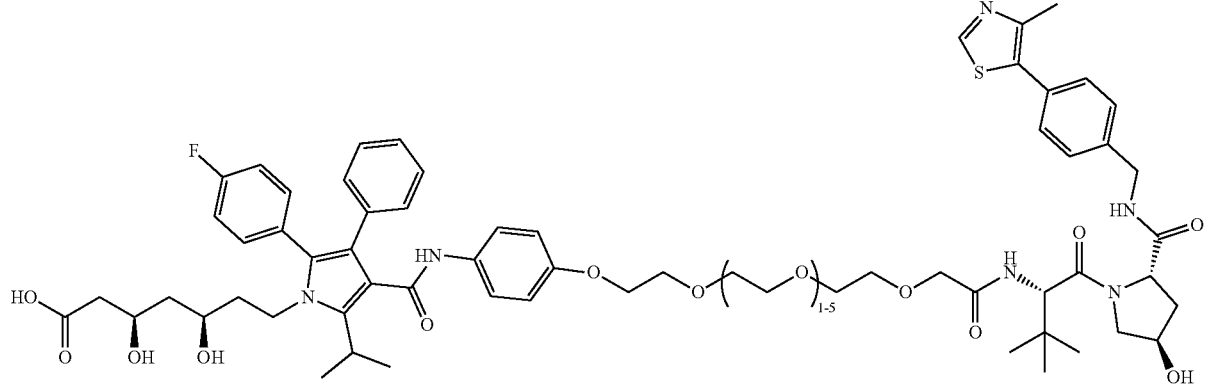

Example 10~14

Use of the HMG-CoA Reductase Degradation Inducing Compounds

An embodiment of the present invention is a composition for inducing HMG-CoA reductase degradation including a compound represented by Formula I or a pharmaceutically acceptable salt thereof. The Formula I is the same as defined above.

HMG-CoA reductase (3-hydroxy-3-methylglutaryl-CoA reductase) is an enzyme present in an endoplasmic reticulum membrane and catalyzes conversion of HMG-CoA to mevalonate which is a rate-limiting step of intracellular cholesterol biosynthesis.

In Examples of the present invention, it was confirmed that the compound according to the present invention effectively induced the degradation of HMG-CoA reductase in a hepatocyte model. Surprisingly, it was confirmed that compounds 1-14 of the present invention had remarkably excellent degradability of HMG-CoA reductase in hepatocytes as compared to the atorvastatin-based PROTAC compound described in International Patent Publication No. WO2019/109415 A1 (FIGS. 1 & 2). Accordingly, the composition including the compound represented by Formula I of the present invention or a pharmaceutically acceptable salt thereof may be effectively employed for inducing degradation of HMG-CoA reductase.

An embodiment of the present invention is a composition for preventing or treating HMG-CoA reductase-related diseases including a compound represented by Formula I or a pharmaceutically acceptable salt thereof. The Formula I is the same as defined above.

In the present invention, the HMGCR-related disease refers to any disease or condition capable of being treated, alleviated, delayed, inhibited or prevented from induction of degradation or inhibition of activity of HMGCR. In an embodiment, the HMG-CoA reductase-related disease may be cardiovascular disease or hyperlipidemia. The cardiovascular disease may include, for example, myocardial infarction, stroke, angina, heart failure, atherosclerosis, or arteriosclerosis, and the hyperlipidemia may include, for example, primary hypercholesterolemia (family and non-family), mixed dyslipidemia, primary dysbetalipoproteinemia, or hypertriglyceridemia. However, examples thereof are not limited thereto.

It was confirmed from compounds 1-14 of the present invention that the compound according to the present invention has an excellent effect of inducing degradation of HMG-CoA reductase (FIGS. 1 & 2). Therefore, the pharmaceutical composition including the compound represented by Formula I or the pharmaceutically acceptable salt thereof may be effectively employed for the prevention or treatment of HMG-CoA-related diseases.

The pharmaceutical composition of the present invention may further include one or more active ingredients exhibiting the same or similar medicinal effects in addition to the compound represented by Formula I above, or the pharmaceutically acceptable salt thereof.

An embodiment of the present invention is a method of degrading HMG-CoA reductase by administering a compound represented by Formula I or a pharmaceutically acceptable salt thereof to mammals including humans.

Another embodiment of the present invention is a method of degrading HMG-CoA reductase by administering the compound represented by Formula I or the pharmaceutically acceptable salt thereof to a sample in vitro. The sample may be a cell, a cell culture, a body fluid or tissue of a mammal including a human, but is not limited thereto.

The compound of the present invention exhibits an effect of inducing protein degradation. Therefore, the pharmaceutical compound of the present invention may be effectively utilized for preventing or treating related diseases.

DETAILED DESCRIPTION OF EMBODIMENTS

Figure 1:
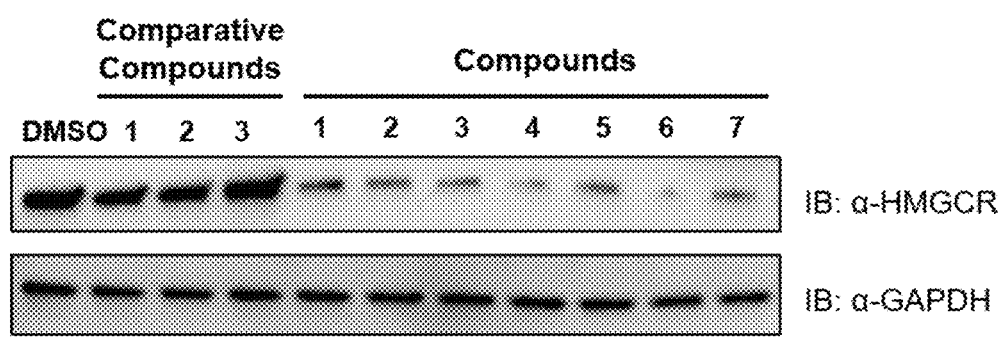
FIG. 1 and FIG. 2 show the results of Western blotting measuring the HMG-CoA reductase degradation ability of the bifunctional compounds according to the present invention.
Figure 2:
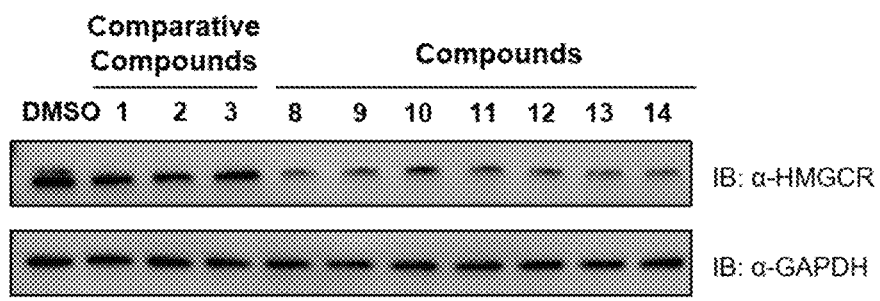

Hereinafter, the constitution and effects of the present invention will be described in more detail through Examples. These Examples are provided for illustrative purposes only, and do not limit the scope of the present invention.

In the examples, compounds 1-14 were synthesized and purified according to the following method and the structure was analyzed.

Instruments
LCMS: Shimadzu LCMS-2020
NMR: BRUKER AVANCE III/400 MHz
HPLC: Shimadzu LC-20AB and Shimadzu LC-20AD
LCSM Analysis LCMS data were recorded with Shimadzu LCMS-2020 equipped with an electron spray ionization device. 0.0375% TFA in water (solvent A) and 0.01875% TFA in acetonitrile (solvent B) were used as mobile phases. As a column, Kinetex EVO C18 (2.1*30) mm, 5um was used.

HPLC Analysis

In HPLC analysis, Shimadzu LC-20AB or Shimadzu LC-20AD was used. 0.0375% TFA in water (solvent A) and 0.01875% TFA in acetonitrile (solvent B) or 0.025% $NH_3 \cdot H_2O$ in water (solvent A) and acetonitrile (Solvent B) was used as the mobile phase. As a column, XBridge C18 (2.1*50) mm, 5um or Kinetex C18 LC column (4.6*50) mm, 5um was used.

NMR Analysis

1H NMR spectrum was recorded with Bruker AVANCE III 400 MHz/5 mm Probe (BBO).

Synthesis of Atorvastatin Intermediate

Step 1: Synthesis of N-(4-(benzyloxy)phenyl)-4-methyl-3-oxopentanamide (3)

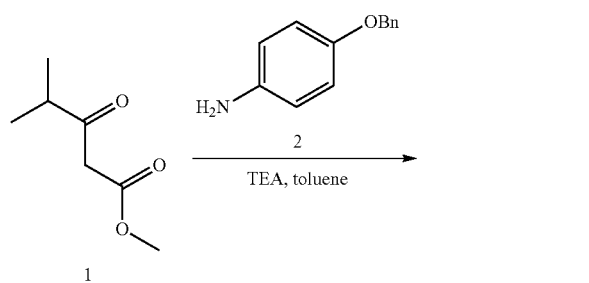

A mixture of methyl 4-methyl-3-oxo-pentanoate (18.09 g, 125.47 mmol, 17.91 mL) and 4-benzyloxyaniline (25 g, 125.47 mmol) in toluene (250 mL) was added TEA (12.70 g, 125.47 mmol, 17.46 mL) and the resulting mixture was stirred at 120° C. for 20 h under nitrogen using a Dean Stark apparatus. TLC (Petroleum ether:Ethyl acetate=1:1) showed a new spot was formed and 4-benzyloxyaniline was consumed. The mixture was concentrated under vacuum. The residue was triturated with methyl tert-butyl ether (150 mL), the filter cake was collected and dried in vacuum to give N-(4-benzyloxyphenyl)-4-methyl-3-oxopentanamide (29 g, 93.14 mmol, 74.23% yield) as white solid. $^1$H NMR (400 MHz, CDCl$_3$) δ 9.09 (s, 1H), 7.48-7.46 (m, 1H), 7.46-7.41 (m, 3H), 7.41-7.31 (m, 3H), 6.97-6.92 (m, 2H), 5.06 (s, 2H), 3.60 (s, 2H), 2.80-2.69 (m, 1H), 1.18 (d, J=7.00 Hz, 6H)

Step 2: Synthesis of 2-benzylidene-N-(4-(benzyloxy)phenyl)-4-methyl-3-oxopentanamide (5)

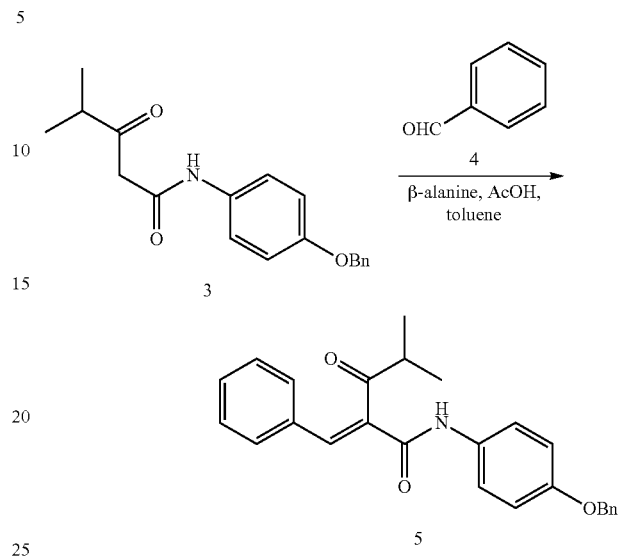

To a mixture of N-(4-(benzyloxy)phenyl)-4-methyl-3-oxopentanamide (26 g, 83.50 mmol), beta-alanine (3.73 g, 41.83 mmol) and benzaldehyde (16.06 g, 151.35 mmol, 15.30 mL) in toluene (200 mL) was added AcOH (519.98 mg, 8.66 mmol, 0.495 mL), the mixture was stirred at 130° C. for 36 h under nitrogen using a Dean Stark apparatus. TLC (PE:EtOAc=5:1) showed three new spots were formed and N-(4-benzyloxyphenyl)-4-methyl-3-oxo-pentanamide was consumed. The mixture was concentrated under vacuum. The residue was purified by silica gel column chromatography (Petroleum ether:Ethyl acetate=1:0 to 15:1) followed by reversed MPLC (water/ACN=2:8, 1‰ FA) to afford 2-benzylidene-N-(4-benzyloxyphenyl)-4-methyl-3-oxopentanamide (11 g, 27.54 mmol, 34.38% yield) as yellow solid. $^1$H NMR (400 MHz, DMSO-d6) δ 10.31 (s, 1H), 7.68 (s, 1H), 7.65-7.63 (m, 2H), 7.53-7.51 (m, 1H), 7.51-7.49 (m, 1H), 7.47-7.43 (m, 2H), 7.42-7.39 (m, 5H), 7.35-7.32 (m, 1H), 7.02-6.97 (m, 2H), 5.08 (s, 2H), 3.43-3.33 (m, 1H), 1.10 (d, J=6.75 Hz, 6H). MS (M+H)$^+$=400.2.

Step 3: Synthesis of N-(4-(benzyloxy)phenyl)-2-(2-(4-fluorophenyl)-2-oxo-1-phenylethyl)-4-methyl-3-oxopentanamide (6)

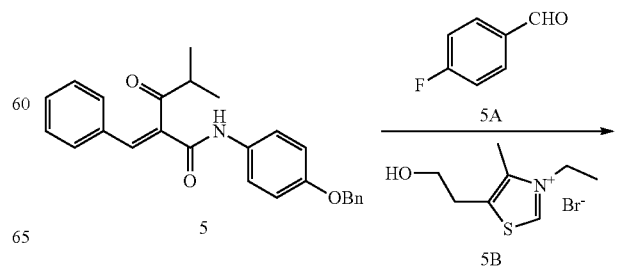

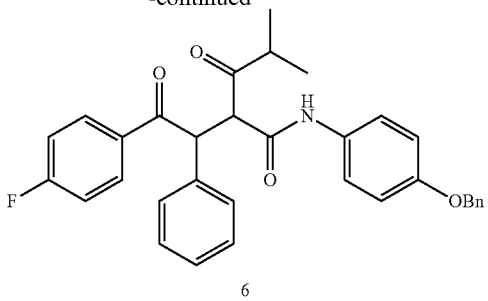

To a mixture of 2-benzylidene-N-(4-(benzyloxy)phenyl)-4-methyl-3-oxopentanamide (8.5 g, 21.28 mmol), 4-fluorobenzaldehyde (5.28 g, 42.56 mmol, 4.48 mL) and TEA (4.31 g, 42.56 mmol, 5.92 mL) in EtOH (80 mL) was added 3-ethyl-5-(2-hydroxyethyl)-4-methylthiazol-3-ium bromide (4.29 g, 17.02 mmol) and the resulting mixture was stirred at 100° C. for 72 h under nitrogen. LCMS showed a peak (34%) with desired mass and 2-benzylidene-N-(4-benzyloxyphenyl)-4-methyl-3-oxo-pentanamide (11%) remained. The mixture was filtered and the filtrate was concentrated under vacuum. The crude product was purified by silica gel column chromatography (PE:EtOAc=9:1 to 6:4) to afford N-(4-(benzyloxy)phenyl)-2-(2-(4-fluorophenyl)-2-oxo-1-phenylethyl)-4-methyl-3-oxopentanamide (7 g, 13.37 mmol, 87.50% yield) as yellow oil. MS (M+H)$^+$=524.2

Step 4: Synthesis of tert-butyl 2-((4R,6R)-6-(2-(3-((4-(benzyloxy)phenyl)carbamoyl)-5-(4-fluoro phenyl)-2-isopropyl-4-phenyl-1H-pyrrol-1-yl)ethyl)-2,2-dimethyl-1,3-dioxan-4-yl)acetate (8)

To a solution of N-(4-(benzyloxy)phenyl)-2-[2-(4-fluorophenyl)-2-oxo-1-phenylethyl]-4-methyl-3-oxopentanamide (7 g, 13.37 mmol) and tert-butyl 2-[(4R,6R)-6-(2-aminoethyl)-2,2-dimethyl-1,3-dioxan-4-yl]acetate (5.46 g, 19.97 mmol) in toluene (150 mL) was added pivalic acid (1.68 g, 16.45 mmol, 1.89 mL) and the resulting mixture was stirred at 100° C. for 18 h under N$_2$. LCMS showed a main peak with desired mass and a little starting material remained. The mixture was washed with sat. aq. NaHCO$_3$ (100 mL×2) and brine (200 mL), concentrated under vacuum. The residue was purified by silica gel column chromatography (PE: EtOAc=95:5 to 87:13) to afford tert-butyl 2-((4R,6R)-6-(2-(3-((4-(benzyloxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (5 g, 6.57 mmol, 49.15% yield) as brown oil. $^1$H NMR (400 MHz, CDCl$_3$) δ 7.43-7.33 (m, 5H), 7.22-7.13 (m, 7H), 7.04-6.97 (m, 4H), 6.82 (d, J=8.93 Hz, 2H), 6.76 (s, 1H), 5.00 (s, 2H), 4.22-4.15 (m, 1H), 4.10-4.02 (m, 1H), 3.88-3.78 (m, 1H), 3.74-3.65 (m, 1H), 3.59-3.52 (m, 1H), 2.44-2.35 (m, 1H), 2.29-2.20 (m, 1H), 1.74-1.63 (m, 2H), 1.53 (d, J=7.09 Hz, 6H), 1.44 (s, 9H), 1.37 (s, 3H), 1.35-1.34 (m, 1H), 1.31 (s, 3H), 1.11-1.00 (m, 1H). MS (M+H)$^+$=761.2

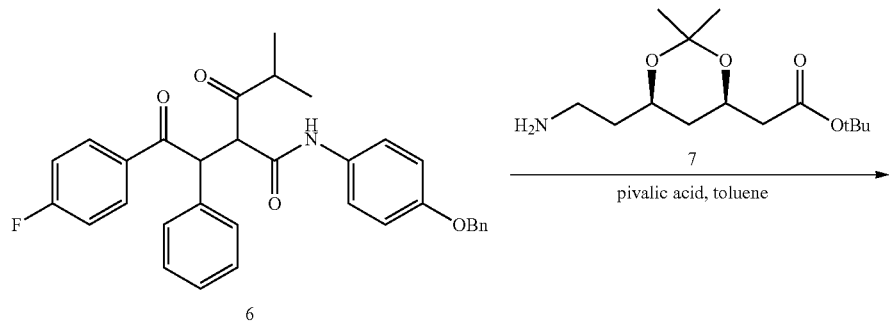

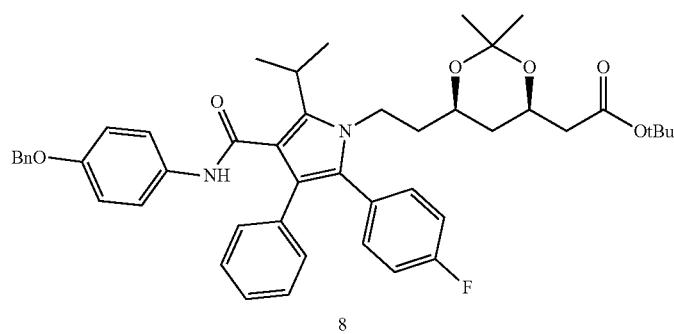

Step 5: Synthesis of tert-butyl 2-((4R,6R)-6-(2-(2-(4-fluorophenyl)-4-((4-hydroxyphenyl)carbamoyl)-5-isopropyl-3-phenyl-1H-pyrrol-1-yl)ethyl)-2,2-dimethyl-1,3-dioxan-4-yl)acetate (9)

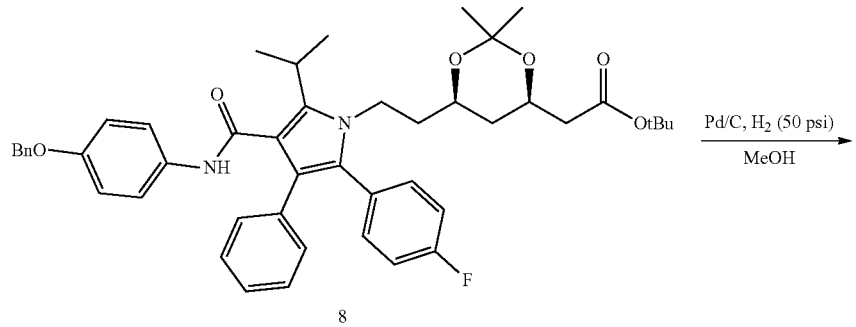

To a mixture of tert-butyl 2-((4R,6R)-6-(2-(3-((4-(benzyloxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (4.8 g, 6.31 mmol) in MeOH (500 mL) was added Pd/C (0.8 g, 6.31 mmol, 10% purity) and the resulting mixture was stirred at 50° C. under $H_2$ (50 psi) for 20 h. LCMS showed a main peak with desired mass and the starting material was consumed. The mixture was filtered through a pad of celite and the filtrate was concentrated. The residue was purified by silica gel column chromatography (100% EA) to afford tert-butyl 2-((4R,6R)-6-(2-(2-(4-fluorophenyl)-4-((4-hydroxyphenyl)carbamoyl)-5-isopropyl-3-phenyl-1H-pyrrol-1-yl)ethyl)-2,2-dimethyl-1,3-dioxan-4-yl)acetate (3.8 g, 5.66 mmol, 89.80% yield) as white solid. $^1$H NMR (400 MHz, DMSO-d6) δ 9.52 (s, 1H), 9.09 (s, 1H), 7.30-7.22 (m, 4H), 7.22-7.15 (m, 2H), 7.11-7.05 (m, 4H), 7.04-6.98 (m, 1H), 6.62 (d, J=8.78 Hz, 2H), 4.16-4.06 (m, 1H), 3.97-3.86 (m, 1H), 3.83-3.70 (m, 2H), 3.22-3.18 (m, 1H), 2.34-2.26 (m, 1H), 2.21-2.13 (m, 1H), 1.66-1.48 (m, 2H), 1.40-1.29 (m, 19H), 1.17 (s, 3H), 0.99-0.86 (m, 1H). MS (M+H)$^+$=671.3

Example 1. Synthesis of (3R,5R)-7-(3-((4-(2-(2-(2-(2-((2-(2,6-dioxopiperidin-3-yl)-1,3-dioxoisoindolin-4-yl)amino)ethoxy)ethoxy)ethoxy)ethoxy)phenyl)carbamoyl)-5-(4-fluorophenyl)-2-isopropyl-4-phenyl-1H-pyrrol-1-yl)-3,5-dihydroxyheptanoic acid (Compound 1)

Step 1: Synthesis of benzyl (2-(2-(2-(2-hydroxyethoxy)ethoxy)ethoxy)ethyl)carbamate (2)

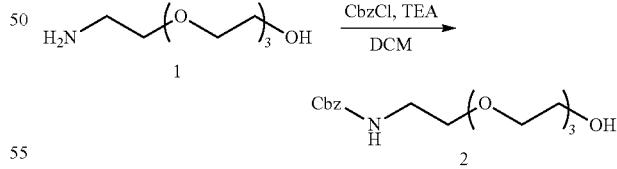

To a mixture of 2-(2-(2-(2-aminoethoxy)ethoxy)ethoxy)ethanol (2 g, 10.35 mmol) and TEA (2.09 g, 20.70 mmol, 2.88 mL) in DCM (20 mL) was added benzyl chloroformate (1.94 g, 11.38 mmol, 1.62 mL). The mixture was stirred at 20° C. for 0.5 h. LCMS showed a main peak with desired mass. The mixture was washed with water (20 mL), and the organic layer was dried over anhydrous $Na_2SO_4$, concentrated to afford benzyl (2-(2-(2-(2-hydroxyethoxy)ethoxy)ethoxy)ethyl)carbamate (3.3 g, crude) as colorless oil, which was used directly in the next step without further purification.

Step 2: Synthesis of 3-oxo-1-phenyl-2,7,10,13-tetraoxa-4-azapentadecan-15-yl 4-methylbenzenesulfonate (3)

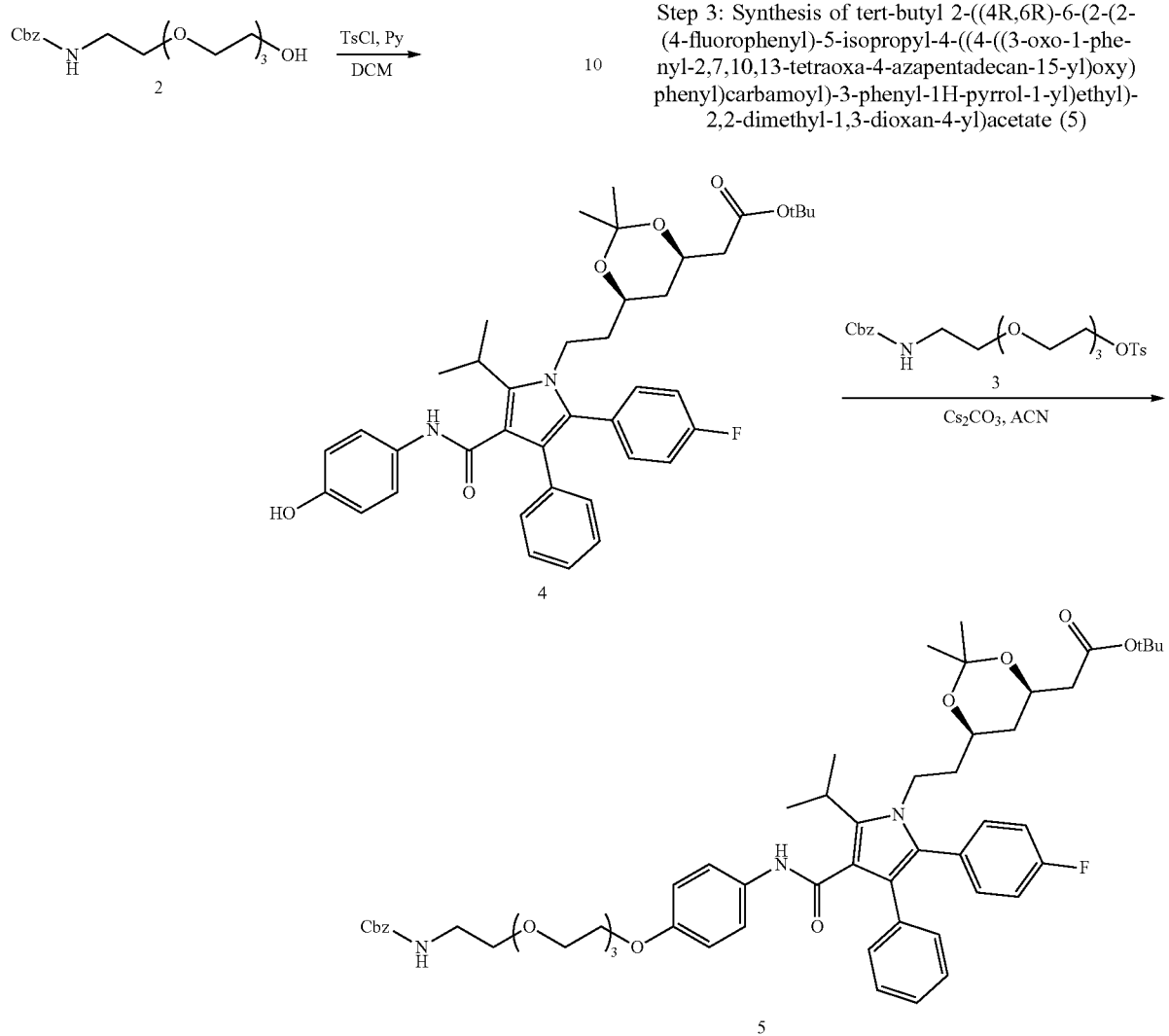

To a mixture of benzyl N-[2-[2-[2-(2-hydroxyethoxy)ethoxy]ethoxy]ethyl]carbamate (3.3 g, 10.08 mmol) and p-toluenesulfonyl chloride (2.88 g, 15.12 mmol) in DCM (30 mL) was added pyridine (1.59 g, 20.16 mmol, 1.63 mL). The mixture was stirred at 20° C. for 16 h. LCMS showed a peak (55%) with desired mass. TLC (Petroleum ether/ethyl acetate=1:1) showed a main new spot was formed. The mixture was washed with water (20 mL), the organic layer was collected and dried over anhydrous $Na_2SO_4$, concentrated. The residue was purified by chromatography (silica gel, eluting with Petroleum ether/ethyl acetate=3:1~1:1) to afford 3-oxo-1-phenyl-2,7,10,13-tetraoxa-4-azapentadecan-15-yl 4-methylbenzenesulfonate (3.7 g, 7.68 mmol, 76.22% yield) as yellow oil.

MS $(M+H)^+ = 482.0$

Step 3: Synthesis of tert-butyl 2-((4R,6R)-6-(2-(2-(4-fluorophenyl)-5-isopropyl-4-((4-((3-oxo-1-phenyl-2,7,10,13-tetraoxa-4-azapentadecan-15-yl)oxy)phenyl)carbamoyl)-3-phenyl-1H-pyrrol-1-yl)ethyl)-2,2-dimethyl-1,3-dioxan-4-yl)acetate (5)

To a solution of 3-oxo-1-phenyl-2,7,10,13-tetraoxa-4-azapentadecan-15-yl 4-methylbenzenesulfonate (789.67 mg, 1.64 mmol) and tert-butyl 2-[(4R,6R)-6-[2-[2-(4-fluorophenyl)-4-[(4-hydroxyphenyl)carbamoyl]-5-isopropyl-3-phenyl-1H-pyrrol-1-yl]ethyl]-2,2-dimethyl-1,3-dioxan-4-yl]acetate (1 g, 1.49 mmol) in ACN (10 mL) was added $Cs_2CO_3$ (1 g, 3.07 mmol). The mixture was stirred at 80° C. for 4 h. LCMS showed a peak (60%) with desired mass and the starting material was consumed. The mixture was filtered and the filtrate was concentrated under vacuum. The residue was purified by reversed-phase HPLC (water:ACN=15:85, 0.1% formic acid condition) to afford tert-butyl 2-((4R,6R)-6-(2-(2-(4-fluorophenyl)-5-isopropyl-4-((4-((3-oxo-1-phenyl-2,7,10,13-tetraoxa-4-azapentadecan-15-yl)oxy)phenyl)carbamoyl)-3-phenyl-1H-pyrrol-1-yl)ethyl)-2,2-dimethyl-1,3-dioxan-4-yl)acetate (1.1 g, 1.12 mmol, 75.28% yield) as yellow oil.

MS $(M+H)^+ = 980.7$

Step 4: Synthesis of tert-butyl 2-((4R,6R)-6-(2-(3-((4-(2-(2-(2-(2-aminoethoxy)ethoxy)ethoxy)ethoxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (6)

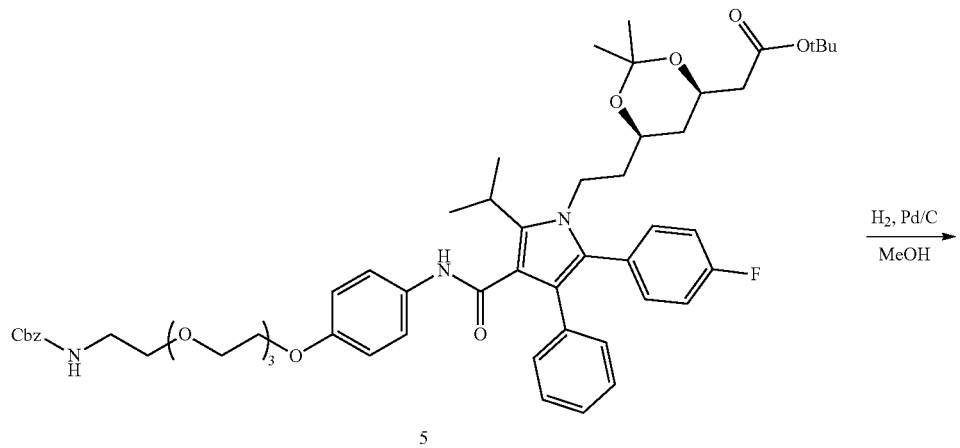

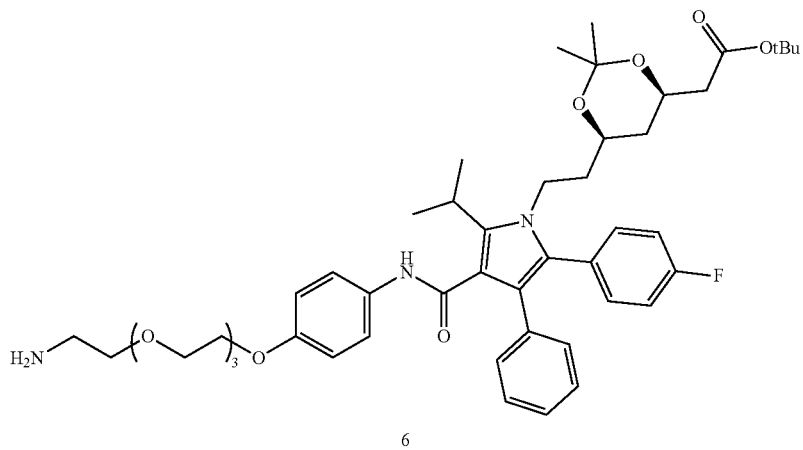

To a solution of tert-butyl 2-((4R,6R)-6-(2-(2-(4-fluorophenyl)-5-isopropyl-4-((4-((3-oxo-1-phenyl-2,7,10,13-tetraoxa-4-azapentadecan-15-yl)oxy)phenyl)carbamoyl)-3-phenyl-1H-pyrrol-1-yl)ethyl)-2,2-dimethyl-1,3-dioxan-4-yl)acetate (1.1 g, 1.12 mmol) in MeOH (5 mL) was added Pd/C (0.11 g, 1.12 mmol, 10% purity) and the resulting mixture was stirred at 30° C. for 4 h under $H_2$. LCMS showed a main peak with desired mass. The mixture was filtered, the filtrate was concentrated under vacuum to give tert-butyl 2-((4R,6R)-6-(2-(3-((4-(2-(2-(2-(2-aminoethoxy)ethoxy)ethoxy)ethoxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (0.55 g, 0.65 mmol, 57.93% yield) as white solid, which was used directly in the next step.

MS $(M+H)^+$=846.7

Step 5: Synthesis of (3R,5R)-7-(3-((4-(2-(2-(2-(2-aminoethoxy)ethoxy)ethoxy)ethoxy)phenyl)carbamoyl)-5-(4-fluorophenyl)-2-isopropyl-4-phenyl-1H-pyrrol-1-yl)-3,5-dihydroxyheptanoic acid (7)

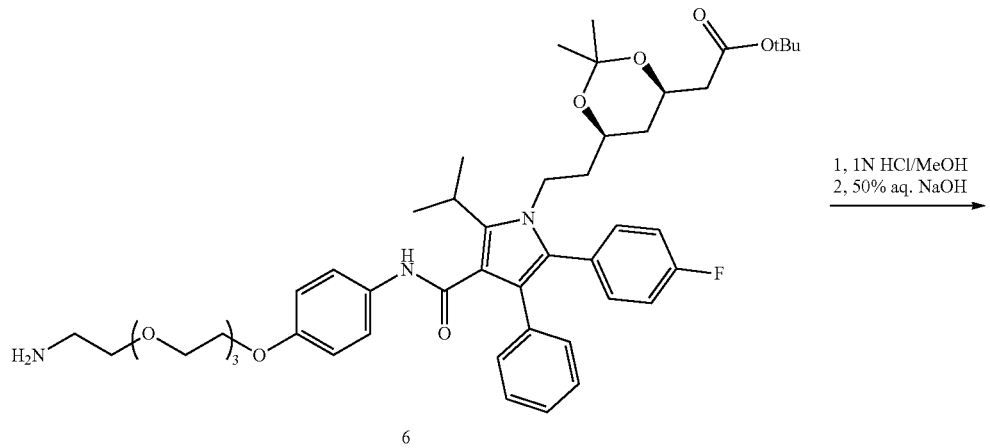

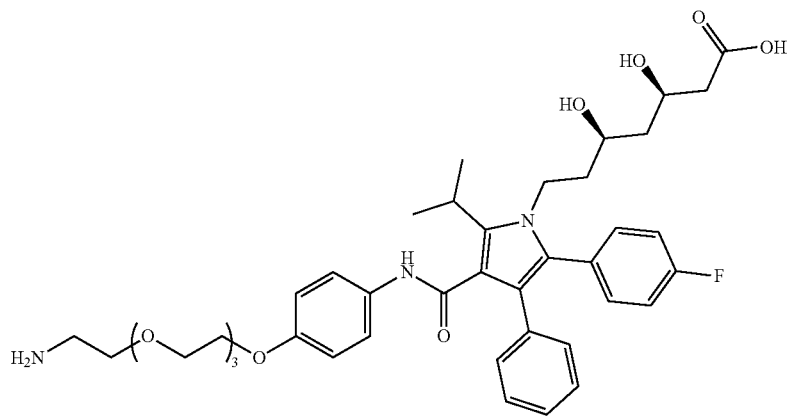

To a solution of tert-butyl 2-((4R,6R)-6-(2-(3-((4-(2-(2-(2-(2-aminoethoxy)ethoxy)ethoxy)ethoxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (0.35 g, 0.41 mmol) in MeOH (3 mL) and THF (3 mL) was added HCl (1 M, 0.83 mL) and the resulting mixture was stirred at 30° C. for 4 h. To the mixture was added a solution of NaOH (99.28 mg, 2.48 mmol) in Water (0.9 mL) and stirred at 30° C. for 1 h. LCMS showed a main peak with desired mass and the starting material was consumed. The pH was adjusted to 8-9 by 1 N HCl. The mixture was purified by reversed-phase HPLC (0.1% $NH_3$—$H_2O$ condition, 35% ACN) to afford (3R,5R)-7-(3-((4-(2-(2-(2-(2-aminoethoxy)ethoxy)ethoxy)ethoxy)phenyl)carbamoyl)-5-(4-fluorophenyl)-2-isopropyl-4-phenyl-1H-pyrrol-1-yl)-3,5-dihydroxyheptanoic acid (0.22 g, 0.293 mmol, 70.92% yield) as yellow solid.

MS $(M+H)^+$=750.3

Step 6: Synthesis of (3R,5R)-7-(3-((4 (2 (2 (2 (2 ((2-(2,6-dioxopiperidin-3-yl)-1,3-dioxoisoindolin-4-yl)amino)ethoxy)ethoxy)ethoxy)ethoxy)phenyl)carbamoyl)-5-(4-fluorophenyl)-2-isopropyl-4-phenyl-1H-pyrrol-1-yl)-3,5-dihydroxyheptanoic acid (Compound 1)

150*25 mm*5 um; mobile phase: [water (10 mM NH₄HCO₃)-ACN]; B %: 24%-54%, 10 min) followed by lyophilization to afford (3R,5R)-7-(3-((4-(2-(2-(2-(2-((2-(2,6-dioxopiperidin-3-yl)-1,3-dioxoisoindolin-4-yl)amino)ethoxy)ethoxy)ethoxy)ethoxy)phenyl)carbamoyl)-5-(4-fluorophenyl)-2-isopropyl-4-phenyl-1H-pyrrol-1-yl)-3,5-

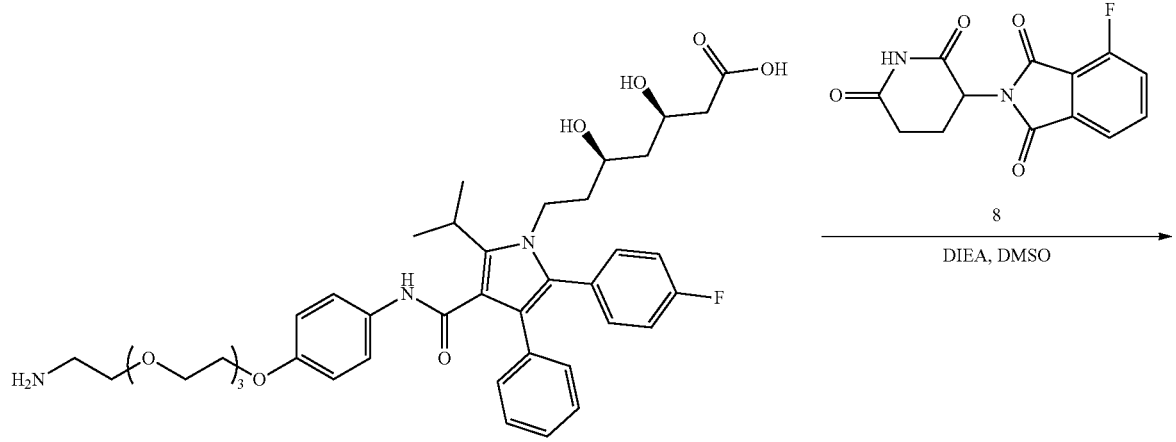

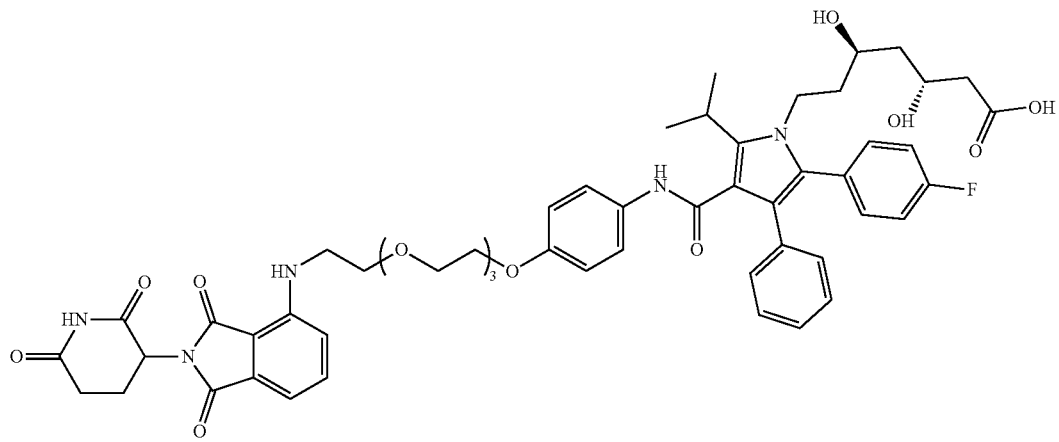

Compound 1

To a solution of (3R,5R)-7-(3-((4-(2-(2-(2-(2-aminoethoxy)ethoxy)ethoxy)ethoxy)phenyl)carbamoyl)-5-(4-fluorophenyl)-2-isopropyl-4-phenyl-1H-pyrrol-1-yl)-3,5-dihydroxyheptanoic acid (0.3 g, 0.4 mmol) and 2-(2,6-dioxo-3-piperidyl)-4-fluoro-isoindoline-1,3-dione (112.50 mg, 407.28 umol) in DMSO (5 mL) was added DIPEA (80 mg, 0.62 mmol, 0.11 mL). The mixture was stirred at 90° C. for 15 h. LCMS showed a peak (53%) with desired mass and (3R,5R)-7-(3-((4-(2-(2-(2-(2-aminoethoxy)ethoxy)ethoxy)ethoxy)phenyl)carbamoyl)-5-(4-fluorophenyl)-2-isopropyl-4-phenyl-1H-pyrrol-1-yl)-3,5-dihydroxyheptanoic acid was consumed. The mixture was filtered and the filtrate was purified directly by prep-HPLC (column: Waters Xbridge dihydroxyheptanoic acid (119.9 mg, 0.114.5 mmol, 28.63% yield, 97.3% purity) as yellow solid.

1H NMR (400 MHz, DMSO-$d_6$) δ 9.65 (s, 1H), 7.61-7.53 (m, 1H), 7.40 (d, J=9.05 Hz, 2H), 7.28-7.21 (m, 2H), 7.21-7.15 (m, 2H), 7.13 (d, J=8.68 Hz, 1H), 7.10-6.97 (m, 6H), 6.80 (d, J=9.05 Hz, 2H), 6.60 (t, J=5.56 Hz, 1H), 5.07-5.03 (m, 1H), 4.04-3.96 (m, 2H), 3.96-3.87 (m, 1H), 3.85-3.73 (m, 2H), 3.72-3.65 (m, 3H), 3.64-3.59 (m, 2H), 3.59-3.50 (m, 11H), 3.49-3.42 (m, 4H), 2.94-2.81 (m, 1H), 2.63-2.55 (m, 1H), 2.27-2.09 (m, 2H), 2.06-1.97 (m, 1H), 1.67-1.47 (m, 2H), 1.46-1.25 (m, 9H).

MS (M+H)⁺=1006.3

Example 2. Synthesis of (3R,5R)-7-(3-((4-(14-((2-(2,6-dioxopiperidin-3-yl)-1,3-dioxoisoindolin-4-yl)amino)-3,6,9,12-tetraoxatetradecyl)oxy)phenyl)carbamoyl)-5-(4-fluorophenyl)-2-isopropyl-4-phenyl-1H-pyrrol-1-yl)-3,5-dihydroxyheptanoic acid (Compound 2)

Step 1: Synthesis of benzyl (14-hydroxy-3,6,9,12-tetraoxatetradecyl)carbamate (2)

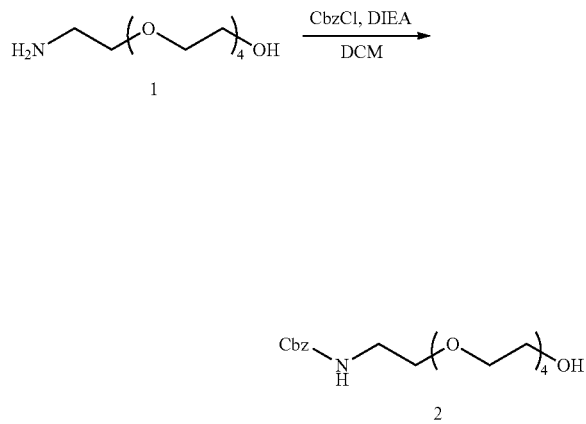

To a mixture of 14-amino-3,6,9,12-tetraoxatetradecan-1-ol (1 g, 4.21 mmol) and TEA (852.87 mg, 8.43 mmol, 1.17 mL) in DCM (10 mL) was added benzyl chloroformate (790.81 mg, 4.64 mmol, 0.659 mL). The mixture was stirred at 20° C. for 0.5 h. LCMS showed a main peak with desired mass. The mixture was washed with water (20 mL). The organic layer was dried over anhydrous Na$_2$SO$_4$, concentrated in vacuo to afford benzyl N-[2-[2-[2-[2-(2-hydroxyethoxy)ethoxy]ethoxy]ethoxy]ethyl]carbamate (1.57 g, crude) as colorless oil, which was used directly in the next step without further purification. MS (M+H)$^+$=372.4

Step 2: Synthesis of 3-oxo-1-phenyl-2,7,10,13,16-pentaoxa-4-azaoctadecan-18-yl 4-methylbenzenesulfonate (3)

To a mixture of benzyl (14-hydroxy-3,6,9,12-tetraoxatetradecyl)carbamate (1.57 g, 4.23 mmol) and 4-methylbenzenesulfonyl chloride (1.21 g, 6.34 mmol) in DCM (30 mL) was added pyridine (668.71 mg, 8.45 mmol, 0.682 mL). The mixture was stirred at 20° C. for 16 h. TLC (Petroleum ether/ethyl acetate=1/1) showed a main new spot was formed. The mixture was washed with water (20 mL), the organic layer was collected and dried over anhydrous Na$_2$SO$_4$, concentrated. The residue was purified by chromatography (silica gel, eluting with Petroleum ether/ethyl acetate=3:1, 1:1) to afford 3-oxo-1-phenyl-2,7,10,13,16-pentaoxa-4-azaoctadecan-18-yl 4-methylbenzenesulfonate (1.8 g, 3.42 mmol, 81.02% yield) as colorless oil.

Step 3: Synthesis of tert-butyl 2-((4R,6R)-6-(2-(2-(4-fluorophenyl)-5-isopropyl-4-((4-((3-oxo-1-phenyl-2,7,10,13,16-pentaoxa-4-azaoctadecan-18-yl)oxy)phenyl)carbamoyl)-3-phenyl-1H-pyrrol-1-yl)ethyl)-2,2-dimethyl-1,3-dioxan-4-yl)acetate (5)

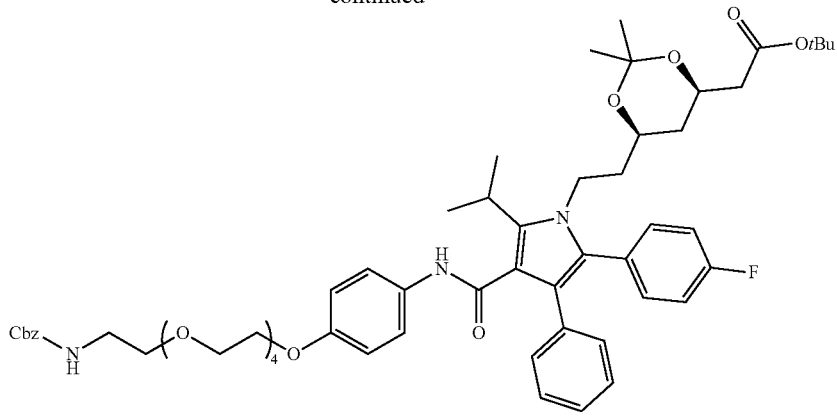

To a mixture of tert-butyl 2-((4R,6R)-6-(2-(2-(4-fluorophenyl)-4-((4-hydroxyphenyl)carbamoyl)-5-isopropyl-3-phenyl-1H-pyrrol-1-yl)ethyl)-2,2-dimethyl-1,3-dioxan-4-yl)acetate (1 g, 1.49 mmol) and 3-oxo-1-phenyl-2,7,10,13,16-pentaoxa-4-azaoctadecan-18-yl 4-methylbenzenesulfonate (783.55 mg, 1.49 mmol) in ACN (10 mL) was added $Cs_2CO_3$ (971.42 mg, 2.98 mmol). The mixture was stirred at 80° C. for 16 h. LCMS showed the starting material was consumed completely and desired mass was detected. The reaction mixture was filtered. The filtrate was concentrated. The crude product was purified by reversed-phase HPLC (90% ACN, 0.1% formic acid condition) to afford tert-butyl 2-((4R,6R)-6-(2-(2-(4-fluorophenyl)-5-isopropyl-4-(4-((3-oxo-1-phenyl-2,7,10,13,16-pentaoxa-4-azaoctadecan-18-yl)oxy)phenyl)carbamoyl)-3-phenyl-1H-pyrrol-1-yl)ethyl)-2,2-dimethyl-1,3-dioxan-4-yl)acetate (1 g, 976.36 umol, 65.49% yield) as a yellow oil. MS $(M+H)^+$=1024.4

Step 4: Synthesis of tert-butyl 2-((4R,6R)-6-(2-(3-((4-((14-amino-3,6,9,12-tetraoxatetradecyl)oxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (6)

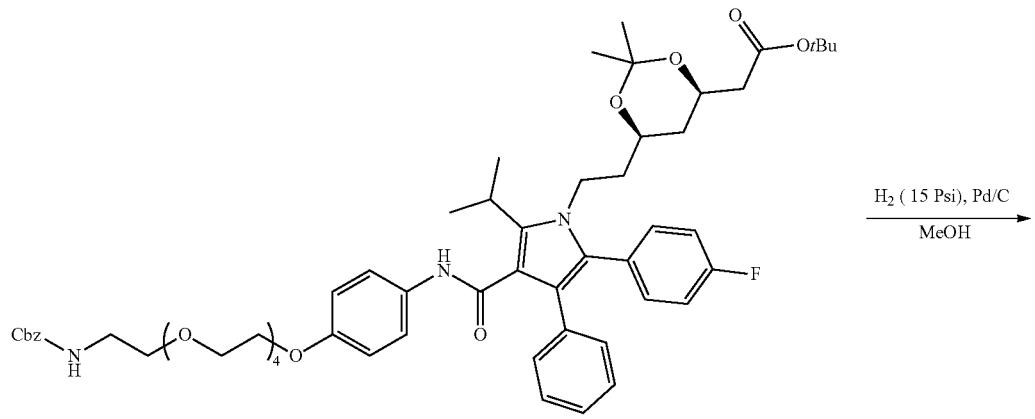

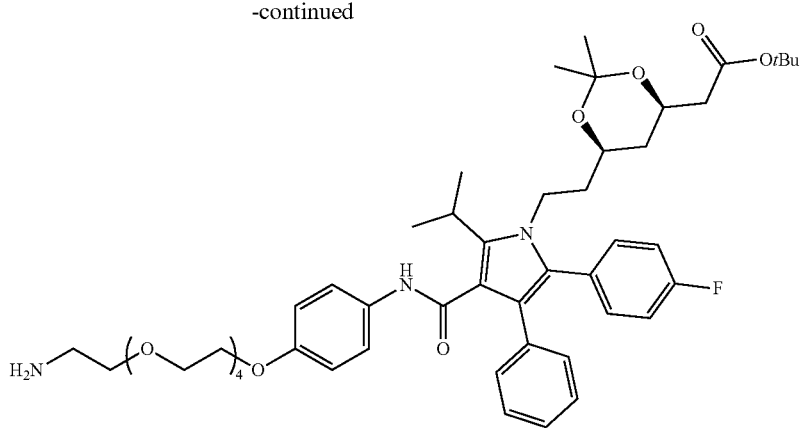

6

A mixture of tert-butyl 2-((4R,6R)-6-(2-(2-(4-fluorophenyl)-5-isopropyl-4-((4-((3-oxo-1-phenyl-2,7,10,13,16-pentaoxa-4-azaoctadecan-18-yl)oxy)phenyl)carbamoyl)-3-phenyl-1H-pyrrol-1-yl)ethyl)-2,2-dimethyl-1,3-dioxan-4-yl)acetate (1 g, 0.976 m mol) and Pd/C (0.1 g, 10% purity) in MeOH (20 mL) was stirred at 30° C. for 3 h under $H_2$ atmosphere (15 psi). LCMS showed the starting material was consumed and desired mass was detected. The reaction mixture was filtered. The filtrate was concentrated under reduced pressure to give tert-butyl 2-((4R,6R)-6-(2-(3-((4-((14-amino-3,6,9,12-tetraoxatetradecyl)oxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (0.75 g, 0.843 mmol, 86.30% yield) as yellow oil, which was used into the next step without further purification.

MS $(M+H)^+$=890.4

Step 5: Synthesis of (3R,5R)-7-(3-((4-((14-amino-3,6,9,12-tetraoxatetradecyl)oxy)phenyl)carbamoyl)-5-(4-fluorophenyl)-2-isopropyl-4-phenyl-1H-pyrrol-1-yl)-3,5-dihydroxyheptanoic acid (7)

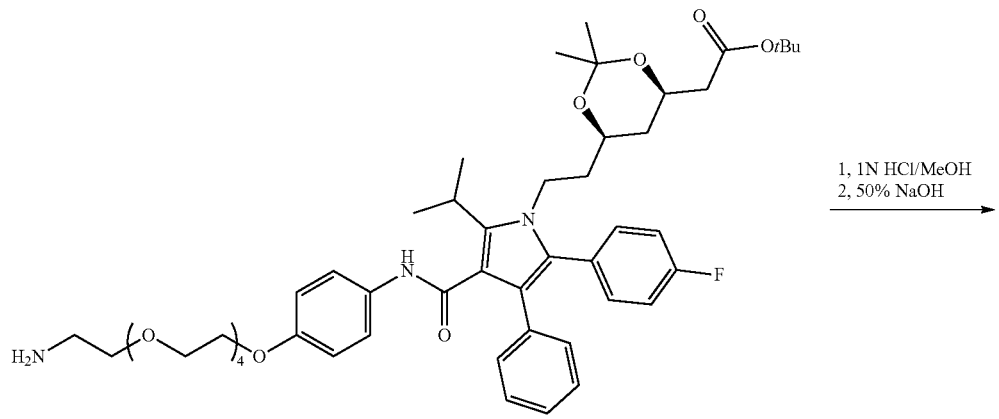

6

1, 1N HCl/MeOH
2, 50% NaOH

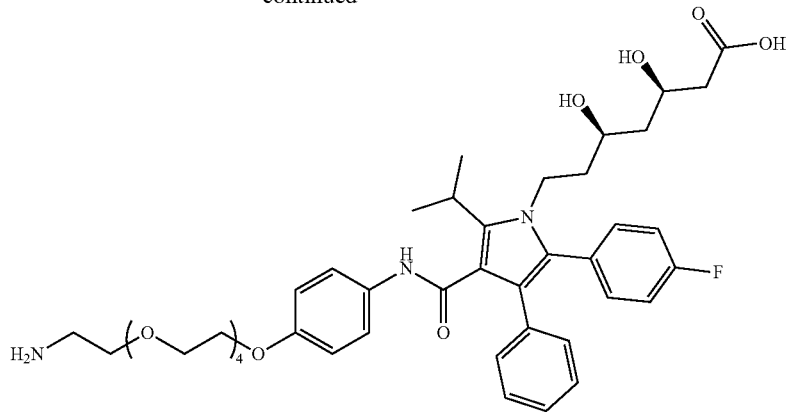

A mixture of tert-butyl 2-[(4R,6R)-6-[2-[3-[[4-[[14-amino-3,6,9,12-tetraoxatetradecyl]oxy]phenyl]carbamoyl]-5-(4-fluorophenyl)-2-isopropyl-4-phenyl-1H-pyrrol-1-yl]ethyl]-2,2-dimethyl-1,3-dioxan-4-yl]acetate (0.75 g, 842.62 umol) in MeOH (7.5 mL) and THF (7.5 mL) was added HCl/$H_2O$ (1 M, 2.11 mL) and stirred at 30° C. for 4 h. LCMS showed one main peak with desired mass was detected. To the mixture was added a solution of NaOH (202.21 mg, 5.06 mmol) in $H_2O$ (4 mL). The mixture was stirred at 30° C. for 10 h. LCMS showed one main peak with desired mass. The pH was adjusted to 8-9 by 1N HCl. The mixture was concentrated in vacuum. The residue was purified by reversed-phase HPLC (0.1% $NH_3$—$H_2O$ condition, 45% ACN) to afford (3R,5R)-7-(3-((4-((14-amino-3,6,9,12-tetraoxatetradecyl)oxy)phenyl)carbamoyl)-5-(4-fluorophenyl)-2-isopropyl-4-phenyl-1H-pyrrol-1-yl)-3,5-dihydroxyheptanoic acid (0.5 g, 0.63 mmol, 74.74% yield) as a white solid. MS $(M+H)^+$=794.3

Step 6: Synthesis of (3R,5R)-7-(3-((4-((14-((2-(2,6-dioxopiperidin-3-yl)-1,3-dioxoisoindolin-4-yl)amino)-3,6,9,12-tetraoxatetradecyl)oxy)phenyl)carbamoyl)-5-(4-fluorophenyl)-2-isopropyl-4-phenyl-1H-pyrrol-1-yl)-3,5-dihydroxyheptanoic acid
(Compound 2)

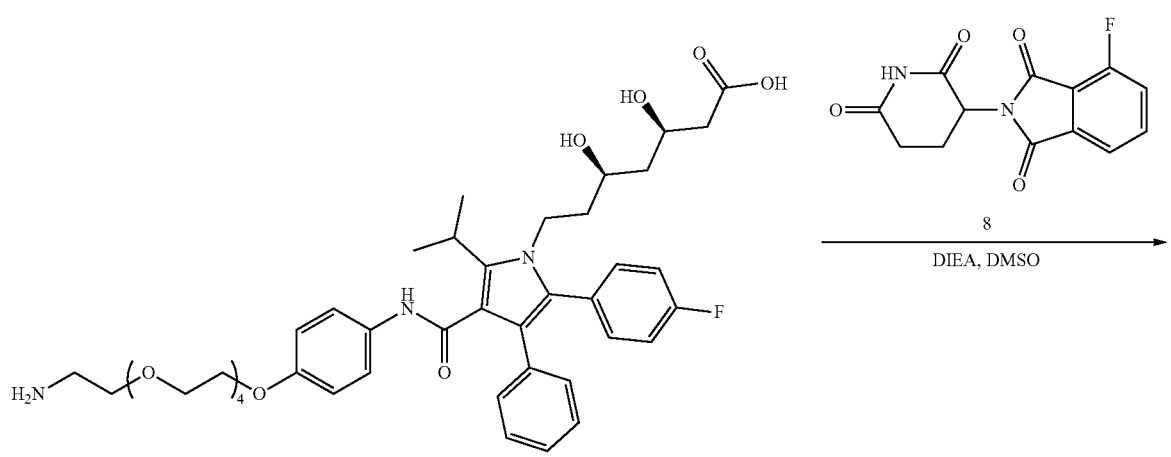

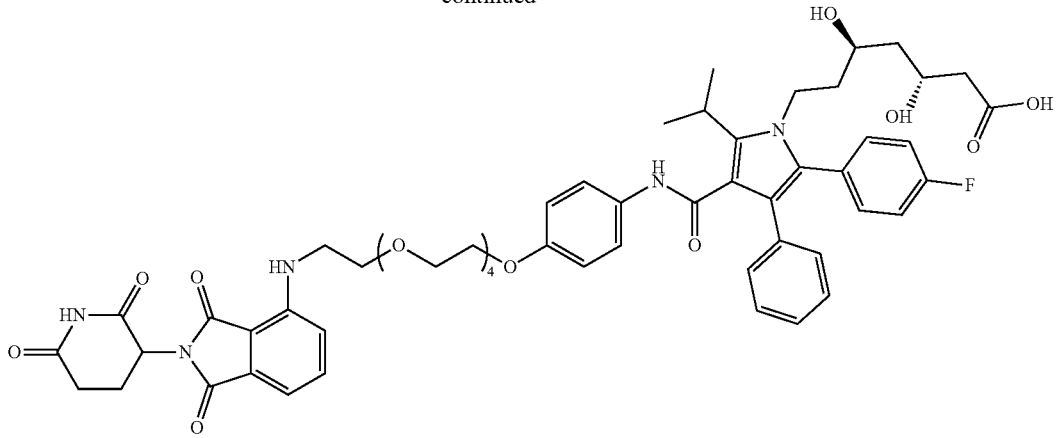

Compound 2

To a solution of (3R,5R)-7-(3-((4-((14-amino-3,6,9,12-tetraoxatetradecyl)oxy)phenyl)carbamoyl)-5-(4-fluorophenyl)-2-isopropyl-4-phenyl-1H-pyrrol-1-yl)-3,5-dihydroxyheptanoic acid (0.3 g, 0.378 mmol) and 2-(2,6-dioxo-3-piperidyl)-4-fluoro-isoindoline-1,3-dione (0.11 g, 0.398 mmol) in DMSO (3 mL) was added DIEA (74.20 mg, 0.574 mmol, 0.1 mL) and the resulting mixture was stirred at 90° C. for 15 h. LCMS showed a main peak with desired mass and starting material was consumed. The pH was adjusted to 8-9 by 1 N HCl. The mixture was filtered and the filtrate was purified directly. The filtrate was purified by prep-HPLC (column: Waters Xbridge 150*25 mm*5 um; mobile phase: [water (10 mM NH$_4$HCO$_3$)-ACN]; B %: 24%-54%, 10 min) followed by lyophilization to afford (3R,5R)-7-(3-((4-((14-((2-(2,6-dioxopiperidin-3-yl)-1,3-dioxoisoindolin-4-yl)amino)-3,6,9,12-tetraoxatetradecyl)oxy)phenyl)carbamoyl)-5-(4-fluorophenyl)-2-isopropyl-4-phenyl-1H-pyrrol-1-yl)-3,5-dihydroxyheptanoic acid (175.8 mg, 0.165 mmol, 43.73% yield, 96.7% purity) as yellow solid. $^1$H NMR (400 MHz, DMSO-d$_6$) δ 9.64 (s, 1H), 7.57 (dd, J=7.15, 8.50 Hz, 1H), 7.40 (d, J=9.05 Hz, 2H), 7.27-7.11 (m, 5H), 7.10-7.05 (m, 4H), 7.05-6.97 (m, 2H), 6.80 (d, J=9.05 Hz, 2H), 6.60 (t, J=5.69 Hz, 1H), 5.05 (dd, J=5.44, 12.90 Hz, 1H), 4.03-3.98 (m, 2H), 3.97-3.88 (m, 1H), 3.87-3.73 (m, 2H), 3.72-3.66 (m, 2H), 3.65-3.58 (m, 2H), 3.58-3.49 (m, 14H), 3.48-3.42 (m, 3H), 3.25-3.17 (m, 3H), 2.94-2.82 (m, 1H), 2.63-2.55 (m, 1H), 2.55-2.52 (m, 1H), 2.29-2.21 (m, 1H), 2.20-2.12 (m, 1H), 2.07-1.97 (m, 1H), 1.68-1.48 (m, 2H), 1.36 (d, J=6.97 Hz, 8H). MS (M+H)$^+$=1050.8

Example 3. Synthesis of (3R,5R)-7-(3-((4-((17-((2-(2,6-dioxopiperidin-3-yl)-1,3-dioxoisoindolin-4-yl)amino)-3,6,9,12,15-pentaoxaheptadecyl)oxy)phenyl)carbamoyl)-5-(4-fluorophenyl)-2-isopropyl-4-phenyl-1H-pyrrol-1-yl)-3,5-dihydroxyheptanoic acid (Compound 3)

Step 1: Synthesis of benzyl (17-hydroxy-3,6,9,12,15-pentaoxaheptadecyl)carbamate (2)

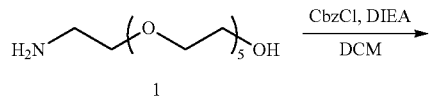

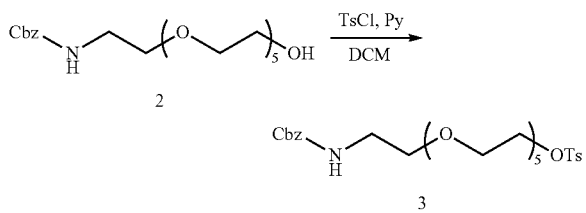

To a mixture of 17-amino-3,6,9,12,15-pentaoxaheptadecan-1-ol (1 g, 3.55 mmol) and TEA (719.33 mg, 7.11 mmol, 0.989 mL) in DCM (10 mL) was added benzyl chloroformate (666.98 mg, 3.91 mmol, 0.5556 mL). The mixture was stirred at 20° C. for 0.5 h. LCMS showed a main peak with desired mass. The mixture was washed with water (20 mL), and the organic layer was dried over anhydrous Na$_2$SO$_4$, concentrated to afford benzyl (17-hydroxy-3,6,9,12,15-pentaoxaheptadecyl)carbamate (1.48 g, crude) as colorless oil, which was used directly in the next step without any purification. MS (M+H)$^+$=416.4

Step 2: Synthesis of 3-oxo-1-phenyl-2,7,10,13,16,19-hexaoxa-4-azahenicosan-21-yl 4-methylbenzenesulfonate (3)

To a mixture of benzyl (17-hydroxy-3,6,9,12,15-pentaoxaheptadecyl)carbamate (1.48 g, 3.56 mmol) and 4-methylbenzenesulfonyl chloride (1.02 g, 5.34 mmol) in DCM (30 mL) was added pyridine (563.54 mg, 7.12 mmol, 575.04 uL). The mixture was stirred at 20° C. for 16 h. TLC (Petroleum ether/ethyl acetate=1/1) showed a main new spot was formed. The mixture was washed with water (20 mL), the organic layer was collected and dried over anhydrous Na$_2$SO$_4$, concentrated. The residue was purified by chromatography (silica gel, eluting with Petroleum ether/ethyl acetate=3/1~1/2) to afford 3-oxo-1-phenyl-2,7,10,13,16,19-hexaoxa-4-azahenicosan-21-yl 4-methylbenzenesulfonate (1.7 g, 2.98 mmol, 83.78% yield) as colorless oil.

Step 3: Synthesis of tert-butyl 2-((4R,6R)-6-(2-(2-(4-fluorophenyl)-5-isopropyl-4-((4-((3-oxo-1-phenyl-2,7,10,13,16,19-hexaoxa-4-azahenicosan-21-yl)oxy)phenyl)carbamoyl)-3-phenyl-1H-pyrrol-1-yl)ethyl)-2,2-dimethyl-1,3-dioxan-4-yl)acetate (5)

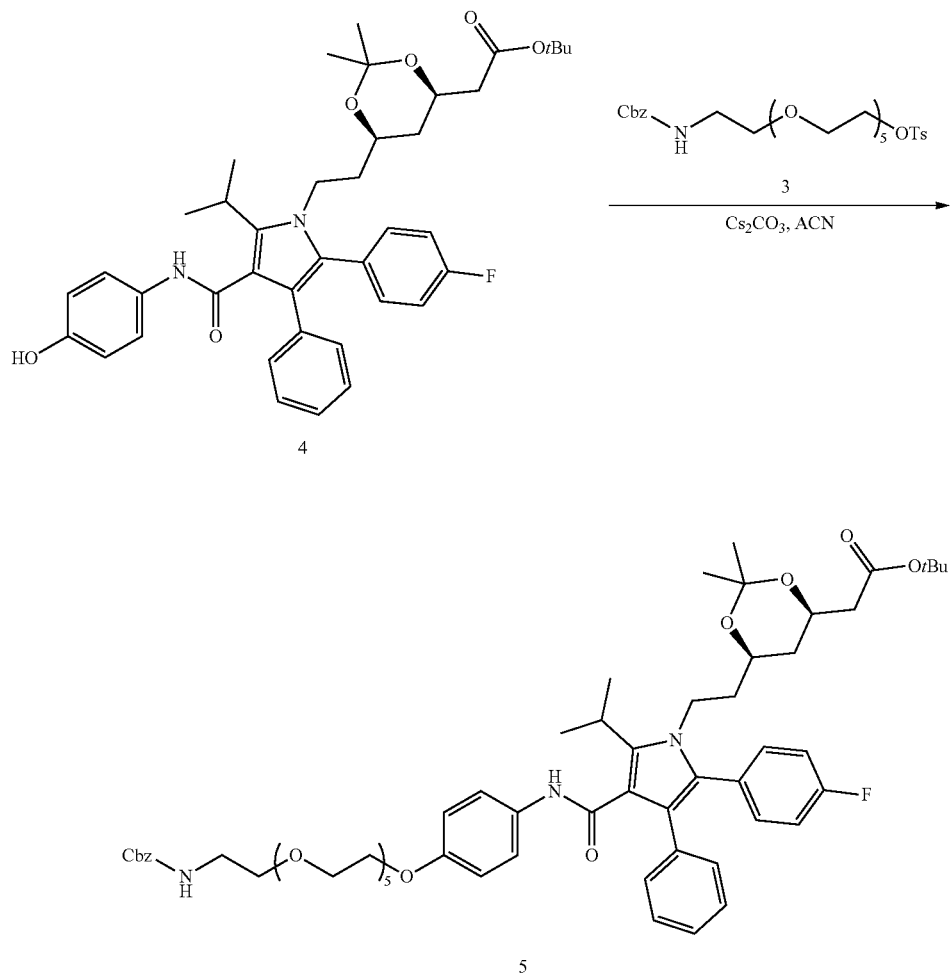

To a solution of tert-butyl 2-((4R,6R)-6-(2-(2-(4-fluorophenyl)-5-isopropyl-4-((4-((3-oxo-1-phenyl-2,7,10,13,16,19-hexaoxa-4-azahenicosan-21-yl)oxy)phenyl)carbamoyl)-3-phenyl-1H-pyrrol-1-yl)ethyl)-2,2-dimethyl-1,3-dioxan-4-yl)acetate (2.00 g, 2.98 mmol) and 3-oxo-1-phenyl-2,7,10,13,16,19-hexaoxa-4-azahenicosan-21-yl 4-methylbenzenesulfonate (1.7 g, 2.98 mmol) in ACN (10 mL) was added $Cs_2CO_3$ (1.94 g, 5.97 mmol). The mixture was stirred at 80° C. for 16 h. LCMS showed 3-oxo-1-phenyl-2,7,10,13,16,19-hexaoxa-4-azahenicosan-21-yl 4-methylbenzenesulfonate was consumed completely and desired mass was detected. The reaction mixture was filtered and mother liquor was obtained. The crude product was purified by reversed-phase HPLC (90% ACN, 0.1% formic acid condition) to give tert-butyl 2-((4R,6R)-6-(2-(2-(4-fluorophenyl)-5-isopropyl-4-((4-((3-oxo-1-phenyl-2,7,10,13,16,19-hexaoxa-4-azahenicosan-21-yl)oxy)phenyl)carbamoyl)-3-phenyl-1H-pyrrol-1-yl)ethyl)-2,2-dimethyl-1,3-dioxan-4-yl)acetate (1.3 g, 1.22 mmol, 40.78% yield) as a yellow oil. MS $(M+H)^+=1068.5$ Step 4: Synthesis of tert-butyl 2-((4R,6R)-6-(2-(3-((4-((17-amino-3,6,9,12,15-pentaoxaheptadecyl)oxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (6)

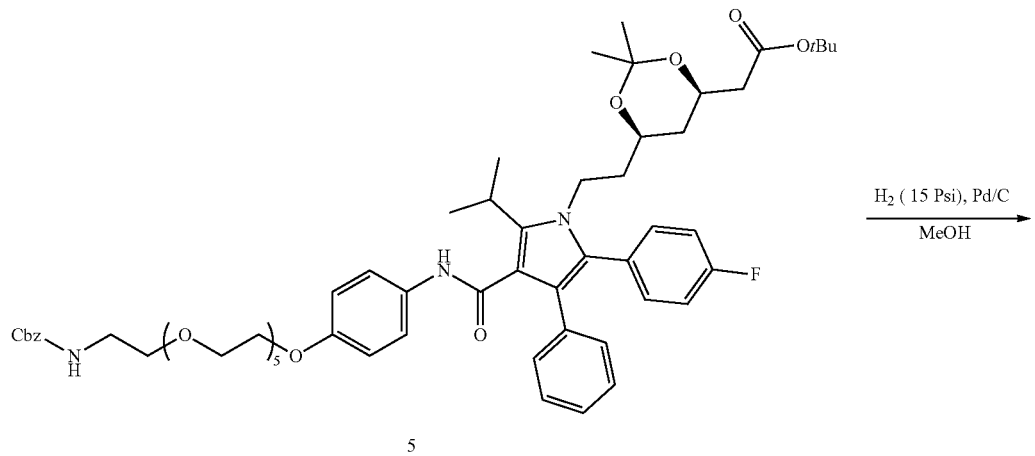

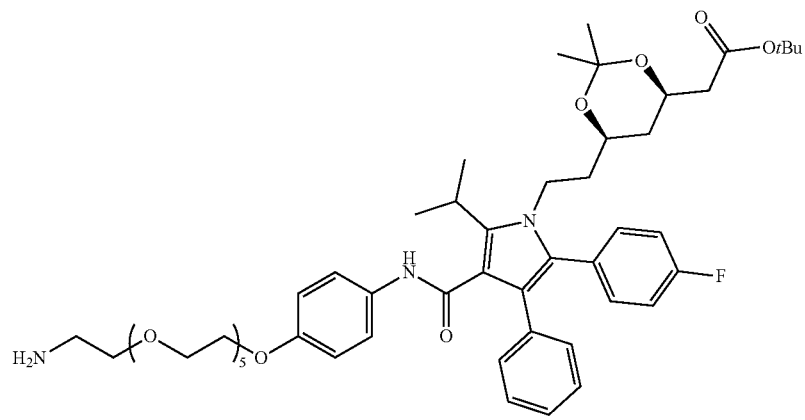

A mixture of tert-butyl 2-((4R,6R)-6-(2-(2-(4-fluorophenyl)-5-isopropyl-4-((4-((3-oxo-1-phenyl-2,7,10,13,16,19-hexaoxa-4-azahenicosan-21-yl)oxy)phenyl)carbamoyl)-3-phenyl-1H-pyrrol-1-yl)ethyl)-2,2-dimethyl-1,3-dioxan-4-yl)acetate (1.3 g, 1.22 mmol) and Pd/C (0.13 g, 10% purity) in MeOH (20 mL) was stirred at 30° C. for 3 h under $H_2$ atmosphere (15 psi). LCMS showed the starting material was consumed completely and desired mass was detected. The reaction mixture was filtered. The filtrate was concentrated under vacuum to afford tert-butyl 2-((4R,6R)-6-(2-(3-((4-((17-amino-3,6,9,12,15-pentaoxaheptadecyl)oxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (1.08 g, 1.16 mmol, 95.01% yield) as yellow oil, which was used into the next step without further purification. MS $(M+H)^+=934.5$ Step 5: Synthesis of (3R,5R)-7-(3-((4-((17-amino-3,6,9,12,15-pentaoxaheptadecyl)oxy)phenyl)carbamoyl)-5-(4-fluorophenyl)-2-isopropyl-4-phenyl-1H-pyrrol-1-yl)-3,5-dihydroxyheptanoic acid (7)

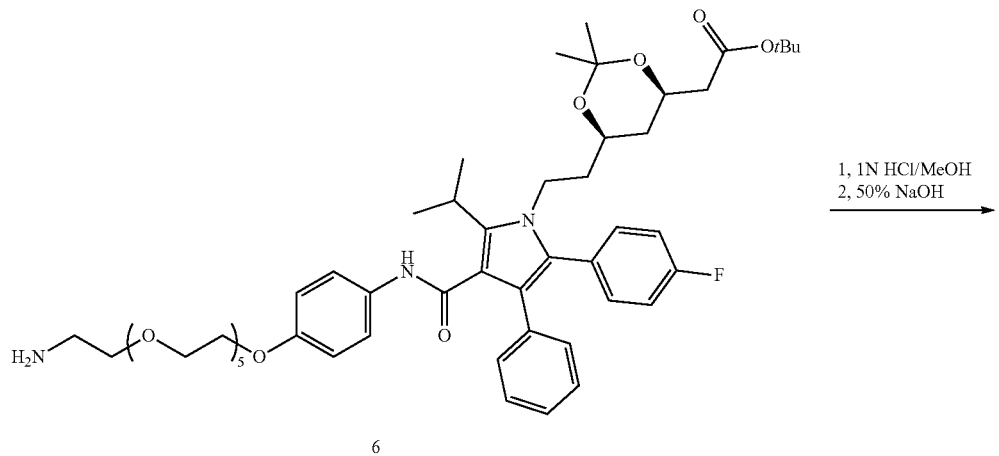

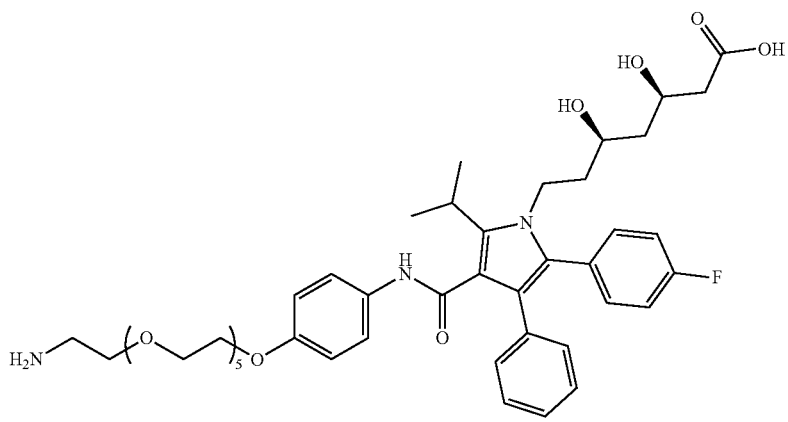

To a mixture of tert-butyl 2-((4R,6R)-6-(2-(3-((4-((17-amino-3,6,9,12,15-pentaoxaheptadecyl)oxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (1.08 g, 1.16 mmol) in MeOH (10 mL) and THF (10 mL) was added HCl (1 M, 2.89 mL) and the resulting mixture was stirred at 30° C. for 5 h. LCMS showed a main peak with desired mass was detected. To the mixture was added a solution of NaOH (277.46 mg, 6.94 mmol) in $H_2O$ (4 mL) and the mixture was stirred at 30° C. for 9 h. LCMS showed one main peak with desired mass. The pH was adjusted to 8-9 by 1N HCl. The mixture was concentrated under vacuum. The crude product was purified by reversed-phase HPLC (0.1% $NH_3.H_2O$, 45% ACN) to afford (3R,5R)-7-(3-((4-((17-amino-3,6,9,12,15-pentaoxaheptadecyl)oxy)phenyl)carbamoyl)-5-(4-fluorophenyl)-2-isopropyl-4-phenyl-1H-pyrrol-1-yl)-3,5-dihydroxyheptanoic acid (0.7 g, 0.835 mmol, 72.25% yield) as a white solid. MS $(M+H)^+$=838.5

Step 6: Synthesis of (3R,5R)-7-(3-((4-((17-((2-(2,6-dioxopiperidin-3-yl)-1,3-dioxoisoindolin-4-yl)amino)-3,6,9,12,15-pentaoxaheptadecyl)oxy)phenyl)carbamoyl)-5-(4-fluorophenyl)-2-isopropyl-4-phenyl-1H-pyrrol-1-yl)-3,5-dihydroxyheptanoic acid (Compound 3)

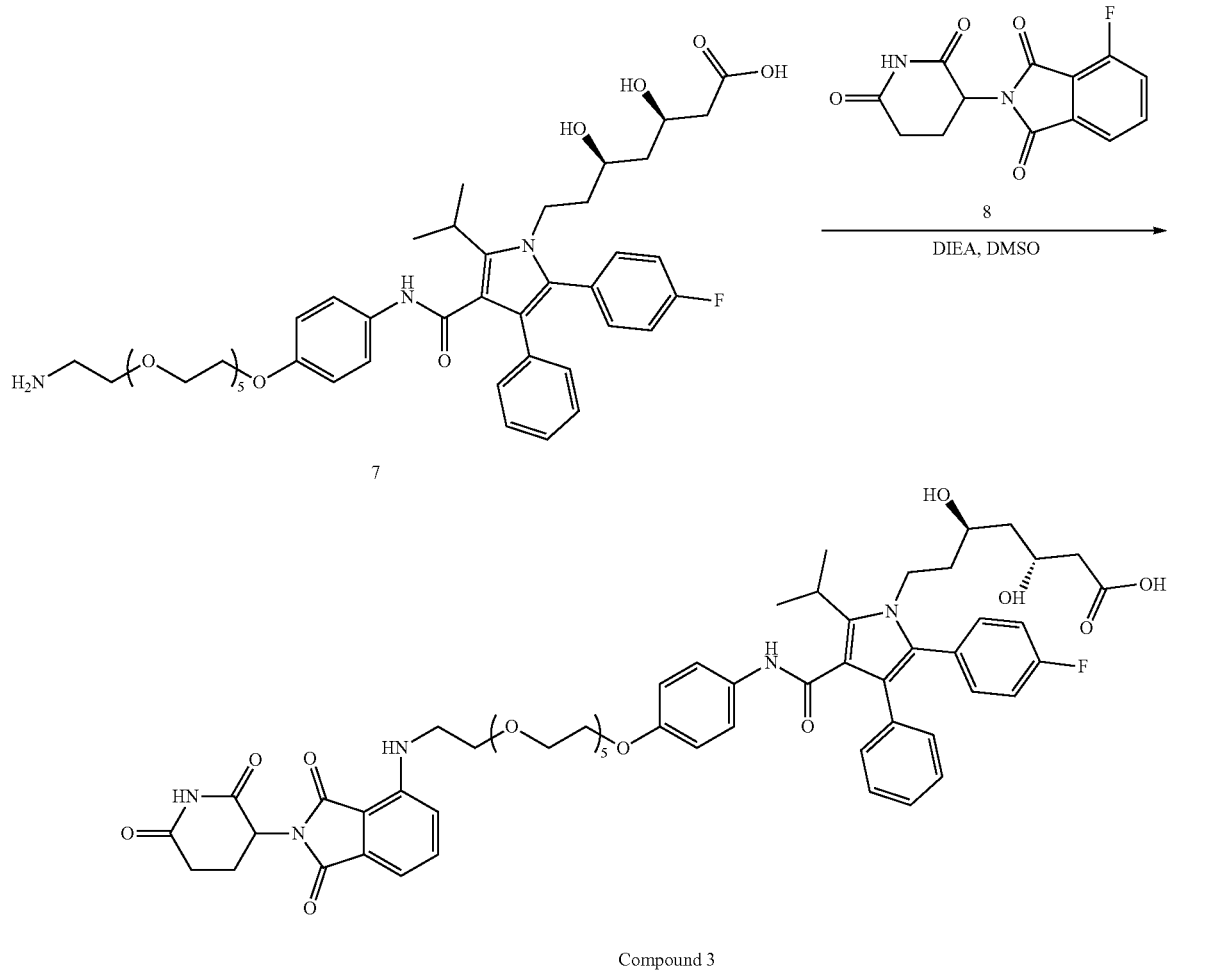

Compound 3

To a solution of (3R,5R)-7-(3-((4-((17-amino-3,6,9,12,15-Pentaoxaheptadecyl)oxy)phenyl)carbamoyl)-5-(4-fluorophenyl)-2-isopropyl-4-phenyl-1H-pyrrol-1-yl)-3,5-dihydroxyheptanoic acid (0.3 g, 0.358 mmol) and 2-(2,6-dioxo-3-piperidyl)-4-fluoro-isoindoline-1,3-dione (0.1 g, 0.362 mmol) in DMSO (3 mL) was added DIEA (69.41 mg, 0.537 mmol) and the resulting mixture was stirred at 90° C. for 15 h. LCMS showed a main peak with desired mass and the starting material was consumed. The pH was adjusted to 8-9 by 1 N HCl and the mixture was filtered. The filtrate was purified by prep-HPLC (column: Waters Xbridge 150*25 mm*5 um; mobile phase: [water (10 mM NH₄HCO₃)-ACN]; B %: 24%-54%, 10 min) followed by lyophilization to afford (3R,5R)-7-(3-((4-((17-((2-(2,6-dioxopiperidin-3-yl)-1,3-dioxoisoindolin-4-yl)amino)-3,6,9,12,15-pentaoxaheptadecyl)oxy)phenyl)carbamoyl)-5-(4-fluorophenyl)-2-isopropyl-4-phenyl-1H-pyrrol-1-yl)-3,5-dihydroxyheptanoic acid (135.4 mg, 0.121 mmol, 33.91% yield, 95.9% purity) as yellow solid. $^1$H NMR (400 MHz, DMSO-d$_6$) δ 9.64 (s, 1H), 7.57 (dd, J=7.15, 8.50 Hz, 1H), 7.40 (d, J=9.05 Hz, 2H), 7.28-7.12 (m, 5H), 7.10-6.97 (m, 6H), 6.81 (d, J=9.05 Hz, 2H), 6.60 (t, J=5.81 Hz, 1H), 5.05 (dd, J=5.44, 12.90 Hz, 1H), 4.04-3.98 (m, 2H), 3.97-3.87 (m, 1H), 3.86-3.73 (m, 2H), 3.73-3.67 (m, 2H), 3.64-3.58 (m, 2H), 3.58-3.43 (m, 20H), 3.25-3.17 (m, 3H), 2.94-2.81 (m, 1H), 2.62-2.55 (m, 1H), 2.55-2.52 (m, 1H), 2.29-2.22 (m, 1H), 2.20-2.13 (m, 1H), 2.07-1.98 (m, 1H), 1.68-1.48 (m, 2H), 1.46-1.27 (m, 8H). MS (M+H)$^+$=1094.8

Example 4. Synthesis of (3R,5R)-7-(3-((4-((20-((2-(2,6-dioxopiperidin-3-yl)-1,3-dioxoisoindolin-4-yl)amino)-3,6,9,12,15,18-hexaoxaicosyl)oxy)phenyl)carbamoyl)-5-(4-fluorophenyl)-2-isopropyl-4-phenyl-1H-pyrrol-1-yl)-3,5-dihydroxyheptanoic acid (Compound 4)

Step 1: Synthesis of benzyl (20-hydroxy-3,6,9,12,15,18-hexaoxaicosyl)carbamate (2)

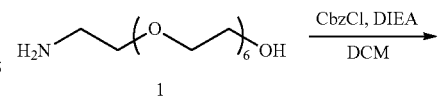

-continued

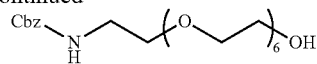

2

To a mixture of 2-[2-[2-[2-[2-[2-(2-aminoethoxy)ethoxy]ethoxy]ethoxy]ethoxy]ethanol (0.7 g, 2.15 mmol) and TEA (435.36 mg, 4.30 mmol, 0.599 mL) in DCM (10 mL) was added benzyl chloroformate (403.68 mg, 2.37 mmol, 336.40 uL) and the resulting mixture was stirred at 20° C. for 0.5 h. LCMS showed a main peak with desired mass. The mixture was washed with water (20 mL), and the organic layer was dried over anhydrous Na$_2$SO$_4$, concentrated to afford benzyl (20-hydroxy-3,6,9,12,15,18-hexaoxaicosyl)carbamate (980 mg, 2.13 mmol, 99.14% yield) as colorless oil, which was used in the next step directly without any purification. MS (M+H)$^+$=460.3

Step 2: Synthesis of 3-oxo-1-phenyl-2,7,10,13,16,19,22-heptaoxa-4-azatetracosan-24-yl 4-methylbenzenesulfonate (3)

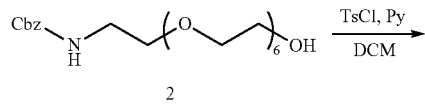

-continued

3

To a mixture of benzyl (20-hydroxy-3,6,9,12,15,18-hexaoxaicosyl)carbamate (980 mg, 2.13 mmol) and 4-methylbenzenesulfonyl chloride (609.87 mg, 3.20 mmol) in DCM (30 mL) was added pyridine (337.38 mg, 4.27 mmol) and the resulting mixture was stirred at 20° C. for 16 h. TLC (Petroleum ether/ethyl acetate=1/1) showed a main new spot was formed. The mixture was washed with water (20 mL), the organic layer was collected and dried over anhydrous Na$_2$SO$_4$, concentrated. The residue was purified by chromatography (silica gel, eluting with Petroleum ether/ethyl acetate=3/1~1/1) to afford 3-oxo-1-phenyl-2,7,10,13,16,19,22-heptaoxa-4-azatetracosan-24-yl 4-methylbenzenesulfonate (1.1 g, 1.79 mmol, 84.05% yield) as colorless oil.

Step 3: Synthesis of tert-butyl 2-((4R,6R)-6-(2-(2-(4-fluorophenyl)-5-isopropyl-4-((4-((3-oxo-1-phenyl-2,7,10,13,16,19,22-heptaoxa-4-azatetracosan-24-yl)oxy)phenyl)carbamoyl)-3-phenyl-1H-pyrrol-1-yl)ethyl)-2,2-dimethyl-1,3-dioxan-4-yl)acetate (5)

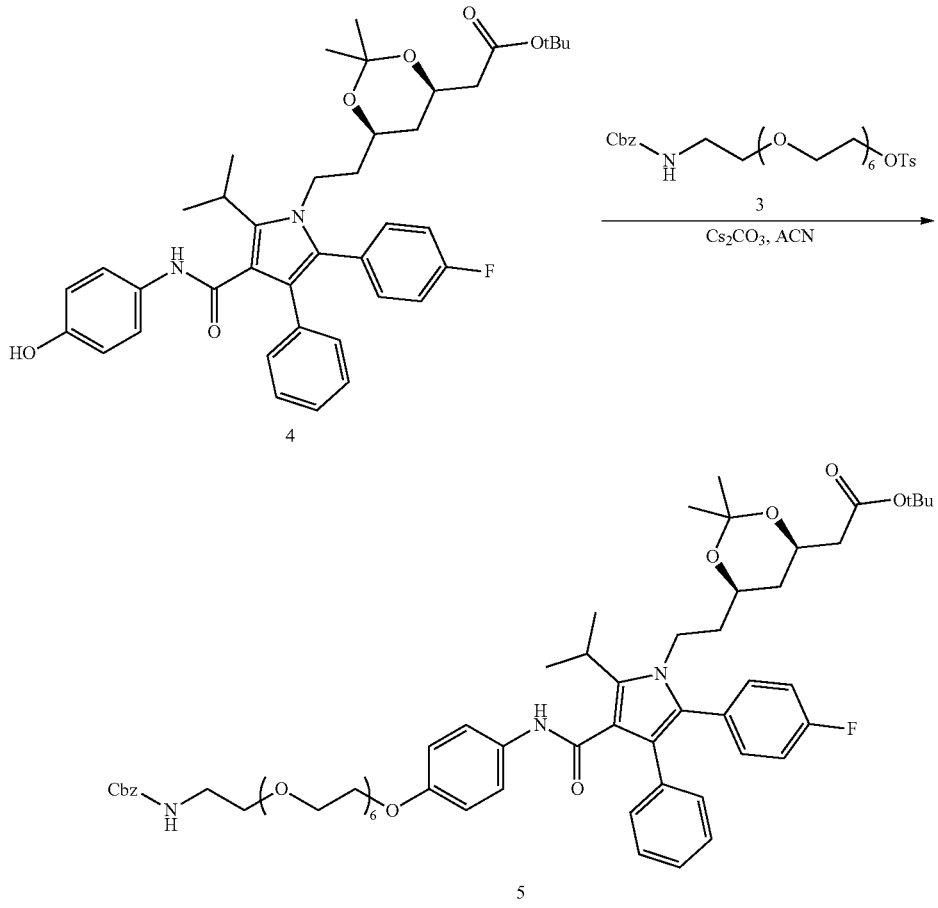

To a mixture of tert-butyl 2-((4R,6R)-6-(2-(2-(4-fluorophenyl)-4-((4-hydroxyphenyl)carbamoyl)-5-isopropyl-3-phenyl-1H-pyrrol-1-yl)ethyl)-2,2-dimethyl-1,3-dioxan-4-yl)acetate (1.20 g, 1.79 mmol) and 3-oxo-1-phenyl-2,7,10,13,16,19,22-heptaoxa-4-azatetracosan-24-yl 4-methylbenzenesulfonate (1.1 g, 1.79 mmol) in ACN (10 mL) was added $Cs_2CO_3$ (1.17 g, 3.58 mmol) and the resulting mixture was stirred at 80° C. for 16 h. LCMS showed the starting material was consumed completely and desired mass was detected. The reaction mixture was filtered. The filtrate was concentrated under vacuum. The residue was purified by reversed-phase HPLC (90% ACN, 0.1% formic acid condition) to afford tert-butyl 2-((4R,6R)-6-(2-(2-(4-fluorophenyl)-5-isopropyl-4-((4-((3-oxo-1-phenyl-2,7,10,13,16,19,22-heptaoxa-4-azatetracosan-24-yl)oxy)phenyl)carbamoyl)-3-phenyl-1H-pyrrol-1-yl)ethyl)-2,2-dimethyl-1,3-dioxan-4-yl)acetate (0.8 g, 0.719 mmol, 40.13% yield) as yellow oil. MS $(M+H)^+=1112.5$ Step 4: Synthesis of tert-butyl 2-((4R,6R)-6-(2-(3-((4-((20-amino-3,6,9,12,15,18-hexaoxaicosyl)oxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (6)

A mixture of tert-butyl 2-((4R,6R)-6-(2-(2-(4-fluorophenyl)-5-isopropyl-4-((4-((3-oxo-1-phenyl-2,7,10,13,16,19,22-heptaoxa-4-azatetracosan-24-yl)oxy)phenyl)carbamoyl)-3-phenyl-1H-pyrrol-1-yl)ethyl)-2,2-dimethyl-1,3-dioxan-4-yl)acetate (0.8 g, 0.719 mmol) and Pd/C (0.1 g, 10% purity) in MeOH (20 mL) was stirred at 30° C. for 3 h under $H_2$ atmosphere (15 psi). LCMS showed the starting material was consumed completely and desired mass was detected. The reaction mixture was filtered. The filtrate was concentrated under reduced pressured to afford tert-butyl 2-((4R,6R)-6-(2-(3-((4-((20-amino-3,6,9,12,15,18-hexaoxaicosyl)oxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (0.65 g, 0.664 mmol, 92.39% yield) as yellow oil, which was used into the next step without further purification. MS $(M+H)^+=978.5$

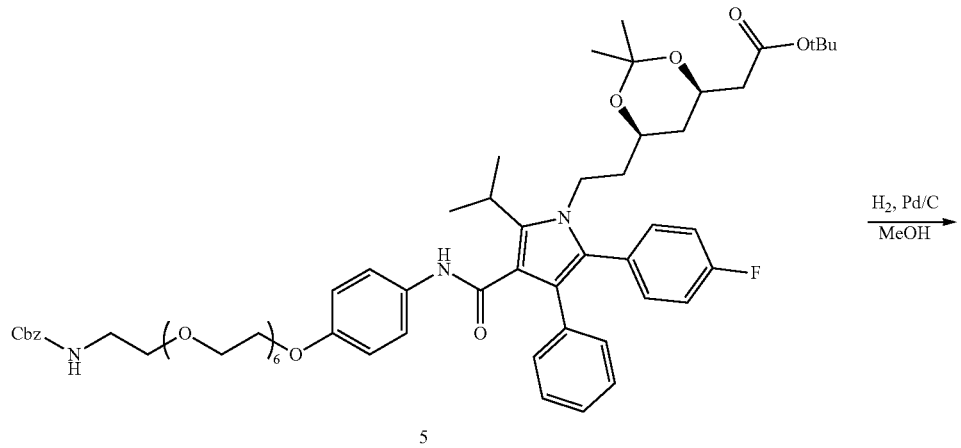

5

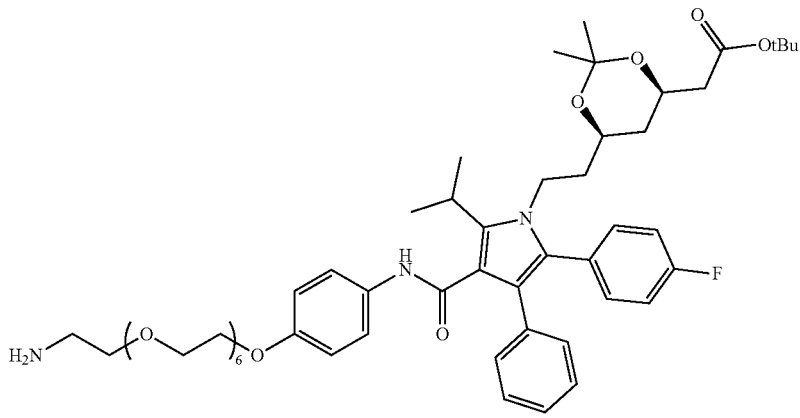

6

Step 5: Synthesis of (3R,5R)-7-(3-((4-((20-amino-3,6,9,12,15,18-hexaoxaicosyl)oxy)phenyl)carbamoyl)-5-(4-fluorophenyl)-2-isopropyl-4-phenyl-1H-pyrrol-1-yl)-3,5-dihydroxyheptanoic acid (7)

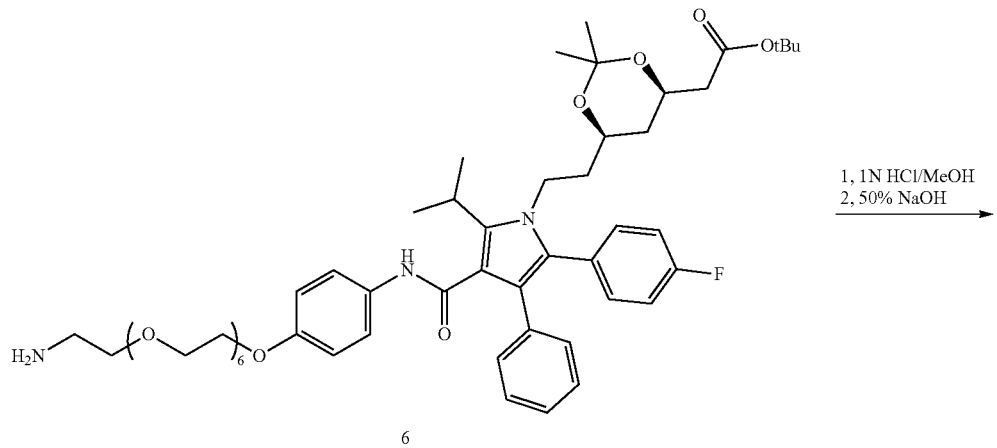

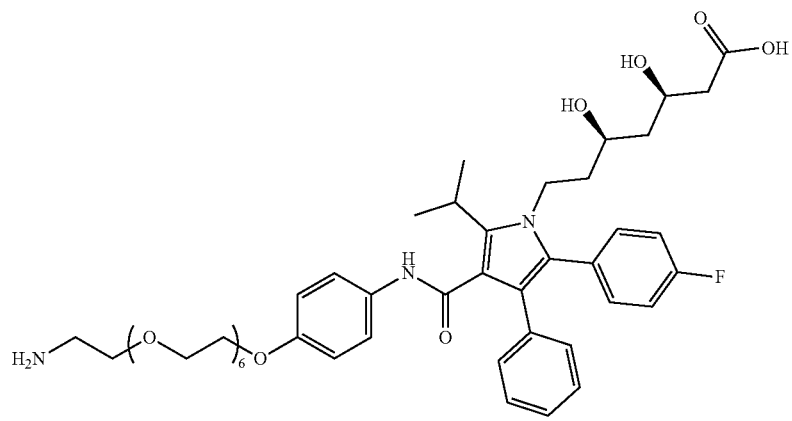

A mixture of tert-butyl 2-((4R,6R)-6-(2-(3-((4-((20-amino-3,6,9,12,15,18-hexaoxaicosyl)oxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (0.65 g, 664.49 umol) in MeOH (6.5 mL) and THF (6.5 mL) was added HCl (1 M, 1.66 mL) and the resulting mixture was stirred at 30° C. for 5 h. LCMS showed one main peak with desired mass was detected. To the mixture was added a solution of NaOH (0.16 g, 4.00 mmol) in H$_2$O (4 mL). The mixture was stirred at 30° C. for 9 h. LCMS showed one main peak with desired mass. The pH was adjusted to 8-9 by 1N HCl. The mixture was concentrated in vacuum. The crude product was purified by reversed-phase HPLC (0.1% NH$_3$—H$_2$O condition, 45% ACN) to afford (3R,5R)-7-(3-((4-((20-amino-3,6,9,12,15,18-hexaoxaicosyl)oxy)phenyl)carbamoyl)-5
4-fluorophenyl)-2-isopropyl-4-phenyl-1H-pyrrol-1-yl)-3,5-dihydroxyheptanoic acid (0.5 g, 0.567 mmol, 85.31% yield) as a white solid. MS (M+H)$^+$=882.5

Step 6: Synthesis of (3R,5R)-7-(3-((4-((20-((2-(2,6-dioxopiperidin-3-yl)-1,3-dioxoisoindolin-4-yl)amino)-3,6,9,12,15,18-hexaoxaicosyl)oxy)phenyl)carbamoyl)-5-(4-fluorophenyl)-2-isopropyl-4-phenyl-1H-pyrrol-1-yl)-3,5-dihydroxyheptanoic acid (Compound 4)

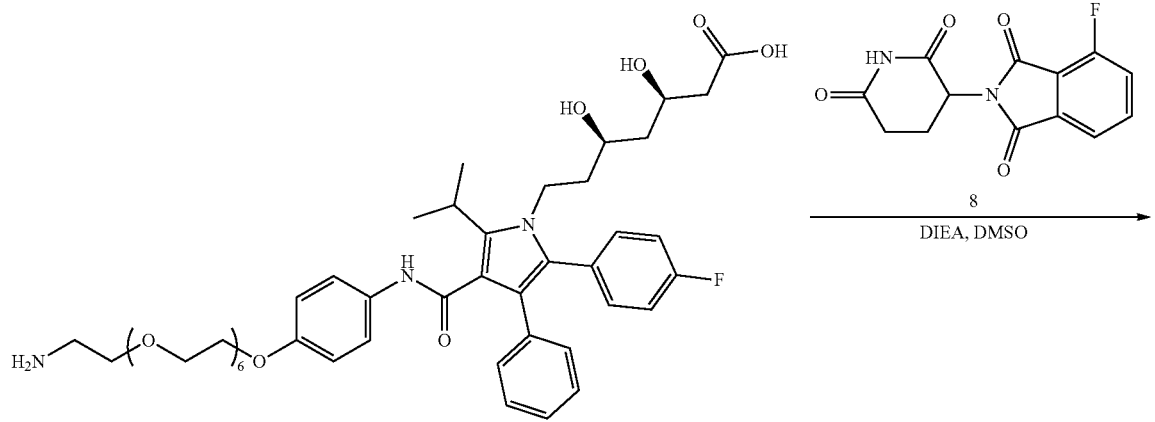

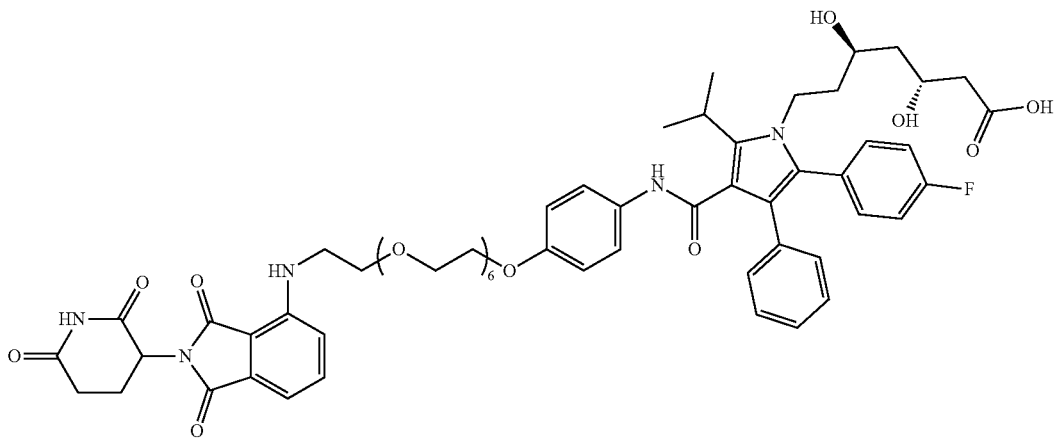

Compouond 4

To a solution of (3R,5R)-7-(3-((4-((20-amino-3,6,9,12,15,18-hexaoxaicosyl)oxy)phenyl)carbamoyl)-5-(4-fluorophenyl)-2-isopropyl-4-phenyl-1H-pyrrol-1-yl)-3,5-dihydroxyheptanoic acid (0.2 g, 0.2267 mmol) and 2-(2,6-dioxo-3-piperidyl)-4-fluoro-isoindoline-1,3-dione (63 mg, 0.228 mmol) in DMSO (3 mL) was added DIEA (43.96 mg, 340.13 umol, 59.24 uL) and the resulting mixture was stirred at 90° C. for 15 h. LCMS showed a main peak with desired mass. The pH was adjusted to 8-9 by 1 N HCl, Then the mixture was filtered. The filtrate was purified by prep-HPLC (column: Waters Xbridge 150*25 mm*5 um; mobile phase: [water (10 mM $NH_4HCO_3$)—ACN]; B %: 24%-54%, 10 min) followed by lyophilization to give (3R,5R)-7-(3-((4-((20-((2-(2,6-dioxopiperidin-3-yl)-1,3-dioxoisoindolin-4-yl)amino)-3,6,9,12,15,18-hexaoxaicosyl)oxy)phenyl)carbamoyl)-5-(4-fluorophenyl)-2-isopropyl-4-phenyl-1H-pyrrol-1-yl)-3,5-dihydroxyheptanoic acid (89.8 mg, 0.078 mmol, 34.27% yield, 97.8% purity) as yellow solid. $^1$H NMR (400 MHz, DMSO-$d_6$) δ 11.05 (s, 1H), 9.64 (s, 1H), 7.57 (dd, J=7.21, 8.44 Hz, 1H), 7.40 (d, J=9.05 Hz, 2H), 7.27-7.12 (m, 5H), 7.11-6.97 (m, 6H), 6.81 (d, J=9.05 Hz, 2H), 6.60 (t, J=5.62 Hz, 1H), 5.05 (dd, J=5.32, 12.90 Hz, 1H), 4.03-3.98 (m, 2H), 3.98-3.87 (m, 1H), 3.85-3.73 (m, 2H), 3.73-3.68 (m, 2H), 3.64-3.59 (m, 2H), 3.58-3.43 (m, 23H), 3.25-3.15 (m, 3H), 2.93-2.81 (m, 1H), 2.62-2.55 (m, 1H), 2.55-2.52 (m, 2H), 2.29-2.21 (m, 1H), 2.19-2.12 (m, 1H), 2.08-1.98 (m, 1H), 1.67-1.49 (m, 2H), 1.46-1.26 (m, 8H). MS (M+H)$^+$=1138.8

Example 5. Synthesis of (3R,5R)-7-(3-((4-((1-((2-(2,6-dioxopiperidin-3-yl)-1,3-dioxoisoindolin-4-yl)oxy)-2-oxo-6,9,12,15,18,21-hexaoxa-3-azatricosan-23-yl)oxy)phenyl)carbamoyl)-5-(4-fluorophenyl)-2-isopropyl-4-phenyl-1H-pyrrol-1-yl)-3,5-dihydroxyheptanoic acid (Compound 5)

Step 1: Synthesis of 2-((2-(2,6-dioxopiperidin-3-yl)-1,3-dioxoisoindolin-4-yl)oxy)acetic acid (2)

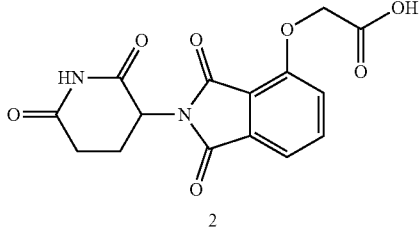

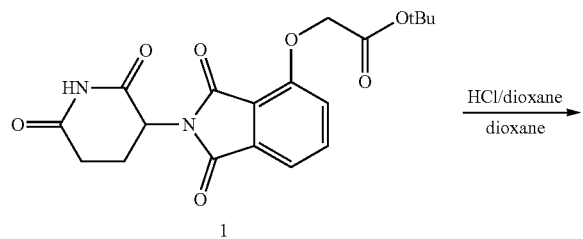

To a mixture of tert-butyl 2-[2-(2,6-dioxo-3-piperidyl)-1,3-dioxo-isoindolin-4-yl]oxyacetate (1 g, 2.29 mmol) in dioxane (15 mL) was added HCl/dioxane (4 M, 20.00 mL). The mixture was stirred at 20° C. for 2 h. LCMS showed a main peak with desired mass. The solvent was evaporated. The residue was purified by reverse MPLC (1‰ formic acid) to give 2-((2-(2,6-dioxopiperidin-3-yl)-1,3-dioxoisoindolin-4-yl)oxy)acetic acid (1.1 g, 3.31 mmol, 100% yield) as white solid. $^1$H NMR (400 MHz, DMSO-$d_6$) δ 11.10 (s, 1H), 7.81-7.79 (m, 1H), 7.47 (d, J=7.2 Hz, 1H), 7.39 (d, J=8.6 Hz, 1H), 5.12-5.08 (m, 1H), 2.94-2.85 (m, 1H), 2.64-2.52 (m, 2H), 2.06-1.99 (m, 1H).

Step 2: Synthesis of (3R,5R)-7-(3-((4-((1-((2-(2,6-dioxopiperidin-3-yl)-1,3-dioxoisoindolin-4-yl)oxy)-2-oxo-6,9,12,15,18,21-hexaoxa-3-azatricosan-23-yl)oxy)phenyl)carbamoyl)-5-(4-fluorophenyl)-2-isopropyl-4-phenyl-1H-pyrrol-1-yl)-3,5-dihydroxyheptanoic acid (Compound 5)

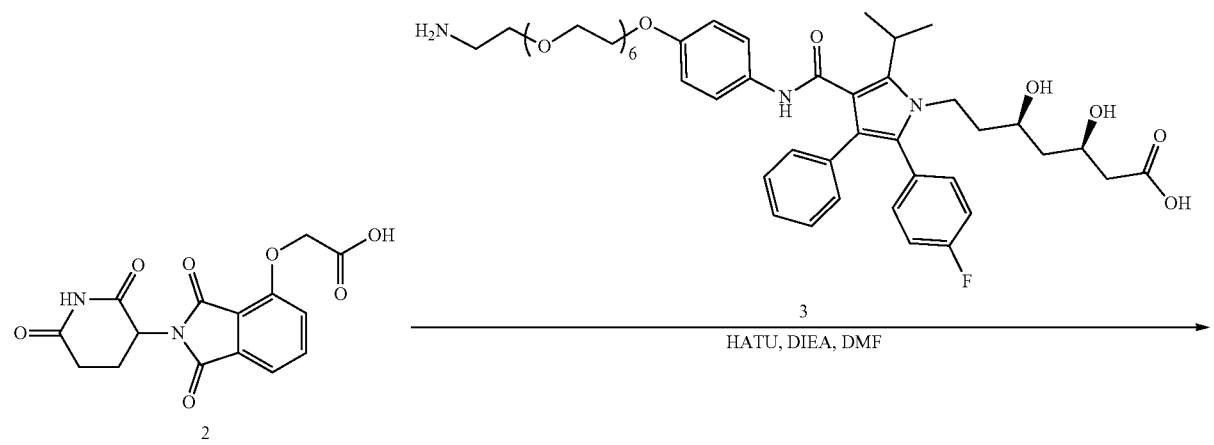

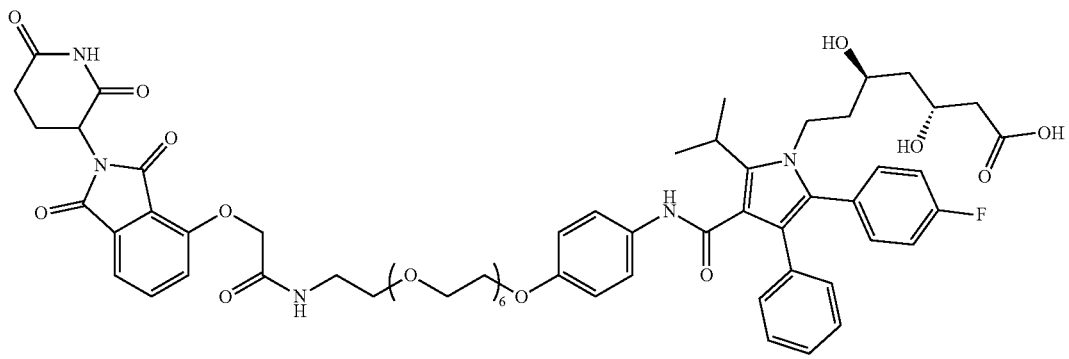

Compound 5

To a solution of 2-((2-(2,6-dioxopiperidin-3-yl)-1,3-dioxoisoindolin-4-yl)oxy)acetic acid (75.34 mg, 0.227 mmol) in DMF (3 mL) was added HATU (86.22 mg, 0.227 mmol) and DIEA (58.61 mg, 0.45 mmol) and the resulting mixture was stirred at 25° C. for 20 min, then a solution of (3R, 5R)-7-(3-((4-((20-amino-3,6,9,12,15,18-hexaoxaicosyl)oxy)phenyl)carbamoyl)-5-(4-fluorophenyl)-2-isopropyl-4-phenyl-1H-pyrrol-1-yl)-3,5-dihydroxyheptanoic acid (0.2 g, 0.227 mmol) in DMF (1 mL) was added. The mixture was stirred at 25° C. for 3 h. LCMS showed a peak (46%) with desired mass. The pH was adjusted to 7-8 by 1N HCl, the mixture was filtered and the filtrate was purified by prep-HPLC (column: Waters Xbridge 150*25 mm*5 um; mobile phase: [water (10 mM NH$_4$HCO$_3$)—ACN]; B %: 15%-45%, 10 min) followed by lyophilization. The product was re-purified by prep-HPLC (column: Welch Xtimate C18 100*25 mm*3 um; mobile phase: [water (0.04% NH$_3$H$_2$O)—ACN]; B %: 13%-43%, 11 min) followed by lyophilization to afford (3R,5R)-7-(3-((4-((1-((2-(2,6-dioxopiperidin-3-yl)-1,3-dioxoisoindolin-4-yl)oxy)-2-oxo-6,
9,12,15,18,21-hexaoxa-3-azatricosan-23-yl)oxy)phenyl)carbamoyl)-5-(4-fluorophenyl)-2-isopropyl-4-phenyl-1H-pyrrol-1-yl)-3,5-dihydroxyheptanoic acid (34.1 mg, 0.0264 mmol, 11.65% yield, 92.7% purity) as white solid. $^1$H NMR (400 MHz, DMSO-d$_6$) δ 9.66 (s, 1H), 8.01 (t, J=5.71 Hz, 1H), 7.84-7.77 (m, 1H), 7.49 (d, J=7.15 Hz, 1H), 7.40 (dd, J=3.83, 8.72 Hz, 3H), 7.27-7.14 (m, 5H), 7.10-7.03 (m, 4H), 7.02-6.98 (m, 1H), 6.81 (d, J=9.03 Hz, 2H), 5.11 (dd, J=5.40, 12.92 Hz, 1H), 4.78 (s, 2H), 4.05-3.98 (m, 2H), 3.97-3.88 (m, 1H), 3.84-3.73 (m, 3H), 3.72-3.67 (m, 3H), 3.59-3.54 (m, 4H), 3.54-3.43 (m, 8H), 3.25-3.17 (m, 4H), 2.96-2.83 (m, 1H), 2.64-2.56 (m, 9H), 2.26-2.19 (m, 1H), 2.17-2.00 (m, 3H), 1.66-1.49 (m, 3H), 1.46-1.33 (m, 8H), 1.32-1.24 (m, 1H), 1.19-1.10 (m, 1H). MS (M+H)$^+$=1196.9

Example 6. Synthesis of (3R,5R)-7-(3-((4-((25-((2-(2,6-dioxopiperidin-3-yl)-1,3-dioxoisoindolin-4-yl)oxy)-19,24-dioxo-3,6,9,12,15-pentaoxa-18,23-diazapentacosyl)oxy)phenyl)carbamoyl)-5-(4-fluorophenyl)-2-isopropyl-4-phenyl-1H-pyrrol-1-yl)-3,5-dihydroxyheptanoic acid (Compound 6)

Step 1: Synthesis of 2-(2,6-dioxopiperidin-3-yl)-4-hydroxyisoindoline-1,3-dione (3)

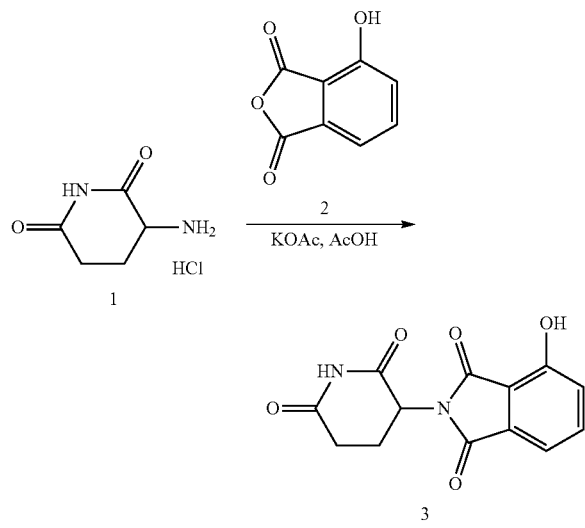

A mixture of 4-hydroxyisobenzofuran-1,3-dione (13.8 g, 84.09 mmol), 3-aminopiperidine-2,6-dione (14.53 g, 88.29 mmol, HCl salt) and KOAc (20.63 g, 210.22 mmol) in AcOH (100 mL) was stirred at 100° C. for 15 h. LCMS showed a main peak with desired mass and the starting material was consumed. The mixture was poured into water (500 mL) slowly, the filter cake was collected by filtration and dried in vacuum to afford 2-(2,6-dioxopiperidin-3-yl)-4-hydroxyisoindoline-1,3-dione (18 g, 65.64 mmol, 78.06% yield) as brown solid. $^1$H NMR (400 MHz, DMSO-d$_6$) δ 11.09 (s, 1H), 7.65 (dd, J=7.32, 8.32 Hz, 1H), 7.31 (d, J=7.00 Hz, 1H), 7.25 (d, J=8.38 Hz, 1H), 5.09-5.05 (m, 1H), 2.94-2.82 (m, 1H), 2.63-2.55 (m, 1H), 2.55-2.51 (m, 1H), 2.07-1.98 (m, 1H).

Step 2: Synthesis of tert-butyl 2-((2-(2,6-dioxopiperidin-3-yl)-1,3-dioxoisoindolin-4-yl)oxy)acetate (5)

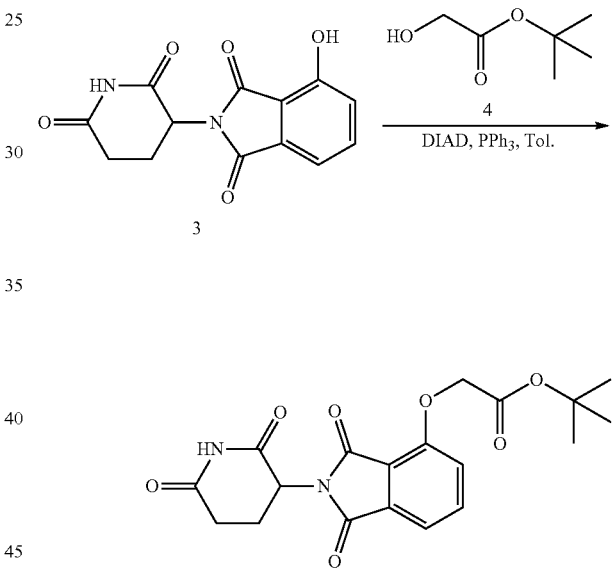

To a mixture of 2-(2,6-dioxo-3-piperidyl)-4-hydroxyisoindoline-1,3-dione (5 g, 18.23 mmol, 1 eq), tert-butyl 2-hydroxyacetate (2.89 g, 21.88 mmol) and PPh$_3$ (7.17 g, 27.35 mmol) in THF (100 mL) was added DIAD (4.42 g, 21.88 mmol) dropwise at 0° C. under N$_2$ protection. Then the mixture was stirred at 20° C. for 16 h. LCMS showed 23% desired mass was detected. The solvent was evaporated. The residue was purified by reversed-phase HPLC (0.1% FA condition) to afford tert-butyl 2-((2-(2,6-dioxopiperidin-3-yl)-1,3-dioxoisoindolin-4-yl)oxy)acetate (4.5 g, 11.59 mmol, 63.55% yield) as white solid. $^1$H NMR (400 MHz, DMSO-d$_6$) δ 11.11 (s, 1H), 7.81 (dd, J=7.3, 8.6 Hz, 1H), 7.52-7.47 (m, 1H), 7.39 (d, J=8.6 Hz, 1H), 5.11 (dd, J=5.4, 12.7 Hz, 1H), 4.97 (s, 2H), 2.97-2.84 (m, 1H), 2.69-2.55 (m, 2H), 2.11-2.01 (m, 1H), 1.44 (s, 9H).

Step 3: Synthesis of 2-((2-(2,6-dioxopiperidin-3-yl)-1,3-dioxoisoindolin-4-yl)oxy)acetic acid (6)

Step 4: Synthesis of tert-butyl 4-(2-((2-(2,6-dioxopiperidin-3-yl)-1,3-dioxoisoindolin-4-yl)oxy)acetamido)butanoate (8)

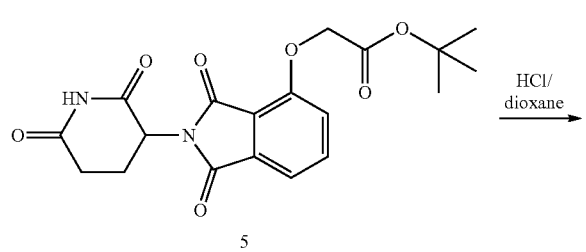

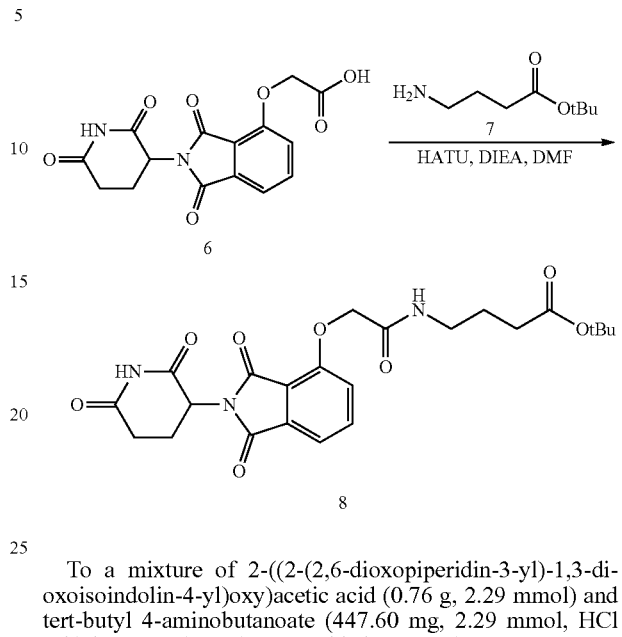

To a mixture of tert-butyl 2-((2-(2,6-dioxopiperidin-3-yl)-1,3-dioxoisoindolin-4-yl)oxy)acetate (1 g, 2.29 mmol) in dioxane (15 mL) was added HCl/dioxane (4 M, 20.00 mL). The mixture was stirred at 20° C. for 2 h. LCMS showed a main peak with desired mass. The solvent was evaporated to afford 2-((2-(2,6-dioxopiperidin-3-yl)-1,3-dioxoisoindolin-4-yl)oxy)acetic acid (760 mg, crude) as white solid, which was used directly in the next step without further purification.

MS (M+H)$^+$=332.9

To a mixture of 2-((2-(2,6-dioxopiperidin-3-yl)-1,3-dioxoisoindolin-4-yl)oxy)acetic acid (0.76 g, 2.29 mmol) and tert-butyl 4-aminobutanoate (447.60 mg, 2.29 mmol, HCl salt) in DMF (5 mL) were added HATU (869.71 mg, 2.29 mmol) and DIEA (295.62 mg, 2.29 mmol, 0.398 mL) and the resulting mixture was stirred at 20° C. for 16 h. LCMS showed a peak with 35.7% desired mass. The solvent was evaporated. The residue was purified by reversed-phase HPLC (0.1% formic acid condition) to afford tert-butyl 4-(2-((2-(2,6-dioxopiperidin-3-yl)-1,3-dioxoisoindolin-4-yl)oxy)acetamido)butanoate (0.8 g, 1.61 mmol, 70.18% yield, 95% purity) as white solid. MS (M+H)$^+$=474.2

Step 5: Synthesis of 4-(2-((2-(2,6-dioxopiperidin-3-yl)-1,3-dioxoisoindolin-4-yl)oxy)acetamido)butanoic acid (9)

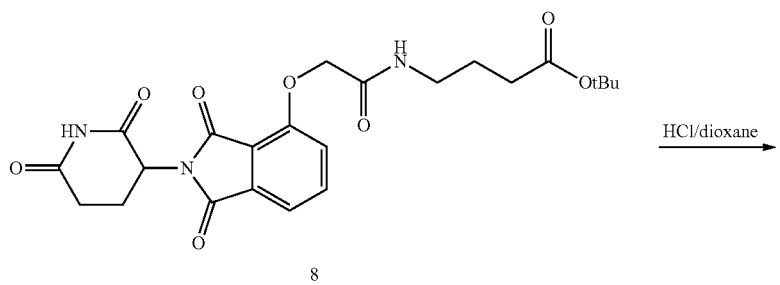

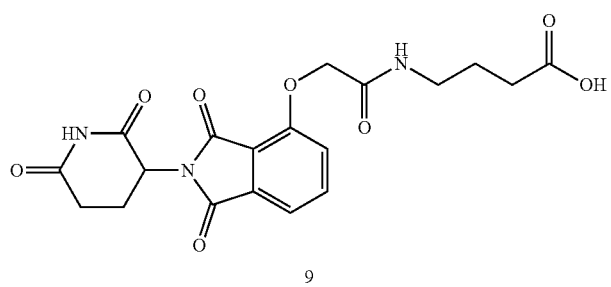

To tert-butyl 4-(2-((2-(2,6-dioxopiperidin-3-yl)-1,3-dioxoisoindolin-4-yl)oxy)acetamido)butanoate (0.8 g, 1.69 mmol) was added HCl/dioxane (4 M, 30 mL) and the resulting mixture was stirred at 20° C. for 3 h. LCMS showed one main peak with desired mass was detected. The mixture was concentrated under reduced pressure. The residue was purified by reversed-phase HPLC (0.1% formic acid condition, 50% ACN) followed by lyophilization to afford 4-(2-((2-(2-(2,6-dioxopiperidin-3-yl)-1,3-dioxoisoindolin-4-yl)oxy)acetamido)butanoic acid (1 g, 2.40 mmol, 83.33% yield) as white solid. $^1$H NMR (400 MHz, DMSO-$d_6$) δ 12.05 (s, 1H), 11.10 (s, 1H), 7.99 (t, J=5.69 Hz, 1H), 7.81 (dd, J=7.40, 8.38 Hz, 1H), 7.50 (d, J=7.21 Hz, 1H), 7.39 (d, J=8.44 Hz, 1H), 5.12 (dd, J=5.32, 12.90 Hz, 1H), 4.77 (s, 2H), 3.19-3.14 (m, 2H), 2.96-2.83 (m, 1H), 2.64-2.54 (m, 2H), 2.23 (t, J=7.40 Hz, 2H), 2.10-1.99 (m, 1H), 1.68-1.63 (m, 2H).

MS (M+H)$^+$=418.1

Step 6: Synthesis of (3R,5R)-7-(3-((4-((25-((2-(2,6-dioxopiperidin-3-yl)-1,3-dioxoisoindolin-4-yl)oxy)-19,24-dioxo-3,6,9,12,15-pentaoxa-18,23-diazapentacosyl)oxy)phenyl)carbamoyl)-5-(4-fluorophenyl)-2-isopropyl-4-phenyl-1H-pyrrol-1-yl)-3,5-dihydroxyheptanoic acid (Compound 6)

a solution of (3R,5R)-7-(3-((4-((17-amino-3,6,9,12,15-pentaoxaheptadecyl)oxy)phenyl)carbamoyl)-5-(4-fluorophenyl)-2-isopropyl-4-phenyl-1H-pyrrol-1-yl)-3,5-dihydroxyheptanoic acid (0.25 g, 0.298 mmol, 1 eq) in DMF (0.5 mL) was added. The mixture was stirred at 25° C. for 3 h. LCMS showed a peak (77%) with desired mass. The mixture was filtered. The filtrate was purified by prep-HPLC (column: Waters Xbridge 150*25 mm*5 um; mobile phase: [water (10 mM NH$_4$HCO$_3$)—ACN]; B %: 20%-47%, 10 min) followed by lyophilization, the crude product was re-purified by prep-HPLC (column: Waters Xbridge 150*25 mm*5 um; mobile phase: [water (10 mM NH$_4$HCO$_3$)—ACN]; B %: 15%-45%, 10 min) followed by lyophilization to afford (3R,5R)-7-(3-((4-((25-((2-(2,6-dioxopiperidin-3-yl)-1,3-dioxoisoindolin-4-yl)oxy)-19,24-dioxo-3,6,9,12,15-pentaoxa-18,23-diazapentacosyl)oxy)phenyl)carbamoyl)-5-(4-fluorophenyl)-2-isopropyl-4-phenyl-1H-pyrrol-1-yl)-3,5-dihydroxyheptanoic acid (77.0 mg, 0.062 mmol, 20.65% yield, 96.7% purity) as white solid. $^1$H NMR (400 MHz, DMSO-$d_6$) δ 9.64 (s, 1H), 7.98 (t, J=5.62 Hz, 1H), 7.87-7.77 (m, 2H), 7.49 (d, J=7.34 Hz, 1H), 7.43-7.33 (m, 3H), 7.27-7.13 (m, 4H), 7.10-7.04 (m, 4H), 7.03-6.97 (m, 1H), 6.81 (d, J=9.05 Hz, 2H), 5.14-5.10 (m, 1H), 4.76 (s, 2H), 4.05-3.99 (m, 2H), 3.97-3.87 (m, 1H), 3.86-3.74 (m, 2H),

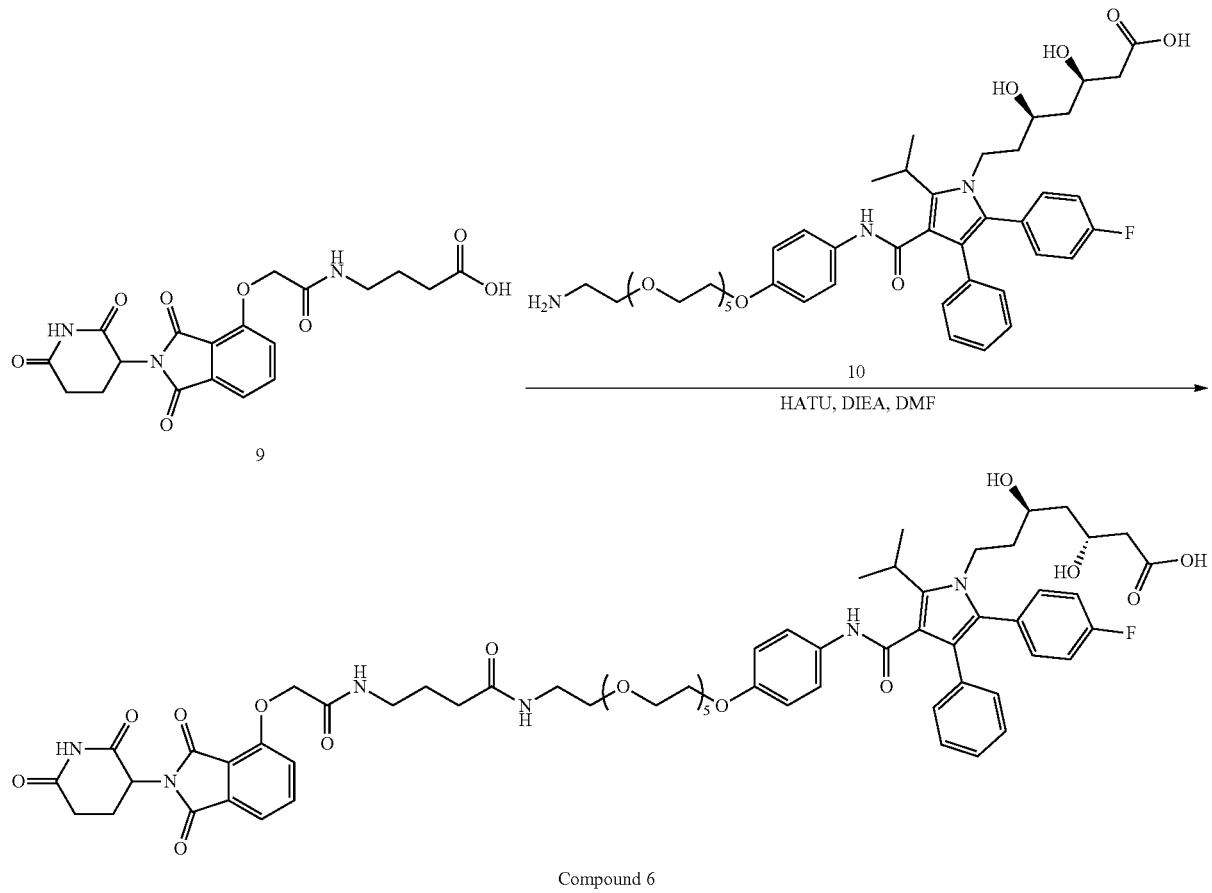

Compound 6

To a solution of 4-(2-((2-(2,6-dioxopiperidin-3-yl)-1,3-dioxoisoindolin-4-yl)oxy)acetamido)butanoic acid (124.52 mg, 0.298 mmol) in DMF (3 mL) was added HATU (113.44 mg, 0.298 mmol) and DIEA (77.12 mg, 596.68 umol, 0.1 mL) and the mixture was stirred at 25° C. for 30 min, then 3.73-3.67 (m, 2H), 3.59-3.47 (m, 19H), 3.41-3.37 (m, 5H), 3.24-3.09 (m, 3H), 2.96-2.83 (m, 1H), 2.64-2.52 (m, 2H), 2.28-2.20 (m, 1H), 2.19-2.12 (m, 1H), 2.12-1.99 (m, 3H), 1.80-1.58 (m, 3H), 1.56-1.48 (m, 1H), 1.46-1.24 (m, 8H).
MS (M+H)$^+$=1237.9

Example 7. Synthesis of (3R,5R)-7-(3-((4-(8-((2-(2, 6-dioxopiperidin-3-yl)-1,3-dioxoisoindolin-4-yl) oxy)-22,27-dioxo-3,6,9,12,15,18-hexaoxa-21,26-diazaoctacosyl)oxy)phenyl)carbamoyl)-5-(4-fluorophenyl)-2-isopropyl-4-phenyl-1H-pyrrol-1-yl)-3,5-dihydroxyheptanoic acid (Compound 7)

Step 1: Synthesis of tert-butyl 2-((4R,6R)-6-(2-(2-(4-fluorophenyl)-5-isopropyl-4-((4-((3-oxo-1-phenyl-2,7,10,13,16,19,22-heptaoxa-4-azatetracosan-24-yl)oxy)phenyl)carbamoyl)-3-phenyl-1H-pyrrol-1-yl) ethyl)-2,2-dimethyl-1,3-dioxan-4-yl)acetate (3)

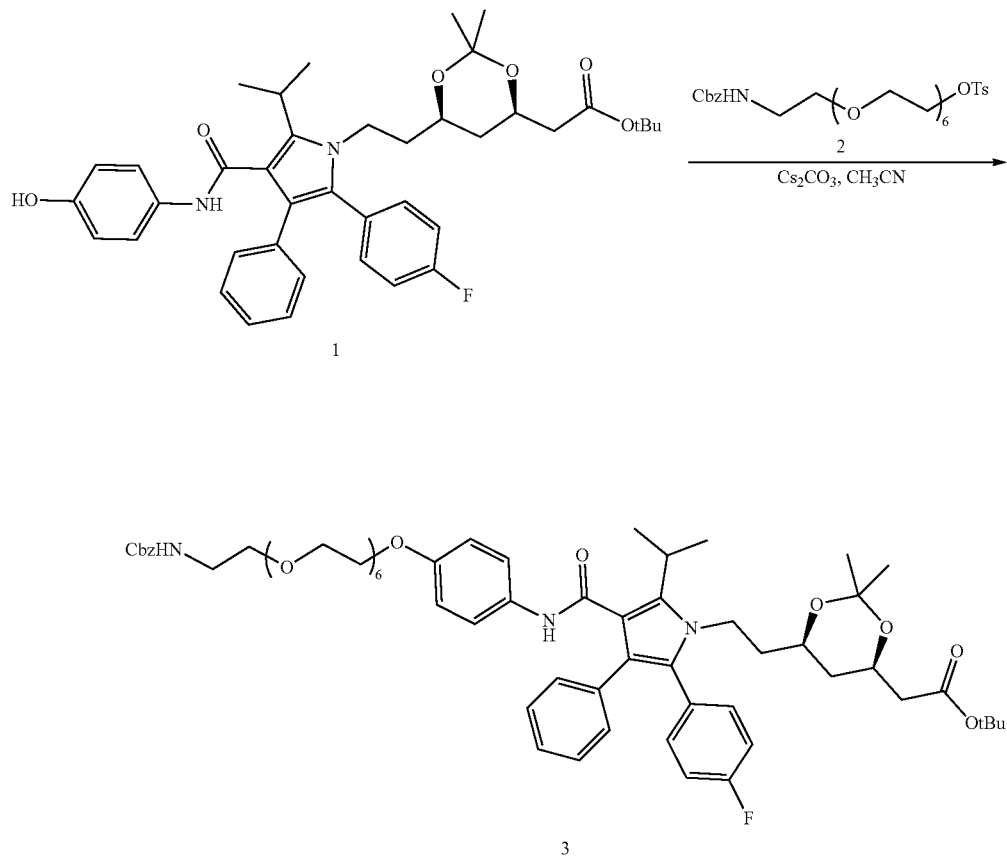

To a mixture of tert-butyl 2-((4R,6R)-6-(2-(2-(4-fluorophenyl)-4-((4-hydroxyphenyl)carbamoyl)-5-isopropyl-3-phenyl-1H-pyrrol-1-yl)ethyl)-2,2-dimethyl-1,3-dioxan-4-yl)acetate (1.20 g, 1.79 mmol) and 3-oxo-1-phenyl-2,7,10,13,16,19,22-heptaoxa-4-azatetracosan-24-yl 4-methylbenzenesulfonate (1.1 g, 1.79 mmol) in MeCN (10 mL) was added $Cs_2CO_3$ (1.17 g, 3.58 mmol). The mixture was stirred at 80° C. for 16 h. LCMS showed the starting material was consumed completely and desired mass was detected. The reaction mixture was filtered and mother liquor was obtained. The crude product was purified by reversed-phase HPLC (90% MeCN, 0.1% formic acid condition) to give tert-butyl 2-((4R,6R)-6-(2-(2-(4-fluorophenyl)-5-isopropyl-4-((4-((3-oxo-1-phenyl-2,7,10,13,16,19, 22-heptaoxa-4-azatetracosan-24-yl)oxy)phenyl) carbamoyl)-3-phenyl-1H-pyrrol-1-yl)ethyl)-2,2-dimethyl-1, 3-dioxan-4-yl)acetate (0.8 g, 0.719 mmol, 40.13% yield) was obtained as a yellow oil. MS $(M+H)^+$=1112.5

Step 2: Synthesis of tert-butyl 2-((4R,6R)-6-(2-(3-((4-((20-amino-3,6,9,12,15,18-hexaoxaicosyl)oxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (4)

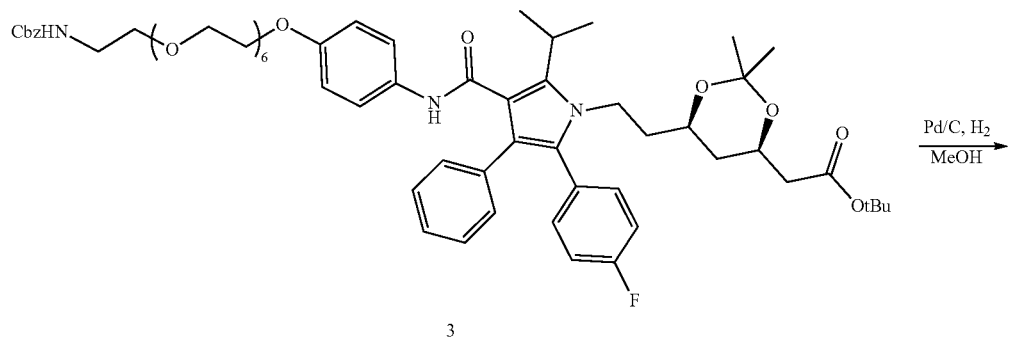

A mixture of tert-butyl 2-((4R,6R)-6-(2-(2-(4-fluorophenyl)-5-isopropyl-4-((4-((3-oxo-1-phenyl-2,7,10,13,16,19,22-heptaoxa-4-azatetracosan-24-yl)oxy)phenyl)carbamoyl)-3-phenyl-1H-pyrrol-1-yl)ethyl)-2,2-dimethyl-1,3-dioxan-4-yl)acetate (0.8 g, 0.719 mmol) and Pd/C (0.1 g, 10% purity) in MeOH (20 mL) was stirred at 30° C. for 3 h under H₂ atmosphere (15 psi). LCMS showed the starting material was consumed completely and desired mass was detected. The reaction mixture was filtered and concentrated under reduced pressured to afford tert-butyl 2-((4R,6R)-6-(2-(3-((4-((20-amino-3,6,9,12,15,18-hexaoxaicosyl)oxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (0.65 g, 0.665 mmol, 92.39% yield) as yellow oil, which was used into the next step without further purification.

Step 3: Synthesis of (3R,5R)-7-(3-((4-((20-amino-3,6,9,12,15,18-hexaoxaicosyl)oxy)phenyl)carbamoyl)-5-(4-fluorophenyl)-2-isopropyl-4-phenyl-1H-pyrrol-1-yl)-3,5-dihydroxyheptanoic acid (5)

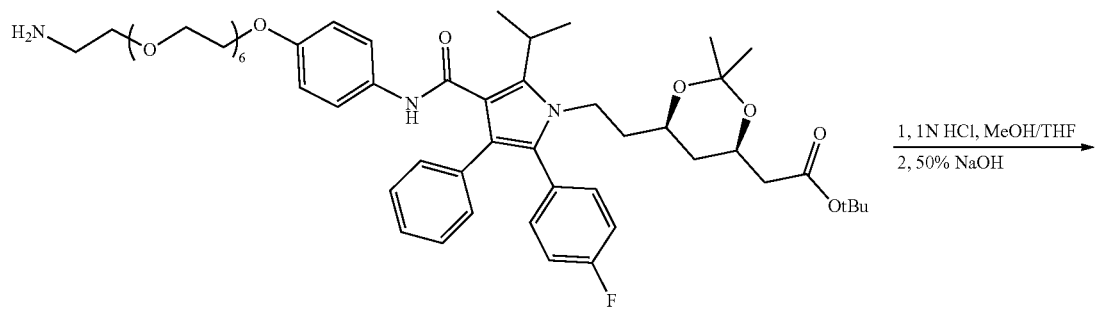

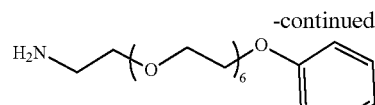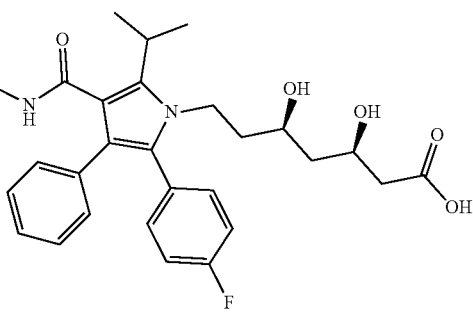

A mixture of tert-butyl 2-((4R,6R)-6-(2-(3-((4-((20-amino-3,6,9,12,15,18-hexaoxaicosyl)oxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (0.65 g, 0.665 mmol) in MeOH (6.5 mL) and THF (6.5 mL) was added HCl (1 M, 1.66 mL) and stirred at 30° C. for 5 h. LCMS showed one main peak with desired mass was detected. To the mixture was added a solution of NaOH (0.16 g, 4.00 mmol, 6.02 eq) in H$_2$O (4 mL). The mixture was stirred at 30° C. for 9 h. LCMS showed one main peak with desired mass. The pH was adjusted to 8-9 by 1N HCl, the mixture was concentrated under vacuum. The crude product was purified by reversed-phase HPLC (0.1% NH$_3$.H$_2$O condition, 45% ACN) to give (3R,5R)-7-(3-((4-((20-amino-3,6,9,12,15,18-hexaoxaicosyl)oxy)phenyl)carbamoyl)-5-(4-fluorophenyl)-2-isopropyl-4-phenyl-1H-pyrrol-1-yl)-3,5-dihydroxyheptanoic acid (0.5 g, 0.567 mmol, 85.31% yield) as a white solid. MS (M+H)$^+$=882.5

Step 4: Synthesis of (3R,5R)-7-(3-((4-((28-((2-(2,6-dioxopiperidin-3-yl)-1,3-dioxoisoindolin-4-yl)oxy)-22,27-dioxo-3,6,9,12,15,18-hexaoxa-21,26-diazaoctacosyl)oxy)phenyl)carbamoyl)-5-(4-fluorophenyl)-2-isopropyl-4-phenyl-1H-pyrrol-1-yl)-3,5-dihydroxyheptanoic acid (Compound 7)

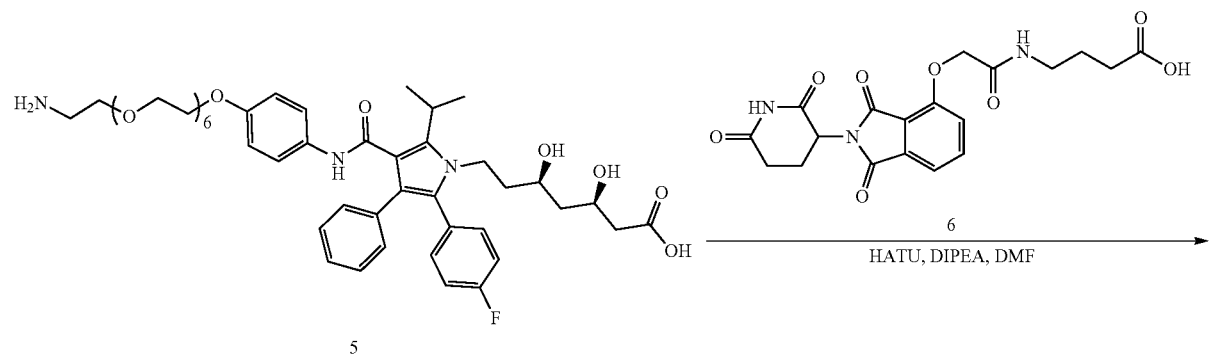

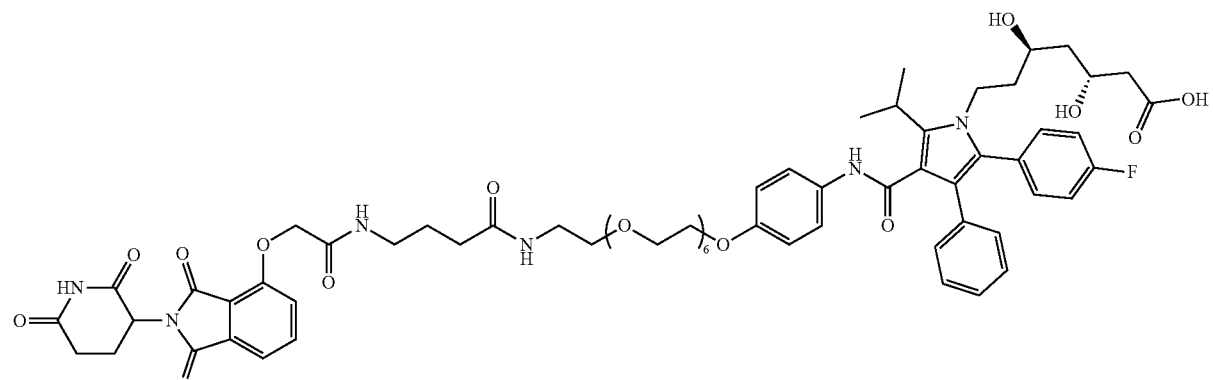

Compound 7

To a solution of 4-(2-((2-(2,6-dioxopiperidin-3-yl)-1,3-dioxoisoindolin-4-yl)oxy)acetamido)butanoic acid (71 mg, 0.17 mmol) in DMF (2 mL) was added HATU (64 mg, 0.168 mmol, 0.989 eq) and DIEA (43.96 mg, 0.34 mmol, 0.059 mL) and the resulting mixture was stirred at 25° C. for 30 min. Then a solution of (3R,5R)-7-(3-((4-((20-amino-3,6,9,12,15,18-hexaoxaicosyl)oxy)phenyl)carbamoyl)-5-(4-fluorophenyl)-2-isopropyl-4-phenyl-1H-pyrrol-1-yl)-3,5-dihydroxyheptanoic acid (0.15 g, 0.17 mmol) in DMF (1 mL) was added. The mixture was stirred at 25° C. for 3 h. LCMS showed a main peak with desired mass and (3R,5R)-7-(3-((4-((20-amino-3,6,9,12,15,18-hexaoxaicosyl)oxy)phenyl)carbamoyl)-5-(4-fluorophenyl)-2-isopropyl-4-phenyl-1H-pyrrol-1-yl)-3,5-dihydroxyheptanoic acid was consumed. The mixture was filtered and the filtrate was purified by prep-HPLC (column: Waters Xbridge 150*25 mm*5 um; mobile phase: [water (10 mM $NH_4HCO_3$)—ACN]; B %: 17%-47%, 10 min) followed by lyophilization, the crude product was re-purified by prep-HPLC (column: Waters Xbridge 150*25 mm*5 um; mobile phase: [water (10 mM $NH_4HCO_3$)—ACN]; B %: 15%-45%, 10 min) followed by lyophilization to give (3R,5R)-7-(3-((4-((28-((2-(2,6-dioxopiperidin-3-yl)-1,3-dioxoisoindolin-4-yl)oxy)-22,27-dioxo-3,6,9,12,15,18-hexaoxa-21,26-diazaoctacosyl)oxy)phenyl)carbamoyl)-5-(4-fluorophenyl)-2-isopropyl-4-phenyl-1H-pyrrol-1-yl)-3,5-dihydroxyheptanoic acid (73.4 mg, 0.057 mmol, 33.44% yield, 97.4% purity) as white solid. $^1$H NMR (400 MHz, DMSO-$d_6$) δ 9.64 (s, 1H), 7.98 (t, J=5.62 Hz, 1H), 7.87-7.76 (m, 2H), 7.49 (d, J=7.21 Hz, 1H), 7.44-7.36 (m, 3H), 7.27-7.14 (m, 4H), 7.11-7.03 (m, 4H), 7.03-6.97 (m, 1H), 6.81 (d, J=9.05 Hz, 2H), 5.14-5.10 (dd, J=5.44, 12.90 Hz, 1H), 4.76 (s, 2H), 4.04-3.99 (m, 2H), 3.98-3.87 (m, 1H), 3.86-3.73 (m, 2H), 3.73-3.68 (m, 2H), 3.60-3.46 (m, 20H), 3.41-3.36 (m, 5H), 3.24-3.09 (m, 3H), 2.94-2.85 (m, 1H), 2.57 (s, 6H), 2.27-2.20 (m, 1H), 2.18-1.99 (m, 4H), 1.69-1.61 (m 3H), 1.52 (d, J=11.74 Hz, 1H), 1.47-1.24 (m, 8H). MS (M+H)$^+$=1281.9

Example 8. Synthesis of (3R,5R)-7-(3-(4-((1-((2-(2,6-dioxopiperidin-3-yl)-1,3-dioxoisoindolin-4-yl)oxy)-2-oxo-6,9,12,15,18,21-hexaoxa-3-azatricosan-23-yl)oxy)phenyl)-2-(4-fluorophenyl)-5-isopropyl-4-(phenylcarbamoyl)-1H-pyrrol-1-yl)-3,5-dihydroxyheptanoic acid (Compound 8)

Step 1: Synthesis of 2-(2,6-dioxopiperidine-3-yl)-4-hydroxy-isoindoline-1,3-dione (3)

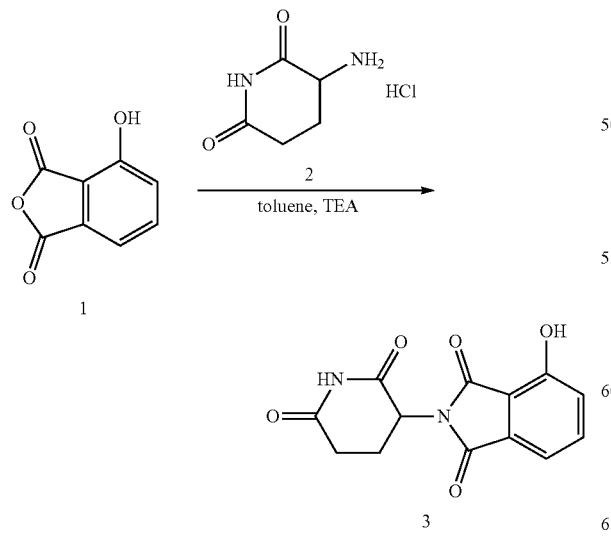

To a solution of 4-hydroxyisobenzofuran-1, 3-dione (20 g, 121.87 mmol) and 3-aminopiperidine-2, 6-dione (20.06 g, 121.87 mmol, HCl salt) in toluene (500 mL) was added TEA (14.54 g, 143.69 mmol, 20 mL). The reaction mixture was stirred for 12 h at 130° C. The reaction solvent was removed under reduced pressure. The residue was triturated in EtOAc/H$_2$O to give 2-(2, 6-dioxo-3-piperidyl)-4-hydroxy-isoindoline-1, 3-dione (23 g, 83.87 mmol, 68.8% yield) as pale green solid. $^1$H NMR (400 MHz, DMSO-$d_6$) δ=11.09 (s, 1H), 7.65 (dd, J=7.2, 8.3 Hz, 1H), 7.40-7.20 (m, 2H), 5.07 (dd, J=5.4, 12.8 Hz, 1H), 2.95-2.82 (m, 1H), 2.62-2.53 (m, 2H), 2.10-1.93 (m, 1H).

Step 2: Synthesis of tert-butyl 2-[2-(2,6-dioxopiperidine-3-yl)-1,3-dioxo-isoindolin-4-yl]oxyacetate (5)

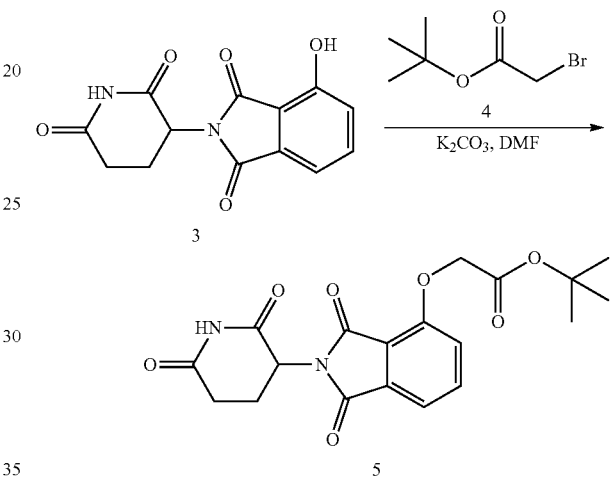

To a solution of 2-(2,6-dioxo-3-piperidyl)-4-hydroxy-isoindoline-1,3-dione (4 g, 14.59 mmol) in DMF (40 mL) was added K$_2$CO$_3$ (3.02 g, 21.88 mmol) and then tert-butyl 2-bromoacetate (3.13 g, 16.05 mmol, 2.37 mL) at 20° C. and the reaction mixture was stirred for 2 h. LCMS showed some the starting material remained, the desired mass was detected. The reaction mixture was filtered and washed with EtOAc (30 mL×3). The filtrate was washed with water (30 mL), brine (30 mL), and then the organic layer was dried over Na$_2$SO$_4$, filtered. The filtrate was concentrated under reduced pressure. The residue was purified by silica gel column (PE/EtOAc=5/1 to 1/1) to afford tert-butyl 2-[2-(2, 6-dioxo-3-piperidyl)-1, 3-dioxo-isoindolin-4-yl]oxyacetate (3.1 g, 7.98 mmol, 54.72% yield) as cream colored solid.

Step 3: Synthesis of 2-[2-(2,6-dioxopiperidine-3-yl)-1, 3-dioxoisoindolin-4-yl]oxyacetic acid (6)

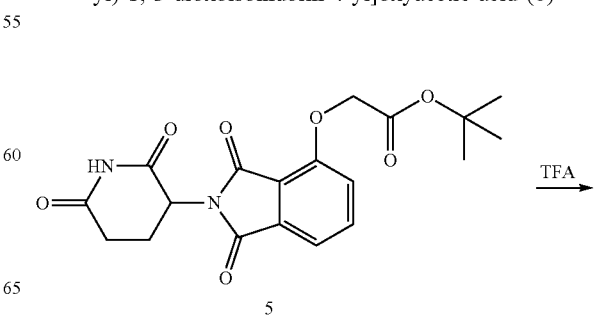

83

-continued

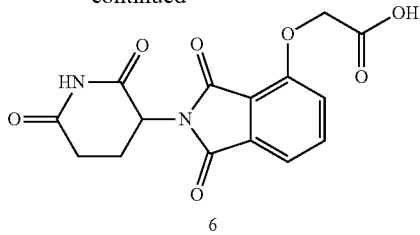

6

A solution of tert-butyl 2-[2-(2,6-dioxopiperidine-3-yl)-1,3-dioxoisoindolin-4-yl]oxyacetate (3 g, 7.72 mmol) in TFA (20 mL) was stirred for 2 h at 20° C. The reaction solvent was removed under reduced pressure. The residue was triturated in EtOAc (10 mL) to give 2-[2-(2, 6-dioxo-3-piperidyl)-1, 3-dioxo-isoindolin-4-yl]oxyacetic acid (1.8 g, 5.42 mmol, 70.13% yield) as white solid. $^1$H NMR (400 MHz, DMSO-d$_6$) δ=11.11 (s, 1H), 7.80 (dd, J=7.3, 8.6 Hz, 1H), 7.48 (d, J=7.0 Hz, 1H), 7.40 (d, J=8.4 Hz, 1H), 5.11 (dd, J=5.4, 12.8 Hz, 1H), 5.00 (s, 2H), 2.97-2.83 (m, 1H), 2.70-2.54 (m, 2H), 2.10-2.00 (m, 1H).

Step 4: Synthesis of perfluorophenyl-2-(2-(2,6-dioxopiperidine-3-yl)-1,3-dioxoisoindolin-4-yl)oxyacetate (8)

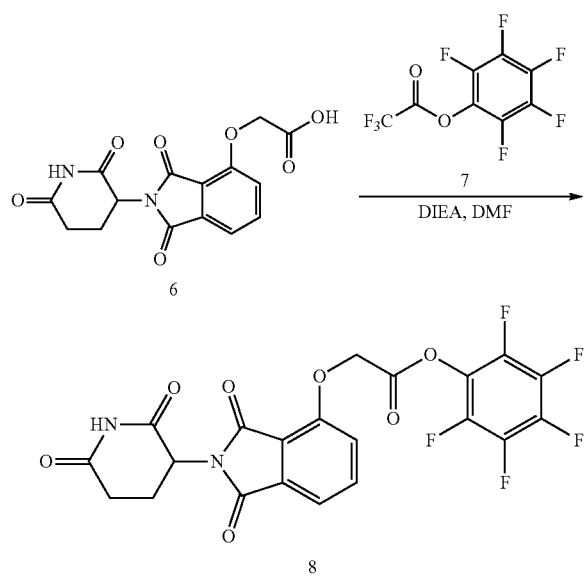

To a solution of 2-[2-(2,6-dioxopiperidine-3-yl)-1,3-dioxoisoindoline-4-yl]oxyacetic acid (0.5 g, 1.50 mmol), DIPEA (1.3 mL) in DMF (10 mL) was added (2,3,4,5,6-pentafluorophenyl) 2,2,2-trifluoroacetate (843 mg, 3.01 mmol) at 0° C. The reaction mixture was stirred for 1 h at 20° C. LCMS showed the reaction was completed. The reaction solvent was removed under reduced pressure. The residue was purified by reverse phase column (0.1% FA) and lyophilized to give (2,3,4,5,6-pentafluorophenyl) 2-[2-(2,6-dioxo-3-piperidyl)-1,3-dioxo-isoindolin-4-yl]oxyacetate (0.25 g, 33% yield) as white solid. $^1$H NMR (400 MHz, CDCl$_3$) δ 7.96 (br s, 1H), 7.74 (dd, J=7.3, 8.4 Hz, 1H), 7.63-7.59 (m, 1H), 7.24 (d, J=8.4 Hz, 1H), 5.32 (d, J=1.2 Hz, 2H), 5.02-4.94 (m, 1H), 2.96-2.73 (m, 3H), 2.20-2.11 (m, 1H).

84

Step 5: Synthesis of 4-methyl-3-oxo-N-phenyl-pentanamide (11)

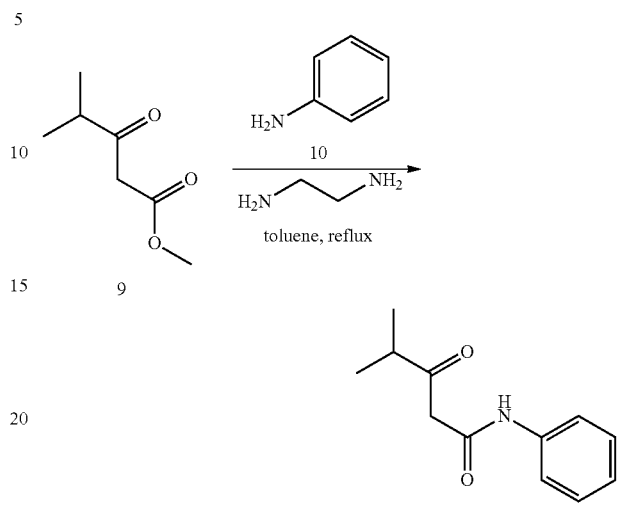

To a solution of methyl 4-methyl-3-oxo-pentanoate (30 g, 208.09 mmol, 29.70 mL) in toluene (300 mL) was added aniline (19.38 g, 208.09 mmol, 19.0 mL), TEA (21.06 g, 208.09 mmol, 28.96 mL) and ethane-1, 2-diamine (1.25 g, 20.81 mmol, 1.39 mL). The reaction mixture was stirred for 12 h for 130° C. TLC showed the starting material remained, the new spot was formed. The reaction solvent was removed under reduced pressure. The residue was purified by silica gel column (PE/EtOAc=60/1 to 5/1) to give 4-methyl-3-oxo-N-phenyl-pentanamide (35 g, 170.52 mmol, 81.95% yield) as yellow oil. $^1$H NMR (400 MHz, CDCl$_3$) δ 9.23 (br s, 1H), 7.57 (d, J=7.7 Hz, 2H), 7.35 (t, J=7.9 Hz, 2H), 7.18-7.10 (m, 1H), 3.63 (s, 2H), 2.76 (td, J=6.9, 13.9 Hz, 1H), 1.20 (d, J=7.0 Hz, 6H).

Step 6: Synthesis of (E)-2-(4-(benzyloxy)benzylidin) 4-methyl-3-oxo-N-phenylpentanamide (13)

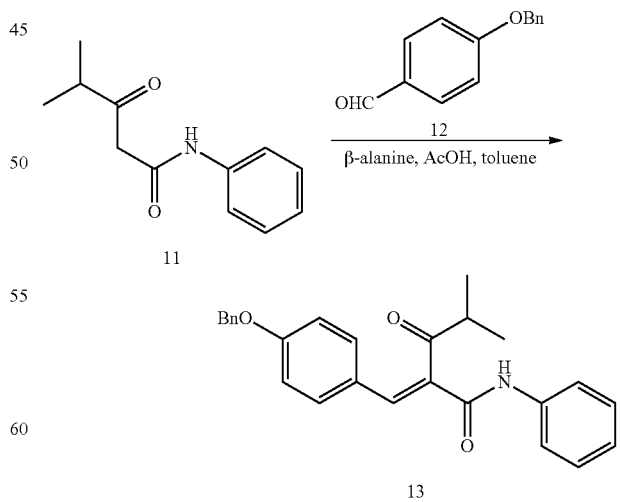

To a solution of 4-methyl-3-oxo-N-phenyl-pentanamide (5 g, 24.36 mmol) and 4-benzyloxybenzaldehyde (9.31 g, 43.85 mmol) in toluene (100 mL) was added BETA-ALA- NINE (1.09 g, 12.18 mmol) and acetic acid (146.29 mg, 2.44 mmol, 139.32 uL). The reaction mixture was heated at 130° C. with a Dean-Stark apparatus for 12 h. LCMS showed the reaction was completed. The reaction solvent was removed under reduced pressure. The residue was purified by silica gel column (PE/EtOAc=60/1 to 5/1) to give (2E)-2-[(4-benzyloxyphenyl)methylene]-4-methyl-3-oxo-N-phenyl-pentanamide (5.2 g, 13.02 mmol, 53.44% yield) as yellow solid. MS [M+H]$^+$=400.2

Step 7: Synthesis of 2-[1-(4-benzyloxyphenyl)-2-(4-fluorophenyl)-2-oxo-ethyl]-4-methyl-3-oxo-N-phenyl-pentanamide (16)

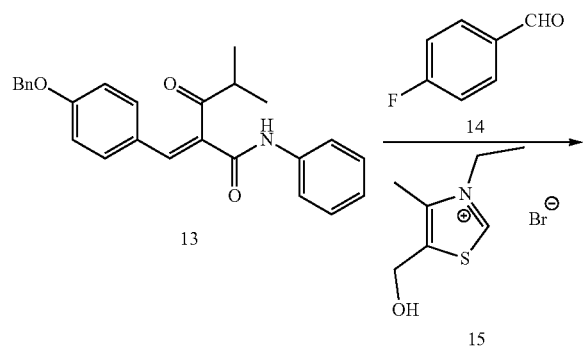

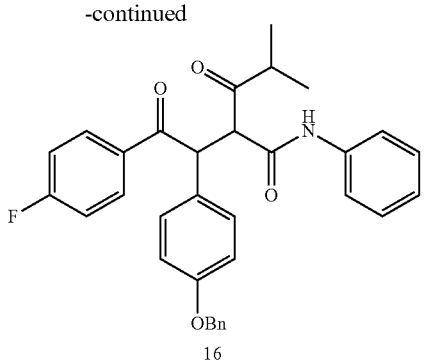

To a mixture of (E)-2-(4-(benzyloxy)benzylidin) 4-methyl-3-oxo-N-phenylpentanamide (4.7 g, 11.77 mmol) and 4-fluorobenzaldehyde (2.19 g, 17.65 mmol, 1.86 mL) was added 3-ethyl-5-(hydroxymethyl)-4-methylthiazol-3-ium bromide (2.97 g, 11.77 mmol) and TEA (2.38 g, 23.53 mmol, 3.28 mL). The reaction mixture was heated at 80° C. for 12 h. LCMS showed the starting material was consumed and the 58% of desired mass was detected. The reaction mixture was cooled to rt, EtOAc (100 mL) and water (30 mL) was added. The organic layer was separated and washed with brine (30 mL), dried over Na$_2$SO$_4$, filtered and the filtrate was concentrated under reduced pressure. The residue was purified by silica gel column (PE/EtOAc=100/1 to 5/1) to afford 2-[1-(4-benzyloxyphenyl)-2-(4-fluorophenyl)-2-oxo-ethyl]-4-methyl-3-oxo-N-phenyl-pentanamide (4.5 g, 8.59 mmol, 73.05% yield) as yellow foam. MS [M+H]$^+$=524.3

Step 8: Synthesis of tert-butyl 2-[(4R,6R)-6-[2-[3-(4-benzyloxyphenyl)-2-(4-fluorophenyl)-5-isopropyl-4-(phenylcarbamoyl)-1H-pyrrol-1-yl]ethyl]-2,2-dimethyl-1,3-dioxan-4-yl]acetate (18)

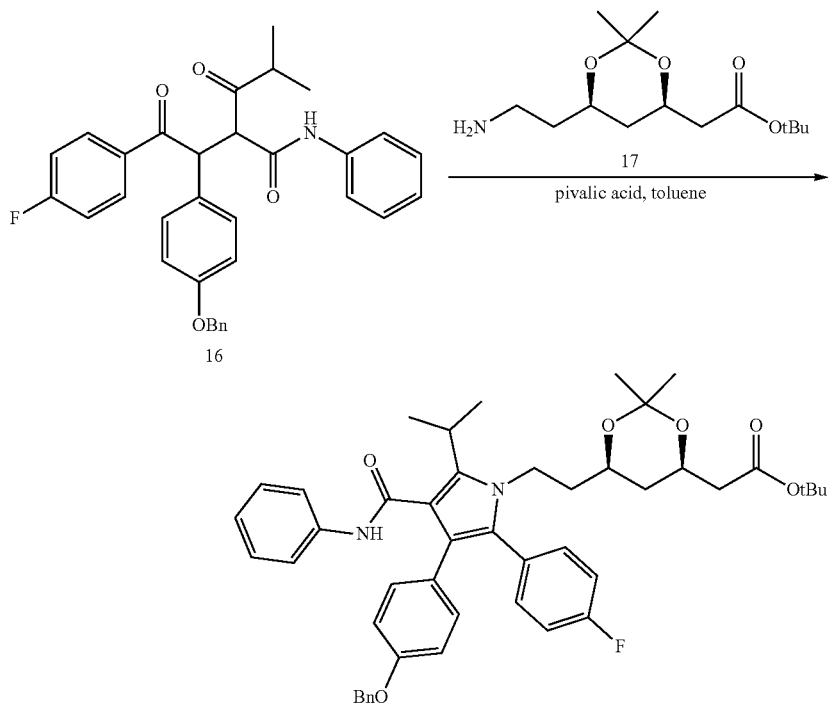

To a solution of 2-[1-(4-benzyloxyphenyl)-2-(4-fluoro-phenyl)-2-oxo-ethyl]-4-methyl-3-oxo-N-phenyl-pentana-mide (4.2 g, 8.02 mmol) and tert-butyl 2-[(4R,6R)-6-(2-aminoethyl)-2,2-dimethyl-1,3-dioxan-4-yl]acetate (3.29 g, 12.03 mmol) in toluene (40 mL) was added pivalic acid (983 mg, 9.63 mmol). The reaction mixture was heated at 100° C. for 12 h. LCMS showed the starting material remained partially and the desired mass was detected. The reaction mixture was quenched with saturated NaHCO₃ solution (30 mL), extracted with EtOAc (100 mL). The organic layer washed with brine (30 mL), dried over Na₂SO₄, filtered and the filtrate was concentrated under reduced pressure. The residue was purified by silica gel column (PE/EtOAc=60/1 to 5/1) to give tert-butyl 2-[(4R,6R)-6-[2-[3-(4-benzyloxy-phenyl)-2-(4-fluorophenyl)-5-isopropyl-4-(phenylcarbam-oyl)pyrrol-1-yl]ethyl]-2,2-dimethyl-1,3-dioxan-4-yl]acetate (4.7 g, 4.20 mmol, 52.36% yield, 68% purity) as yellow foam. MS [M+H]+=761.5

Step 9: Synthesis of tert-butyl 2-[(4R,6R)-6-[2[2-(4-fluorophenyl)-3-(4-hydroxyphenyl)-5-isopropyl-4-(phenylcarbamoyl)-1H-pyrrol-1-yl]ethyl]-2,2-dim-ethyl-1,3-dioxan-4-yl]acetate (19)

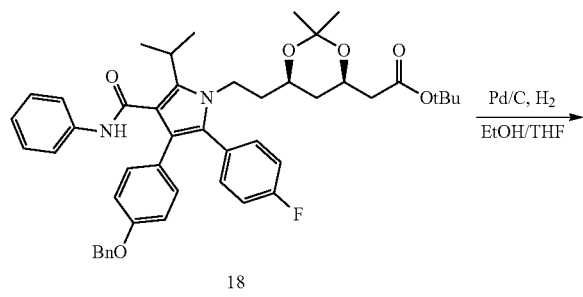

18

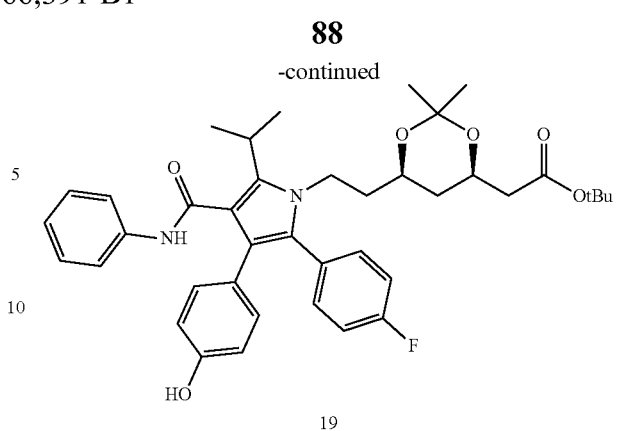

19

To a solution of tert-butyl 2-[(4R,6R)-6-[2-[3-(4-benzy-loxyphenyl)-2-(4-fluorophenyl)-5-isopropyl-4-(phenylcar-bamoyl)-1H-pyrrol-1-yl]ethyl]-2,2-dimethyl-1,3-dioxan-4-yl]acetate (4.5 g, 4.08 mmol) in THF (1 mL) and EtOH (0.5 mL) was added Pd/C (0.01 g, 10% purity). The reaction mixture was degassed under vacuum and purged with H₂ several times. The reaction mixture was stirred for 12 h at 80° C. under H₂ (50 Psi). TLC showed the completion of the reaction. The reaction mixture was cooled to rt, then filtered through a pad of celite. The filtrate was concentrated under reduced pressure. The residue was purified by silica gel column (PE/EtOAc=30/1 to 5/1) to give tert-butyl2-[(4R,6R)-6-[2-[2-(4-fluorophenyl)-3-(4-hydroxyphenyl)-5-iso-propyl-4-(phenylcarbamoyl)pyrrol-1-yl]ethyl]-2,2-dim-ethyl-1,3-dioxan-4-yl]acetate (2.2 g, 3.08 mmol, 75.55% yield, 94% purity) as white foam. MS [M+H]+=671.4

Step 10: Synthesis of tert-butyl 2-((4R,6R)-6-(2-(2-(4-fluorophenyl)-5-isopropyl-3-(4-((3-oxo-1-phenyl-2,7,10,13,16,19,22-heptaoxa-4-azatetracosan-24-yl)oxy)phenyl)-4-(phenylcarbamoyl)-1H-pyrrol-1-yl)ethyl)-2,2-dimethyl-1,3-dioxan-4-yl)acetate (21)

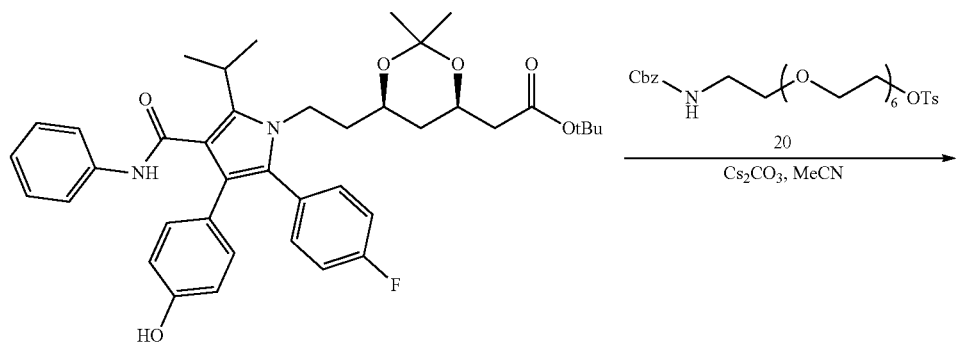

19

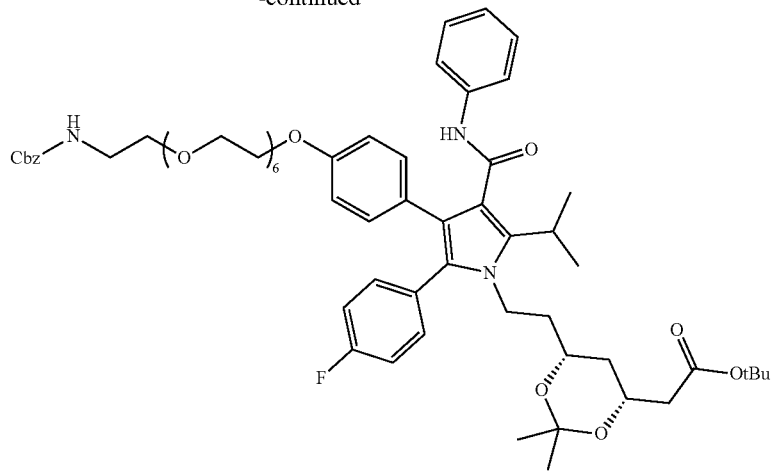

21

To a solution of tert-butyl 2-[(4R,6R)-6-[2-[2-(4-fluorophenyl)-3-(4-hydroxyphenyl)-5-isopropyl-4-(phenylcarbamoyl)-1H-pyrrol-1-yl]ethyl]-2,2-dimethyl-1,3-dioxan-4-yl]acetate (0.25 g, 372.69 umol) in MeCN (3 mL) was added Cs$_2$CO$_3$ (242.86 mg, 745.37 umol), 2-[2-[2-[2-[2-[2-[2-(benzyloxycarbonylamino)ethoxy]ethoxy]ethoxy]ethoxy]ethoxy]ethoxy]ethyl 4-methylbenzenesulfonate (0.25 g, 407.36 umol). The reaction mixture was heated at 90° C. for 12 h. LCMS showed the starting material was consumed and the 36% of desired mass was detected. The reaction mixture was filtered and the filtrate was concentrated under reduced pressure to afford tert-butyl 2-[(4R,6R)-6-[2-[3-[4-[2-[2-[2-[2-[2-[2-[2-(benzyloxycarbonylamino)ethoxy]ethoxy]ethoxy]ethoxy]ethoxy]ethoxy]ethoxy]phenyl]-2-(4-fluorophenyl)-5-isopropyl-4-(phenylcarbamoyl)pyrrol-1-yl]ethyl]-2,2-dimethyl-1,3-dioxan-4-yl]acetate (0.3 g, 269.71 umol, 72.37% yield) as yellow solid, which was used for next step without purification. MS [M+H]$^+$=1112.9

Step 11: Synthesis of tert-butyl 2-[(4R,6R)-6-[2-[3-[4-[2-[2-[2-[2-[2-(2 aminoethoxy)ethoxy]ethoxy]ethoxy]ethoxy]ethoxy]ethoxy]phenyl]-2-(4-fluorophenyl)-5-isopropyl-4-(phenylcarbamoyl)pyrrol-1-yl]ethyl]-2,2-dimethyl-1,3-dioxan-4-yl]acetate (22)

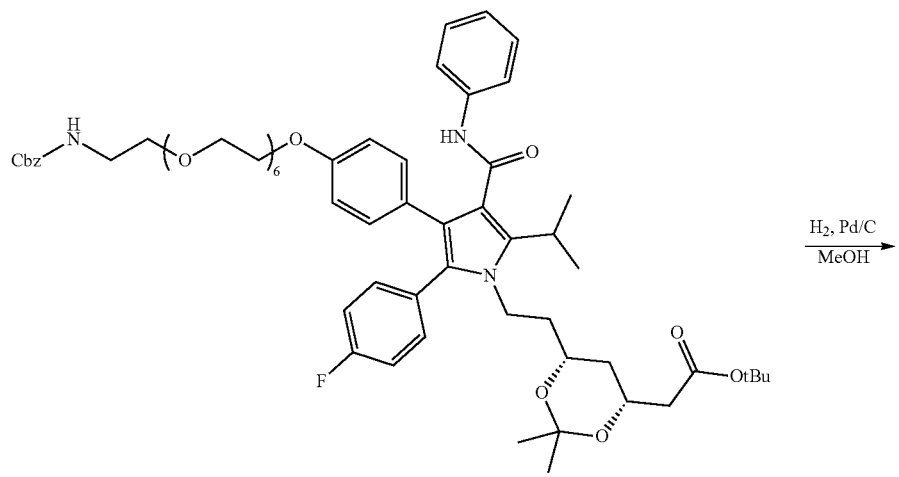

21

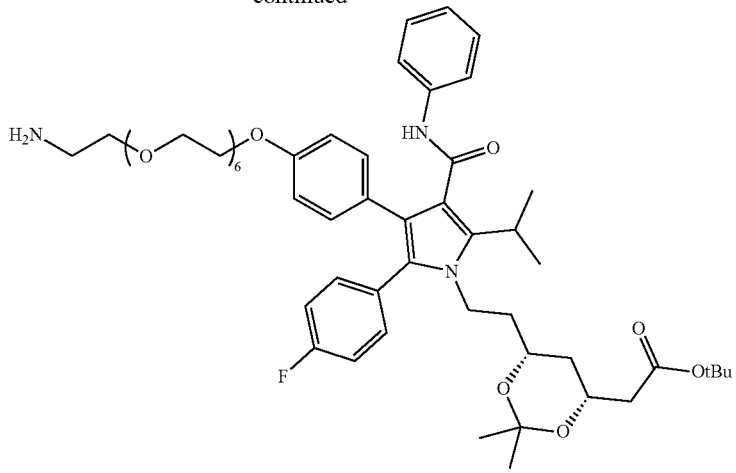

22

To a solution of tert-butyl 2-[(4R,6R)-6-[2-[3-[4-[2-[2-[2-[2-[2-[2-[2-(benzyloxycarbonylamino)ethoxy]ethoxy]ethoxy]ethoxy]ethoxy]ethoxy]ethoxy]phenyl]-2-(4-fluorophenyl)-5-isopropyl-4-(phenylcarbamoyl)pyrrol-1-yl]ethyl]-2,2-dimethyl-1,3-dioxan-4-yl]acetate (300 mg, 269.71 umol) in MeOH (1 mL) was added Pd/C (100 mg, 10% purity). The reaction mixture was degassed under vacuum and purged with $H_2$ several times, then the resulting mixture was stirred at 20° C. for 2 h under $H_2$ (15 psi). LCMS showed completion of the reaction. The reaction mixture was filtered through a pad of celite and washed with MeOH (5 mL×3). The filtrate was concentrated under reduced pressure. The residue was purified by silica gel column (DCM/MeOH=100/1 to 30/1) to give tert-butyl 2-[(4R,6R)-6-[2-[3-[4-[2-[2-[2-[2-[2-[2-(2-aminoethoxy)ethoxy]ethoxy]ethoxy]ethoxy]ethoxy]ethoxy]phenyl]-2-(4-fluorophenyl)-5-isopropyl-4-(phenylcarbamoyl)pyrrol-1-yl]ethyl]-2,2-dimethyl-1,3-dioxan-4-yl]acetate (0.19 g, 137.91 umol, 51.13% yield, 71% purity) as yellow oil. MS [M+H]+= 978.4

Step 12: Synthesis of (3R,5R)-7-[3-[4-[2-[2-[2-[2-[2-[2 (2 aminoethoxy)ethoxy]ethoxy]ethoxy]ethoxy]ethoxy]ethoxy]phenyl]-2-(4-fluorophenyl)-5-isopropyl-4-(phenylcarbamoyl)pyrrol-1-yl]-3,5-dihydroxyheptanoic acid (23)

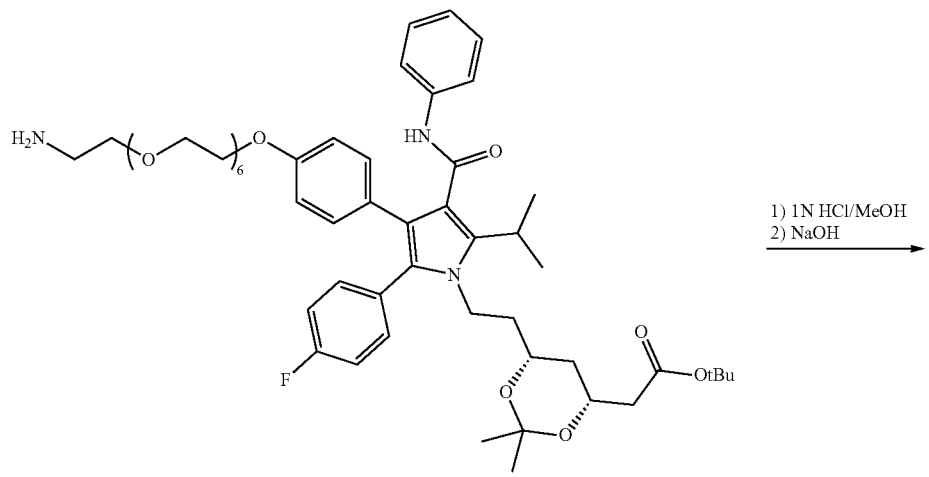

22

1) 1N HCl/MeOH
2) NaOH

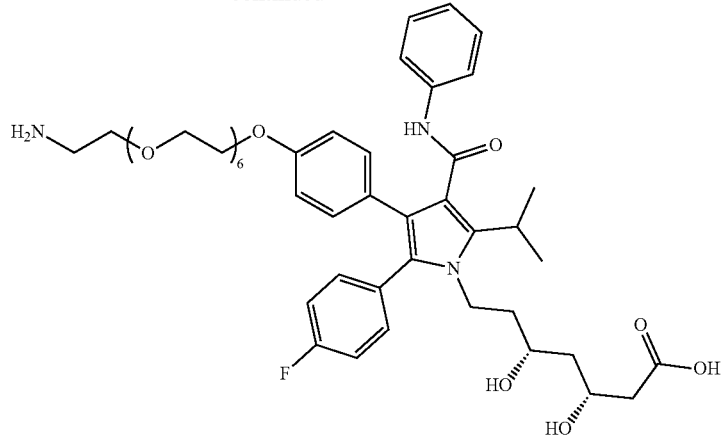

23

To a solution of tert-butyl 2-[(4R,6R)-6-[2-[3-[4-[2-[2-[2-[2-[2-[2-(2-aminoethoxy)ethoxy]ethoxy]ethoxy]ethoxy]ethoxy]phenyl]-2-(4-fluorophenyl)-5-isopropyl-4-(phenylcarbamoyl)pyrrol-1-yl]ethyl]-2,2-dimethyl-1,3-dioxan-4-yl]acetate (190 mg, 194.24 umol) in MeOH (1 mL) and THF (1 mL) was added HCl (1 M, 388.47 uL) at 20° C. The reaction mixture was stirred for 2 h at 20° C. Then NaOH (2 M, 582.71 uL) was added and the resulting mixture was stirred for 12 h. LCMS showed completion of the reaction. The reaction solvent was removed in vacuum. The reaction mixture was purified by reverse phase (0.1% $NH_3 \cdot H_2O$) and lyophilized to give (3R,5R)-7-[3-[4-[2-[2-[2-[2-[2-[2-(2-aminoethoxy)ethoxy]ethoxy]ethoxy]ethoxy]ethoxy]phenyl]-2-(4-fluorophenyl)-5-isopropyl-4-(phenylcarbamoyl)pyrrol-1-yl]-3,5-dihydroxy-heptanoic acid (90 mg, 97.96 umol, 50.43% yield, 96% purity) as white solid. MS [M+H]$^+$ 882.7

Step 13: Synthesis of (3R,5R)-7-(3-(4-((1-((2-(2,6-dioxopiperidin-3-yl)-1,3-dioxoisoindolin-4-yl)oxy)-2-oxo-6,9,12,15,18,21-hexaoxa-3-azatricosan-23-yl)oxy)phenyl)-2-(4-fluorophenyl)-5-isopropyl-4-(phenylcarbamoyl)-1H-pyrrol-1-yl)-3,5-dihydroxyheptanoic acid (Compound 8)

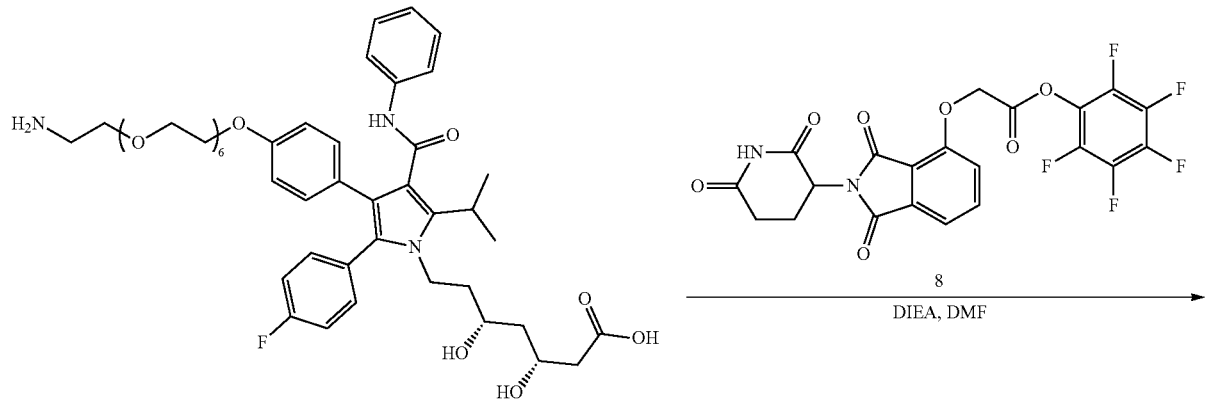

23

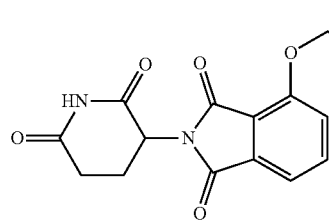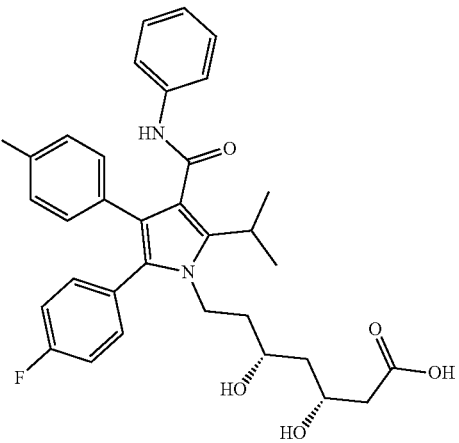

Compound 8

To a solution of (3R,5R)-7-[3-[4-[2-[2-[2-[2-[2-[2-(2-aminoethoxy)ethoxy]ethoxy]ethoxy]ethoxy]ethoxy]ethoxy]phenyl]-2-(4-fluorophenyl)-5-isopropyl-4-(phenylcarbamoyl)pyrrol-1-yl]-3,5-dihydroxy-heptanoic acid (0.05 g, 56.69 umol) and DIPEA (36 mg, 283.44 umol, 49.37 uL) in DMF (4 mL) was added (2,3,4,5,6-pentafluorophenyl) 2-[2-(2,6-dioxo-3-piperidyl)-1,3-dioxo-isoindolin-4-yl]oxyacetate (28 mg, 56.69 umol). The resulting mixture was stirred for 2 h. LCMS showed the starting material was consumed and the desired mass was detected. The reaction solvent was removed under reduced pressure. The residue was purified by prep-HPLC (neutral) to give (3R,5R)-7-[3-[4-[2-[2-[2-[2-[2-[2-[[2-[2-(2,6-dioxo-3-piperidyl)-1,3-dioxo-isoindolin-4-yl]oxyacetyl]amino]ethoxy]ethoxy]ethoxy]ethoxy]ethoxy]ethoxy]phenyl]-2-(4-fluorophenyl)-5-isopropyl-4-(phenylcarbamoyl)pyrrol-1-yl]-3,5-dihydroxy-heptanoic acid (5.3 mg, 4.14 umol, 7.7% yield, 99% purity) as white solid. $^1$H NMR (400 MHz, DMSO-d$_6$) δ 9.78 (s, 1H), 8.01 (t, J=5.6 Hz, 1H), 7.80 (dd, J=7.4, 8.4 Hz, 1H), 7.51 (dd, J=7.7, 13.6 Hz, 3H), 7.39 (d, J=8.4 Hz, 1H), 7.26-7.12 (m, 6H), 7.02-6.95 (m, 3H), 6.65 (d, J=8.8 Hz, 2H), 5.11 (dd, J=5.5, 12.9 Hz, 1H), 4.78 (s, 2H), 3.99-3.59 (m, 9H), 3.56-3.42 (m, 21H), 3.01-2.81 (m, 2H), 2.69-2.54 (m, 3H), 2.39-1.96 (m, 6H), 1.66-1.24 (m, 11H). MS (M+H)$^+$=1196.7

Example 9. Synthesis of (3R,5R)-7-(2-(2-((1-((2-(2,6-dioxopiperidin-3-yl)-1,3-dioxoisoindolin-4-yl)oxy)-2-oxo-6,9,12,15,18,21-hexaoxa-3-azatricosan-23-yl)oxy)-4-fluorophenyl)-5-isopropyl-3-phenyl-4-(phenylcarbamoyl)-1H-pyrrol-1-yl)-3,5-dihydroxyheptanoic acid (Compound 9)

Step 1: Synthesis of 2-benzyloxy-4-fluoro-benzaldehyde (3a)

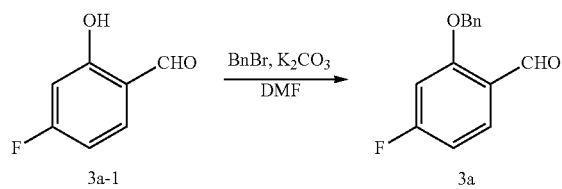

To a solution of 4-fluoro-2-hydroxy-benzaldehyde (5 g, 35.69 mmol) in DMF (100 mL) was added bromomethyl-benzene (7.32 g, 42.82 mmol, 5.09 mL) and K$_2$CO$_3$ (12.33 g, 89.21 mmol) at 20° C. The reaction mixture heated at 80° C. for 4 h. LCMS showed the reaction was completed. The reaction mixture was quenched with water (100 mL), extracted with methyl tert-butyl ether (300 mL). The organic layer was washed with brine (100 mL), dried over Na$_2$SO$_4$, filtered and the filtrate was concentrated under reduced pressure. The residue was purified by silica gel column (PE/EtOAc=100/1 to 10/1) to give 2-benzyloxy-4-fluoro-benzaldehyde (6.5 g, 28.23 mmol, 79.11% yield) as colorless oil.

$^1$H NMR (400 MHz, CDCl$_3$) δ 10.44 (s, 1H), 7.94-7.85 (m, 1H), 7.49-7.34 (m, 5H), 6.81-6.70 (m, 2H), 5.17 (s, 2H).

Step 2: Synthesis of (E)-2-benzylidene-4-methyl-3-oxo-N-phenylpentanamide (3)

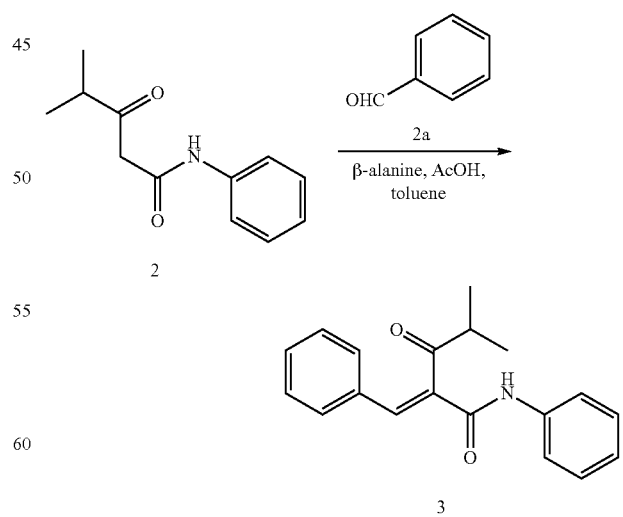

To a solution of 4-methyl-3-oxo-N-phenyl-pentanamide (10 g, 48.72 mmol) and benzaldehyde (9.31 g, 87.70 mmol) in toluene (100 mL) was added BETA-ALANINE (868.13 mg, 9.74 mmol) and acetic acid (1.76 g, 29.23 mmol, 1.67 mL) at 20° C. The reaction mixture was heated at 130° C. for 12 h. TLC showed the trace starting material remained and desired spot was detected. The reaction solvent was removed under reduced pressure. The residue was purified by silica gel column (PE/EtOAc=60/1 to 5/1) followed by trituration with TBME (10 mL) and dried to give (2E)-2-benzylidene-4-methyl-3-oxo-N-phenyl-pentanamide (4.3 g, 14.22 mmol, 29.18% yield, 97% purity) as white solid. $^1$H NMR (400 MHz, CDCl$_3$) δ 7.64 (s, 1H), 7.58-7.49 (m, 3H), 7.47 (m, 2H), 7.38-7.34 (m, 5H), 7.13 (m, 1H), 3.39-3.30 (m, 1H), 1.22 (d, J=6.8 Hz, 6H).

Step 3: Synthesis of 2-[2-(2-benzyloxy-4-fluoro-phenyl)-2-oxo-1-phenyl-ethyl]-4-methyl-3-oxo-N-phenyl-pentanamide (4)

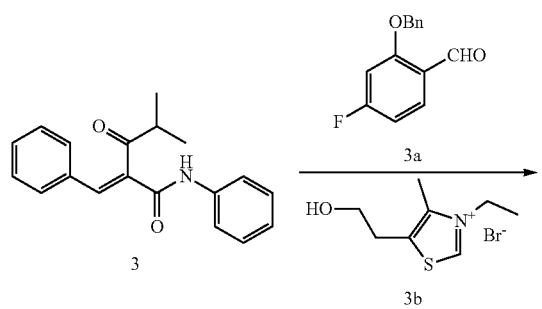

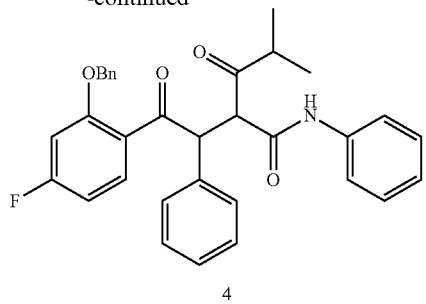

4

A mixture of (E)-2-benzylidene-4-methyl-3-oxo-N-phenylpentanamide (3 g, 10.23 mmol), 2-benzyloxy-4-fluoro-benzaldehyde (3.53 g, 15.34 mmol), 3-ethyl-5-(2-hydroxy-ethyl)-4-methylthiazol-3-ium bromide (2.58 g, 10.23 mmol) and TEA (2.07 g, 20.45 mmol, 2.85 mL) was heated at 80° C. for 12 h in neat reaction. The reaction mixture was dissolved in EtOAc (200 mL) and water (60 mL). The organic layer was separated and washed with brine (60 mL), dried over Na$_2$SO$_4$, filtered. The filtrate was concentrated under reduced pressure. The residue was purified by silica gel column (PE/EtOAc=20/1 to 5/1) followed by pre-HPLC (TFA) to give 2-[2-(2-benzyloxy-4-fluoro-phenyl)-2-oxo-1-phenyl-ethyl]-4-methyl-3-oxo-N-phenyl-pentanamide (0.529 g, 1.01 mmol, 9.88% yield) as light yellow solid.

Step 4: Synthesis of tert-butyl 2-[(4R,6R)-6-[2-[2-(2-benzyloxy-4-fluoro-phenyl)-5-isopropyl-3-phenyl-4-(phenylcarbamoyl)pyrrol-1-yl]ethyl]-2,2-dimethyl-1,3-dioxan-4-yl]acetate (5)

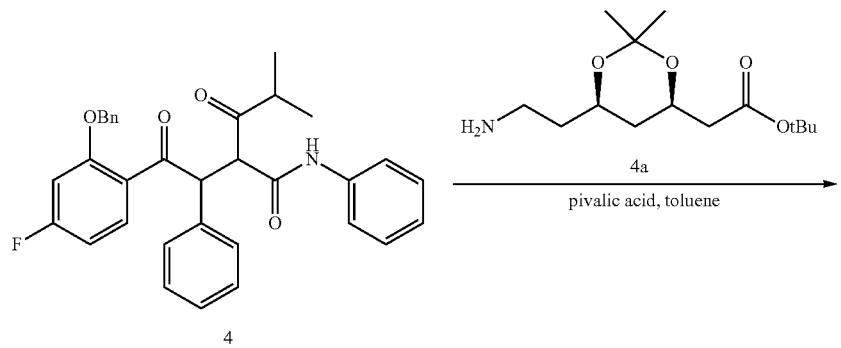

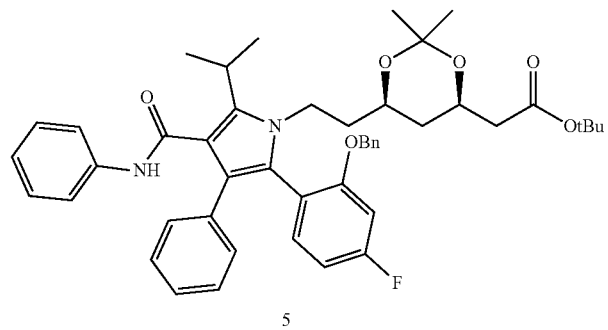

To a solution of 2-[2-(2-benzyloxy-4-fluoro-phenyl)-2-oxo-1-phenyl-ethyl]-4-methyl-3-oxo-N-phenyl-pentanamide (0.529 g, 1.01 mmol) and tert-butyl 2-[(4R,6R)-6-(2-aminoethyl)-2,2-dimethyl-1,3-dioxan-4-yl]acetate (414.29 mg, 1.52 mmol) in toluene (5 mL) was added PIVALIC ACID (123.82 mg, 1.21 mmol, 139.28 uL). The reaction mixture was heated at 110° C. for 12 h. LCMS showed the starting material was consumed and 57% of desired mass was detected. The reaction mixture was quenched with saturated NaHCO₃ solution (60 mL) and extracted with EtOAc (100 mL). The organic layer was washed with brine (60 mL), dried over Na₂SO₄, filtered and the filtrated was concentrated under reduced pressure. The residue was purified by silica gel column (PE/EtOAc=60/1 to 8/1) to give tert-butyl 2-[(4R,6R)-6-[2-[2-(2-benzyloxy-4-fluoro-phenyl)-5-isopropyl-3-phenyl-4-(phenylcarbamoyl)pyrrol-1-yl]ethyl]-2,2-dimethyl-1,3-dioxan-4-yl]acetate (0.41 g, 538.81 umol, 53.33% yield) as yellow oil. MS (M+H)⁺=761.3

Step 5: Synthesis of tert-butyl 2-[(4R,6R)-6-[2-[2-(4-fluoro-2-hydroxy-phenyl)-5-isopropyl-3-phenyl-4-(phenylcarbamoyl)-1H-pyrrol-1-yl]ethyl]-2,2-dimethyl-1,3-dioxan-4-yl]acetate (6)

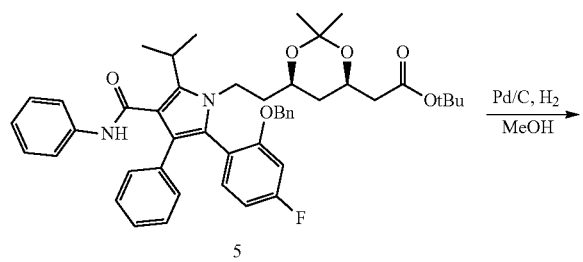

To a solution of tert-butyl 2-[(4R,6R)-6-[2-[2-(2-benzyloxy-4-fluoro-phenyl)-5-isopropyl-3-phenyl-4-(phenylcarbamoyl)-1H-pyrrol-1-yl]ethyl]-2,2-dimethyl-1,3-dioxan-4-yl]acetate (0.49 g, 643.95 umol) in MeOH (5 mL) was added Pd/C (0.05 g, 10% purity) under N₂. The reaction mixture was degassed under vacuum and purged with H₂ for three times and the resulting mixture was heated at 80° C. for 12 h under H₂ (50 Psi). LCMS showed the reaction was completed. The reaction mixture was cooled to rt, and filtered through a pad of celite, washed with MeOH (10 mL×5). The filtrate was concentrated under reduced pressure. The crude tert-butyl 2-[(4R,6R)-6-[2-[2-(4-fluoro-2-hydroxy-phenyl)-5-isopropyl-3-phenyl-4-(phenylcarbamoyl)pyrrol-1-yl]ethyl]-2,2-dimethyl-1,3-dioxan-4-yl]acetate (374 mg, 557.54 umol, 86.58% yield) as white foam, which was used for next step without purification. MS (M+H)⁺=671.5

Step 6: Synthesis of tert-butyl 2-[(4R,6R)-6-[2-[2-[2-[2-[2-[2-[2-[2-[2 (benzyloxycarbonylamino) ethoxy]ethoxy]ethoxy]ethoxy]ethoxy]ethoxy]ethoxy]-4-fluoro-phenyl]-5-isopropyl-3-phenyl-4-(phenylcarbamoyl)pyrrol-1-yl]ethyl]-2,2-dimethyl-1,3-dioxan-4-yl]acetate (7)

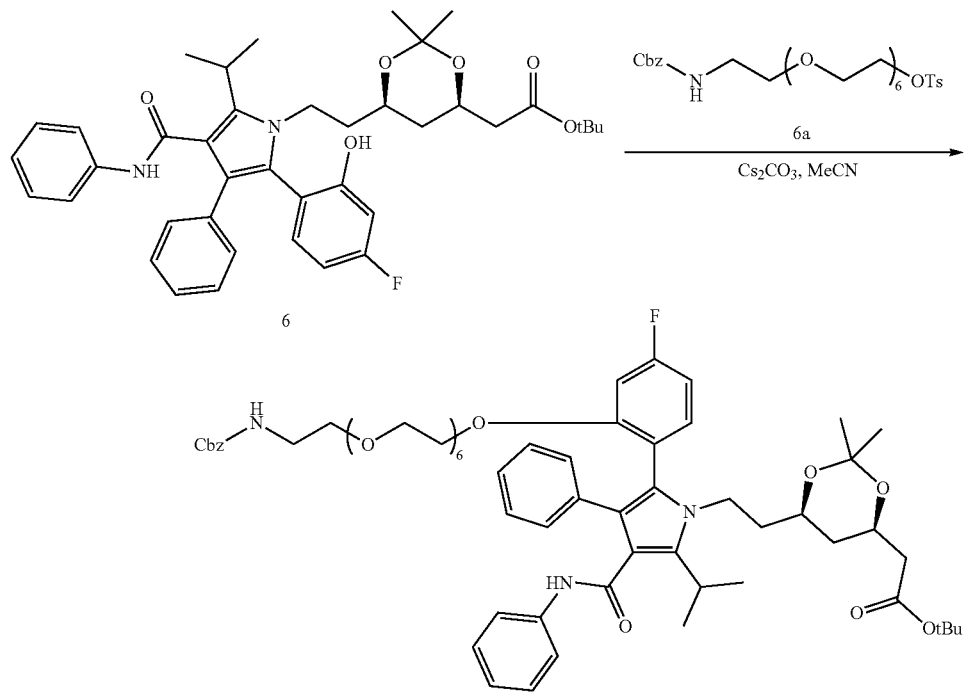

To a solution of tert-butyl 2-[(4R,6R)-6-[2-[2-(4-fluoro-2-hydroxy-phenyl)-5-isopropyl-3-phenyl-4-(phenylcarbamoyl)-1H-pyrrol-1-yl]ethyl]-2,2-dimethyl-1,3-dioxan-4-yl]acetate (320 mg, 477.04 umol) in MeCN (1 mL) was added Cs$_2$CO$_3$ (310.86 mg, 954.07 umol), 2-[2-[2-[2-[2-[2-[2-(benzyloxycarbonylamino)ethoxy]ethoxy]ethoxy]ethoxy]ethoxy]ethyl 4-methylbenzenesulfonate (319.11 mg, 519.97 umol) and the reaction mixture was heated at 90° C. for 12 h. LCMS showed the starting material was consumed and the desired mass was detected. The reaction mixture was filtered and the filtrate was concentrated under reduced pressure. The residue was purified by silica gel column (PE/EtOAc=5/1 to 0/1) to give tert-butyl 2-[(4R,6R)-6-[2-[2-[2-[2-[2-[2-[2-[2-[2-(benzyloxycarbonylamino)ethoxy]ethoxy]ethoxy]ethoxy]ethoxy]ethoxy]ethoxy]-4-fluoro-phenyl]-5-isopropyl-3-phenyl-4-(phenylcarbamoyl)pyrrol-1-yl]ethyl]-2,2-dimethyl-1,3-dioxan-4-yl]acetate (410 mg, 328.05 umol, 68.77% yield, 89% purity) as yellow oil. MS [M+H]$^+$=1112.3

Step 7: Synthesis of tert-butyl 2-[(4R,6R)-6-[2-[2-[2-[2-[2-[2-[2-[2-(2 aminoethoxy)ethoxy]ethoxy]ethoxy]ethoxy]ethoxy]ethoxy]-4-fluoro-phenyl]-5-isopropyl-3-phenyl-4-(phenylcarbamoyl)pyrrol-1-yl]ethyl]-2,2-dimethyl-1,3-dioxan-4-yl]acetate (8)

To a solution of tert-butyl 2-((4R,6R)-6-(2-(2-(4-fluoro-2-((3-oxo-1-phenyl-2,7,10,13,16,19,22-heptaoxa-4-azatetracosan-24-yl)oxy)phenyl)-5-isopropyl-3-phenyl-4-(phenylcarbamoyl)-1H-pyrrol-1-yl)ethyl)-2,2-dimethyl-1,3-dioxan-4-yl)acetate (410 mg, 368.60 umol) in MeOH (10 mL) was added Pd/C (40 mg, 10% purity) under N$_2$. The suspension was degassed in vacuum and purged with H$_2$ for three times. The reaction mixture was stirred for 2 h at 20° C. under H$_2$ (15 psi). LCMS showed the reaction was completed. The reaction mixture was filtered through a pad of celite and washed with MeOH (10 mL×5). The filtrate was concentrated under reduced pressure. The residue was purified by silica gel column (DCM\MeOH=100\1 to 10\1) to give tert-butyl 2-[(4R,6R)-6-[2-[2-[2-[2-[2-[2-[2-[2-(2-aminoethoxy)ethoxy]ethoxy]ethoxy]ethoxy]ethoxy]ethoxy]-4-fluoro-phenyl]-5-isopropyl-3-phenyl-4-(phenylcarbamoyl)pyrrol-1-yl]ethyl]-2,2-dimethyl-1,3-dioxan-4-yl]acetate (176 mg, 169.13 umol, 45.88% yield, 94% purity) as colorless oil. MS (M+H)$^+$=978.7

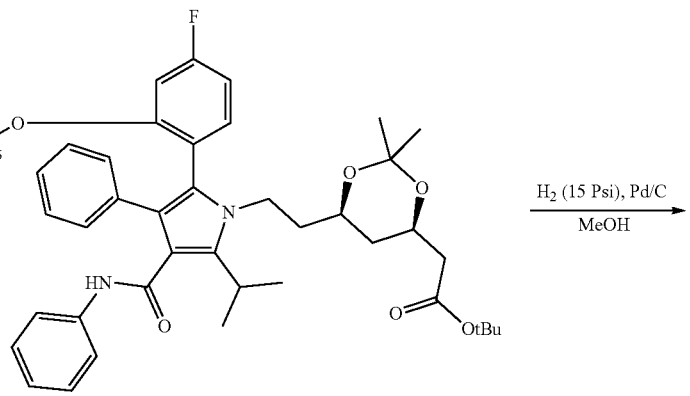

7

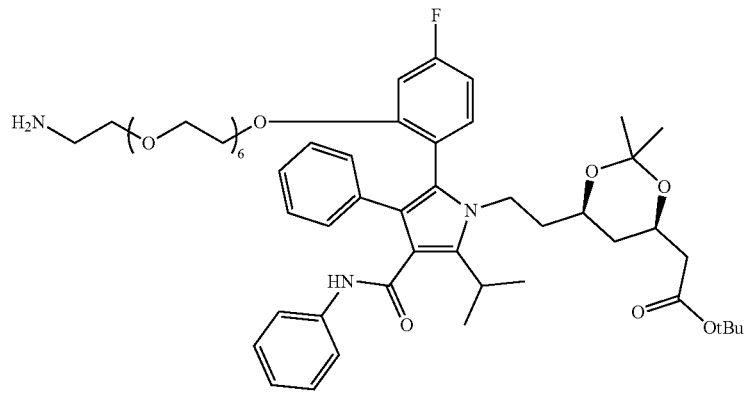

8

Step 8: Synthesis of (3R,5R)-7-[2-[2-[2-[2-[2-[2-[2-[2-(2 aminoethoxy)ethoxy]ethoxy]ethoxy]ethoxy]ethoxy]ethoxy]-4-fluoro-phenyl]-5-isopropyl-3-phenyl-4-(phenylcarbamoyl)pyrrol-1-yl]-3,5-dihydroxy-heptanoic acid (9)

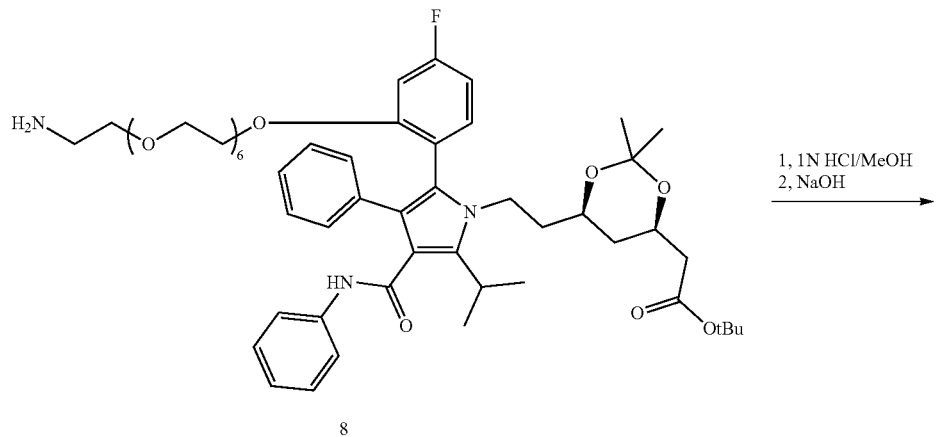

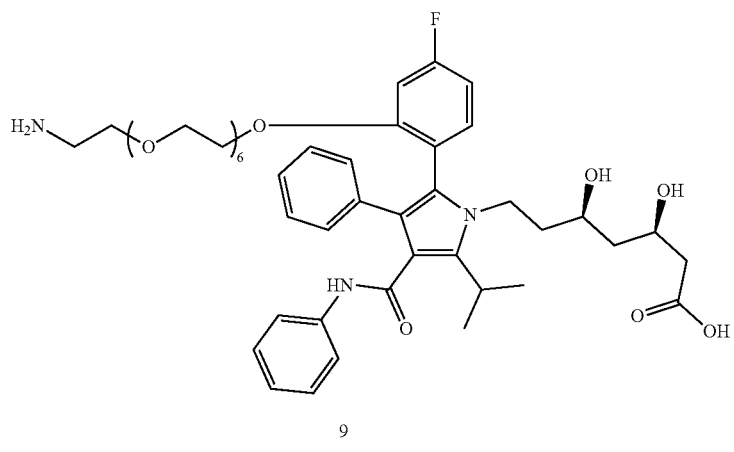

To a solution of tert-butyl 2-[(4R,6R)-6-[2-[2-[2-[2-[2-[2-[2-[2-[2-(2-aminoethoxy)ethoxy]ethoxy]ethoxy]ethoxy]ethoxy]ethoxy]-4-fluoro-phenyl]-5-isopropyl-3-phenyl-4-(phenylcarbamoyl)pyrrol-1-yl]ethyl]-2,2-dimethyl-1,3-dioxan-4-yl]acetate (176 mg, 179.92 umol) in THF (1 mL) and MeOH (1 mL) was added HCl (1 M, 359.85 uL) at 20° C. and the reaction mixture was stirred at 20° C. for 2 h. Then NaOH (43.18 mg, 1.08 mmol) was added and the resulting mixture was stirred at 20° C. for 12 h. LCMS showed the reaction was completed. The reaction solvent was removed under reduced pressure. The residue was purified by reverse phase column (deionized water) to give (3R,5R)-7-[2-[2-[2-[2-[2-[2-[2-[2-(2-aminoethoxy)ethoxy]ethoxy]ethoxy]ethoxy]ethoxy]ethoxy]-4-fluoro-phenyl]-5-isopropyl-3-phenyl-4-(phenylcarbamoyl)pyrrol-1-yl]-3,5-dihydroxy-heptanoic acid (138 mg, 154.89 umol, 86.09% yield, 99% purity) as white solid. MS (M+H)$^+$=882.5

Step 9: Synthesis of (3R,5R)-7-(2-(2-((1-((2-(2,6-dioxopiperidin-3-yl)-1,3-dioxoisoindolin-4-yl)oxy)-2-oxo-6,9,12,15,18,21-hexaoxa-3-azatricosan-23-yl)oxy)-4-fluorophenyl)-5-isopropyl-3-phenyl-4-(phenylcarbamoyl)-1H-pyrrol-1-yl)-3,5-dihydroxyheptanoic acid (Compound 9)

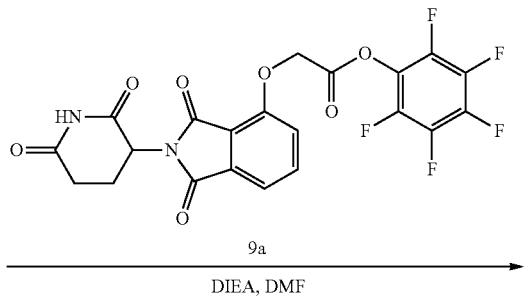

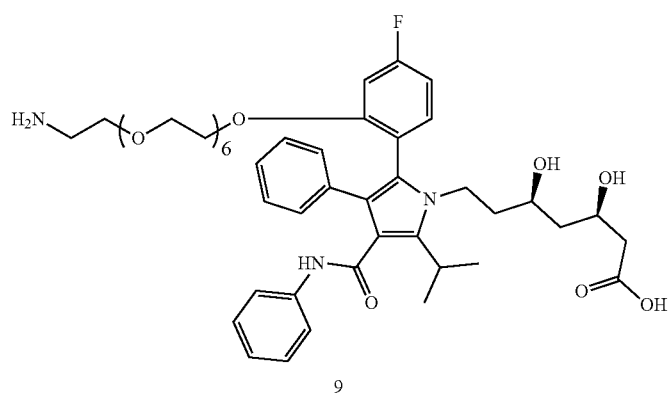

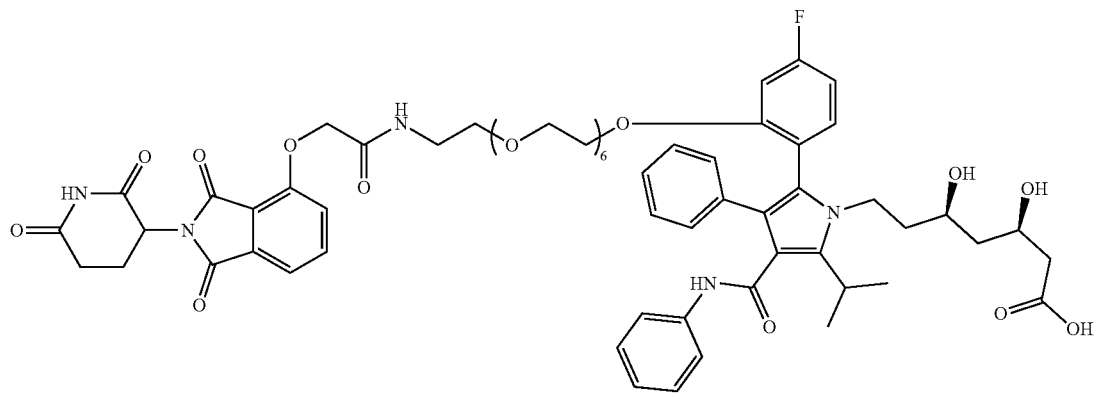

Compound 9

To a solution (3R,5R)-7-[2-[2-[2-[2-[2-[2-[2-[2-(2-aminoethoxy)ethoxy]ethoxy]ethoxy]ethoxy]ethoxy]ethoxy]-4-fluoro-phenyl]-5-isopropyl-3-phenyl-4-(phenylcarbamoyl)pyrrol-1-yl]-3,5-dihydroxy-heptanoic acid (0.128 g, 145.12 umol) and DIEA (94 mg, 725.61 umol, 126.39 uL) in DMF (1 mL) was added (2,3,4,5,6-pentafluorophenyl) 2-[2-(2,6-dioxo-3-piperidyl)-1,3-dioxo-isoindolin-4-yl]oxyacetate (72 mg, 145.12 umol) at 20° C. The reaction mixture was stirred at 20° C. for 2 h. LCMS showed the reaction was completed. The solvent was removed under reduced pressure. The residue was purified with another batch (100 mg scale) by prep-HPLC (neutral) to give (3R,5R)-7-[2-[2-[2-[2-[2-[2-[2-[2-[2-[[2-[2-(2,6-dioxo-3-piperidyl)-1,3-dioxo-isoindolin-4-yl]oxyacetyl]amino]ethoxy]ethoxy]ethoxy]ethoxy]ethoxy]ethoxy]ethoxy]-4-fluoro-phenyl]-5-isopropyl-3-phenyl-4-(phenylcarbamoyl)pyrrol-1-yl]-3,5-dihydroxy-heptanoic acid (48.7 mg, 38.67 umol, 26.65% yield, 95% purity) as white solid. $^1$H NMR (400 MHz, DMSO-$d_6$) δ 9.68 (s, 1H), 8.02 (br s, 1H), 7.80 (br t, J=7.8 Hz, 1H), 7.56-7.35 (m, 4H), 7.21 (br t, J=7.5 Hz, 2H), 7.11-6.95 (m, 8H), 6.76-6.62 (m, 1H), 5.11 (br dd, J=5.1, 13.0 Hz, 1H), 4.78 (s, 2H), 4.20-4.01 (m, 3H), 3.93-3.18 (m, 30H), 2.95-2.82 (m, 2H), 2.69-2.56 (m, 2H), 2.23-1.97 (m, 4H), 1.68-1.11 (m, 12H). MS (M+H)$^+$=1196.2

Example 10. Synthesis of (3S,5S)-7-(2-(4-fluorophenyl)-4-((4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)phenyl)carbamoyl)-5-isopropyl-3-phenyl-1H-pyrrol-1-yl)-3,5-dihydroxyheptanoic acid (Compound 10)

Step 1: Synthesis of tert-butyl 4-bromobenzylcarbamate (2)

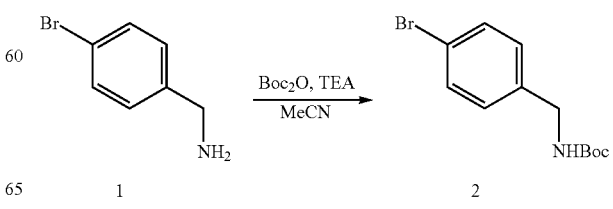

To a solution of (4-bromophenyl)methanamine (20 g, 107.50 mmol, 13.61 mL) and TEA (21.76 g, 215.00 mmol, 29.93 mL) in CH₃CN (200 mL) was added Boc₂O (23.5 g, 107.68 mmol, 24.74 mL) and the resulting mixture was stirred at 20° C. for 15 h. LCMS showed a main peak with desired mass and the starting material was consumed. The mixture was concentrated under vacuum. The crude product was triturated with petroleum ether (100 mL), the filter cake was dried in vacuum to afford tert-butyl 4-bromobenzylcarbamate (25 g, 87.36 mmol, 81.27% yield) as white solid. ¹H NMR (400 MHz, CDCl₃) δ 7.47-7.45 (m, 1H), 7.45-7.43 (m, 1H), 7.17 (s, 1H), 7.15 (s, 1H), 4.89 (s, 1H), 4.27 (d, J=5.75 Hz, 2H), 1.46 (s, 9H).

Step 2: Synthesis of tert-butyl 4-(4-methylthiazol-5-yl)benzylcarbamate (4)

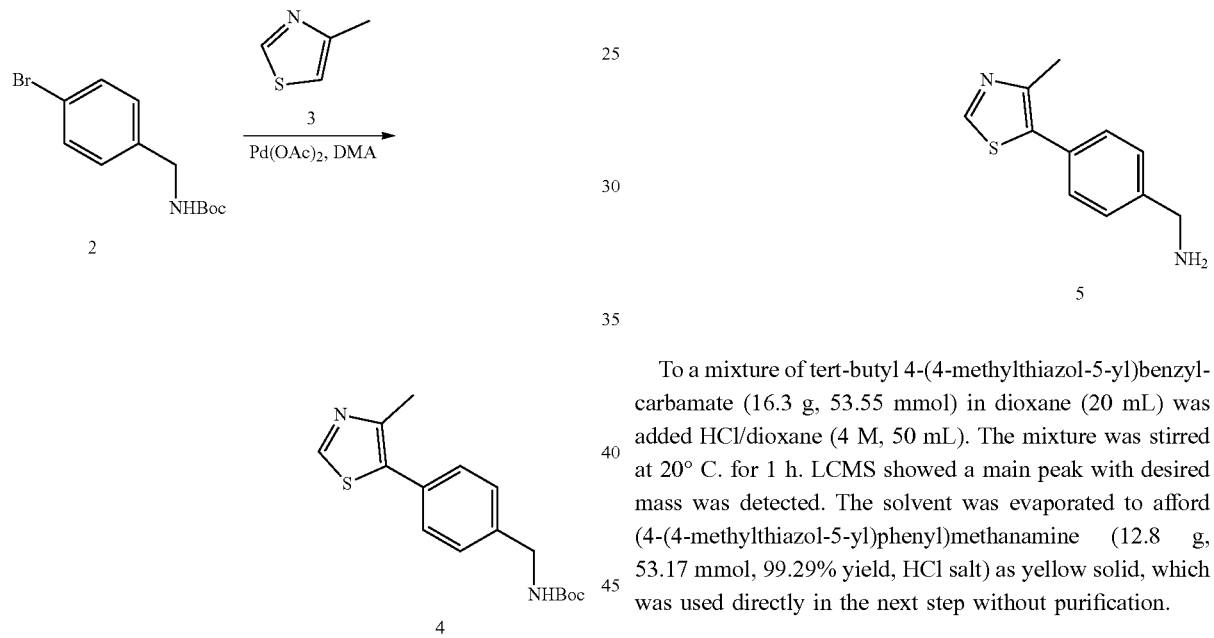

To a stirred solution of tert-butyl 4-bromobenzylcarbamate (25 g, 87.36 mmol) in DMA (150 mL) under N₂ was added 4-methylthiazole (17.32 g, 174.72 mmol, 15.89 mL), KOAc (17.15 g, 174.72 mmol) and Pd(OAc)₂ (980.68 mg, 4.37 mmol) and the resulting mixture was stirred at 120° C. for 15 h. LCMS showed a main peak with desired mass and the starting material was consumed. The mixture was filtered. The filtrate was poured into water (500 mL) and extracted with EtOAc (200 mL×3). The combined organic phase was washed with brine (500 mL×3) and concentrated under vacuum. The residue was purified by silica gel column chromatography (Petroleum ether:Ethyl acetate=1:0 to 3:1) to give tert-butyl 4-(4-methylthiazol-5-yl)benzylcarbamate (19 g, 62.42 mmol, 71.45% yield) as yellow solid.

MS (M+H)⁺=305.1

Step 3: Synthesis of (4-(4-methylthiazol-5-yl)phenyl)methanamine (5)

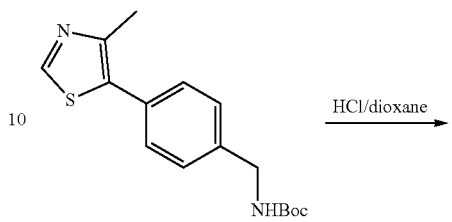

To a mixture of tert-butyl 4-(4-methylthiazol-5-yl)benzylcarbamate (16.3 g, 53.55 mmol) in dioxane (20 mL) was added HCl/dioxane (4 M, 50 mL). The mixture was stirred at 20° C. for 1 h. LCMS showed a main peak with desired mass was detected. The solvent was evaporated to afford (4-(4-methylthiazol-5-yl)phenyl)methanamine (12.8 g, 53.17 mmol, 99.29% yield, HCl salt) as yellow solid, which was used directly in the next step without purification.

Step 4: Synthesis of (2S,4R)-tert-butyl 4-hydroxy-2-((4-(4-methylthiazol-5-yl)benzyl)carbamoyl)pyrrolidine-1-carboxylate (7)

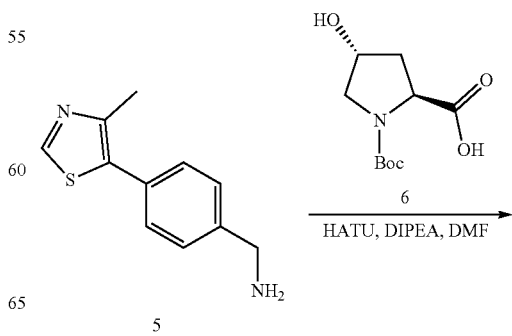

-continued

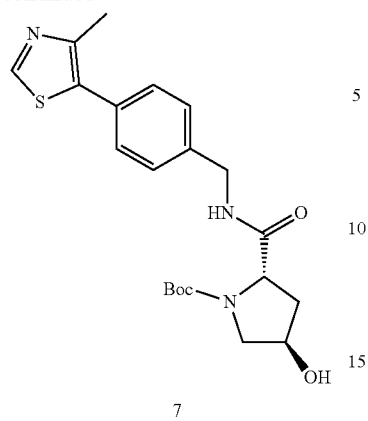

7

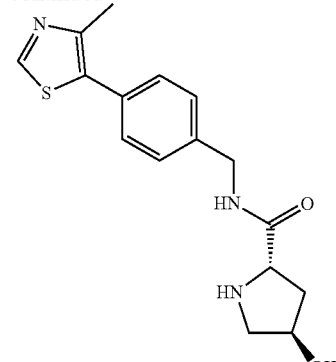

8

To a mixture of (4-(4-methylthiazol-5-yl)phenyl)methanamine (12.8 g, 53.17 mmol, HCl salt) and (2S,4R)-1-(tert-butoxycarbonyl)-4-hydroxypyrrolidine-2-carboxylic acid (12.29 g, 53.17 mmol) in DMF (100 mL) were added HATU (24.26 g, 63.80 mmol) and DIPEA (13.74 g, 106.33 mmol, 18.52 mL). The mixture was stirred at 20° C. for 16 h. LCMS showed a main peak with desired mass was detected. TLC (ethyl acetate/MeOH=10:1) showed a main new spot was formed. The mixture was poured into water (500 mL) and extracted with ethyl acetate (300 mL×2). The combined organic layer was dried over Na$_2$SO$_4$, concentrated. The residue was purified by chromatography (silica gel, eluting with ethyl acetate/MeOH=10:1) to afford (2S,4R)-tert-butyl 4-hydroxy-2-((4-(4-methylthiazol-5-yl)benzyl)carbamoyl)pyrrolidine-1-carboxylate (18 g, 43.11 mmol, 81.09% yield) as yellow oil. MS (M+H)$^+$=418.1

Step 5: Synthesis of (2S,4R)-4-hydroxy-N-(4-(4-methylthiazol-5-yl)benzyl)pyrrolidine-2-carboxamide (8)

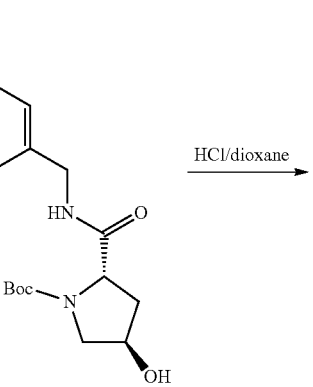

7

A mixture of (2S,4R)-tert-butyl 4-hydroxy-2-((4-(4-methylthiazol-5-yl)benzyl)carbamoyl)pyrrolidine-1-carboxylate (18 g, 43.11 mmol) and HCl/dioxane (4 M, 100 mL, 9.28 eq) was stirred at 20° C. for 2 h. LCMS showed a main peak with desired mass. The solvent was evaporated to afford (2S,4R)-4-hydroxy-N-(4-(4-methylthiazol-5-yl)benzyl)pyrrolidine-2-carboxamide (15 g, 42.39 mmol, 98.32% yield, HCl salt) as light yellow solid, which was used directly in the next step.

Step 6: Synthesis of tert-butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate (10)

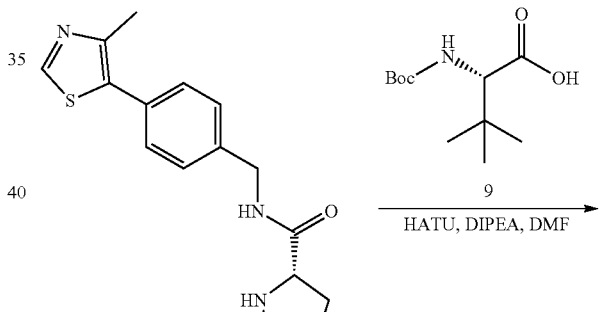

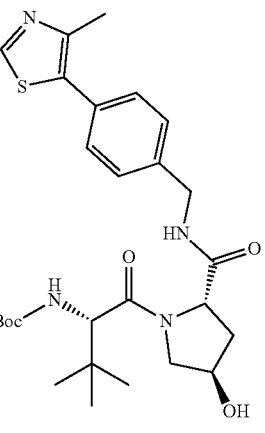

10

To a mixture of (2S,4R)-4-hydroxy-N-(4-(4-methylthiazol-5-yl)benzyl)pyrrolidine-2-carboxamide (15 g, 42.39 mmol, HCl salt) and (2S)-2-(tert-butoxycarbonylamino)-3,3-dimethyl-butanoic acid (9.80 g, 42.39 mmol) in DMF (100 mL) were added HATU (17.73 g, 46.63 mmol) and DIEA (10.96 g, 84.78 mmol, 14.77 mL). The mixture was stirred at 20° C. for 16 h. LCMS showed a main peak with desired mass. TLC (Petroleum ether/ethyl acetate=0:1) showed a main new spot was formed. The mixture was poured into water (300 mL) and extracted with DCM (200 mL×2). The combined organic layer was dried over Na$_2$SO$_4$, concentrated. The residue was purified by chromatography (silica gel, eluting with petroleum ether/ethyl acetate=1:1 to 0:1) to afford tert-butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate (19 g, 35.80 mmol, 84.46% yield) as light yellow solid. MS (M+H)$^+$=531.2

Step 7: Synthesis of (2S,4R)-1-((S)-2-amino-3,3-dimethylbutanoyl)-4-hydroxy-N-(4-(4-methylthiazol-5-yl)benzyl)pyrrolidine-2-carboxamide (11)

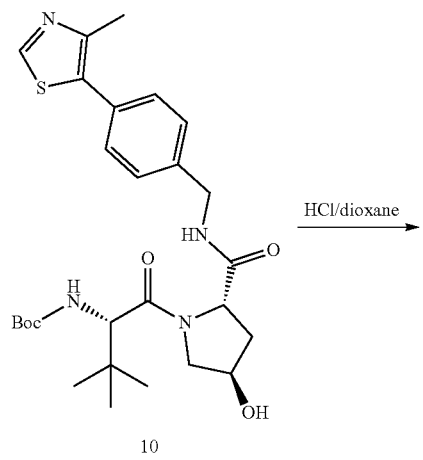

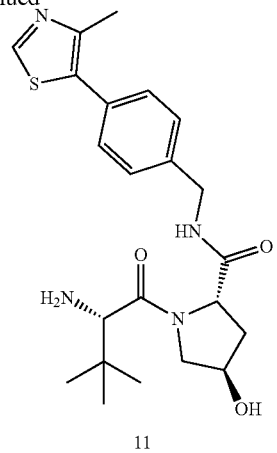

A mixture of tert-butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate (19 g, 35.80 mmol) and HCl/dioxane (4 M, 100 mL) was stirred at 20° C. for 3 h. LCMS showed a main peak with desired mass. The solvent was evaporated to afford (2S,4R)-1-((S)-2-amino-3,3-dimethylbutanoyl)-4-hydroxy-N-(4-(4-methylthiazol-5-yl)benzyl)pyrrolidine-2-carboxamide (16.7 g, 35.76 mmol, 99.87% yield, HCl salt) as light yellow solid, which was used directly in the next step without any purification. MS (M+H)$^+$=431.3

Step 8: Synthesis of (S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl 4-methylbenzenesulfonate (13)

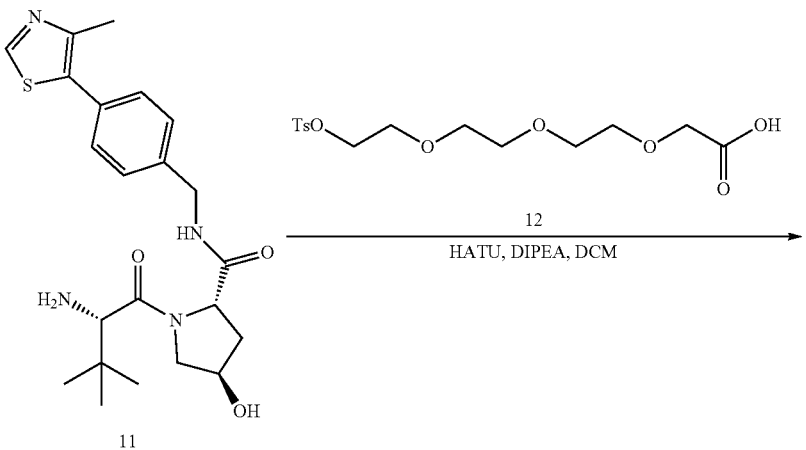

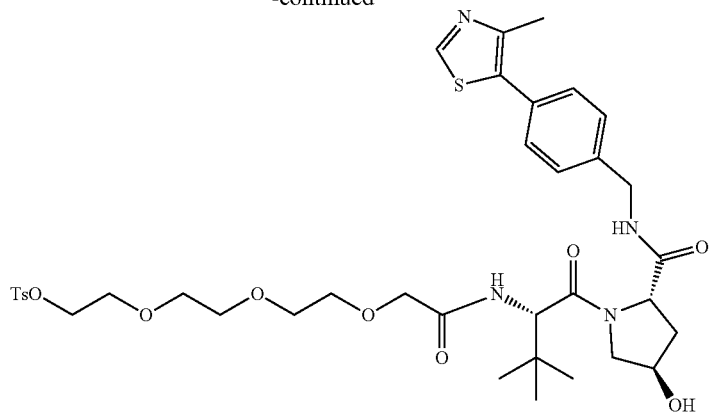

13

To a mixture of 2-(2-(2-(2-(tosyloxy)ethoxy)ethoxy)ethoxy)acetic acid (1.13 g, 3.12 mmol) and (2S,4R)-1-((S)-2-amino-3,3-dimethylbutanoyl)-4-hydroxy-N-(4-(4-methylthiazol-5-yl)benzyl)pyrrolidine-2-carboxamide (1.46 g, 3.12 mmol, HCl salt) in DCM (20 mL) were added HATU (1.30 g, 3.43 mmol) and DIEA (1.21 g, 9.35 mmol, 1.63 mL). The mixture was stirred at 20° C. for 1 h. LCMS showed a peak with 34% desired mass. The solvent was evaporated. The residue was poured into water (20 mL) and extracted with ethyl acetate (20 mL×2). The combined organic layer was dried over anhydrous Na$_2$SO$_4$, filtrated and concentrated. The residue was purified by reversed-phase HPLC (0.1% FA condition) to afford (S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl 4-methylbenzenesulfonate (550 mg, 0.696 mmol, 22.31% yield, 98% purity) as brown oil.

Step 9: Synthesis of tert-butyl 2-((4R,6R)-6-(2-(2-(4-fluorophenyl)-4-((4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)phenyl)carbamoyl)-5-isopropyl-3-phenyl-1H-pyrrol-1-yl)ethyl)-2,2-dimethyl-1,3-dioxan-4-yl)acetate (15)

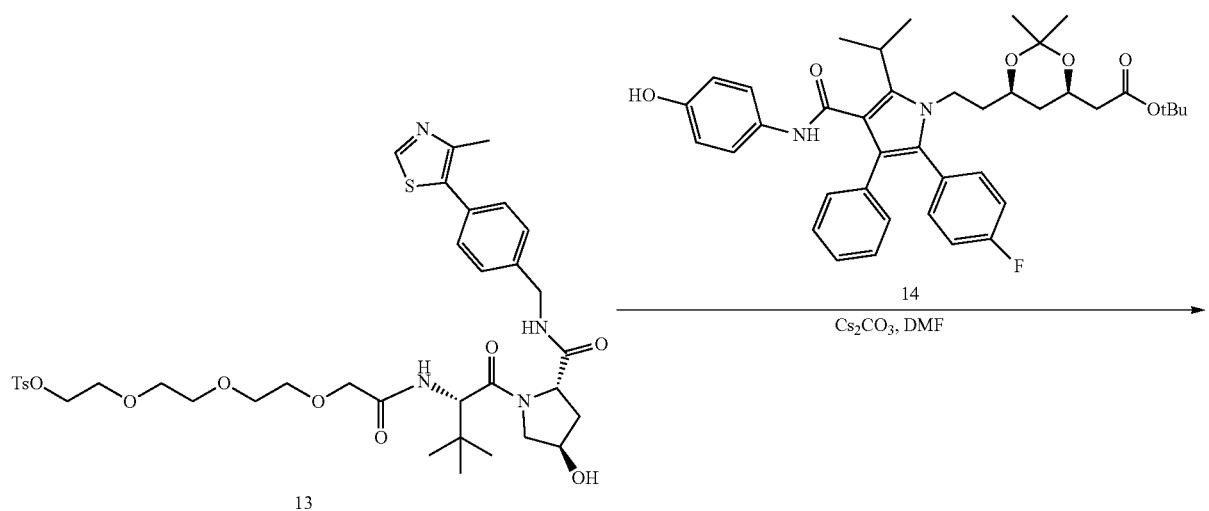

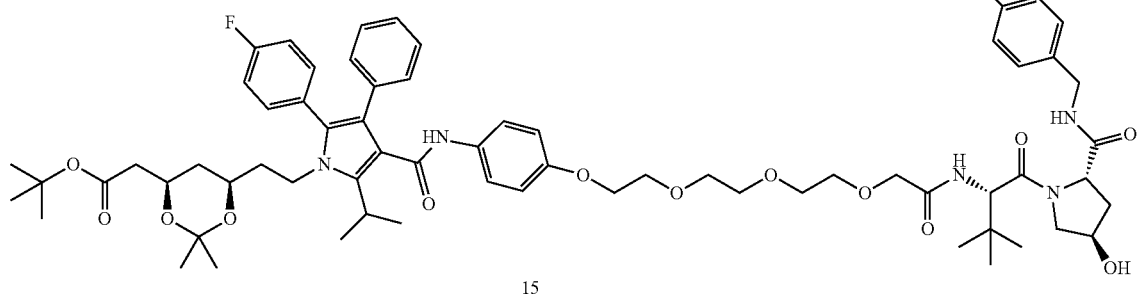

To a solution of (S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl 4-methylbenzenesulfonate (0.2 g, 0.258 mmol) and tert-butyl 2-((4R,6R)-6-(2-(2-(4-fluorophenyl)-4-((4-hydroxyphenyl)carbamoyl)-5-isopropyl-3-phenyl-1H-pyrrol-1-yl)ethyl)-2,2-dimethyl-1,3-dioxan-4-yl)acetate (173.12 mg, 0.258 mmol) in DMF (4 mL) was added $Cs_2CO_3$ (168.18 mg, 0.516 mmol) and the resulting mixture was stirred at 90° C. for 16 h. LCMS showed a peak (59%) with desired mass. The mixture was filtered and the filtrate was concentrated under vacuum. The residue was purified by reverse MPLC ($H_2O$:ACN=1:9, 1‰ FA) to give tert-butyl 2-((4R,6R)-6-(2-(2-(4-fluorophenyl)-4-((4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)phenyl)carbamoyl)-5-isopropyl-3-phenyl-1H-pyrrol-1-yl)ethyl)-2,2-dimethyl-1,3-dioxan-4-yl)acetate (150 mg, 0.118 mmol, 45.64% yield) as yellow solid. MS $(M+H)^+$=1273.6

Step 10: Synthesis of tert-butyl 2-(2-(2-(2-(tosyloxy)ethoxy)ethoxy)ethoxy)acetate (17)

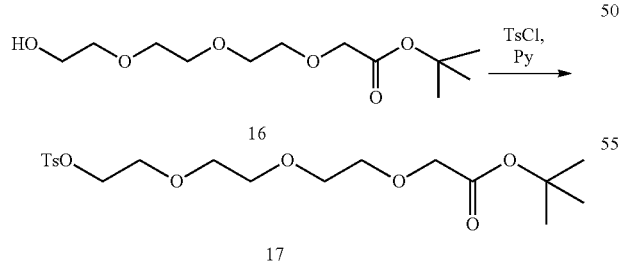

To a mixture of tert-butyl 2-[2-[2-(2-hydroxyethoxy)ethoxy]ethoxy]acetate (1 g, 3.78 mmol) in pyridine (10 mL) was added 4-methylbenzenesulfonyl chloride (1.08 g, 5.68 mmol) and the mixture was stirred at 20° C. for 16 h. LCM showed a main peak with desired mass. TLC (Petroleum ether/ethyl acetate=1:1) showed a main spot was formed. The mixture was poured into water (20 mL) and extracted with ethyl acetate (30 mL). The organic layer was washed with 1 N HCl aqueous solution (20 mL), dried over anhydrous $Na_2SO_4$, concentrated. The residue was purified by chromatography (silica gel, eluting with petroleum ether/ethyl acetate=5:1 to 1:1) to afford tert-butyl 2-(2-(2-(2-(tosyloxy)ethoxy)ethoxy)ethoxy)acetate (1.3 g, 3.11 mmol, 82.10% yield) as colorless oil. $^1$H NMR (400 MHz, $CDCl_3$) δ 7.80 (d, J=8.0 Hz, 2H), 7.34 (d, J=8.0 Hz, 2H), 4.16-4.15 (m, 2H), 4.01 (s, 2H), 3.70-3.67 (m, 4H), 3.68-3.66 (m, 2H), 3.59 (m, 4H), 2.45 (s, 3H), 1.47 (s, 9H).

Step 11: Synthesis of 2-(2-(2-(2-(tosyloxy)ethoxy)ethoxy)ethoxy)acetic acid (12)

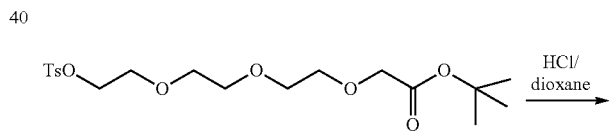

A mixture of tert-butyl 2-(2-(2-(2-(tosyloxy)ethoxy)ethoxy)ethoxy)acetate (1.3 g, 3.11 mmol) and HCl/dioxane (4 M, 10 mL) was stirred at 20° C. for 3 h. LCMS showed a main peak with desired mass. The solvent was evaporated to afford 2-(2-(2-(2-(tosyloxy)ethoxy)ethoxy)ethoxy)acetic acid (1.13 g, crude) as colorless oil, which was used directly in the next step without further purification.

Step 12: Synthesis of (3R,5R)-7-(2-(4-fluorophenyl)-4-((4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)phenyl)carbamoyl)-5-isopropyl-3-phenyl-1H-pyrrol-1-yl)-3,5-dihydroxyheptanoic acid (Compound 10)

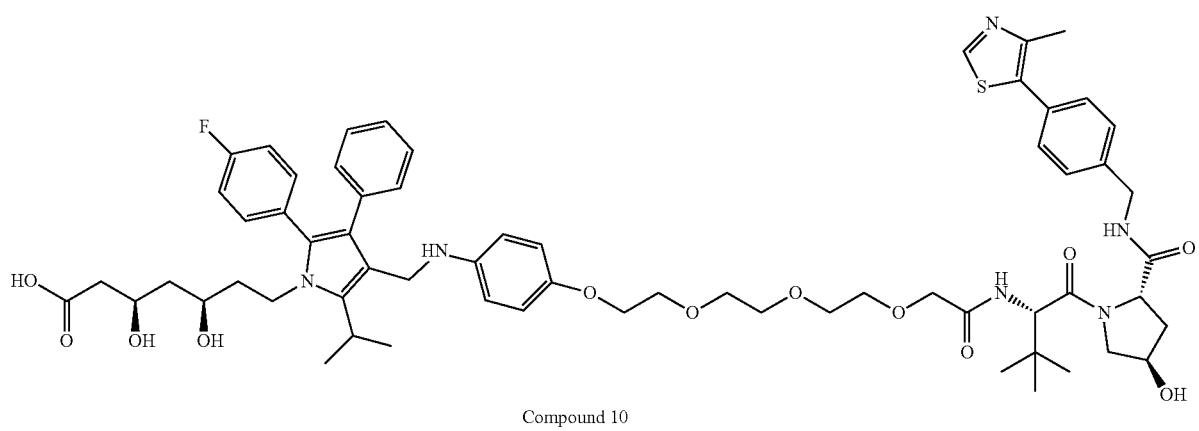

To a solution of tert-butyl 2-((4R,6R)-6-(2-(2-(4-fluorophenyl)-4-((4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)phenyl)carbamoyl)-5-isopropyl-3-phenyl-1H-pyrrol-1-yl)ethyl)-2,2-dimethyl-1,3-dioxan-4-yl)acetate (0.15 g, 0.118 mmol) in THF (8 mL) and MeOH (8 mL) was added HCl (1 M, 0.24 mL) and the resulting mixture was stirred at 30° C. for 3 h. LCMS showed a main peak with mass of intermediate. To the mixture was added a solution of NaOH (28.27 mg, 0.77 mmol) in water (0.3 mL), the mixture was stirred at 30° C. for 1 h. LCMS showed a peak (78%) with desired mass. The mixture was concentrated under vacuum. The residue was purified by prep-HPLC (column: Xtimate C18 10u 250 mm*80 mm; mobile phase: [water (0.05% ammonia hydroxide v/v)—ACN]; B %: 20%-40%, 10 min) followed by lyophilization to give (3R,5R)-7-(2-(4-fluorophenyl)-4-((4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)phenyl)carbamoyl)-5-isopropyl-3-phenyl-1H-pyrrol-1-yl)-3,5-dihydroxyheptanoic acid (92.5 mg, 0.078 mmol, 66.30% yield, 99.4% purity) as white solid.

$^1$H NMR (400 MHz, DMSO-d$_6$) δ 9.72 (s, 1H), 8.98-8.95 (m, 1H), 8.60 (t, J=5.90 Hz, 1H), 7.49 (s, 1H), 7.44-7.37 (m, 7H), 7.27-7.21 (m, 2H), 7.21-7.15 (m, 2H), 7.07 (d, J=4.14 Hz, 4H), 7.02-6.95 (m, 1H), 6.79 (d, J=8.78 Hz, 2H), 5.18 (s, 1H), 4.84 (s, 1H), 4.57 (d, J=9.54 Hz, 1H), 4.48-4.32 (m, 3H), 4.30-4.21 (m, 1H), 4.02-3.88 (m, 5H), 3.82-3.64 (m, 5H), 3.63-3.48 (m, 10H), 3.27-3.17 (m, 1H), 2.44 (s, 3H), 2.13-2.01 (m, 1H), 1.99-1.86 (m, 2H), 1.76 (dd, J=7.91, 14.93 Hz, 1H), 1.65-1.44 (m, 2H), 1.36 (d, J=6.65 Hz, 7H), 1.20-1.09 (m, 1H), 1.00-0.89 (m, 9H). MS (M+H)$^+$=1177.5

Example 11. Synthesis of (3S,5S)-7-(2-(4-fluorophenyl)-4-((4-(((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl)oxy)phenyl)carbamoyl)-5-isopropyl-3-phenyl-1H-pyrrol-1-yl)-3,5-dihydroxyheptanoic acid (Compound 11)

Step 1: Synthesis of tert-butyl 14-(tosyloxy)-3,6,9,12-tetraoxatetradecan-1-oate (2)

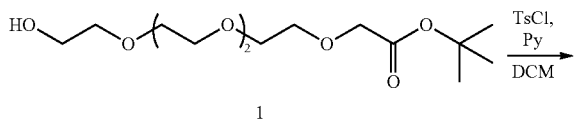

-continued

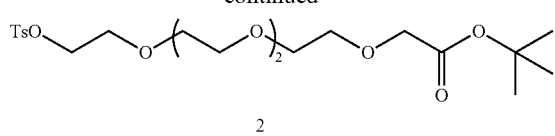

To a mixture of tert-butyl 14-hydroxy-3,6,9,12-tetraoxa-tetradecan-1-oate (1 g, 3.24 mmol) and 4-methylbenzene-sulfonyl chloride (927.37 mg, 4.86 mmol) in DCM (5 mL) was added Pyridine (513.02 mg, 6.49 mmol, 0.5 mL). The mixture was stirred at 20° C. for 16 h. LCMS showed a main peak with desired mass. TLC (Petroleum ether/ethyl acetate=1:1) showed a main new spot was formed. The mixture was poured into water (20 mL) and extracted with ethyl acetate (30 mL). The organic layer was washed with HCl (1 N, 20 mL), dried over Na$_2$SO$_4$, concentrated. The residue was purified by chromatography (silica gel, eluting with petroleum ether/ethyl acetate=1:1) to afford tert-butyl 2-[2-[2-[2-[2-(p-tolylsulfonyloxy)ethoxy]ethoxy]ethoxy]ethoxy]acetate (1.4 g, 3.03 mmol, 93.33% yield) as colorless oil.

Step 2: Synthesis of 14-(tosyloxy)-3,6,9,12-tetraoxatetradecan-1-oic acid (Linker 2)

A mixture of tert-butyl 14-(tosyloxy)-3,6,9,12-tetraoxa-tetradecan-1-oate (1.4 g, 3.03 mmol) and HCl/dioxane (4 M, 10 mL) was stirred at 20° C. for 3 h. LCMS showed a main peak with desired mass. The solvent was evaporated to afford 2-[2-[2-[2-[2-(p-tolylsulfonyloxy)ethoxy]ethoxy]ethoxy]ethoxy]acetic acid (1.2 g, 2.95 mmol, 97.55% yield) as colorless oil, which was used directly in the next step without further purification. MS (M+H)$^+$=407.3

Step 3: Synthesis of (S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl 4-methylbenzenesulfonate (3)

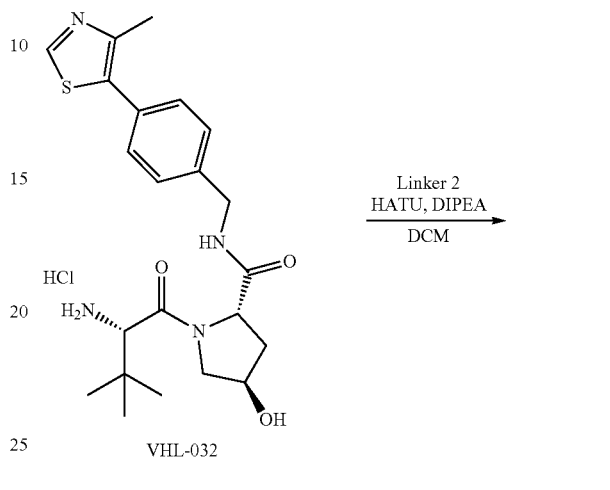

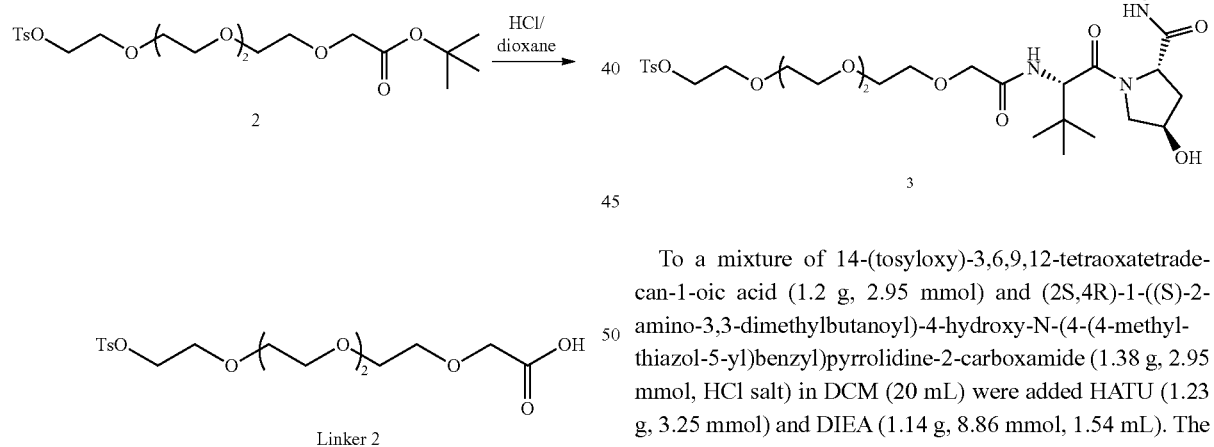

To a mixture of 14-(tosyloxy)-3,6,9,12-tetraoxatetrade-can-1-oic acid (1.2 g, 2.95 mmol) and (2S,4R)-1-((S)-2-amino-3,3-dimethylbutanoyl)-4-hydroxy-N-(4-(4-methyl-thiazol-5-yl)benzyl)pyrrolidine-2-carboxamide (1.38 g, 2.95 mmol, HCl salt) in DCM (20 mL) were added HATU (1.23 g, 3.25 mmol) and DIEA (1.14 g, 8.86 mmol, 1.54 mL). The mixture was stirred at 20° C. for 3 h. LCMS showed a peak (26.9%) with desired mass. The solvent was evaporated. The residue was diluted with water (20 mL) and extracted with ethyl acetate (20 mL×2). The combined organic layer was dried over anhydrous Na$_2$SO$_4$, concentrated. The residue was purified by reversed-phase HPLC (0.1% FA condition) to afford (S)-16-((2S,4R)-4-hydroxy-2-((4-(4-methylthi-azol-5-yl)benzyl)carbamoyl)pyrrolidine-1-carbonyl)-17,17-dimethyl-14-oxo-3,6,9,12-tetraoxa-15-azaoctadecyl 4-methylbenzenesulfonate (650 mg, 0.786 mmol, 26.61% yield, 99% purity) as light yellow oil. MS (M+H)$^+$=819.3

Step 4: Synthesis of tert-butyl 2-((4R,6R)-6-(2-(2-(4-fluorophenyl)-4-((4-(((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl)oxy)phenyl)carbamoyl)-5-isopropyl-3-phenyl-1H-pyrrol-1-yl)ethyl)-2,2-dimethyl-1,3-dioxan-4-yl)acetate (5)

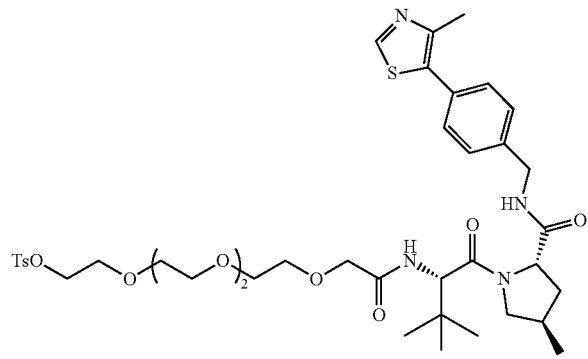
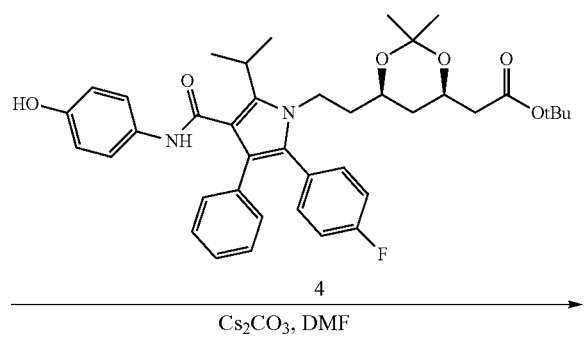

etate (245.72 mg, 0.366 mmol) in DMF (2 mL) and ACN (2 mL) was added Cs₂CO₃ (0.24 g, 0.74 mmol) The mixture was stirred at 80° C. for 6 h. LCMS showed a peak (46%) with desired mass. The combined mixture was filtered and the filtrate was concentrated under vacuum. The residue was purified by reverse MPLC (water:ACN=15:85, 1‰ FA) to give tert-butyl 2-((4R,6R)-6-(2-(2-(4-

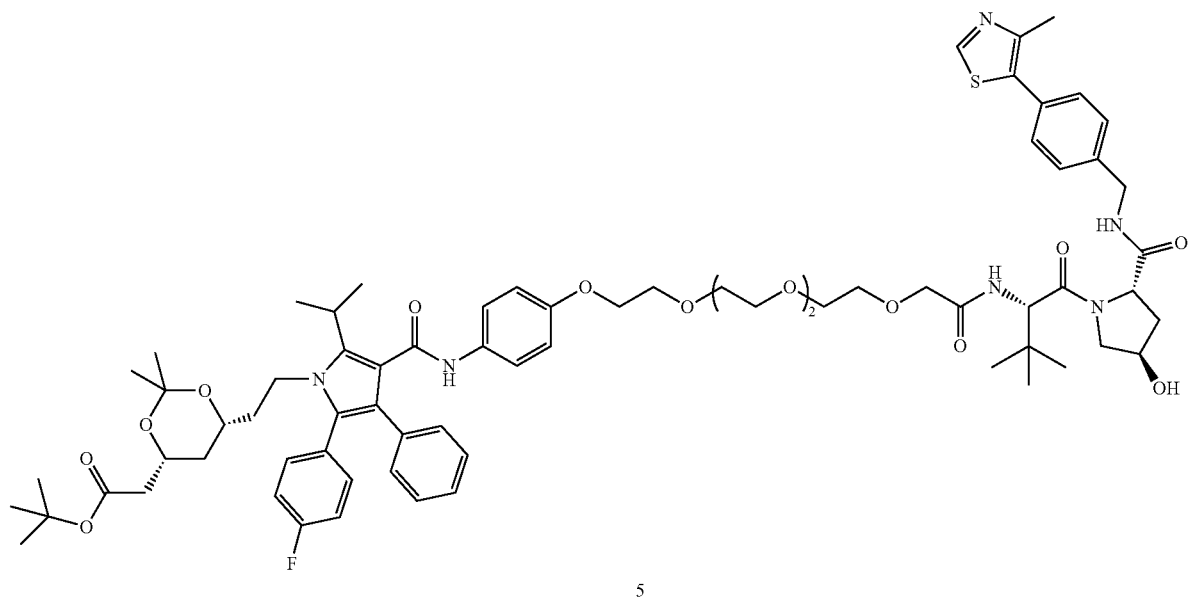

Two batches in parallel: To a solution of (S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl 4-methylbenzenesulfonate (0.3 g, 0.37 mmol) and tert-butyl 2-((4R,6R)-6-(2-(2-(4-fluorophenyl)-4-((4-hydroxyphenyl)carbamoyl)-5-isopropyl-3-phenyl-1H-pyrrol-1-yl)ethyl)-2,2-dimethyl-1,3-dioxan-4-yl)ac- (((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl)oxy)phenyl)carbamoyl)-5-isopropyl-3-phenyl-1H-pyrrol-1-yl)ethyl)-2,2-dimethyl-1,3-dioxan-4-yl)acetate (0.33 g, 0.25 mmol, 34.19% yield) as yellow solid. MS (M+H)⁺=1317.6

Step 5: Synthesis of (3R,5R)-7-(2-(4-fluorophenyl)-4-((4-(((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl)oxy)phenyl)carbamoyl)-5-isopropyl-3-phenyl-1H-pyrrol-1-yl)-3,5-dihydroxyheptanoic acid (Compound 11)

and concentrated under vacuum. The residue was purified by prep-HPLC (column: Waters Xbridge C18 150*50 mm*10 um; mobile phase: [water (10 mM NH₄HCO₃)—ACN]; B %: 17%-47%, 11.5 min) followed by lyophilization to give (3R,5R)-7-(2-(4-fluorophenyl)-4-((4-(((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-

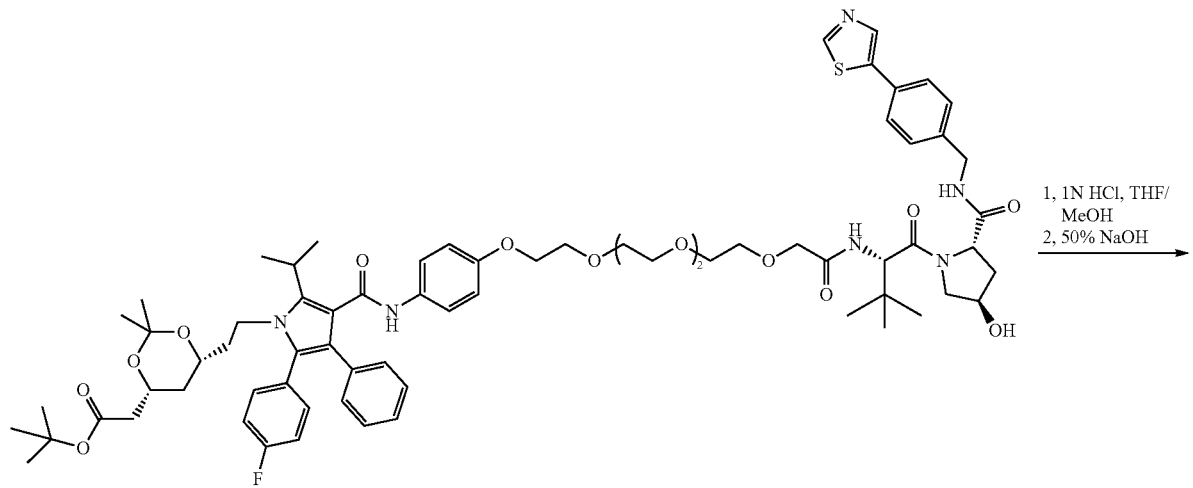

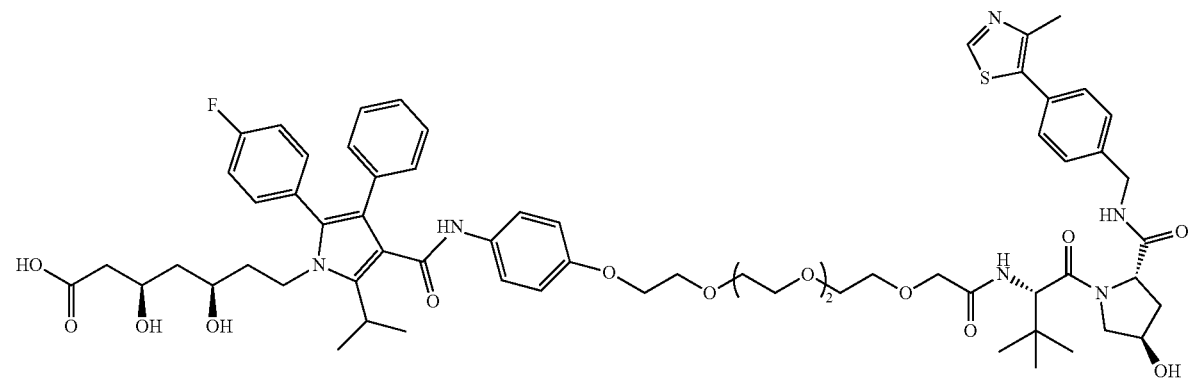

Compound 11

To a solution of tert-butyl 2-((4R,6R)-6-(2-(2-(4-fluorophenyl)-4-((4-(((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl)oxy)phenyl)carbamoyl)-5-isopropyl-3-phenyl-1H-pyrrol-1-yl)ethyl)-2,2-dimethyl-1,3-dioxan-4-yl)acetate (0.33 g, 0.25 mmol) in THF (2 mL) and MeOH (2 mL) was added HCl (1 M, 0.5 mL) and the resulting mixture was stirred at 30° C. for 3 h. LCMS showed a main peak with mass of intermediate. To the mixture was added a solution of NaOH (60.10 mg, 1.50 mmol) in water (0.6 mL) and the mixture was stirred at 30° C. for 1 h. LCMS showed a main peak with desired mass. The pH was adjusted to 8-9 with HCl (1 N) tetraoxa-15-azaoctadecyl)oxy)phenyl)carbamoyl)-5-isopropyl-3-phenyl-1H-pyrrol-1-yl)-3,5-dihydroxyheptanoic acid (212.9 mg, 0.173 mmol, 69.18% yield, 99.4% purity) as white solid. $^1$H NMR (400 MHz, DMSO-$d_6$) δ 9.65 (s, 1H), 9.01-8.92 (m, 1H), 8.59 (t, J=5.93 Hz, 1H), 7.46-7.37 (m, 7H), 7.28-7.14 (m, 4H), 7.10-7.04 (m, 4H), 7.03-6.97 (m, 1H), 6.80 (d, J=9.05 Hz, 2H), 5.15 (s, 1H), 4.56 (d, J=9.66 Hz, 1H), 4.48-4.32 (m, 3H), 4.30-4.21 (m, 1H), 4.04-3.88 (m, 5H), 3.86-3.73 (m, 2H), 3.72-3.64 (m, 3H), 3.63-3.48 (m, 16H), 3.26-3.16 (m, 3H), 2.45-2.43 (m, 3H), 2.28-2.20 (m, 1H), 2.19-2.11 (m, 1H), 2.09-2.02 (m, 1H), 1.93-1.87 (m, 1H), 1.68-1.49 (m, 2H), 1.47-1.24 (m, 9H), 1.00-0.89 (m, 9H). MS (M+H)$^+$=1221.2

Example 12. Synthesis of (3S,5S)-7-(2-(4-fluorophenyl)-4-((4-(((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)oxy)phenyl)carbamoyl)-5-isopropyl-3-phenyl-1H-pyrrol-1-yl)-3,5-dihydroxyheptanoic acid (Compound 12)

Step 1: Synthesis of ethyl 17-hydroxy-3,6,9,12,15-pentaoxaheptadecan-1-oate (2)

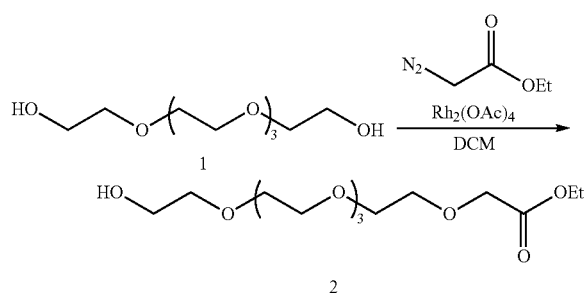

To a solution of 2-[2-[2-[2-(2-hydroxyethoxy)ethoxy]ethoxy]ethoxy]ethanol (5 g, 20.98 mmol) and Rh₂(OAc)₄ (0.5 g, 1.13 mmol) in DCM (300 mL) was added (2-ethoxy-2-oxo-ethyl)iminioazanide (2.5 g, 21.53 mmol) drop-wise, the mixture was stirred at 25° C. for 2 h. TLC (EtOAc:MeOH=10:1) showed three new spots and the starting material remained. The mixture was concentrated under vacuum. The residue was purified by silica gel column chromatography (PE:EtOAc=1:1 to 0:1) to give ethyl 17-hydroxy-3,6,9,12,15-pentaoxaheptadecan-1-oate (1.8 g, 5.55 mmol, 26.45% yield) as blue oil.

Step 2: Synthesis of ethyl 17-(tosyloxy)-3,6,9,12,15-pentaoxaheptadecan-1-oate (3)

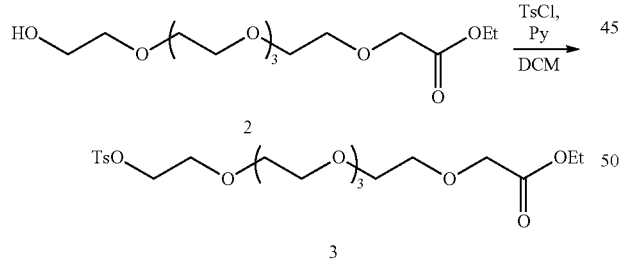

To a solution of ethyl 17-hydroxy-3,6,9,12,15-pentaoxaheptadecan-1-oate (1.8 g, 5.55 mmol) and TosCl (1.38 g, 7.21 mmol) in DCM (20 mL) was added Pyridine (980.00 mg, 12.39 mmol, 1 mL) and the mixture was stirred at 25° C. for 16 h. LCMS showed a peak with desired mass. The mixture was concentrated under vacuum. The residue was purified by silica gel chromatography (PE:EtOAc=1:1 to 1:9) to give ethyl 17-(tosyloxy)-3,6,9,12,15-pentaoxaheptadecan-1-oate (0.6 g, 1.25 mmol, 22.53% yield) as light yellow oil and ethyl 17-(tosyloxy)-3,6,9,12,15-pentaoxaheptadecan-1-oate (2.4 g, crude) as yellow oil. MS (M+H)⁺= 479.1

Step 3: Synthesis of 17-(tosyloxy)-3,6,9,12,15-pentaoxaheptadecan-1-oic acid (Linker 2)

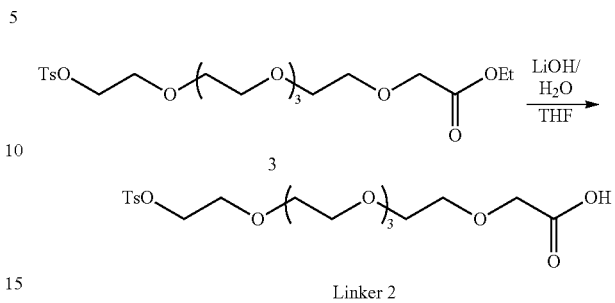

To a solution of ethyl 17-(tosyloxy)-3,6,9,12,15-pentaoxaheptadecan-1-oate (3 g, 6.27 mmol) in THF (5 mL) was added a solution of LiOH.H₂O (500.00 mg, 11.92 mmol) in Water (5 mL) and the mixture was stirred at 25° C. for 1 h. LCMS showed a main peak with desired mass. The pH was adjusted to 3-7 with HCl (5 N), the mixture was concentrated under vacuum to give 17-(tosyloxy)-3,6,9,12,15-pentaoxaheptadecan-1-oic acid (3 g, crude, Li salt) as yellow oil, which was used into the next step directly.

Step 4: Synthesis of (5)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl 4-methylbenzenesulfonate (4)

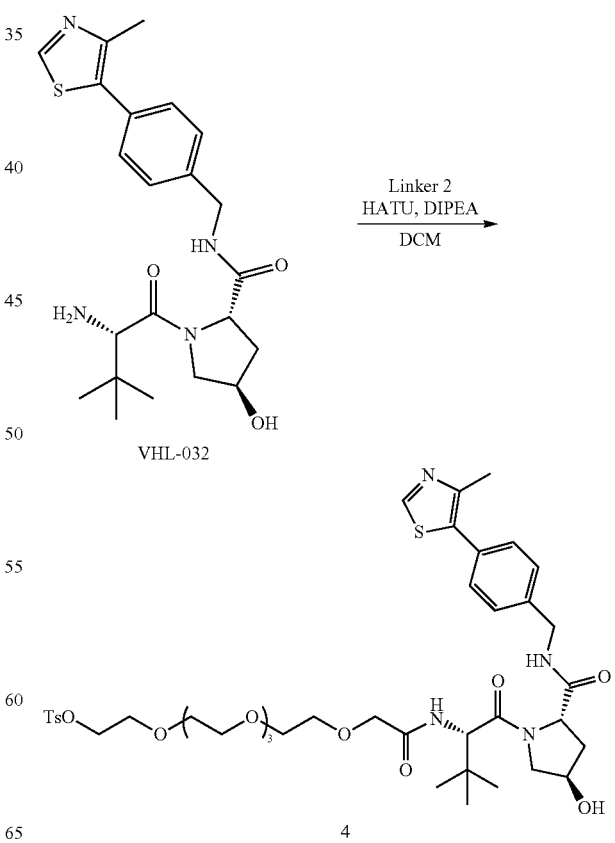

To a solution of 17-(tosyloxy)-3,6,9,12,15-pentaoxaheptadecan-1-oic acid (2.3 g, 5.03 mmol, Li salt), (2S,4R)-1-[(2S)-2-amino-3,3-dimethyl-butanoyl]-4-hydroxy-N-[ [4-(4-methylthiazol-5-yl)phenyl]methyl]pyrrolidine-2-carboxamide (3.48 g, 7.45 mmol, HCl salt) and DIEA (2.60 g, 20.12 mmol, 3.50 mL) in DCM (50 mL) was added HATU (2.29 g, 6.04 mmol) and the mixture was stirred at 25° C. for 15 h. LCMS showed a peak with desired mass. The mixture was concentrated under vacuum. The residue was purified by reversed-phase HPLC (0.1% FA condition, 70% ACN) to give (S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl 4-methylbenzenesulfonate (0.6 g, 695.21 umol, 13.82% yield) as yellow oil. MS $(M+H)^+=863.4$ Step 5: Synthesis of tert-butyl 2-((4R,6R)-6-(2-(2-(4-fluorophenyl)-4-((4-(((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)oxy)phenyl)carbamoyl)-5-isopropyl-3-phenyl-1H-pyrrol-1-yl)ethyl)-2,2-dimethyl-1,3-dioxan-4-yl)acetate (6)

To a solution of (S)-19-((2S,4R)-4-hydroxy-2-((4-(4-methylthiazol-5-yl)benzyl)carbamoyl)pyrrolidin-1-carbonyl)-20,20-dimethyl-17-oxo-3,6,9,12,15-pentaoxa-18-azahenicosyl 4-methylbenzenesulfonate (0.6 g, 695.21 umol) and tert-butyl 2-[(4R,6R)-6-[2-[2-(4-fluorophenyl)-4-[(4-hydroxyphenyl)carbamoyl]-5-isopropyl-3-phenyl-pyrrol-1-yl]ethyl]-2,2-dimethyl-1,3-dioxan-4-yl]acetate (466.35 mg, 695.21 umol) in ACN (10 mL) was added $Cs_2CO_3$ (453.03 mg, 1.39 mmol) and the resulting mixture was stirred at 90° C. for 16 h. LCMS showed a peak (65%) with desired mass and a little starting material remained. The mixture was filtered. The filtrate was purified by reversed-phase HPLC (0.1% FA condition, 85% ACN) to give tert-butyl 2-((4R,6R)-6-(2-(2-(4-fluorophenyl)-4-(((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)oxy)phenyl)carbamoyl)-5-isopropyl-3-phenyl-1H-pyrrol-1-yl)ethyl)-2,2-dimethyl-1,3-dioxan-4-yl)acetate (0.45 g, 330.48 umol, 47.54% yield) as yellow oil. MS $(M+H)^+=1361.8$

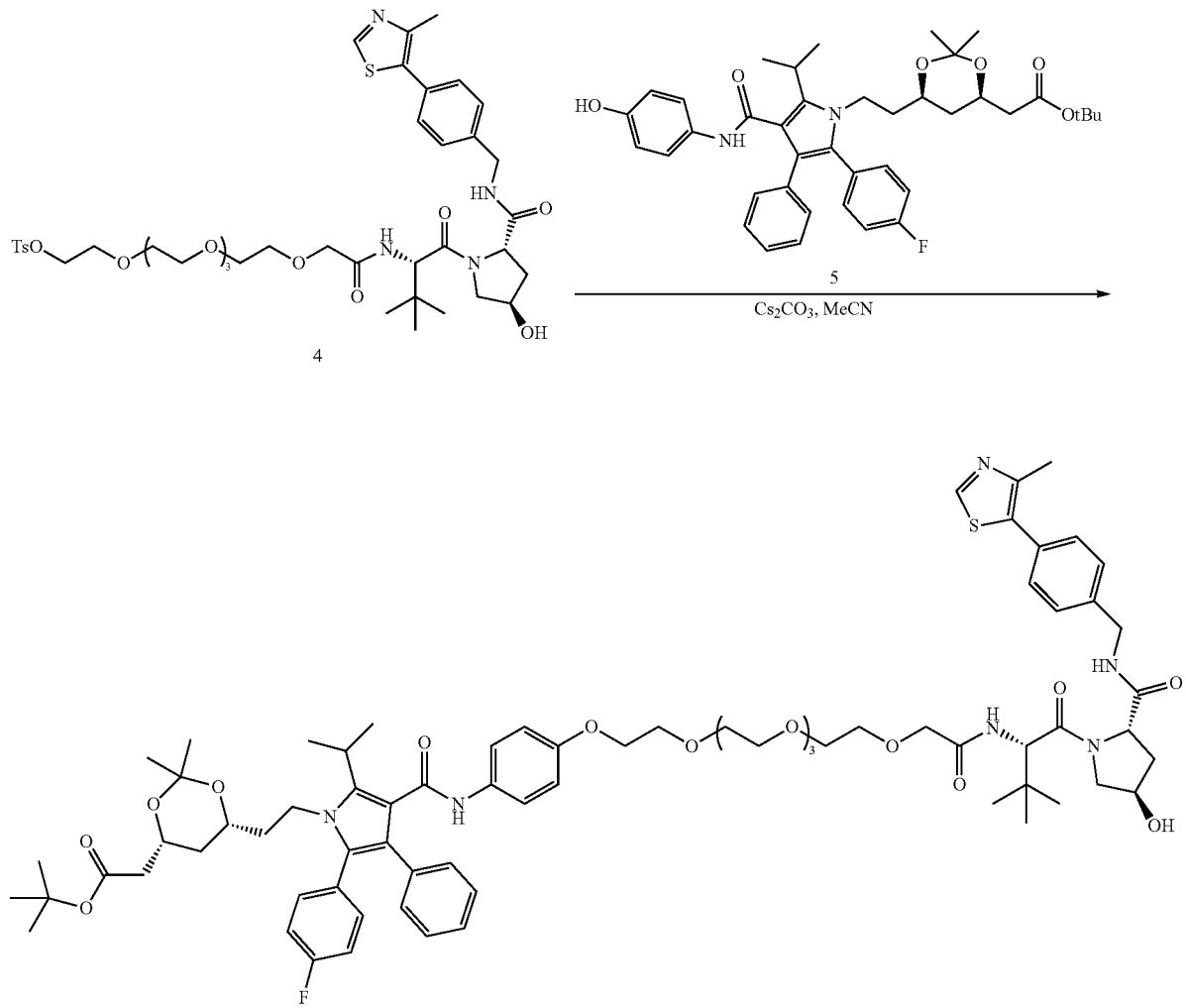

Step 6: Synthesis of (3R,5R)-7-(2-(4-fluorophenyl)-4-((4-(((S)-19-((2S,4R)-4-hydroxy-2-((4-(4-methyl-thiazol-5-yl)benzyl)carbamoyl)pyrrolidine-1-carbonyl)-20,20-dimethyl-17-oxo-3,6,9,12,15-pentaoxa-18-azahenicosyl)oxy)phenyl)carbamoyl)-5-isopropyl-3-phenyl-1H-pyrrol-1-yl)-3,5-dihydroxyheptanoic acid (Compound 12)

100*25 mm*3 um; mobile phase: [water (0.04% NH₃H₂O)—ACN]; B %: 16%-46%, 10 min) followed by lyophilization to give (3R,5R)-7-(2-(4-fluorophenyl)-4-(((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)oxy)phenyl)carbamoyl)-5-isopropyl-3-phenyl-1H-pyrrol-1-yl)-3,5-

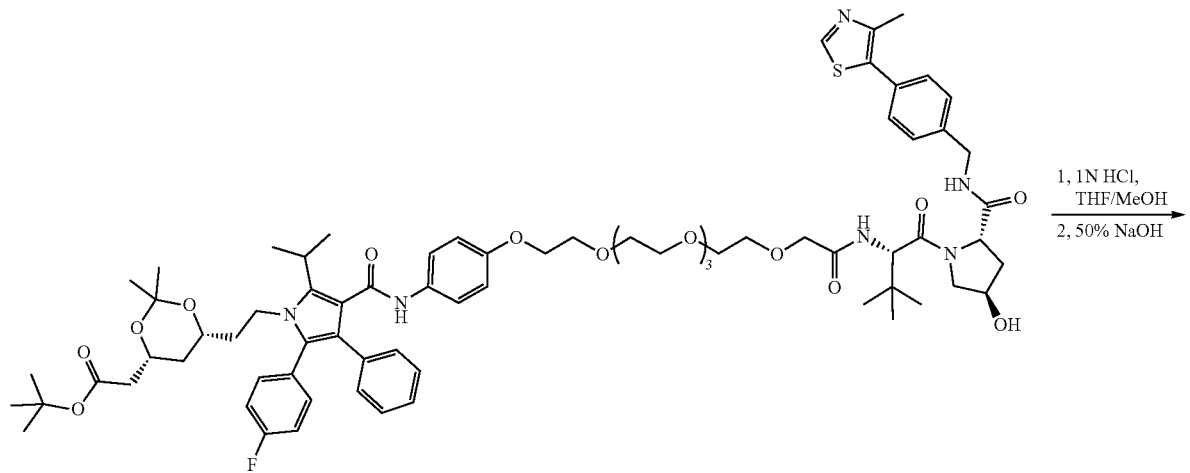

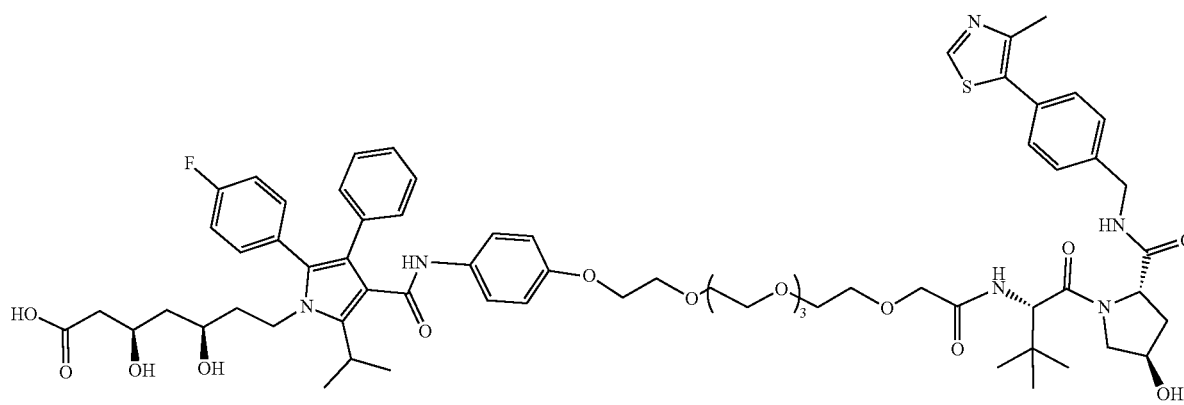

Compound 12

To a solution of tert-butyl 2-((4R,6R)-6-(2-(2-(4-fluorophenyl)-4-((4-(((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)oxy)phenyl)carbamoyl)-5-isopropyl-3-phenyl-1H-pyrrol-1-yl)ethyl)-2,2-dimethyl-1,3-dioxan-4-yl)acetate (0.23 g, 168.91 umol) in THF (2 mL) and MeOH (2 mL) was added HCl (1 M, 337.82 uL) and the mixture was stirred at 30° C. for 3 h. LCMS showed a main peak with mass of intermediate. To the mixture was added a solution of NaOH (40.54 mg, 1.01 mmol) in Water (0.05 mL), the mixture was stirred at 30° C. for 1 h. LCMS showed a main peak with desired mass. The pH was adjusted to 7-9 by 1N HCl, the mixture was filtered. The filtrate was purified by prep-HPLC (column: Welch Xtimate C18 dihydroxyheptanoic acid (125.4 mg, 0.098 mmol, 58.25% yield, 99.3% purity) as white solid.

1H NMR (400 MHz, DMSO-d6) δ 9.70 (s, 1H), 8.99-8.96 (m, 1H), 8.61 (t, J=5.96 Hz, 1H), 7.45-7.37 (m, 7H), 7.28-7.14 (m, 4H), 7.10-7.04 (m, 4H), 7.03-6.96 (m, 1H), 6.80 (d, J=9.03 Hz, 2H), 5.22 (s, 1H), 4.57 (d, J=9.54 Hz, 1H), 4.48-4.33 (m, 3H), 4.29-4.21 (m, 1H), 4.04-3.98 (m, 2H), 3.96 (s, 2H), 3.94-3.88 (m, 1H), 3.78 (dd, J=4.45, 10.60 Hz, 1H), 3.72-3.64 (m, 4H), 3.63-3.58 (m, 3H), 3.58-3.49 (m, 13H), 3.48 (s, 3H), 3.26-3.17 (m, 1H), 2.46-2.43 (m, 3H), 2.11-2.03 (m, 1H), 1.99 (dd, J=4.20, 15.00 Hz, 1H), 2.01-1.96 (m, 1H), 1.85-1.75 (m, 1H), 1.66-1.44 (m, 2H), 1.36 (d, J=6.40 Hz, 7H), 1.19-1.13 (m, 1H), 1.00-0.87 (m, 9H). MS (M+H)+=1265.0

Example 13. Synthesis of (3S,5S)-7-(2-(4-fluoro-phenyl)-4-((4-(((((S)-22-((2S,4R)-4-hydroxy-2-((4-(4-methylthiazol-5-yl)benzyl)carbamoyl)pyrrolidine-1-carbonyl)-23,23-dimethyl-20-oxo-3,6,9,12,15,18-hexaoxa-21-azatetracosyl)oxy)phenyl)carbamoyl)-5-isopropyl-3-phenyl-1H-pyrrol-1-yl)-3,5-dihydroxyheptanoic acid (Compound 13)

Step 1: Synthesis of ethyl 20-hydroxy-3,6,9,12,15,18-hexaoxaicosan-1-oate (2)

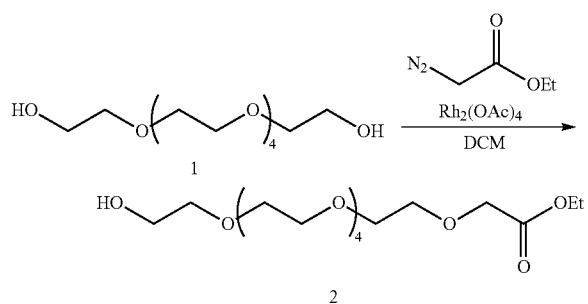

To a solution of 3,6,9,12,15-pentaoxaheptadecane-1,17-diol (5 g, 17.71 mmol) and Rh$_2$(OAc)$_4$ (0.7 g, 1.58 mmol) in DCM (200 mL) was added (2-ethoxy-2-oxo-ethyl)iminioazanide (2.60 g, 21.25 mmol) drop-wise, the mixture was stirred at 20° C. for 16 h. TLC (Ethyl acetate:Methanol=10:1) showed two new spots and the starting material remained. The mixture was concentrated under vacuum. The residue was purified by silica gel column chromatography (Ethyl acetate:Methanol=1:0 to 10:1) to give ethyl 20-hydroxy-3,6,9,12,15,18-hexaoxaicosan-1-oate (2.5 g, 6.79 mmol, 38.32% yield) as blue liquid.

Step 2: Synthesis of ethyl 20-(tosyloxy)-3,6,9,12,15,18-hexaoxaicosan-1-oate (3)

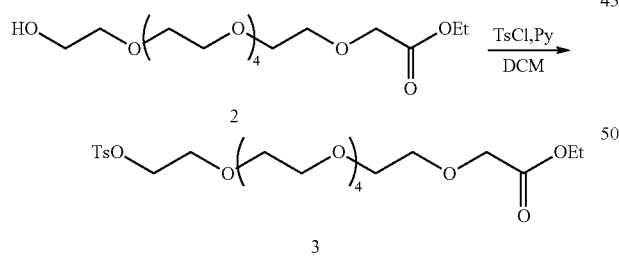

To a solution of ethyl 20-hydroxy-3,6,9,12,15,18-hexaoxaicosan-1-oate (2.5 g, 6.79 mmol) in DCM (25 mL) was added Tosyl chloride (1.80 g, 9.44 mmol) and Pyridine (1.07 g, 13.57 mmol, 1.10 mL) drop-wise, the mixture was stirred at 20° C. for 4 h. LCMS showed a peak with desired mass. Then the mixture was stirred at 20° C. for 12 h. The mixture was concentrated under vacuum. The residue was purified by silica gel chromatography (PE:EtOAc=1:1 to 0:1) to give ethyl 20-(tosyloxy)-3,6,9,12,15,18-hexaoxaicosan-1-oate (2 g, 3.83 mmol, 56.40% yield) as yellow oil. MS (M+H)$^+$=523.2

Step 3: Synthesis of 20-(tosyloxy)-3,6,9,12,15,18-hexaoxaicosan-1-oic acid (Linker 2)

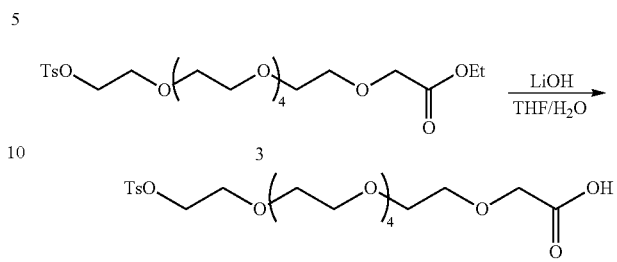

To a solution of ethyl 20-(tosyloxy)-3,6,9,12,15,18-hexaoxaicosan-1-oate (1 g, 1.91 mmol) in THF (10 mL) was added a solution of LiOH.H$_2$O (160.00 mg, 3.81 mmol) in Water (10 mL), the mixture was stirred at 25° C. for 1 h. LCMS showed a main peak with desired mass. The pH was adjusted to 6-7 by HCl (1 N), then the mixture was concentrated under vacuum to give 20-(tosyloxy)-3,6,9,12,15,18-hexaoxaicosan-1-oic acid (1 g, crude, Li salt) as yellow oil, which was used directly in the next step. MS (M+H)$^+$=495.2

Step 4: Synthesis of (S)-22-((2S,4R)-4-hydroxy-2-((4-(4-methylthiazol-5-yl)benzyl)carbamoyl)pyrrolidine-1-carbonyl)-23,23-dimethyl-20-oxo-3,6,9,12,15,18-hexaoxa-21-azatetracosyl 4-methylbenzenesulfonate (4)

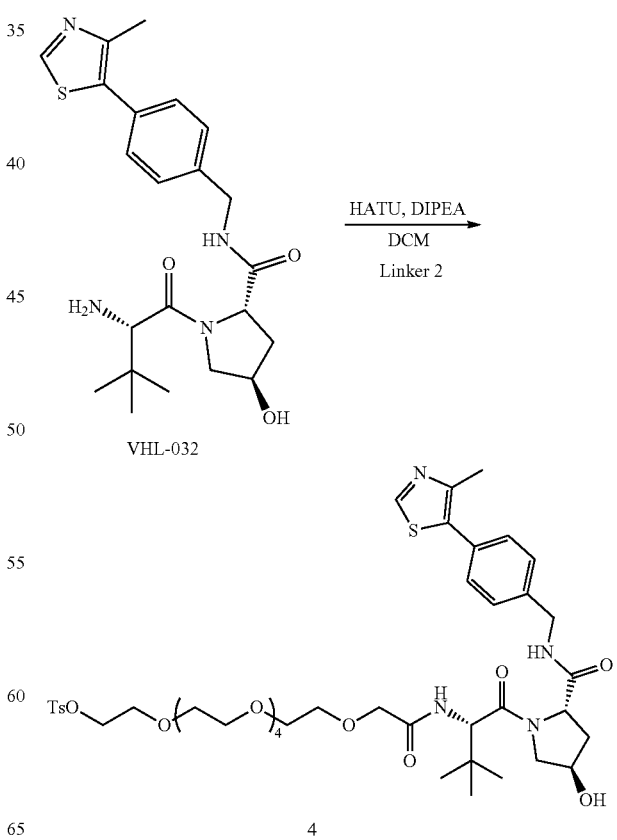

To a solution of 20-(tosyloxy)-3,6,9,12,15,18-hexaoxaicosan-1-oic acid (1 g, crude Li salt), HATU (0.9 g, 2.37 mmol) and DIEA (1.29 g, 9.97 mmol, 1.74 mL) in DCM (20 mL) was added (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (0.94 g, 2.01 mmol, HCl salt) and the mixture was stirred at 25° C. for 3 h. LCMS showed a peak (60%) with desired mass. The mixture was washed with water (10 mL×3) and concentrated under vacuum. The residue was purified by reversed-phase HPLC (0.1% FA condition, 55% ACN) to give (S)-22-((2S,4R)-4-hydroxy-2-((4-(4-methylthiazol-5-yl)benzyl)carbamoyl)pyrrolidine-1-carbonyl)-23,23-dimethyl-20-oxo-3,6,9,12,15,18-hexaoxa-21-azatetracosyl 4-methylbenzenesulfonate (0.3 g, 330.72 umol, 16.59% yield) as yellow oil. MS (M+H)$^+$=907.5

Step 5: Synthesis of tert-butyl 2-((4R,6R)-6-(2-(2-(4-fluorophenyl)-4-((4-(((S)-22-((2S,4R)-4-hydroxy-2-((4-(4-methylthiazol-5-yl)benzyl)carbamoyl)pyrrolidine-1-carbonyl)-23,23-dimethyl-20-oxo-3,6,9,12,15,18-hexaoxa-21-azatetracosyl)oxy)phenyl)carbamoyl)-5-isopropyl-3-phenyl-1H-pyrrol-1-yl)ethyl)-2,2-dimethyl-1,3-dioxan-4-yl)acetate (6)

To a solution of (S)-22-((2S,4R)-4-hydroxy-2-((4-(4-methylthiazol-5-yl)benzyl)carbamoyl)pyrrolidine-1-carbonyl)-23,23-dimethyl-20-oxo-3,6,9,12,15,18-hexaoxa-21-azatetracosyl 4-methylbenzenesulfonate (0.3 g, 0.33 mmol) and tert-butyl 2-[(4R,6R)-6-[2-[2-(4-fluorophenyl)-4-[(4-hydroxyphenyl)carbamoyl]-5-isopropyl-3-phenyl-pyrrol-1-yl]ethyl]-2,2-dimethyl-1,3-dioxan-4-yl]acetate (221.85 mg, 330.72 umol) in ACN (10 mL) was added Cs$_2$CO$_3$ (215.51 mg, 0.66 mmol), the mixture was stirred at 90° C. for 15 h. LCMS showed a peak (40%) with desired mass. The mixture was filtered and the filtrate was concentrated under vacuum. The residue was purified by reversed-phase HPLC (0.1% FA condition, 85% ACN) to give tert-butyl 2-((4R,6R)-6-(2-(2-(4-fluorophenyl)-4-((4-(((S)-22-((2S,4R)-4-hydroxy-2-((4-(4-methylthiazol-5-yl)benzyl)carbamoyl)pyrrolidine-1-carbonyl)-23,23-dimethyl-20-oxo-3,6,9,12,15,18-hexaoxa-21-azatetracosyl)oxy)phenyl)carbamoyl)-5-isopropyl-3-phenyl-1H-pyrrol-1-yl)ethyl)-2,2-dimethyl-1,3-dioxan-4-yl)acetate (0.2 g, 0.142 mmol, 43.02% yield) as brown oil.

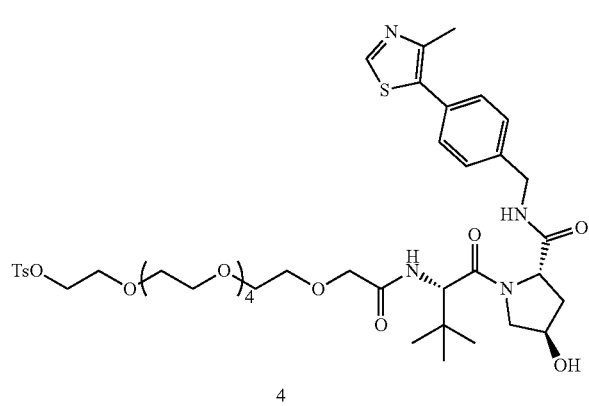

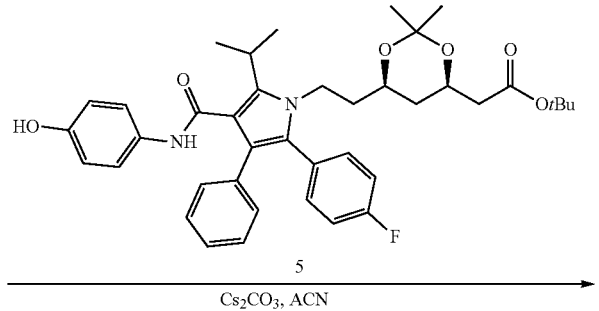

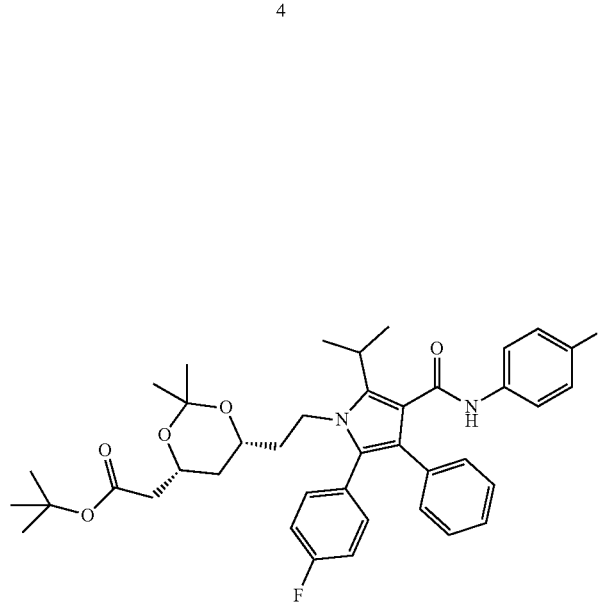

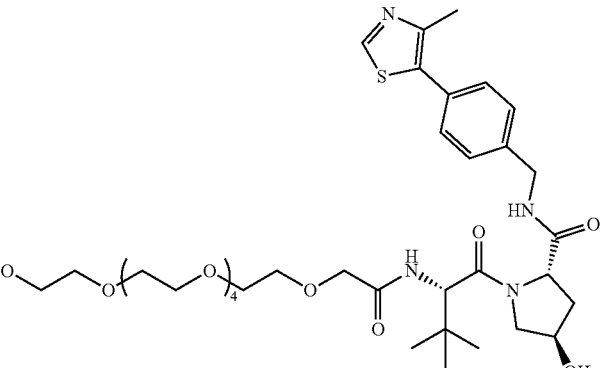

Step 6: Synthesis of (3R,5R)-7-(2-(4-fluorophenyl)-4-((4-(((S)-22-((2S,4R)-4-hydroxy-2-((4-(4-methyl-thiazol-5-yl)benzyl)carbamoyl)pyrrolidine-1-carbonyl)-23,23-dimethyl-20-oxo-3,6,9,12,15,18-hexaoxa-21-azatetracosyl)oxy)phenyl)carbamoyl)-5-isopropyl-3-phenyl-1H-pyrrol-1-yl)-3,5-dihydroxyheptanoic acid (Compound 13)

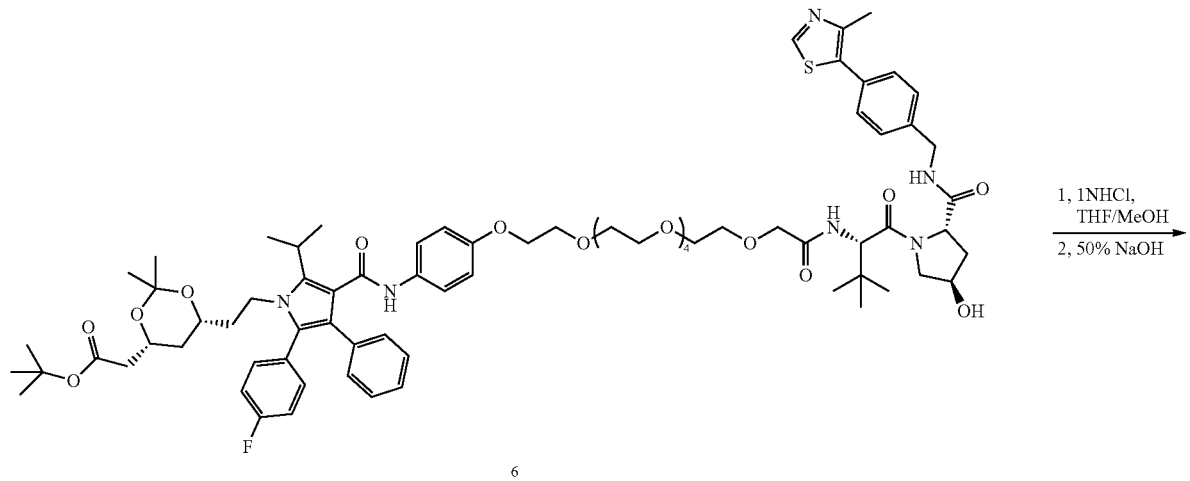

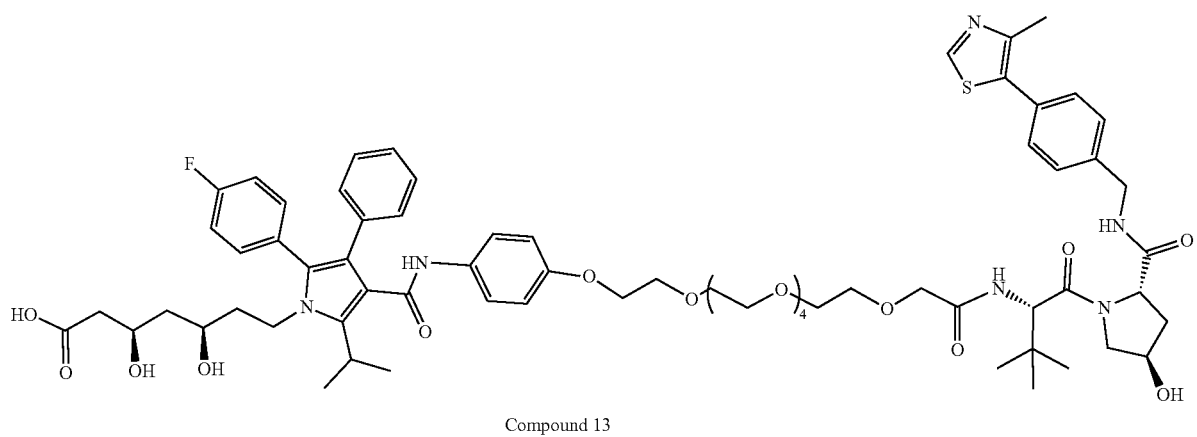

Compound 13

To a solution of tert-butyl 2-((4R,6R)-6-(2-(2-(4-fluorophenyl)-4-((4-(((S)-22-((2S,4R)-4-hydroxy-2-((4-(4-methylthiazol-5-yl)benzyl)carbamoyl)pyrrolidine-1-carbonyl)-23,23-dimethyl-20-oxo-3,6,9,12,15,18-hexaoxa-21-azatetracosyl)oxy)phenyl)carbamoyl)-5-isopropyl-3-phenyl-1H-pyrrol-1-yl)ethyl)-2,2-dimethyl-1,3-dioxan-4-yl)acetate (0.2 g, 0.142 mmol) in THF (2 mL) and MeOH (2 mL) was added HCl (1 M, 0.28 5 mL), the mixture was stirred at 30° C. for 3 h. LCMS showed a peak with mass of intermediate. To the mixture was added a solution of NaOH (34.15 mg, 853.66 umol) in Water (0.05 mL), the mixture was stirred at 30° C. for 1 h. LCMS showed a main peak with desired mass. The pH was adjusted to 7-9 by HCl (1 N), the mixture was filtered. The filtrate was purified by prep-HPLC (column: Welch Xtimate C18 100*25 mm*3 um; mobile phase: [water (0.04% $NH_3H_2O$)—ACN]; B %: 15%-45%, 10 min) to give a solution. Combined of the solution and another batches product (38.5 mg) was lyophilized to give (3R,5R)-7-(2-(4-fluorophenyl)-4-((4-(((S)-22-((2S,4R)-4-hydroxy-2-((4-(4-methylthiazol-5-yl)benzyl)carbamoyl)pyrrolidine-1-carbonyl)-23,23-dimethyl-20-oxo-3,6,9,12,15,18-hexaoxa-21-azatetracosyl)oxy)phenyl)carbamoyl)-5-isopropyl-3-phenyl-1H-pyrrol-1-yl)-3,5-dihydroxyheptanoic acid (124.3 mg, 0.094 mmol, 66.31% yield, 99.4% purity) as white solid.

1H NMR (400 MHz, DMSO-d6) δ 9.72 (s, 1H), 8.99-8.96 (m, 1H), 8.60 (t, J=5.90 Hz, 1H), 7.54 (s, 1H), 7.46-7.36 (m, 7H), 7.27-7.14 (m, 4H), 7.07 (d, J=4.27 Hz, 4H), 7.02-6.97 (m, 1H), 6.80 (d, J=9.03 Hz, 2H), 5.20 (s, 1H), 4.84 (s, 1H), 4.56 (d, J=9.54 Hz, 1H), 4.48-4.32 (m, 3H), 4.29-4.21 (m, 1H), 4.03-3.99 (m, 2H), 3.96 (s, 2H), 3.94-3.88 (m, 1H), 3.81-3.73 (m, 1H), 3.72-3.67 (m, 2H), 3.67-3.58 (m, 5H), 3.56 (dd, J=2.57, 5.08 Hz, 5H), 3.54-3.48 (m, 11H), 3.47 (s, 3H), 3.30 (s, 1H), 3.25-3.18 (m, 1H), 2.45-2.43 (m, 3H), 2.11-2.02 (m, 1H), 1.99-1.86 (m, 2H), 1.76 (dd, J=8.03, 14.93 Hz, 1H), 1.63-1.43 (m, 2H), 1.40-1.29 (m, 7H), 1.17-1.11 (m, 1H), 0.98-0.90 (m, 9H).

Example 14. Synthesis of (3S,5S)-7-(2-(4-fluorophenyl)-4-((4-(((S)-25-((2S,4R)-4-hydroxy-2-((4-(4-methylthiazol-5-yl)benzyl)carbamoyl)pyrrolidine-1-carbonyl)-26,26-dimethyl-23-oxo-3,6,9,12,15,18,21-heptaoxa-24-azaheptacosyl)oxy)phenyl)carbamoyl)-5-isopropyl-3-phenyl-1H-pyrrol-1-yl)-3,5-dihydroxyheptanoic acid (Compound 14)

Step 1: Synthesis of ethyl 23-hydroxy-3,6,9,12,15,18,21-heptaoxatricosan-1-oate (2)

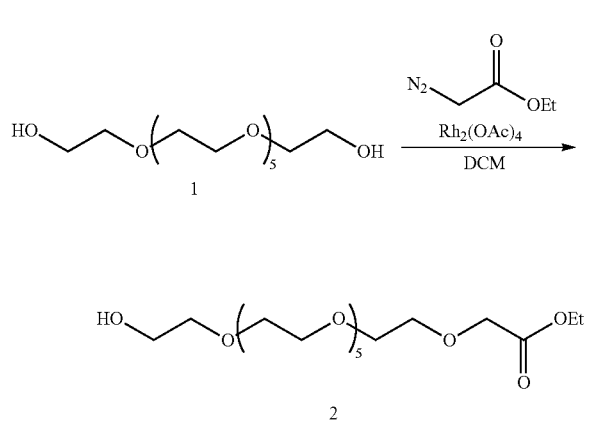

To a solution of 3,6,9,12,15,18-hexaoxaicosane-1,20-diol (5 g, 15.32 mmol) and Rh₂(OAc)₄ (0.6 g, 1.36 mmol) in DCM (200 mL) was added (2-ethoxy-2-oxo-ethyl)iminioazanide (2.2 g, 18.00 mmol), the mixture was stirred at 20° C. for 16 h. TLC (Ethyl acetate:Methanol=10:1) showed two new spots and the starting material remained. The mixture was concentrated under vacuum. The residue was purified by silica gel column chromatography (Ethyl acetate:Methanol=1:0 to 10:1) to give ethyl 23-hydroxy-3,6,9,12,15,18,21-heptaoxatricosan-1-oate (2.5 g, 6.06 mmol, 39.56% yield) as blue liquid.

Step 2: Synthesis of ethyl 23-(tosyloxy)-3,6,9,12,15,18,21-heptaoxatricosan-1-oate (3)

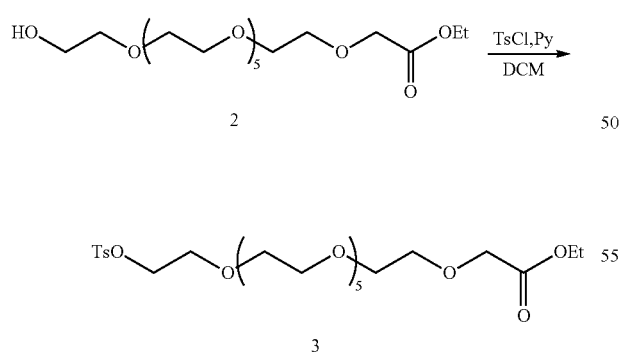

To a solution of ethyl 23-hydroxy-3,6,9,12,15,18,21-heptaoxatricosan-1-oate (2.5 g, 6.06 mmol) and Tosyl chloride (1.50 g, 7.88 mmol) in CH₂Cl₂ (25 mL) was added Pyridine (980.00 mg, 12.39 mmol, 1 mL), the mixture was stirred at 20° C. for 4 h. LCMS showed a peak with desired mass. Then the mixture was stirred at 20° C. for 12 h. The mixture was concentrated under vacuum. The residue was purified by silica gel column chromatography (PE:EtOAc=1:1 to 0:1) to give ethyl 23-(tosyloxy)-3,6,9,12,15,18,21-heptaoxatricosan-1-oate (2.1 g, 3.71 mmol, 61.14% yield) as yellow oil. MS (M+H)⁺=567.2

Step 3: Synthesis of 23-(tosyloxy)-3,6,9,12,15,18,21-heptaoxatricosan-1-oic acid (Linker 2)

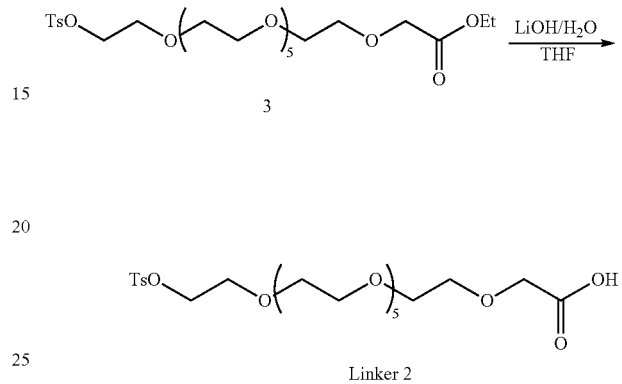

To a solution of ethyl 23-(tosyloxy)-3,6,9,12,15,18,21-heptaoxatricosan-1-oate (1 g, 1.76 mmol) in THF (10 mL) was added a solution of LiOH.H₂O (0.148 g, 3.53 mmol) in H₂O (10 mL), the mixture was stirred at 25° C. for 3 h. LCMS showed a main peak with desired mass. The pH was adjusted to 6-7 by HCl (1 N), then the mixture was concentrated under vacuum to give a aqueous phase. The aqueous phase was lyophilized to give 23-(tosyloxy)-3,6,9,12,15,18,21-heptaoxatricosan-1-oic acid (1 g, crude, Li salt) as yellow solid.

MS (M+H)+=539.3

Step 4: Synthesis of (S)-25-((2S,4R)-4-hydroxy-2-((4-(4-methylthiazol-5-yl)benzyl)carbamoyl)pyrrolidine-1-carbonyl)-26,26-dimethyl-23-oxo-3,6,9,12,15,18,21-heptaoxa-24-azaheptacosyl 4-methylbenzenesulfonate (4)

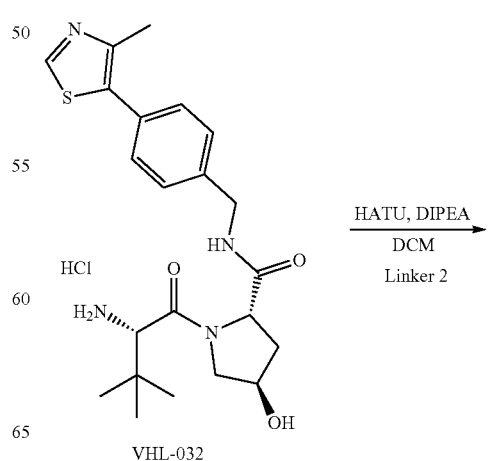

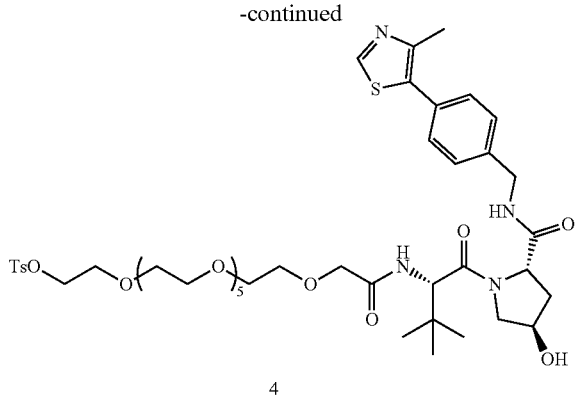

4

To a solution of 23-(tosyloxy)-3,6,9,12,15,18,21-heptaoxatricosan-1-oic acid (0.5 g, 0.916 mmol, Li salt), HATU (388.27 mg, 1.02 mmol) and DIEA (479.92 mg, 3.71 mmol, 0.65 mL) in DCM (15 mL) was added (2S,4R)-1-[(2S)-2-amino-3,3-dimethyl-butanoyl]-4-hydroxy-N-[[4-(4-methyl-thiazol-5-yl)phenyl]methyl]pyrrolidine-2-carboxamide (433.55 mg, 0.928 mmol, HCl salt), the mixture was stirred at 25° C. for 3 h. LCMS showed a peak (33%) with desired mass. The combined of mixture was washed with water (10 mL×3) and concentrated under vacuum. The residue was purified by reversed-phase HPLC (0.1% FA condition, 64% ACN) to give (S)-25-((2S,4R)-4-hydroxy-2-((4-(4-methyl-thiazol-5-yl)benzyl)carbamoyl)pyrrolidine-1-carbonyl)-26,26-dimethyl-23-oxo-3,6,9,12,15,18,21-heptaoxa-24-azaheptacosyl 4-methylbenzenesulfonate (0.35 g, 0.368 mmol, 19.82% yield) as yellow oil. MS (M+H)$^+$=951.7

Step 5: Synthesis of tert-butyl 2-((4R,6R)-6-(2-(2-(4-fluorophenyl)-4-((4-(((S)-25-((2S,4R)-4-hydroxy-2-((4-(4-methylthiazol-5-yl)benzyl)carbamoyl)pyrrolidine-1-carbonyl)-26,26-dimethyl-23-oxo-3,6,9,12,15,18,21-heptaoxa-24-azaheptacosyl)oxy)phenyl)carbamoyl)-5-isopropyl-3-phenyl-1H-pyrrol-1-yl)ethyl)-2,2-dimethyl-1,3-dioxan-4-yl)acetate (6)

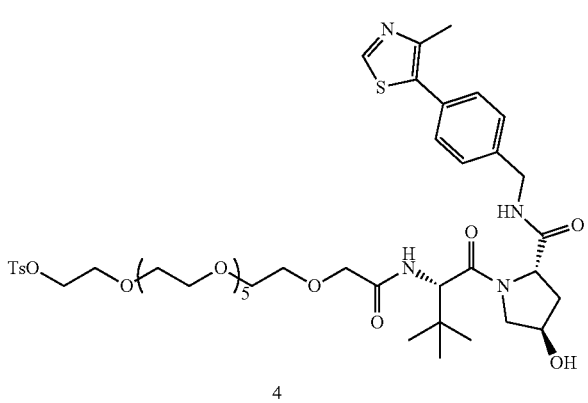

4

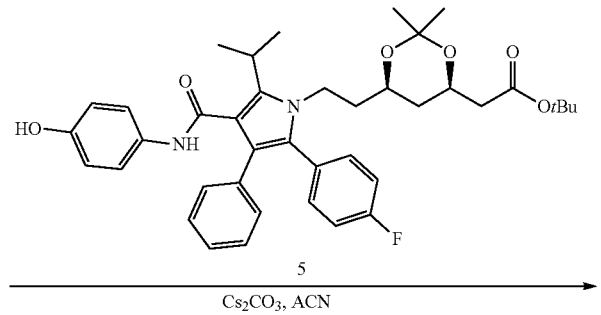

5

Cs$_2$CO$_3$, ACN

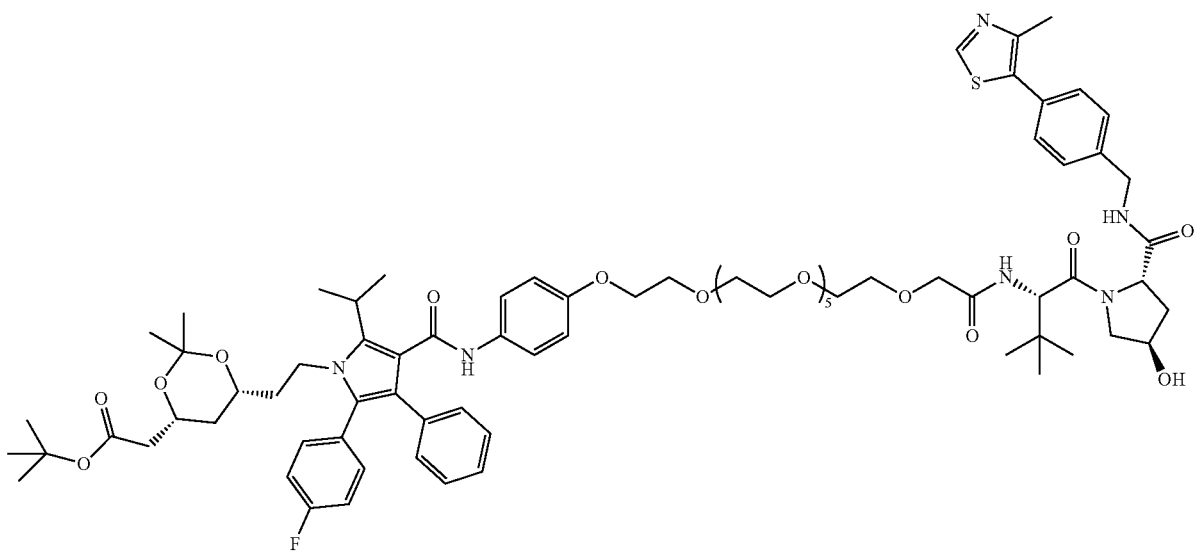

6

To a solution of (S)-25-((2S,4R)-4-hydroxy-2-((4-(4-methylthiazol-5-yl)benzyl)carbamoyl)pyrrolidine-1-carbonyl)-26,26-dimethyl-23-oxo-3,6,9,12,15,18,21-heptaoxa-24-azaheptacosyl 4-methylbenzenesulfonate (0.35 g, 0.368 mmol) and tert-butyl 2-[(4R,6R)-6-[2-[2-(4-fluorophenyl)-4-[(4-hydroxyphenyl)carbamoyl]-5-isopropyl-3-phenyl-pyrrol-1-yl]ethyl]-2,2-dimethyl-1,3-dioxan-4-yl]acetate (246.84 mg, 0.368 mmol) in ACN (10 mL) was added Cs$_2$CO$_3$ (239.79 mg, 735.95 umol), the mixture was stirred at 90° C. for 15 h. LCMS showed a peak (43%) with desired mass and the starting material remained. The mixture was filtered and the filtrate was purified by reversed-phase HPLC (0.1% FA condition, 85% ACN) to give tert-butyl 2-((4R,6R)-6-(2-(2-(4-fluorophenyl)-4-((4-(((S)-25-((2S,4R)-4-hydroxy-2-((4-(4-methylthiazol-5-yl)benzyl)carbamoyl)pyrrolidine-1-carbonyl)-26,26-dimethyl-23-oxo-3,6,9,12,15,18,21-heptaoxa-24-azaheptacosyl)oxy)phenyl)carbamoyl)-5-isopropyl-3-phenyl-1H-pyrrol-1-yl)ethyl)-2,2-dimethyl-1,3-dioxan-4-yl)acetate (0.22 g, 0.103 mmol, 28.04% yield, 68% purity) as brown oil. MS (M+H)$^+$=1449.9

Step 6: Synthesis of (3R,5R)-7-(2-(4-fluorophenyl)-4-((4-(((S)-25-((2S,4R)-4-hydroxy-2-((4-(4-methylthiazol-5-yl)benzyl)carbamoyl)pyrrolidine-1-carbonyl)-26,26-dimethyl-23-oxo-3,6,9,12,15,18,21-heptaoxa-24-azaheptacosyl)oxy)phenyl)carbamoyl)-5-isopropyl-3-phenyl-1H-pyrrol-1-yl)-3,5-dihydroxyheptanoic acid (Compound 14)

To a solution of tert-butyl 2-((4R,6R)-6-(2-(2-(4-fluorophenyl)-4-((4-(((S)-25-((2S,4R)-4-hydroxy-2-((4-(4-methylthiazol-5-yl)benzyl)carbamoyl)pyrrolidine-1-carbonyl)-26,26-dimethyl-23-oxo-3,6,9,12,15,18,21-heptaoxa-24-azaheptacosyl)oxy)phenyl)carbamoyl)-5-isopropyl-3-phenyl-1H-pyrrol-1-yl)ethyl)-2,2-dimethyl-1,3-dioxan-4-yl)acetate (0.22 g, 0.152 mmol) in THF (2 mL) and MeOH (2 mL) was added HCl (1 M, 0.3 mL), the mixture was stirred at 30° C. for 3 h. LCMS showed a peak with mass of intermediate. To the mixture was added a solution of NaOH (36.42 mg, 0.91 mmol) in Water (0.05 mL), the mixture was stirred at 30° C. for 1 h. LCMS showed a peak (58%) with desired mass and intermediate was consumed. The mixture was filtered and the filtrate was purified by prep-HPLC (column: Welch Xtimate C18 100*25 mm*3 um; mobile phase: [water (0.04% NH$_3$H$_2$O)—ACN]; B %: 16%-46%, 10 min) followed by lyophilization to give (3R,5R)-7-(2-(4-fluorophenyl)-4-((4-(((S)-25-((2S,4R)-4-hydroxy-2-((4-(4-methylthiazol-5-yl)benzyl)carbamoyl)pyrrolidine-1-carbonyl)-26,26-dimethyl-23-oxo-3,6,9,12,15,18,21-heptaoxa-24-azaheptacosyl)oxy)phenyl)carbamoyl)-5-isopropyl-3-phenyl-1H-pyrrol-1-yl)-3,5-dihydroxyheptanoic acid (81.3 mg, 0.0599 mmol, 39.50% yield, 99.8% purity) as white solid.

$^1$H NMR (400 MHz, DMSO-d$_6$) δ 9.74 (s, 1H), 8.99-8.96 (m, 1H), 8.63 (t, J=5.99 Hz, 1H), 7.46-7.36 (m, 7H), 7.27-7.15 (m, 4H), 7.09-7.04 (m, 4H), 7.02-6.96 (m, 1H), 6.80 (d, J=9.05 Hz, 2H), 5.21 (s, 1H), 4.56 (d, J=9.66 Hz,

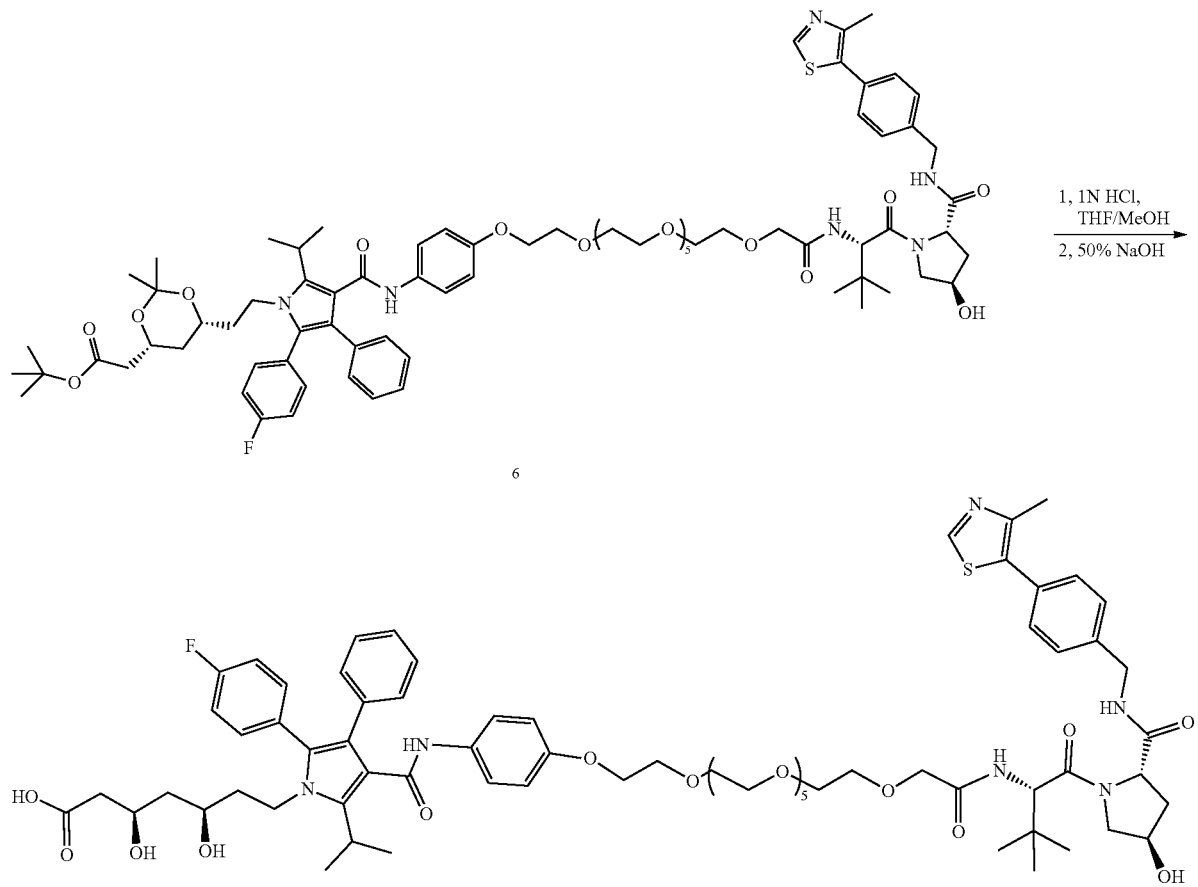

Compound 14

1H), 4.47-4.32 (m, 3H), 4.28-4.20 (m, 1H), 4.03-3.98 (m, 2H), 3.96 (s, 2H), 3.93-3.87 (m, 1H), 3.76 (d, J=10.03 Hz, 1H), 3.72-3.67 (m, 2H), 3.67-3.58 (m, 5H), 3.58-3.45 (m, 26H), 3.25-3.17 (m, 1H), 2.44 (s, 3H), 2.10-2.01 (m, 1H), 1.98 (dd, J=4.40, 14.92 Hz, 1H), 1.91-1.87 (m, 1H), 1.83-1.74 (m, 1H), 1.63-1.45 (m, 2H), 1.35 (d, J=6.97 Hz, 7H), 1.18-1.12 (m, 1H), 0.99-0.89 (m, 9H).

Comparative Example 1. Synthesis of (3R,5R)-7-(3-(3-(3-(1-(14-((2-(2,6-dioxopiperidine-3-yl)-1,3-dioxoisoinoline-4-yl)amino)-3,6,9,12-tetraoxatetradecyl)-1H-1,2,3-triazol-4-yl)propoxy)phenyl)-2-(4-fluorophenyl)-5-isopropyl-4-(phenylcarbamoyl)-1H-pyrrol-1-yl)-3,5-dihydroxyheptanoic acid (Comparative Compound 1)

Comparative Compound 1 is a compound described by Formula 4 in International Patent Publication No. WO2019/109415 A1. The compound may be prepared according to the preparation method described in the above document.

Comparative Example 2. Synthesis of (3R,5R)-7-(3-(3-((5-(1-(2-(2-(2-((2-(2,6-dioxopiperidine-3-yl)-1,3-dioxoisoindoline-4-yl)amino)ethoxy)ethoxy)ethyl)-1H-1,2,3-triazol-4-yl)pentyl)oxy)phenyl)-2-(4-fluorophenyl)-5-isopropyl-4-(phenylcarbamoyl)-1H-pyrrol-1-yl)-3,5-dihydroxyheptanoic acid (Comparative Compound 2)

Comparative Compound 2 is a compound described by Formula 7 in International Patent Publication No. WO2019/109415 A1. The compound may be prepared according to the preparation method described in the above document.

Comparative Example 3. Synthesis of (3R,5R)-7-(3-((4-(2,5,8,11,14,17,20-heptaoxadocosan-22-yloxy)phenyl)carbamoyl)5-(4-fluorophenyl)-2-isopropyl-4-phenyl-1H-pyrrol-1-yl)-3,5-dihydroxyheptanoic acid (Comparative Compound 3)

Step 1: Synthesis of tert-butyl 2-((4R,6R)-6-(2-(3-((4-(2,5,8,11,14,17,20-heptaoxadocosan-22-yloxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (11)

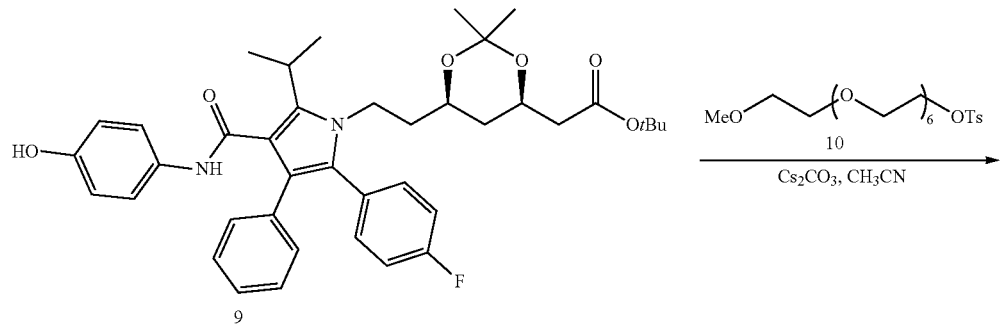

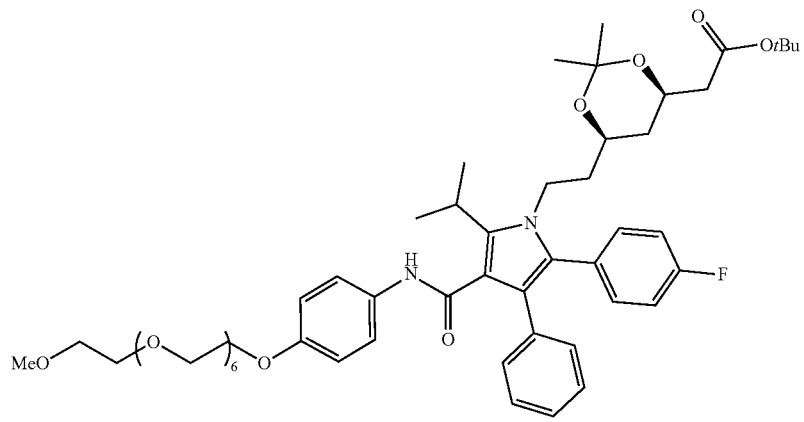

To a solution of tert-butyl 2-((4R,6R)-6-(2-(2-(4-fluorophenyl)-4-((4-hydroxyphenyl)carbamoyl)-5-isopropyl-3-phenyl-1H-pyrrol-1-yl)ethyl)-2,2-dimethyl-1,3-dioxan-4-yl)acetate (0.17 g, 0.253 mmol) and 2,5,8,11,14,17,20-heptaoxadocosan-22-yl 4-methylbenzenesulfonate (0.15 g, 0.303 mmol) in ACN (8 mL) was added Cs$_2$CO$_3$ (165.14 mg, 0.507 mmol), the mixture was stirred at 80° C. for 16 h. LCMS showed a main peak with desired mass. The mixture was filtered and the filtrate was concentrated in vacuum. The residue was purified by reverse MPLC (water:ACN=3:7, 1‰ FA) followed by lyophilization to afford tert-butyl 2-((4R,6R)-6-(2-(3-((4-(2,5,8,11,14,17,20-heptaoxadocosan-22-yloxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (0.23 g, 0.232 mmol, 91.38% yield) as yellow oil. MS (M+H)$^+$=993.3

Step 2: Synthesis of (3R,5R)-7-(3-((4-(2,5,8,11,14,17,20-heptaoxadocosan-22-yloxy)phenyl) carbamoyl)-5-(4-fluorophenyl)-2-isopropyl-4-phenyl-1H-pyrrol-1-yl)-3,5-dihydroxyheptanoic acid
(Comparative Compound 3)

To a mixture of tert-butyl 2-((4R,6R)-6-(2-(3-((4-(2,5,8,11,14,17,20-heptaoxadocosan-22-yloxy)phenyl)carbamoyl)-5-(4-fluorophenyl)-2-isopropyl-4-phenyl-1H-pyrrol-1-yl)ethyl)-2,2-dimethyl-1,3-dioxan-4-yl)acetate (0.21 g, 211.44 umol) in THF (2 mL) and MeOH (2 mL) was added HCl (1 M, 0.423 mL), the mixture was stirred at 30° C. for 3 h. TLC (Petroleum ether:Ethyl acetate=1:1) showed two new spots were formed. Then a solution of NaOH (50.74 mg, 1.27 mmol) in Water (0.5 mL) was added and the mixture was stirred at 30° C. for 1 h. LCMS showed a main peak with desired mass. The mixture was concentrated under vacuum. The residue was purified by prep-HPLC (column: Xtimate C18 10u 250 mm*80 mm; mobile phase: [water (0.05% ammonia hydroxide v/v)—ACN]; B %: 12%-42%, 10 min) followed by lyophilization to afford (3R,5R)-7-(3-((4-(2,5,8,11,14,17,20-heptaoxadocosan-22-yloxy)phenyl)carbamoyl)-5-(4-fluorophenyl)-2-isopropyl-4-phenyl-1H-pyrrol-1-yl)-3,5-dihydroxyheptanoic acid (113 mg, 0.123 mmol, 58.03% yield, 97.4% purity) as white solid. $^1$H NMR (400 MHz, DMSO-d$_6$) δ 9.65 (s, 1H), 8.36 (s, 1H), 7.40 (d, J=9.03 Hz, 2H), 7.27-7.15 (m, 4H), 7.10-7.04 (m, 4H), 7.03-6.96 (m, 1H), 6.81 (d, J=9.03 Hz, 2H), 4.05-3.99 (m, 2H), 3.98-3.87 (m, 1H), 3.84-3.74 (m, 1H), 3.73-3.68 (m, 2H), 3.60-3.52 (m, 3H), 3.52-3.47 (m, 21H), 3.43-3.41 (m,

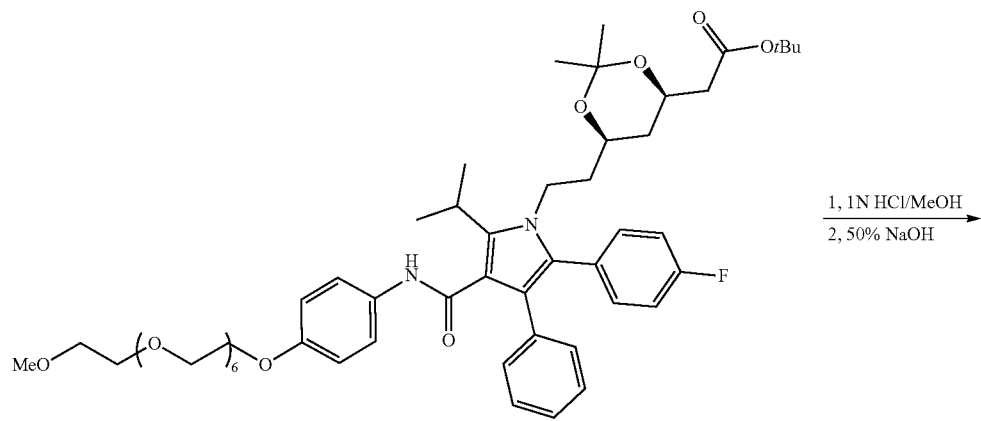

11

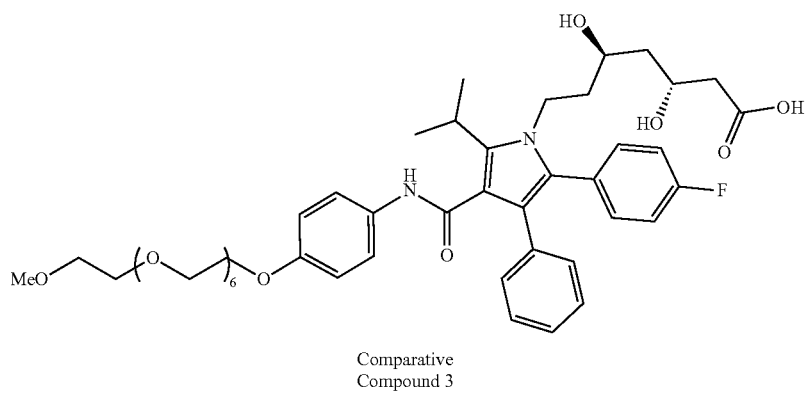

Comparative
Compound 3

2H), 3.23 (s, 4H), 2.24-2.06 (m, 3H), 1.69-1.47 (m, 2H), 1.46-1.22 (m, 9H). MS (M+H)⁺=897.4

The structures of Compounds 1-14 are summarized in the Table 1.

TABLE 1

| No. | Structure |
| --- | --- |
| 1 | 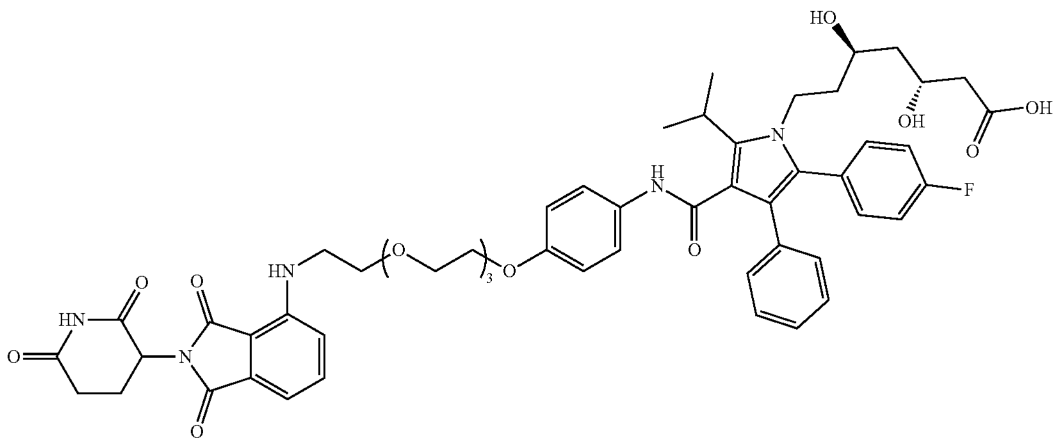 |
| 2 | 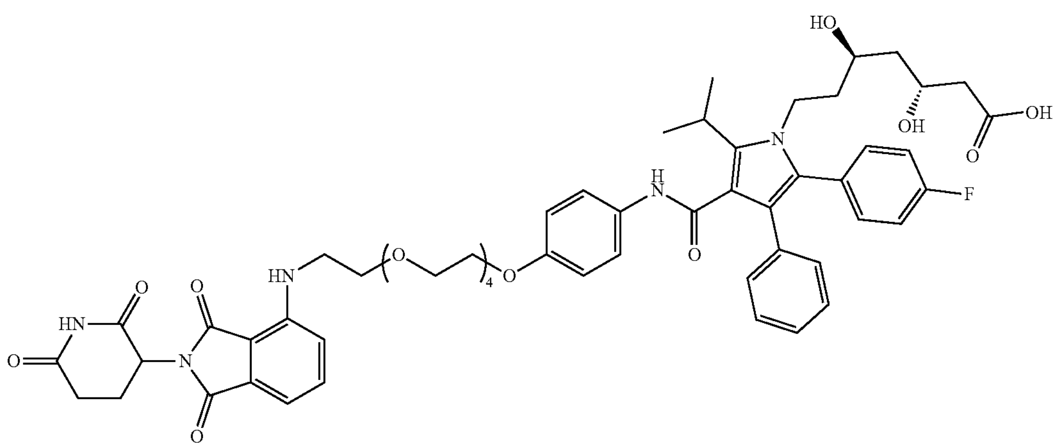 |
| 3 | 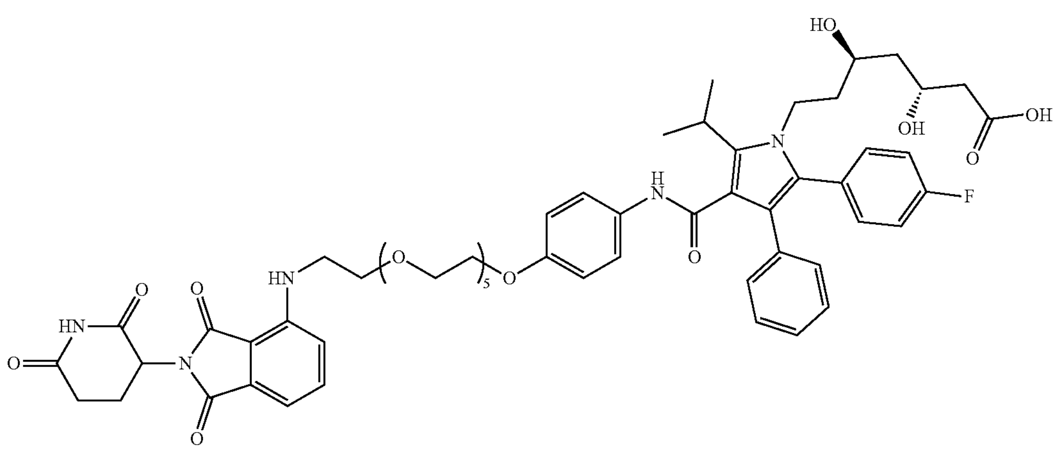 |

TABLE 1-continued
| No. | Structure |
|---|---|
| 4 | 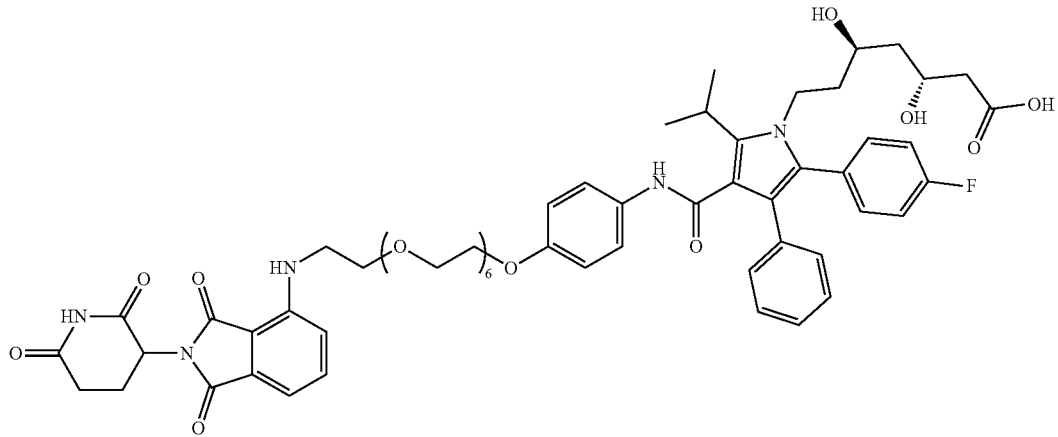 |
| 5 | 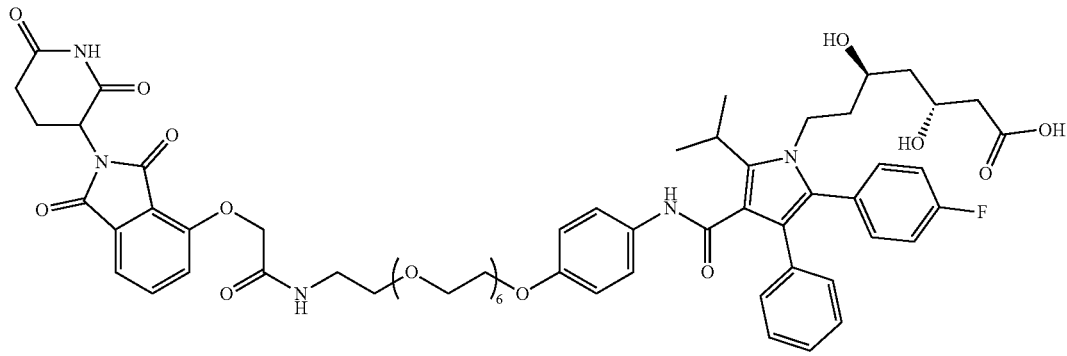 |
| 6 | 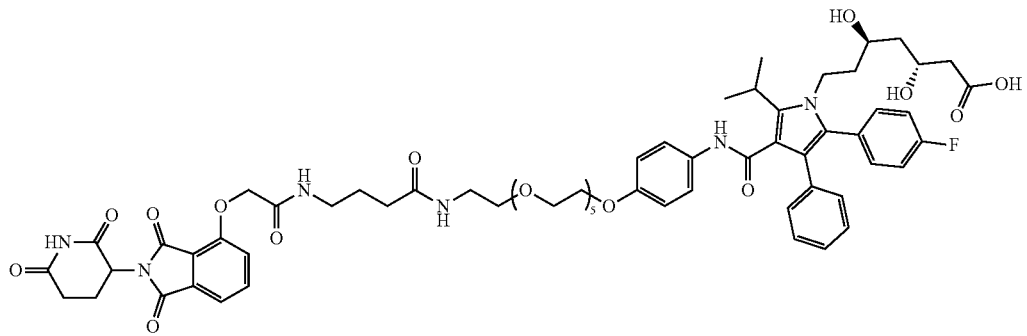 |
| 7 | 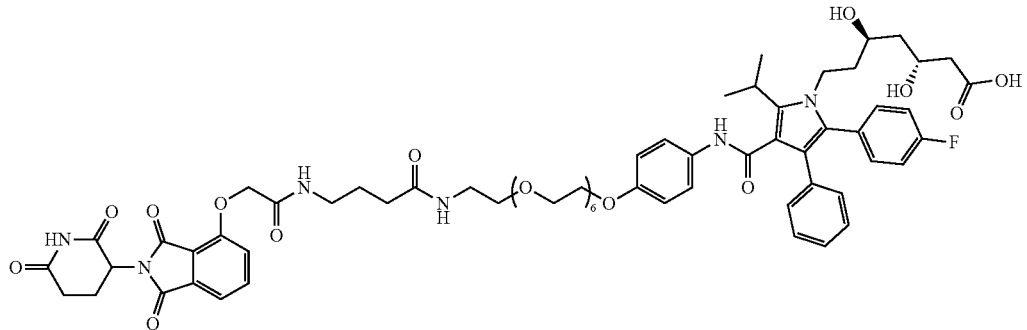 |

| No. | Structure |
|---|---|
| 8 | 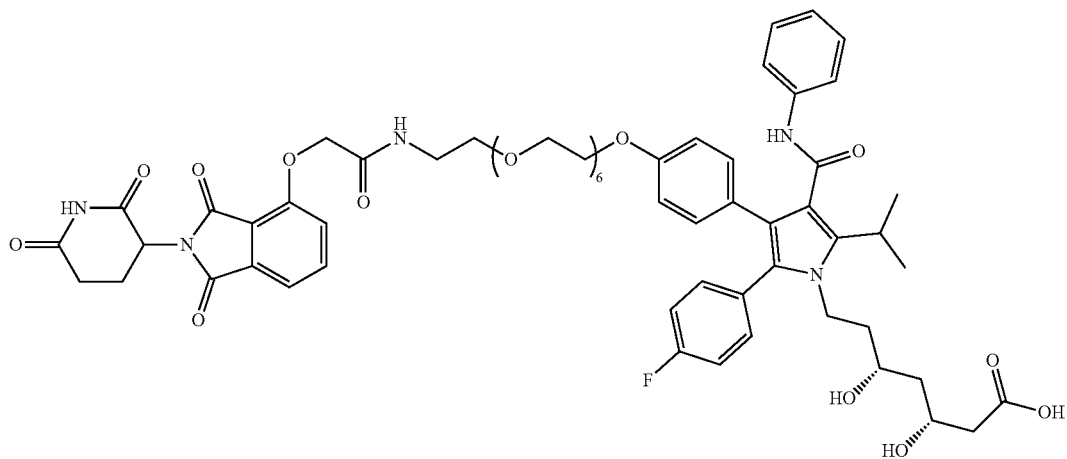 |
| 9 | 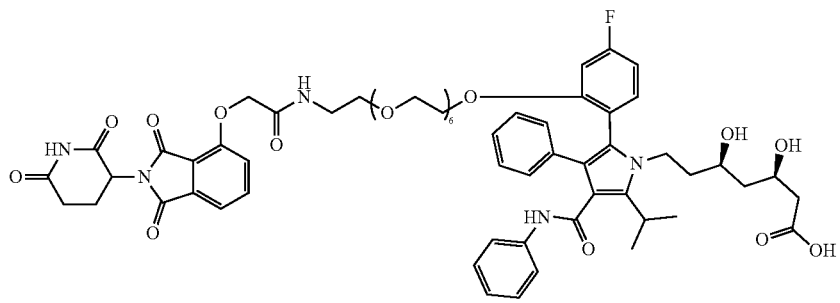 |
| 10 | 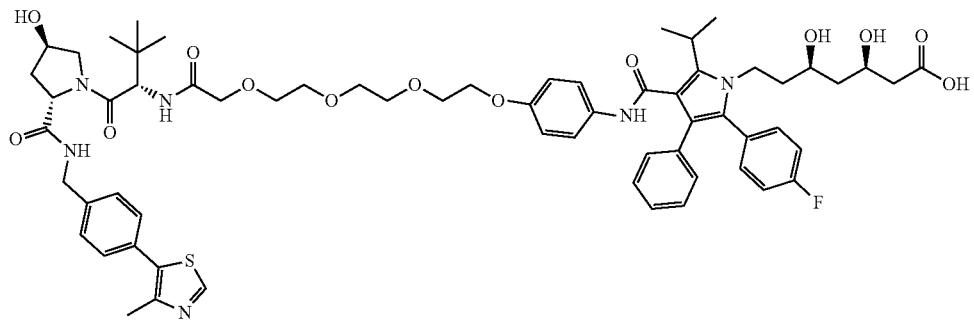 [SMILES: Cc1ncsc1-c1ccc(CNC(=O)[C@@H]2C[C@@H](O)CN2C(=O)[C@@H](NC(=O)COCCOCCOCCOc2ccc(NC(=O)c3c(-c4ccccc4)c(-c4ccc(F)cc4)n(CC[C@@H](O)C[C@@H](O)CC(=O)O)c3C(C)C)cc2)C(C)(C)C)cc1] |
| 11 | 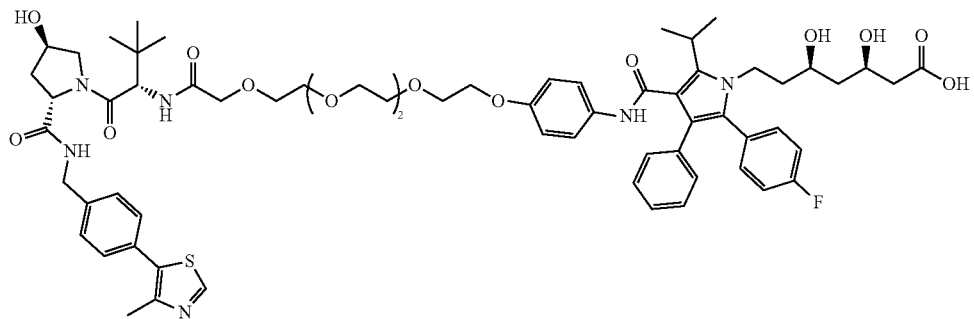 |

TABLE 1-continued

| No. | Structure |
|---|---|
| 12 | 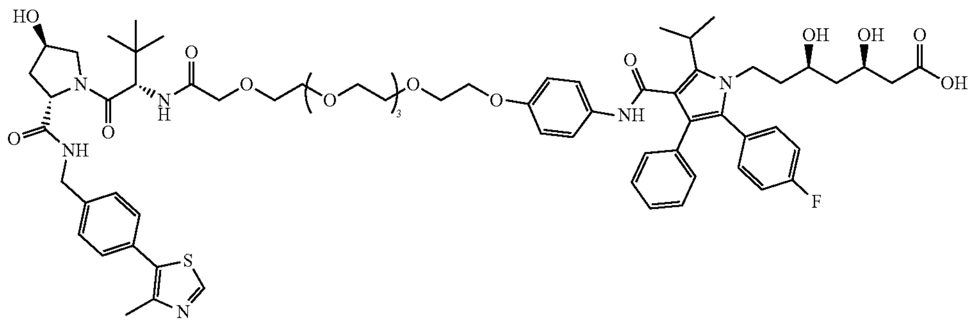 |
| 13 | 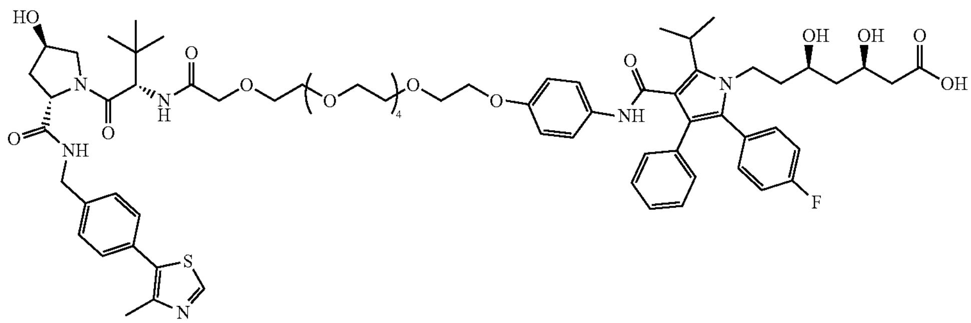 |
| 14 | 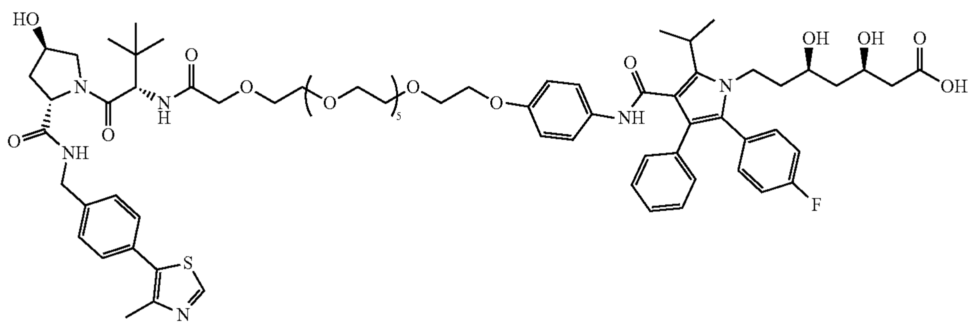 |

The structures of Comparative Compounds 1-3 are summarized in the Table 2.

TABLE 2

| No. | Structure |
|---|---|
| 1 | 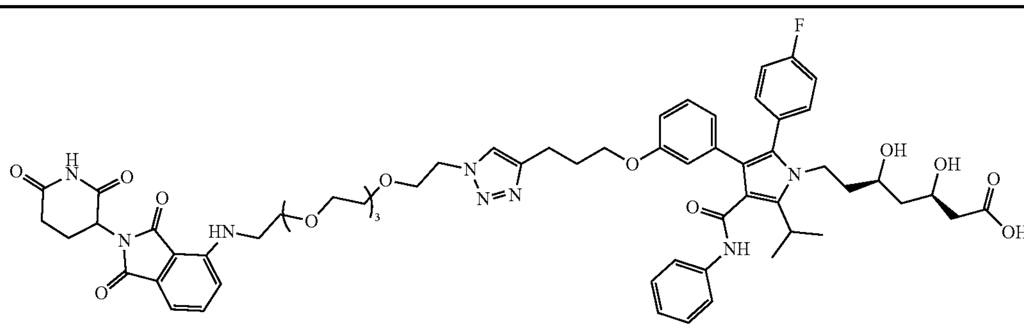 |

| No. | Structure |
|---|---|
| 2 | 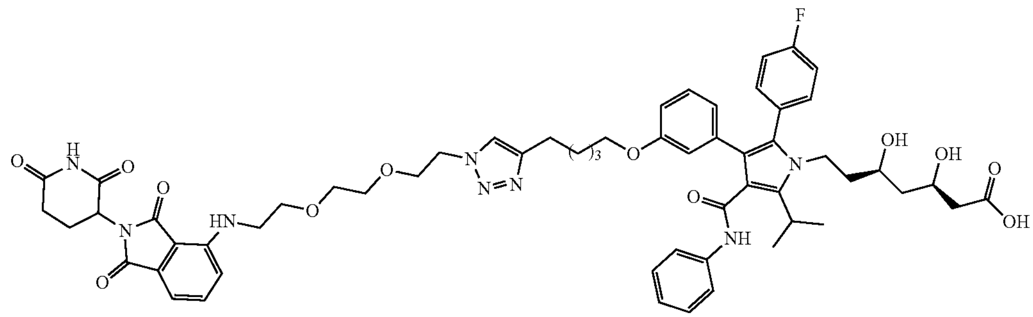 |
| 3 | 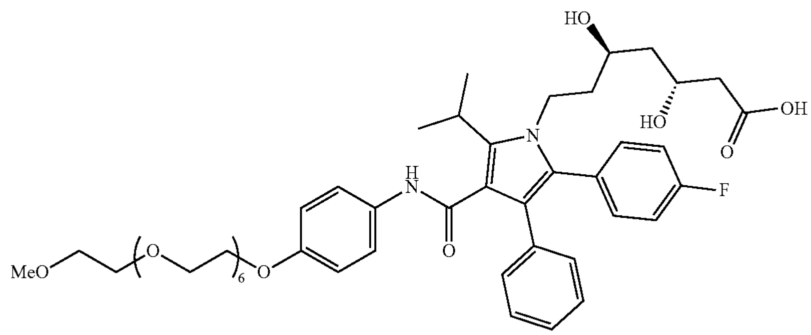 |

Experimental Example

1. Culture of HepG2 Cell Line

HepG2, a human liver cancer cell line, was purchased from the Korea Cell Line Bank (KCLB), Seoul, Korea. The passage in cell culture was maintained at P105 to P110.

For cell counting, cell counter (Thermo Fisher Scientific Inc., Catalog #AMQAX1000) and 0.4% trypan blue solution were used.

For cell culture, Dulbecco's Modified Eagle's medium (DMEM; Gibco, Cat. No. 1195-65; Lot. No. 2085318), Fetal Bovine Serum (FBS; Gibco, Cat. No. 16000-044; Lot. No. 2097593), Penicillin/Streptomycin (PS) (Gibco, Cat. No. 15140-122; Lot. No. 2058855), 100 mm$^2$ cell culture dish (SPL, Cat. No. 20100), 150 mm$^2$ cell culture dish (SPL, Cat. No. 20150), 12-well culture plate (SPL, Cat. No. 30012), PBS pH 7.4 (Gibco, Cat. No. 10010-023; Lot. No. 2085080), TrypLE™ Express (Gibco, Cat. No. 12605-010; Lot No. 2070638), Counting Chamber (Hematocytometer) (Hirschmann, Cat. No. 8100204), and 0.4% Trypan Blue Solution (DYNEBIO, Cat. No. CBT3710; Lot. No. 20190723) were used.

2. Treatment of Compounds of the Present Invention

The compounds in Comparative Examples and Examples were completely dissolved in DMSO and used in the experiment. 2×10$^5$ cells were seeded for each well of a 12-well plate (SPL), and the cells were cultured in the culture medium in a total volume of 2 ml. Each of the compounds of the present invention and comparative compounds was treated at a concentration of 100 nM for 18 hours.

3. Western Blotting

For SDS-PAGE and Western blotting, 1×RIPA lysis buffer (Rockland, Cat. No. MB-030-0050; Lot no. 39751), 100× Protease Inhibitor Cocktail (Quartett, Cat. No. PPI1015; Lot no. PC050038424), Pierce™ BCA protein assay kit (ThermoScientific, Cat. No. 23225; Lot no. UC276876), albumin standard (ThermoScientific, Cat. No. 23209; Lot no. UB269561), 4-15% Mini-PROTEAN TGX stain-free gel (Bio-rad, Cat. No. 4568085; Lot no. L007041B), 10× Tris/Glycine/SDS buffer (Bio-rad, Cat. No. 1610732; Lot no. 10000044375B); 10×TBS (Bio-rad, Cat. No. 1706435; Lot no. 1000045140B), 10% Tween 20 (Cat. No. 1610781; Lot no. L004152B), Color protein standard broad range (NEB, Cat. No. P7719S; Lot no. 10040349), 4× Laemmli sample buffer (Bio-rad, Cat. No. 1610747; Lot no. L004133B), β-mercaptoethanol (Sigma-Aldrich, Cat. No. M3148; Lot no. 60-24-2), SuperBlock™ T20 (TBS) blocking buffer (ThermoScientific, Cat. No. 37536; Lot no. UC282578), 1M sodium azide solution (Sigma-Aldrich, Cat. No. 08591-1 mL-F; Lot no. BCBV4989), α-Rabbit pAb to Ms IgG (abcam, Cat. No. ab97046; Lot no. GR3252115-1), α-Goat pAb to Rb IgG (CST, Cat. No. 7074S; Lot no. 28), α-GAPDH (abcam, Cat. No. ab8245), α-HMGCR (GeneTex, Cat. No. GTX54088; Lot no. 821903509), ECL™ Prime western blotting reagents (GE Healthcare, Cat. No. RPN2232; Lot no. 17001655), Ponceau S solution (Sigma-Aldrich, Cat. No. P7170; Lot no. SLBV4112), Difco™ Skim milk (BD, Cat. No. 232100; Lot no. 8346795), and iBlot® 2 NC Regular stacks (Invitrogen, Cat. No. IB23001; Lot no. 2NR110619-02), were used.

For cell harvesting, the cells were first separated from the plate using trypsin and then washed with the medium and PBS. Specifically, the medium was suctioned off and washed with 1 mL of PBS, and PBS was suctioned off. The cells were treated with 0.5 mL TrypLE™ Express at 37° C. for 7 minutes to separate the cells, and then 0.5 mL of complete medium was added to collect 1 mL of cell culture solution. Then, 1 mL of the cell collection solution was centrifuged at 8,000 rpm for 120 seconds, and the supernatant was removed. After washing with 0.2 mL of PBS, the PBS was removed.

For cell lysis, a lysis buffer was added and cell debris was removed to obtain a cell lysate. Specifically, the cells were treated with 70 μL of 1×RIPA buffer containing a protease inhibitor and incubated for 30 minutes on ice. Then, the cells were centrifuged at 4° C. and 15,000 rpm for 10 minutes to obtain a cell lysate.

Then, a standard curve was obtained using the BCA assay, and the protein mass in the lysate was quantified by substituting the curve. The mixture was incubated at 37° C. for 30 minutes using 20 μL of standard or sample solution, and 200 μL of BCA or Bradford solution, and measured at 562 nm absorbance. Samples were prepared by adding 4× sample buffer so that the quantity of sample added to each well was 15 μg.

Sodium dodecyl sulfate polyacrylamide gel electrophoresis (SDS-PAGE) was performed by setting a running time of 100 minutes at 120 V on a 4-15% Mini-PROTEAN TGX stain-free gel (15 well). Transferring was performed on iBlot® 2 NC Mini stacks at P0 mode of the dry blotting system. After staining using Ponceau S solution, blocking was performed for 1 hour with a blocking buffer (Thermo Fisher Scientific Inc.). After washing with 1×TBS containing 0.05% Tween 20, the product was reacted at 4° C. for 16 hours with anti-HMGCR antibody (1:500) in skim milk or anti-GAPDH (abcam) antibody (1:20000) in 1×TBS-T as a primary antibody. After washing three times for 10 minutes with 1×TBS containing 0.05% Tween 20, the product was reacted at room temperature for 1 hour with anti-mouse antibody (abcam) (1:10000) or anti-rabbit antibody (CST) (1:5000) in 1×TBS-T as a secondary antibody. Then, after washing three times for 10 minutes with 1×TBS containing 0.05% Tween 20, the product was detected with an ECL working solution (1:1).

To analyze the results, an image analyzer (GE) was used to obtain final blot data.

4. Confirmation of HMGCR Degradability of the Compounds of the Present Invention As a result of Western blotting, it was confirmed that all compounds of Examples of the present invention had remarkably excellent HMGCR degradability in hepatocyte line as compared to not only a negative control group using an aniline group instead of the E3 ubiquitin ligase ligand (Comparative Example 3), but also the PROTAC compounds described in International Patent Publication WO2019/109415 A1 (Comparative Examples 1 and 2).

REFERENCES

Ito, Takumi, et al. Science 327.5971 (2010): 1345-1350.
Chamberlain, Philip P., and Brian E. Cathers. Drug Discovery Today: Technologies (2019).
Akuffo, Afua A., et al. Journal of Biological Chemistry 293.16 (2018): 6187-6200.]
Burslem, George M., et al. ChemMedChem 13.15 (2018): 1508-1512.
Schneekloth, John S., et al. Journal of the American Chemical Society 126.12 (2004): 3748-3754.
Rodriguez-Gonzalez, A., et al. Oncogene 27.57 (2008): 7201.
Buckley, Dennis L., et al. Journal of the American Chemical Society 134.10 (2012): 4465-4468.
Buckley, Dennis L., et al. Angewandte Chemie International Edition 51.46 (2012): 11463-11467.
Galdeano, Carles, et al. Journal of medicinal chemistry 57.20 (2014): 8657-8663.
Soares, Pedro, et al. Journal of medicinal chemistry 61.2 (2017): 599-618.

What is claimed is:

1. A compound represented by the following Formula I:

ULM-Linker-PTM, [Formula I]

wherein:

ULM is CRBN or VHL E3 ubiquitin ligase binding moiety,

PTM is

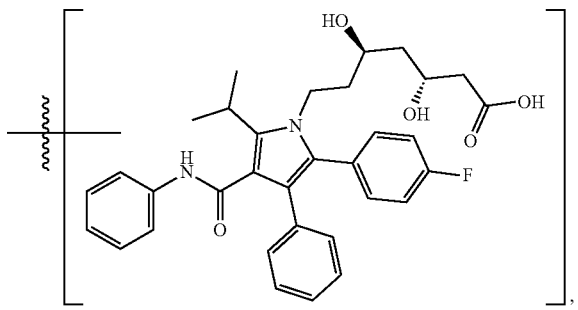

Linker is a group that chemically links ULM and PTM, wherein the compound is selected from the group consisting of:

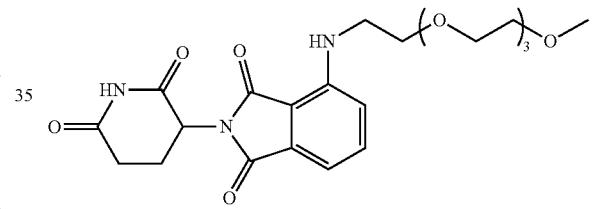

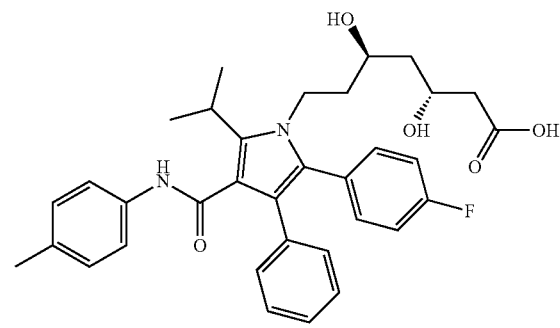

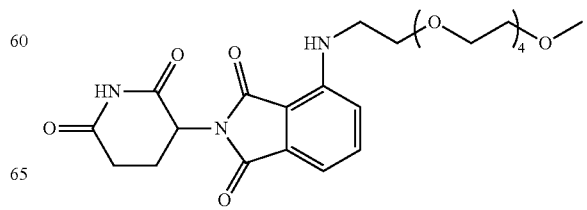

159
-continued
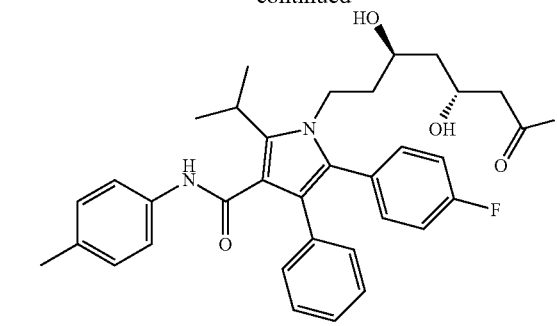
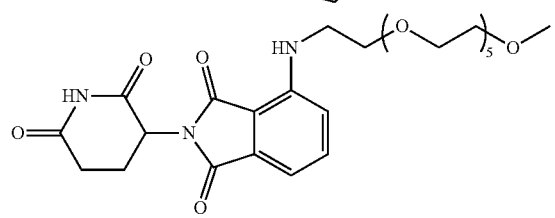
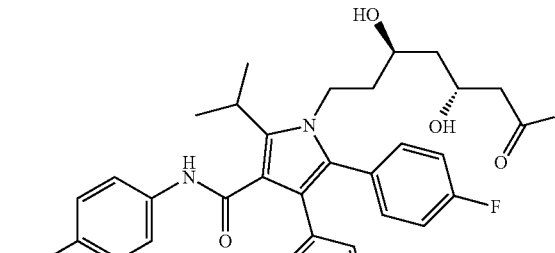
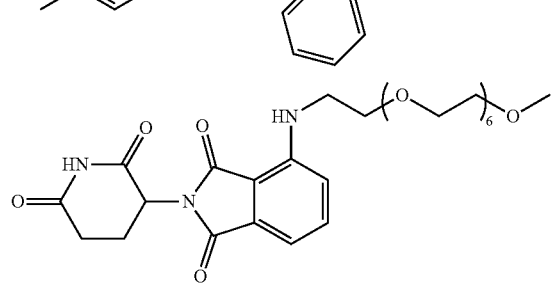
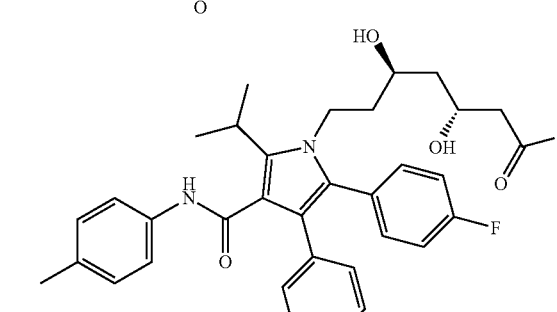
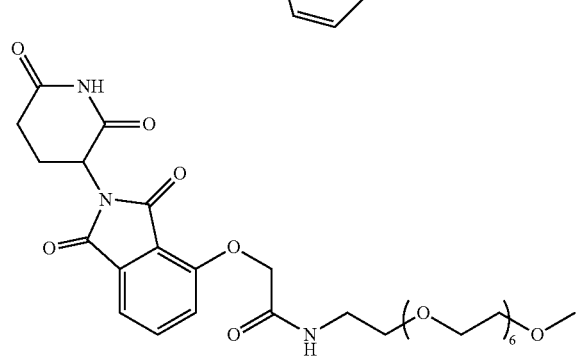
160
-continued
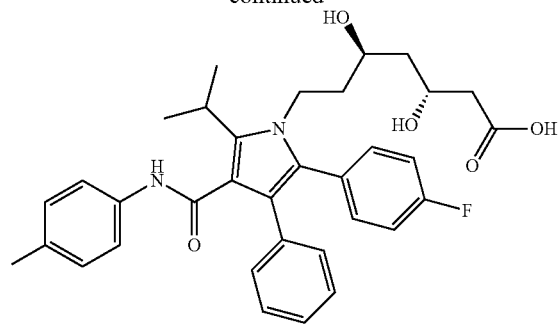
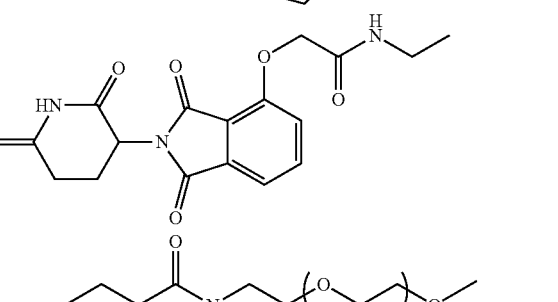
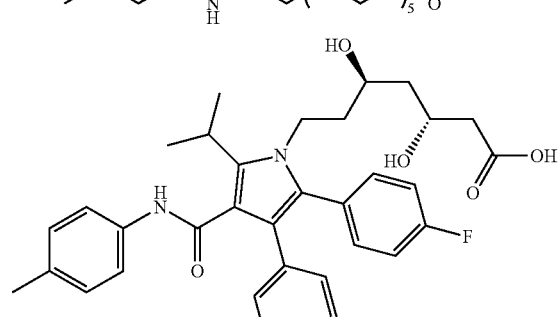
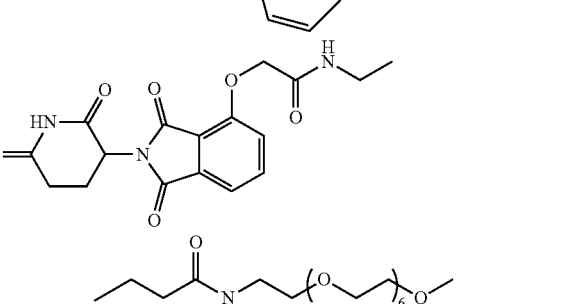
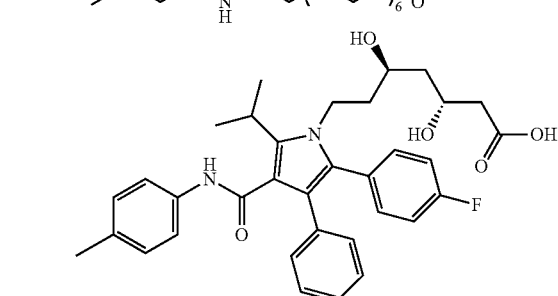
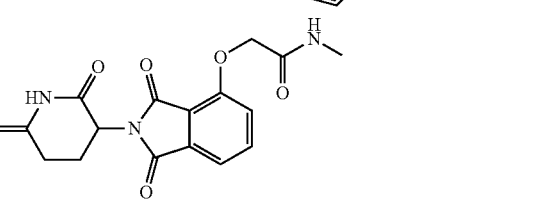

161
-continued
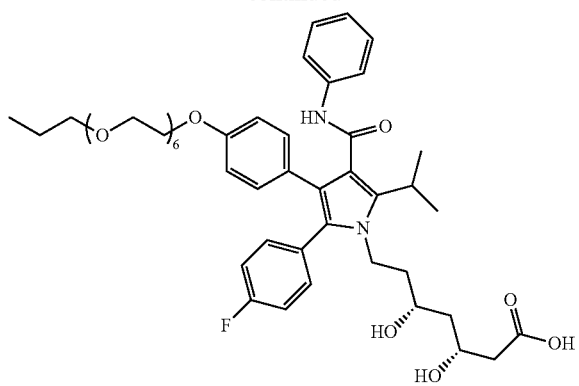
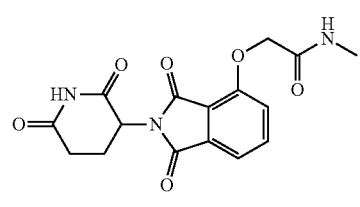
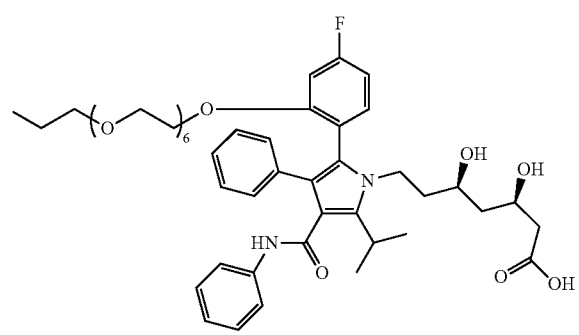
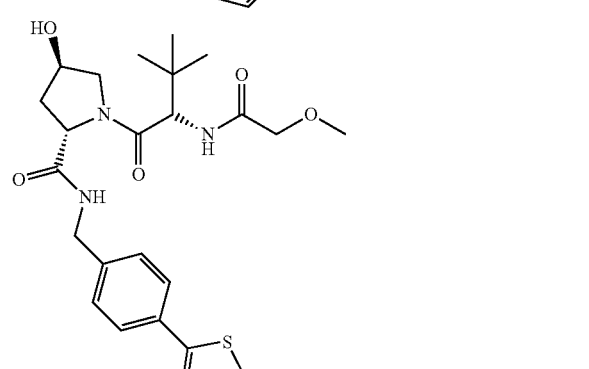
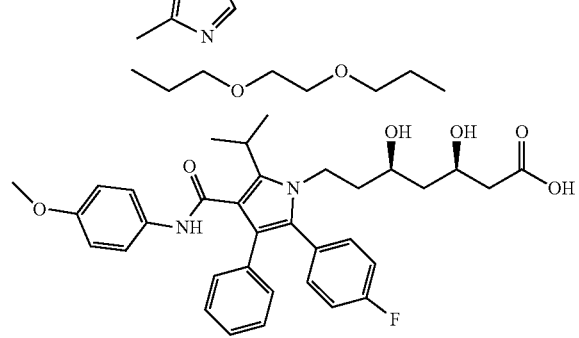
162
-continued
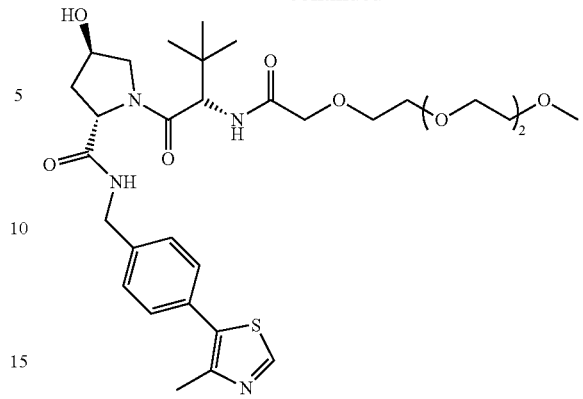
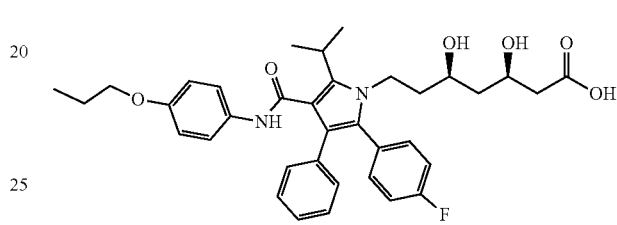
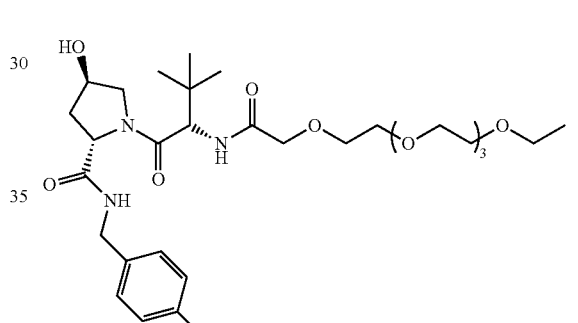
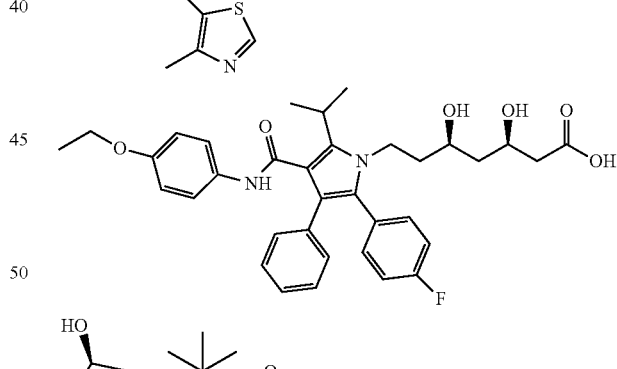
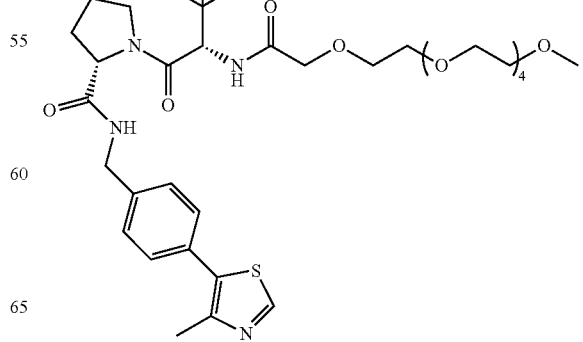

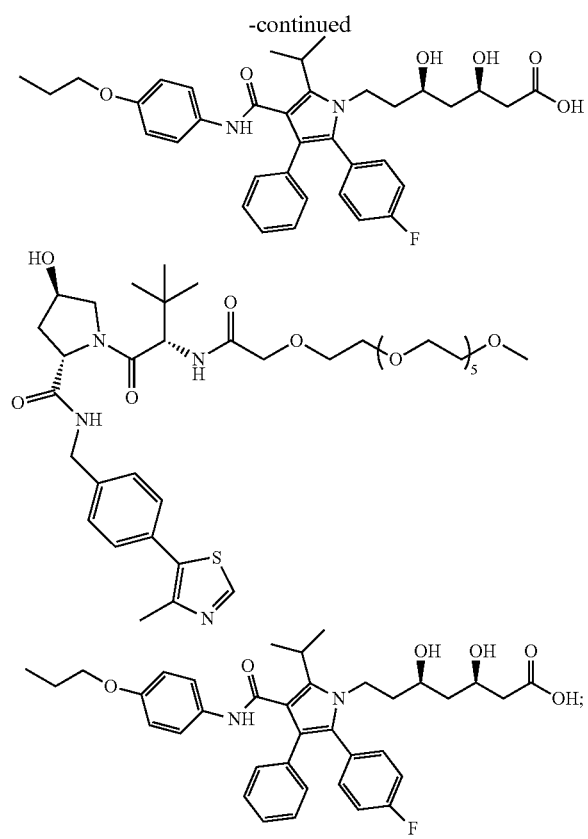
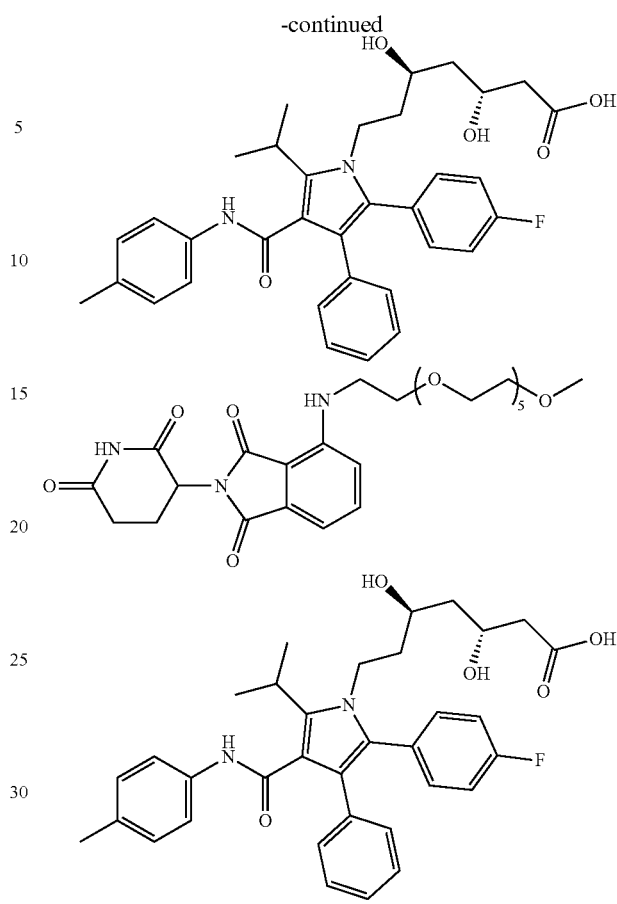
or a pharmaceutically acceptable salt thereof.
2. The compound of claim 1, wherein the compound is selected from the group consisting of:
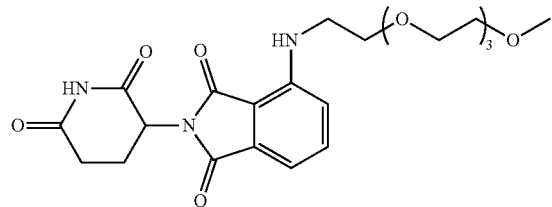
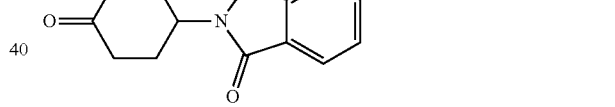
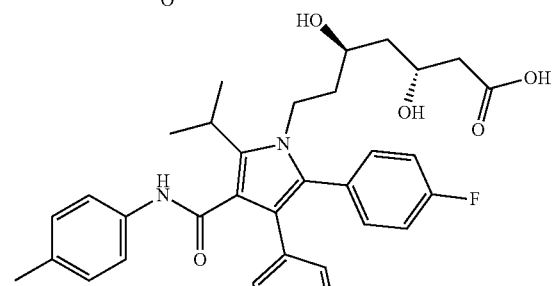
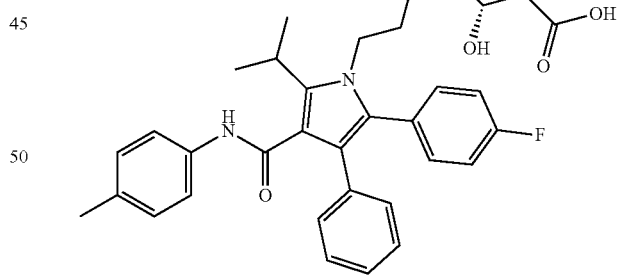
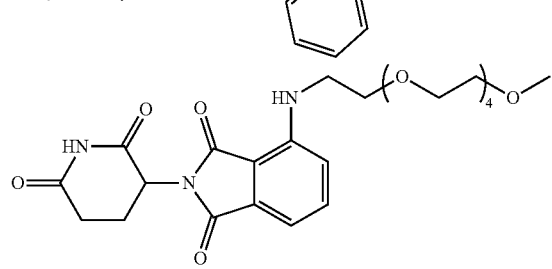
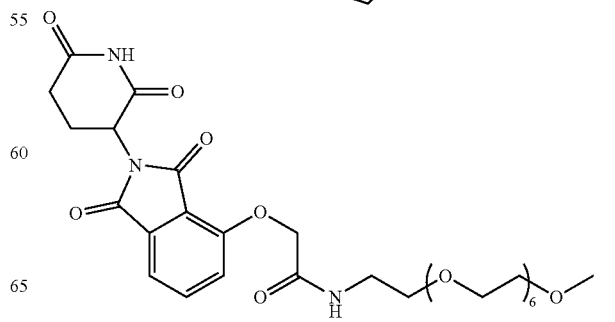

165
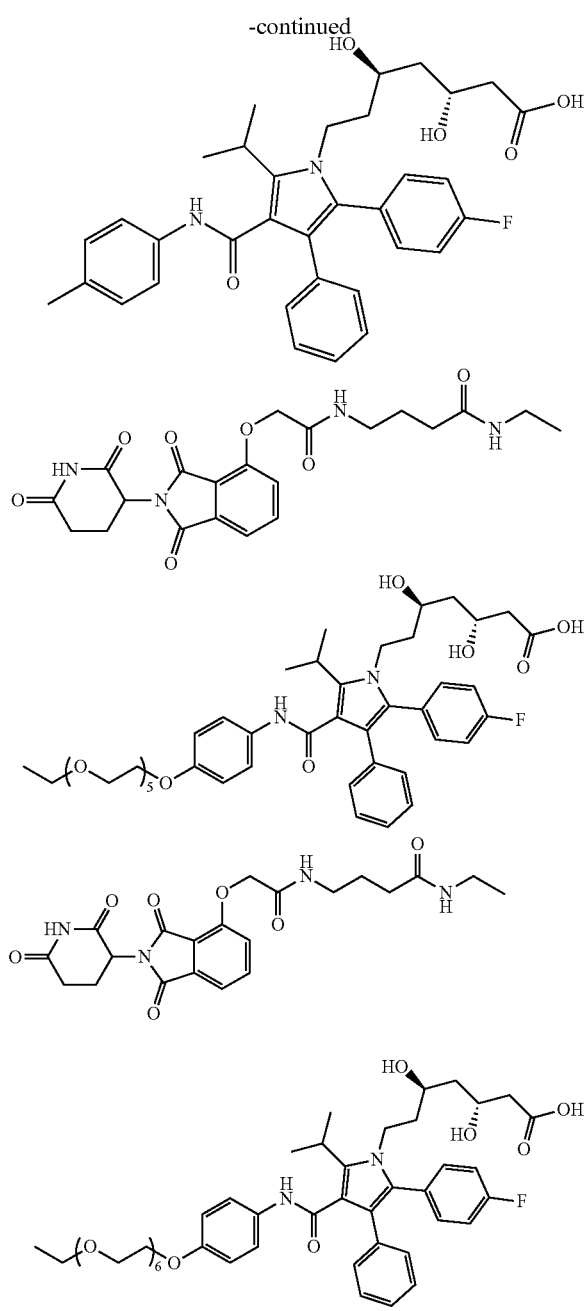
166
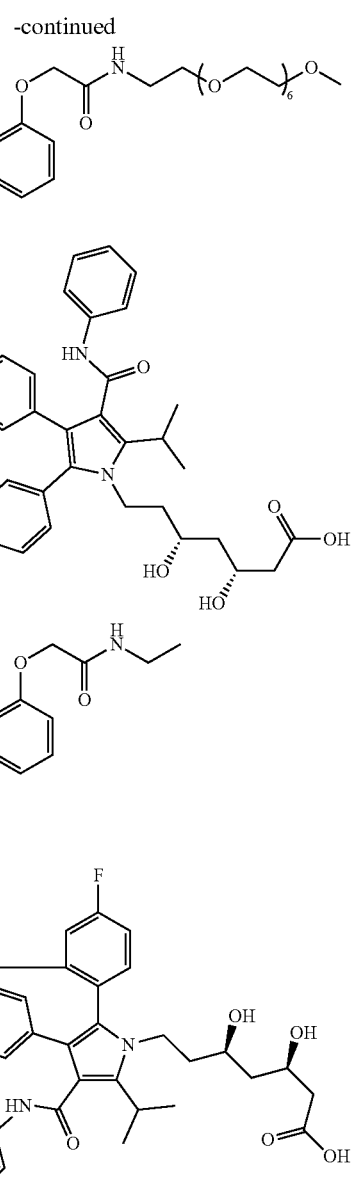
or a pharmaceutically acceptable salt thereof.
3. The compound of claim 1, wherein the compound is selected from the group consisting of:
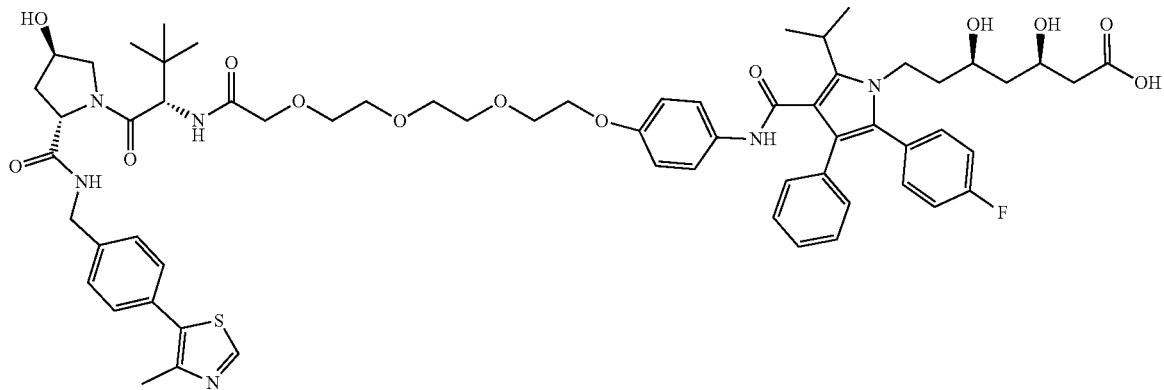

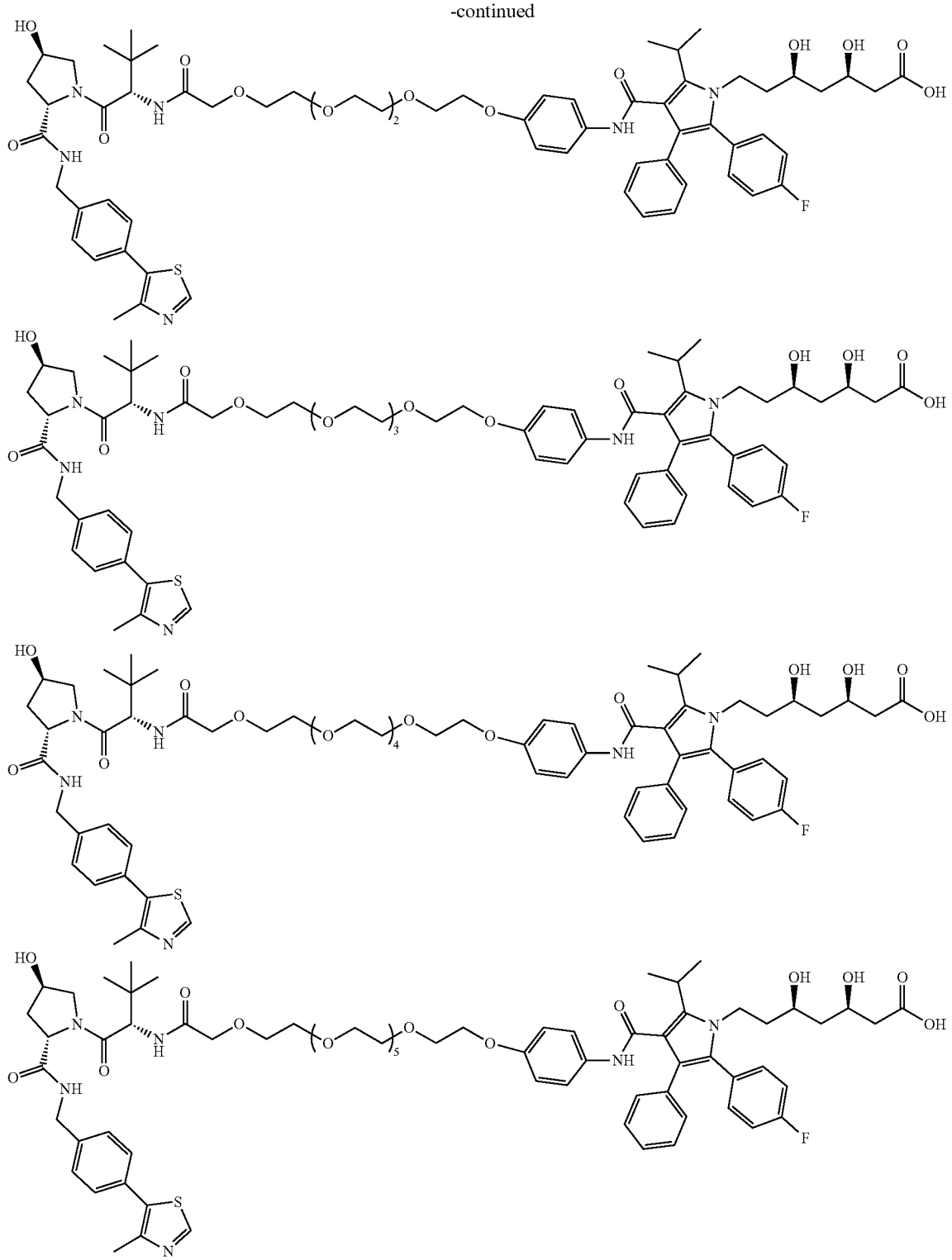
or a pharmaceutically acceptable salt thereof.
* * * * *